United States Patent
Lapierre et al.

(10) Patent No.: US 7,501,430 B2
(45) Date of Patent: Mar. 10, 2009

(54) RAF INHIBITORS AND THEIR USES

(75) Inventors: Jean-Marc Lapierre, Pelham, NH (US);
Nivedita D. Namdev, Westford, MA (US); Mark A. Ashwell, Carlisle, MA (US); Dennis S. France, Carlisle, MA (US); Hui Wu, Malden, MA (US); Patrick M. Hutchins, Denver, CO (US); Manish Tandon, Framingham, MA (US); Yanbin Liu, Acton, MA (US); Jeff S. Link, Londonderry, NH (US); Syed M. Ali, North Andover, MA (US); Chris J. Brassard, Somerville, MA (US); Robb B. Nicewonger, Tyngsboro, MA (US); Anton Filikov, Stoneham, MA (US); Rebecca J. Carazza, Winchester, MA (US)

(73) Assignee: ArQule, Inc., Woburn, MA (US)

( * ) Notice: Subject to any disclaimer, the term of this patent is extended or adjusted under 35 U.S.C. 154(b) by 0 days.

(21) Appl. No.: 11/785,163

(22) Filed: Apr. 16, 2007

(65) Prior Publication Data

US 2007/0281955 A1 Dec. 6, 2007

Related U.S. Application Data

(60) Provisional application No. 60/792,314, filed on Apr. 17, 2006.

(51) Int. Cl.
*C07D 498/04* (2006.01)
*C07D 513/04* (2006.01)
*A61K 31/429* (2006.01)
*A61K 31/4188* (2006.01)

(52) U.S. Cl. ...................... 514/275; 544/333

(58) Field of Classification Search ................. 544/333; 514/275
See application file for complete search history.

(56) References Cited

FOREIGN PATENT DOCUMENTS

WO WO 2004/110990 * 12/2004
WO WO 2006/044869 4/2006

OTHER PUBLICATIONS

Simone, Oncology: Introduction, Cecil Textbook of Medicine, 20th Edition, vol. 1, pp. 1004-1010, 1996.*
Bundgaard, Design of Prodrugs, p. 1, 1985.*
Wolff, Some consideration for prodrug design, Burger's Medicinal Chemistry and Drug Discovery, 5th Edition, vol. I: Principles and Practice, pp. 975-977, 1995.*
Banker et al., Prodrugs, Modern Pharmaceutics, Third Edition, Revised and Expanded, pp. 451 and 596.*
Allen et al., "CI-1040 (PD184352), A Targeted Signal Transduction Inhibitor of MEK (MAPKK)," *Semin. Oncol.* 30(5 Suppl 16):105-116 (2003).
Davies et al., "Mutations of the BRAF Gene in Human Cancer," *Nature*, 417:949-954 (2002).
Hoeflich et al., "Oncogenic BRAF Is Required for Tumor Growth and Maintenance in Melanoma Models," *Cancer Res.*, 66(2):999-1006 (2006).
Li et al., "Selective Killing of Cancer Cells by Beta-Lapachone: Direct Checkpoint Activation as a Strategy Against Cancer," *Proc. Natl. Acad. Sci. USA.*, 100(5):2674-2678 (2003).
Marais et al., "Control of the ERK MAP Kinase Cascade by Ras and Raf," *Cancer Surv.*, 27:101-125 (1996).
Robinson et al., "Mitogen-Activated Protein Kinase Pathways," *Curr. Opin. Cell Biol.*, 9:180-186 (1997).
Sharma et al., "Mutant $^{V599E}$B-Raf Regulates Growth and Vascular Development of Malignant Melanoma Tumors," *Cancer Res.*, 65(6):2412-2421 (2005).
Tuveson et al., "BRAF as a Potential Therapeutic Target in Melanoma and Other Malignacies," *Cancer Cell*, 4:95-98 (2003).
Wellbrock et al., "$^{V599E}$B-RAF Is an Oncogene in Melanocytes," *Cancer Res.*, 64:2338-2342 (2004).
Xing, "BRAF Mutation in Thyroid Cancer," *Endocrine-Related Cancer*, 12:245-262 (2005).
International Search Report for International Application No. PCT/US2007/009348, mailed Oct. 10, 2007.

* cited by examiner

*Primary Examiner*—Deepak Rao
(74) *Attorney, Agent, or Firm*—Bromberg & Sunstein LLP

(57) ABSTRACT

The present invention provides imidazooxazole and imidazothiazole compounds and their synthesis. The compounds of the present invention are capable of inhibiting the activity of RAF kinase, such as B-RAF$^{V600E}$. The compounds are useful for the treatment of cell proliferative disorders such as cancer.

10 Claims, 6 Drawing Sheets

Figure 1: Synthesis of compounds of formula XI

Figure 2: Preparation of the guanidinium salts of formula IX

Figure 3: Transformation of intermediate XI to compounds of formulas XII to XV

Figure 4: Preparation of phenols of formula XVII and carboxylic acids of formula XIX

RAF INHIBITORS AND THEIR USES

CROSS-REFERENCE TO RELATED APPLICATION

This application claims the benefit of U.S. Provisional Application No. 60/792,314, filed Apr. 17, 2006, the contents of which are incorporated herein by reference in their entirety.

BACKGROUND OF THE INVENTION

There are three RAF isoforms in humans: A-RAF, B-RAF and C-RAF (Marais and Marshall. *Cancer Surv.* 27:101-125 (1996)). These serine/threonine protein kinases are components of a conserved signaling pathway downstream of the membrane-bound small G protein RAS, which is activated by growth factors, hormones, and cytokines (Robinson and Cobb, *Curr. Opin. Cell Biol.* 9:180-186 (1997)). RAS stimulates RAF activation, which then leads to activation of the MEK kinase and subsequently the ERK kinase. Depending on the cellular context, this pathway mediates diverse biological functions such as cell growth, survival and differentiation predominantly through the regulation of transcription, metabolism and cytoskeletal rearrangements.

The RAS-RAF signaling pathway has long been associated with human cancers because oncogenic mutations in the ras gene occur in at least 15% of all human cancers (Davies, H. et al., *Nature* 417:949-954 (2002)), and the downstream kinase ERK is hyperactivated in 30% of cancers (Allen, et al., *Semin. Oncol.* 30:105-116 (2003)). However, for more than a decade, the RAF proteins had been considered to be important in cancer only because of their position downstream of RAS. This view was changed radically when activating mutations of B-RAF were found at a high frequency in human cancer, implicating B-RAF as a critical initiator and promoter of malignancy (Davies, H. et al., *Nature* 417:949-954 (2002)).

Activating mutations in the B-RAF protooncogene underlie 70% of melanomas, 50% of papillary thyroid cancers and 10% of colon cancers (Tuveson, et al., *Cancer Cell* 4:95-98 (2003); and Xing, *Endocrine-Related Cancer:* 12:245-262 (2005). Approximately 90% of these mutations occur as a single-nucleotide substitution that converts a valine to glutamate at amino acid 600 (V600E) in the kinase domain of B-RAF. This mutation increases the basal kinase activity of B-RAF, resulting in the activation of the MEK and ERK proteins that ultimately leads to uncontrolled tumor cell growth. Significantly, B-RAF and RAS mutations are usually mutually exclusive in the same tumor types, suggesting that these genes are on the same oncogenic signaling pathway and that RAS acts to activate B-RAF in these tumors.

Recent studies have found that knockdown of mutant B-RAF by small interference RNA in human melanoma cells inhibits both MEK and ERK kinases, causing growth arrest and ultimately promoting apoptosis (Sharma, et al., *Cancer Res.* 65:2412-2421 (2005); and Wellbrock et al., *Cancer Res.* 64:2338-2342 (2004)). In addition, data obtained from a short-hairpin RNA xenograft models targeting mutant B-RAF have shown that tumor regression resulting from B-RAF suppression is inducible, reversible, and tightly regulated (Hoeflich et al., *Cancer Res.* 66:999-1006 (2006). Taken together, gain-of-function B-RAF signaling is strongly associated with in vivo tumorigenicity, confirming B-RAF as an important target for cancer therapeutics.

The references cited herein are not admitted to be prior art to the claimed invention.

SUMMARY OF THE INVENTION

The present invention provides a compound of formula I or pharmaceutically acceptable salts thereof

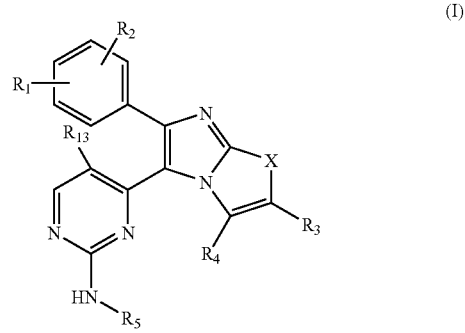

(I)

wherein

X is O, S(O)$_p$;

p is an integer from 0 to 2;

$R_1$ is halogen, —CN, —NO$_2$, —OH, —O—($C_1$-$C_8$ substituted or unsubstituted alkyl), —O—($C_1$-$C_8$ fluoroalkyl), —(CH$_2$)$_{0-3}$—CO$_2$H, —(CH$_2$)$_{0-3}$—C(O)O-alkyl, —($C_1$-$C_8$ substituted or unsubstituted alkyl), —($C_1$-$C_8$ fluoroalkyl), —($C_3$-$C_8$ cycloalkyl), —($C_3$-$C_8$ fluorocycloalkyl), O-aryl (substituted or unsubstituted), —O-heteroaryl (substituted or unsubstituted), —NR$_6$R$_7$, —NR$_8$—C(O)R$_9$, —NR$_8$—C(O)-fluoroalkyl, —NR$_8$—C(O)-aryl (substituted or unsubstituted), —(CH$_2$)$_{0-3}$—C(O)NR$_6$R$_7$, —NR$_8$SO$_2$R$_9$, —NR$_8$C(O)NR$_6$R$_7$, —NR$_8$C(S)NR$_6$R$_7$, —OSO$_2$NR$_6$R$_7$, —C(N—OH)NH$_2$, —C(N—OH)R$_8$, —CH$_2$OR$_8$, —OC(O)NR$_6$R$_7$, —SR$_9$, or —C(O)NR$_8$SO$_2$R$_9$;

$R_2$ is hydrogen, halogen, —CN, —NO$_2$, —OH, —O—($C_1$-$C_8$ substituted or unsubstituted alkyl), —O—($C_1$-$C_8$ fluoroalkyl), —(CH$_2$)$_{0-3}$—CO$_2$H, —(CH$_2$)$_{0-3}$—C(O)O-alkyl, —($C_1$-$C_8$ substituted or unsubstituted alkyl), —($C_1$-$C_8$ fluoroalkyl), —($C_3$-$C_8$ cycloalkyl), —($C_3$-$C_8$ fluorocycloalkyl), O-aryl (substituted or unsubstituted), —O-heteroaryl (substituted or unsubstituted), —NR$_6$R$_7$, —NR$_8$—C(O)R$_9$, —NR$_8$—C(O)-fluoroalkyl, —NR$_8$—C(O)-aryl (substituted or unsubstituted), —(CH$_2$)$_{0-3}$—C(O)NR$_6$R$_7$, —NR$_8$SO$_2$R$_9$, —NR$_8$C(O)NR$_6$R$_7$, —NR$_8$C(S)NR$_6$R$_7$, —OSO$_2$NR$_6$R$_7$, —C(N—OH)NH$_2$, —C(N—OH)R$_8$, —CH$_2$OR$_8$, —OC(O)NR$_6$R$_7$, —SR$_9$, or —C(O)NR$_8$SO$_2$R$_9$, or $R_1$, $R_2$, taken together, may form a ring;

$R_3$ and $R_4$ are independently hydrogen, substituted or unsubstituted lower alkyl, —COOH, —COOR$_8$, or —C(O)NR$_{10}$R$_{11}$;

$R_5$ is selected from the group consisting of $C_1$-$C_{10}$ alkyl, $C_3$-$C_{10}$ cycloalkyl, heterocyclyl, and aryl; wherein said $C_1$-$C_{10}$ alkyl, $C_3$-$C_{10}$ cycloalkyl, heterocyclyl, and aryl groups may be substituted with one or more substituents independently selected from the group consisting of: hydroxyl group, —COOH, oxo, fluorine, thiol, cyano, nitro, —NR$_6$R$_7$, $C_1$-$C_6$ alkylthio, arylthio, $C_1$-$C_6$ alkyl, $C_1$-$C_8$ fluoro-substituted alkyl, $C_1$-$C_6$ alkoxy, $C_1$-$C_8$ fluoro-substituted alkoxy, —O-aryl, —OC(=O)-alkyl, —OC(=O)-aryl, $C_3$-$C_8$ cycloalkyl, $C_3$-$C_8$ fluoro-substituted cycloalkyl, $C_3$-$C_8$ cycloalkyloxy, $C_3$-$C_8$ fluoro-substituted cycloalkyloxy, $C_2$-$C_6$ alkenyl, $C_2$-$C_6$ alkynyl, aryl, —C(=O)—NR$_8$R$_9$, $C_1$-$C_6$ alkylcarbonyl, $C_3$-$C_8$ cycloalkylcarbonyl, heterocyclylcarbonyl, —C(=O)-aryl, —C(=O)—O-aryl, $C_1$-$C_6$ alkoxycarbonyl, $C_1$-$C_6$ fluoro-substituted alkoxycarbonyl, $C_3$-$C_8$ cycloalkyloxycarbonyl, heterocyclyloxycarbonyl, $C_1$-$C_6$ alkylsulfonyl, arylsulfonyl, and heterocyclyl;

wherein when $R_5$ is aryl, said one or more substituents further include chlorine, bromine and iodine; and wherein when $R_5$ is a heterocycle having an endocyclic nitrogen atom or endocyclic nitrogen atoms, said endocyclic nitrogen atom or endocyclic nitrogen atoms may be substituted with one or more substituents independently selected from the group consisting of: hydrogen, $C_1$-$C_6$ alkyl, $C_3$-$C_8$ cycloalkyl, $C_2$-$C_6$ alkenyl, $C_2$-$C_6$ alkynyl, aryl, —C(=O)—$NR_8R_9$, $C_1$-$C_6$ alkylcarbonyl, —C(=O)-aryl, —C(=O)—O-aryl, $C_1$-$C_6$ alkoxycarbonyl, $C_1$-$C_6$ alkylsulfonyl, arylsulfonyl, and heterocyclyl;

each $R_6$ and each $R_7$ are independently hydrogen, substituted or unsubstituted alkyl, substituted or unsubstituted aryl, or substituted or unsubstituted heterocyclyl, or $R_6$ and $R_7$, taken together, may form a ring;

each $R_8$ is independently hydrogen, or substituted or unsubstituted lower alkyl;

each $R_9$ is independently substituted or unsubstituted alkyl, substituted or unsubstituted aryl, substituted or unsubstituted heterocyclyl, or substituted or unsubstituted heteroaryl;

$R_{10}$ is substituted or unsubstituted lower alkyl, or substituted or unsubstituted aryl;

$R_{11}$ is hydrogen, substituted or unsubstituted alkyl, substituted or unsubstituted aryl, or substituted or unsubstituted heterocyclyl, or substituted or unsubstituted heteroaryl, or $R_{11}$, taken together with $R_{10}$, may form a ring; and $R_{13}$ is selected from the group consisting of hydrogen, $C_1$-$C_8$ alkyl, $C_1$-$C_8$ fluoro-substituted alkyl, $C_3$-$C_8$ cycloalkyl, $C_3$-$C_8$ fluoro-substituted cycloalkyl, aryl, halogen-substituted aryl, heteroaryl, and halogen-substituted heteroaryl.

In an embodiment, $R_5$ is

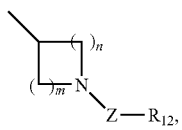

wherein m is an integer from 1 to 3; n is an integer from 1 to 3; Z is hydrogen, a bond, —C(O)—, —C(O)$NR_{11}$—, —S(O)$_2$—, —C(O)NH—S(O)$_2$—, or CH(OH)—CH$_2$—Y—, wherein Y is CH$_2$, O, S, NH, or a bond; and $R_{12}$ is substituted or unsubstituted alkyl, substituted or unsubstituted aryl, substituted or unsubstituted heterocyclyl, or substituted or unsubstituted heteroaryl.

In an embodiment, $R_3$ and $R_4$ are hydrogen.

In an embodiment, $R_{13}$ is hydrogen.

In an embodiment, m+n=4, if m is not equal to n, then the preferred configuration is R.

In an embodiment, Z is —S(O)$_2$— and $R_{12}$ is 4-chlorophenyl, 4-fluorophenyl, 4-cyanophenyl, methyl, or cyclopropyl.

In an embodiment, $R_1$ is —(CH$_2$)$_{0-3}$—C(O)NR$_6$R$_7$, —NR$_8$SO$_2$R$_9$, —NR$_8$C(O)NR$_6$R$_7$, —NR$_8$C(S)NR$_6$R$_7$, —OSO$_2$NR$_6$R$_7$, —C(N—OH)NH$_2$, —C(N—OH)R$_8$, —CH$_2$OR$_8$, —OC(O)NR$_6$R$_7$, —SR$_9$, or —C(O)NR$_8$SO$_2$R$_9$; and $R_2$ is hydrogen, —(CH$_2$)$_{0-3}$—C(O)NR$_6$R$_7$, —NR$_8$SO$_2$R$_9$, —NR$_8$C(O)NR$_6$R$_7$, —NR$_8$C(S)NR$_6$R$_7$, —OSO$_2$NR$_6$R$_7$, —C(N—OH)NH$_2$, —C(N—OH)R$_8$, —CH$_2$OR$_8$, —OC(O)NR$_6$R$_7$, —SR$_9$, or —C(O)NR$_8$SO$_2$R$_9$, or $R_1$ or $R_2$, taken together, may form a ring.

The present invention also provides a pharmaceutical composition comprising a compound of formula I or a pharmaceutically acceptable salt thereof together with one or more pharmaceutically acceptable carriers or excipients. In an embodiment, the pharmaceutical composition further comprises a second chemotherapeutic agent.

The present invention further provides a method of treating a cell proliferative disorder. The method comprises administering to a subject in need thereof a therapeutically effective amount of a compound of formula I, or a pharmaceutically acceptable salt thereof, or a prodrug or metabolite thereof, in combination with a pharmaceutically acceptable carrier, wherein said cell proliferative disorder is treated.

In an embodiment, the cells with proliferative disorder contain DNA encoding a RAF, mutant or wild type. In a further embodiment, the cells have a constitutively enhanced RAF activity. The RAF can be A-RAF, B-RAF, or C-RAF. In an embodiment, B-RAF is a mutant, more specifically, B-RAF$^{V600E}$.

The cell proliferative disorder can be a precancerous condition, or a cancer. In an embodiment, the cell proliferative disorder is melanoma, papillary thyroid cancers, colon cancer, or Congenital Nevi.

The present invention further provides a method of modulating B-RAF activity. The method comprises contacting a cell containing B-RAF gene with an effective amount of a compound of formula II, or a pharmaceutically acceptable salt thereof, or a prodrug, metabolite, analog or derivative thereof, wherein said contacting results in said inhibiting B-RAF activity. In an embodiment, The B-RAF activity is the kinase activity of B-RAF. In an embodiment, the B-RAF is B-RAF$^{V600E}$.

Other features and advantages of the present invention are apparent from the additional descriptions provided herein including the different examples. The provided examples illustrate different components and methodology useful in practicing the present invention. The examples do not limit the claimed invention. Based on the present disclosure the skilled artisan can identify and employ other components and methodology useful for practicing the present invention.

DETAILED DESCRIPTION OF THE INVENTION

1. The Compounds

Figure 1:
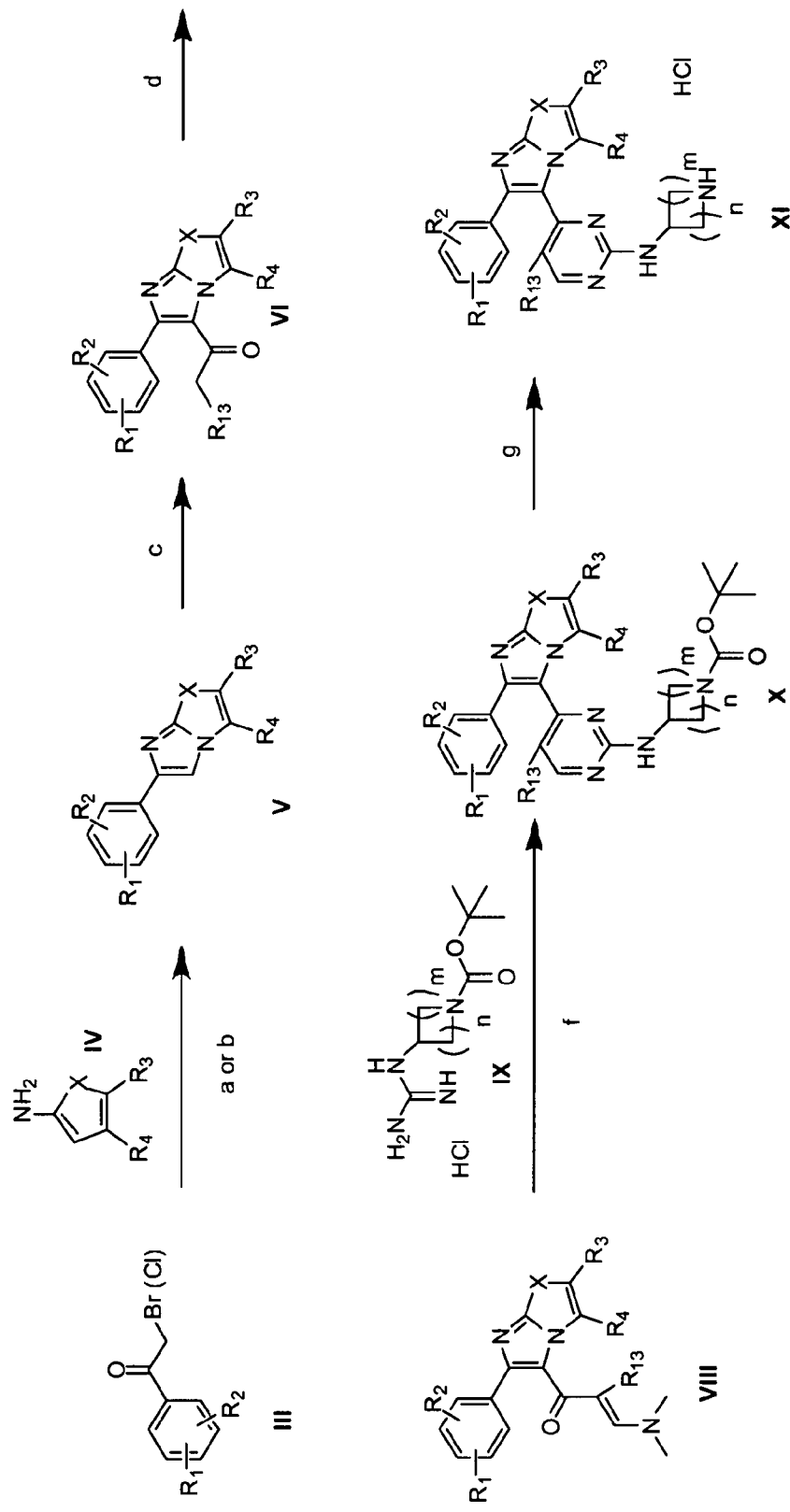
FIG. 1: Synthesis of compounds of formula XI.

The present invention provides imidazooxazole and / or imidazothiazole compounds and their synthesis.

In an embodiment, the present invention provides compounds of formula I and their synthesis.

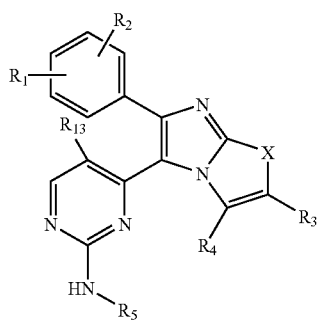

(I)

wherein

X is O, S(O)$_p$;

p is an integer from 0 to 2;

R$_1$ is halogen, —CN, —NO$_2$, —OH, —O—(C$_1$-C$_8$ substituted or unsubstituted alkyl), —O—(C$_1$-C$_8$ fluoroalkyl), —(CH$_2$)$_{0-3}$—CO$_2$H, —(CH$_2$)$_{0-3}$—C(O)O-alkyl, —(C$_1$-C$_8$ substituted or unsubstituted alkyl), —(C$_1$-C$_8$ fluoroalkyl), —(C$_3$-C$_8$ cycloalkyl), —(C$_3$-C$_8$ fluorocycloalkyl), O-aryl (substituted or unsubstituted), —O-heteroaryl (substituted or unsubstituted), —NR$_6$R$_7$, —NR$_8$—C(O)R$_9$, —NR$_8$—C(O)-fluoroalkyl, —NR$_8$—C(O)-aryl (substituted or unsubstituted), —(CH$_2$)$_{0-3}$—C(O)NR$_6$R$_7$, —NR$_8$SO$_2$R$_9$, —NR$_8$C(O)NR$_6$R$_7$, —NR$_8$C(S)NR$_6$R$_7$, —OSO$_2$NR$_6$R$_7$, —C(N—OH)NH$_2$, —C(N—OH)R$_8$, —CH$_2$OR$_8$, —OC(O)NR$_6$R$_7$, —SR$_9$, or —C(O)NR$_8$SO$_2$R$_9$;

R$_2$ is hydrogen, halogen, —CN, —NO$_2$, —OH, —O—(C$_1$-C$_8$ substituted or unsubstituted alkyl), —O—(C$_1$-C$_8$ fluoroalkyl), —(CH$_2$)$_{0-3}$—CO$_2$H, —(CH$_2$)$_{0-3}$—C(O)O-alkyl, —(C$_1$-C$_8$ substituted or unsubstituted alkyl), —(C$_1$-C$_8$ fluoroalkyl), —(C$_3$-C$_8$ cycloalkyl), —(C$_3$-C$_8$ fluorocycloalkyl), O-aryl (substituted or unsubstituted), —O-heteroaryl (substituted or unsubstituted), —NR$_6$R$_7$, —NR$_8$—C(O)R$_9$, —NR$_8$—C(O)-fluoroalkyl, —NR$_8$—C(O)-aryl (substituted or unsubstituted), —(CH$_2$)$_{0-3}$—C(O)NR$_6$R$_7$, —NR$_8$SO$_2$R$_9$, —NR$_8$C(O)NR$_6$R$_7$, —NR$_8$C(S)NR$_6$R$_7$, —OSO$_2$NR$_6$R$_7$, —C(N—OH)NH$_2$, —C(N—OH)R$_8$, —CH$_2$OR$_8$, —OC(O)NR$_6$R$_7$, —SR$_9$, or —C(O)NR$_8$SO$_2$R$_9$, or R$_1$, R$_2$, taken together, may form a ring;

R$_3$ and R$_4$ are independently hydrogen, substituted or unsubstituted lower alkyl, —COOH, —COOR$_8$, or —C(O)NR$_{10}$R$_{11}$;

R$_5$ is independently selected from the group consisting of C$_1$-C$_{10}$ alkyl, C$_3$-C$_{10}$ cycloalkyl, heterocyclyl, and aryl; wherein said C$_1$-C$_{10}$ alkyl, C$_3$-C$_{10}$ cycloalkyl, heterocyclyl, and aryl groups may be substituted with one or more substituents independently selected from the group consisting of: hydroxyl group, —COOH, oxo, fluorine, thiol, cyano, nitro, —NR$_6$R$_7$, C$_1$-C$_6$ alkylthio, arylthio, C$_1$-C$_6$ alkyl, C$_1$-C$_8$ fluoro-substituted alkyl, C$_1$-C$_6$ alkoxy, C$_1$-C$_8$ fluoro-substituted alkoxy, —O-aryl, —OC(═O)-alkyl, —OC(═O)-aryl, C$_3$-C$_8$ cycloalkyl, C$_3$-C$_8$ fluoro-substituted cycloalkyl, C$_3$-C$_8$ cycloalkyloxy, C$_3$-C$_8$ fluoro-substituted cycloalkyloxy, C$_2$-C$_6$ alkenyl, C$_2$-C$_6$ alkynyl, aryl, —C(═O)—NR$_8$R$_9$, C$_1$-C$_6$ alkylcarbonyl, C$_3$-C$_8$ cycloalkylcarbonyl, heterocyclylcarbonyl, —C(═O)-aryl, —C(═O)—O-aryl, C$_1$-C$_6$ alkoxycarbonyl, C$_1$-C$_6$ fluoro-substituted alkoxycarbonyl, C$_3$-C$_8$ cycloalkyloxycarbonyl, heterocyclyloxycarbonyl, C$_1$-C$_6$ alkylsulfonyl, arylsulfonyl, and heterocyclyl;

wherein when R$_5$ is aryl, said one or more substitutents further include chlorine, bromine and iodine; and wherein when R$_5$ is a heterocycle having an endocyclic nitrogen atom or endocyclic nitrogen atoms, said endocyclic nitrogen atom or endocyclic nitrogen atoms may be substituted with one or more substituents independently selected from the group consisting of: hydrogen, C$_1$-C$_6$ alkyl, C$_3$-C$_8$ cycloalkyl, C$_2$-C$_6$ alkenyl, C$_2$-C$_6$ alkynyl, aryl, —C(═O)—NR$_8$R$_9$, C$_1$-C$_6$ alkylcarbonyl, —C(═O)-aryl, —C(═O)—O-aryl, C$_1$-C$_6$ alkoxycarbonyl, C$_1$-C$_6$ alkylsulfonyl, arylsulfonyl, and heterocyclyl;

each R$_6$ and each R$_7$ are independently hydrogen, substituted or unsubstituted alkyl, substituted or unsubstituted aryl, or substituted or unsubstituted heterocyclyl, or R$_6$ and R$_7$, taken together, may form a ring;

each R$_8$ is independently hydrogen, or substituted or unsubstituted lower alkyl;

each R$_9$ is independently substituted or unsubstituted alkyl, substituted or unsubstituted aryl, substituted or unsubstituted heterocyclyl, or substituted or unsubstituted heteroaryl;

R$_{10}$ is substituted or unsubstituted lower alkyl, or substituted or unsubstituted aryl;

R$_{11}$ is hydrogen, substituted or unsubstituted alkyl, substituted or unsubstituted aryl, Or substituted or unsubstituted heterocyclyl, or substituted or unsubstituted heteroaryl, or R$_{11}$, taken together with R$_{10}$, may form a ring; and R$_{13}$ is independently selected from the group consisting of hydrogen, C$_1$-C$_8$ alkyl, C$_1$-C$_8$ fluoro-substituted alkyl, C$_3$-C$_8$ cycloalkyl, C$_3$-C$_8$ fluoro-substituted cycloalkyl, aryl, halogen-substituted aryl, heteroaryl, and halogen-substituted heteroaryl.

The present invention also provides for compounds of formula II and their synthesis.

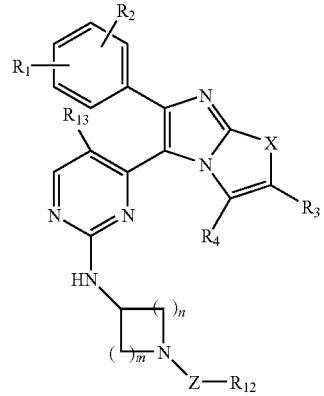

(II)

wherein

X is O, S(O)$_p$;

m is an integer from 1 to 3;

n is an integer from 1 to 3;

p is an integer from 0 to 2;

Z is hydrogen, a bond, —C(O)—, —C(O)NR$_{11}$—, —S(O)$_2$—, —C(O)NH—S(O)$_2$—, or CH(OH)—CH$_2$—Y—, wherein Y is CH$_2$, O, S, NH, or a bond;

R$_1$ is halogen, —CN, —NO$_2$, —OH, —O—(C$_1$-C$_8$ substituted or unsubstituted alkyl), —O—(C$_1$-C$_8$ fluoroalkyl), —(CH$_2$)$_{0-3}$—CO$_2$H, —(CH$_2$)$_{0-3}$—C(O)O-alkyl, —(C$_1$-C$_8$ substituted or unsubstituted alkyl), —(C$_1$-C$_8$ fluoroalkyl), —(C$_3$-C$_8$ cycloalkyl), —(C$_3$-C$_8$ fluorocycloalkyl), O-aryl (substituted or unsubstituted), —O-heteroaryl (substituted or unsubstituted), —NR$_6$R$_7$, —NR$_8$—C(O)R$_9$, —NR$_8$—C(O)- fluoroalkyl, $-NR_8-C(O)$-aryl (substituted or unsubstituted), $-(CH_2)_{0-3}-C(O)NR_6R_7$, $-NR_8SO_2R_9$, $-NR_8C(O)NR_6R_7$, $-NR_8C(S)NR_6R_7$, $-OSO_2NR_6R_7$, $-C(N-OH)NH_2$, $-C(N-OH)R_8$, $-CH_2OR_8$, $-OC(O)NR_6R_7$, $-SR_9$, or $-C(O)NR_8SO_2R_9$;

$R_2$ is hydrogen, halogen, $-CN$, $-NO_2$, $-OH$, $-O-(C_1-C_8$ substituted or unsubstituted alkyl), $-O-(C_1-C_8$ fluoroalkyl), $-(CH_2)_{0-3}-CO_2H$, $-(CH_2)_{0-3}-C(O)O$-alkyl, $-(C_1-C_8$ substituted or unsubstituted alkyl), $-(C_1-C_8$ fluoroalkyl), $-(C_3-C_8$ cycloalkyl), $-(C_3-C_8$ fluorocycloalkyl), O-aryl (substituted or unsubstituted), $-O$-heteroaryl (substituted or unsubstituted), $-NR_6R_7$, $-NR_8-C(O)R_9$, $-NR_8-C(O)$-fluoroalkyl, $-NR_8-C(O)$-aryl (substituted or unsubstituted), $-(CH_2)_{0-3}-C(O)NR_6R_7$, $-NR_8SO_2R_9$, $-NR_8C(O)NR_6R_7$, $-NR_8C(S)NR_6R_7$, $-OSO_2NR_6R_7$, $-C(N-OH)NH_2$, $-C(N-OH)R_8$, $-CH_2OR_8$, $-OC(O)NR_6R_7$, $-SR_9$, or $-C(O)NR_8SO_2R_9$, or $R_1$, $R_2$, taken together, may form a ring;

$R_3$ and $R_4$ are independently hydrogen, substituted or unsubstituted lower alkyl, $-COOH$, $-COOR_8$, or $-C(O)NR_{10}R_{11}$;

each $R_6$ and each $R_7$ are independently hydrogen, substituted or unsubstituted alkyl, substituted or unsubstituted aryl, or substituted or unsubstituted heterocyclyl, or $R_6$ and $R_7$, taken together, may form a ring;

each $R_8$ is independently hydrogen, or substituted or unsubstituted lower alkyl;

each $R_9$ is independently substituted or unsubstituted alkyl, substituted or unsubstituted aryl, substituted or unsubstituted heterocyclyl, or substituted or unsubstituted heteroaryl;

$R_{10}$ is substituted or unsubstituted lower alkyl, or substituted or unsubstituted aryl;

$R_{11}$ is hydrogen, substituted or unsubstituted alkyl, substituted or unsubstituted aryl, or substituted or unsubstituted heterocyclyl, or substituted or unsubstituted heteroaryl, or $R_{11}$, taken together with $R_{10}$, may form a ring;

$R_{12}$ is substituted or unsubstituted alkyl, substituted or unsubstituted aryl, substituted or unsubstituted heterocyclyl, or substituted or unsubstituted heteroaryl; and $R_{13}$ is independently selected from the group consisting of hydrogen, $C_1-C_8$ alkyl, $C_1-C_8$ fluoro-substituted alkyl, $C_3-C_8$ cycloalkyl, $C_3-C_8$ fluoro-substituted cycloalkyl, aryl, halogen-substituted aryl, heteroaryl, and halogen-substituted heteroaryl.

In an embodiment, $R_1$ is $-(CH_2)_{0-3}-C(O)NR_6R_7$, $-NR_8SO_2R_9$, $-NR_8C(O)NR_6R_7$, $-NR_8C(S)NR_6R_7$, $-OSO_2NR_6R_7$, $-C(N-OH)NH_2$, $-C(N-OH)R_8$, $-CH_2OR_8$, $-OC(O)NR_6R_7$, $-SR_9$, or $-C(O)NR_8SO_2R_9$; and $R_2$ is hydrogen, $-(CH_2)_{0-3}-C(O)NR_6R_7$, $-NR_8SO_2R_9$, $-NR_8C(O)NR_6R_7$, $-NR_8C(S)NR_6R_7$, $-OSO_2NR_6R_7$, $-C(N-OH)NH_2$, $-C(N-OH)R_8$, $-CH_2OR_8$, $-OC(O)NR_6R_7$, $-SR_9$, or $-C(O)NR_8SO_2R_9$, or $R_1$, $R_2$, taken together, may form a ring.

The term "alkyl" refers to radicals containing carbon and hydrogen, without unsaturation. Alkyl radicals can be straight or branched. Exemplary alkyl radicals include, without limitation, methyl, ethyl, propyl, isopropyl, hexyl, t-butyl, sec-butyl and the like. Alkyl groups may be denoted by a range, thus, for example, a $(C_1-C_6)$alkyl group is an alkyl group having from one to six carbon atoms in the straight or branched alkyl backbone. Substituted and unsubstituted alkyl groups may independently be $(C_1-C_5)$ alkyl, $(C_1-C_6)$alkyl, $(C_1-C_{10})$alkyl, $(C_3-C_{10})$alkyl, or $(C_5-C_{10})$alkyl. Unless expressly stated, the term "alkyl" does not include "cycloalkyl." The term "lower alkyl" refers to unbranched or branched $(C_1-C_6)$alkyl.

A "cycloalkyl" group refers to a cyclic alkyl group having the indicated number of carbon atoms in the "ring portion," where the "ring portion" may consist of one or more ring structures either as fused, spiro, or bridged ring structures. For example, a C3 to C6 cycloalkyl group (e.g., $(C_3-C_6)$ cycloalkyl) is a ring structure having between 3 and 6 carbon atoms in the ring. When no range is given, then cycloalkyl has between three and nine carbon atoms $((C_3-C_9)$cycloalkyl) in the ring portion. Exemplary cycloalkyl groups include, but are not limited to cyclopropyl, cyclobutyl, cyclopentyl, cyclohexyl, cycloheptyl, and adamantyl. Preferred cycloalkyl groups have three, four, five, six, seven, eight, nine, or from three to nine carbon atoms in the ring structure.

The term substituted alkyl and substituted cycloalkyl, refer to alkyl and cycloalkyl groups, as defined above, substituted with one or more substituents independently selected from the group consisting of fluorine, aryl, heteroaryl, $-O-(C_1-C_6)$alkyl, and $-NR5R6$, where R5 and R6 are independently selected from the group consisting of hydrogen and $-C_1-C_6)$ alkyl.

The term "aryl" refers to an aromatic carbocyclic group, having one, two, or three aromatic rings. Exemplary aryl groups include, without limitation, phenyl, naphthyl, and the like. Aryl groups include one, two, or three aromatic rings structures fused with one or more additional nonaromatic carbocyclic or hetercyclic rings having from 4-9 members. Examples of fused aryl groups include benzocyclobutanyl, indanyl, tetrahydronapthylenyl, 1,2,3,4-tetrahydrophenanthrenyl, tetrahydroanthracenyl, 1,4-dihydro-1,4-methanonaphthalenyl, benzodioxolyl.

The term "heteroaryl" refers to a heteroaromatic (heteroaryl) group having one, two, or three aromatic rings containing from 1-4 heteroatoms (such as nitrogen, sulfur, or oxygen) in the aromatic ring. Heteroaryl groups include one, two, or three aromatic rings structures containing from 1-4 heteroatoms fused with one or more additional nonaromatic rings having from 4-9 members. Heteroaryl groups containing a single type of hetroatom in the aromatic ring are denoted by the type of hetero atom they contain, thus, nitrogen-containing heteroaryl, oxygen-containing heteroaryl and sulfur-containing heteroaryl denote heteroaromatic groups containing one or more nitrogen, oxygen or sulfur atoms respectively. Exemplary heteroaryl groups include, without limitation, pyridyl, pyrimidinyl, triazolyl, quinolyl, quinazolinyl, thiazolyl, benzo[b]thiophenyl, furanyl, imidazolyl, indolyl, and the like.

The terms "heterocyclyl" or "heterocycle" refers to either saturated or unsaturated, stable non-aromatic ring structures that may be fused, spiro or bridged to form additional rings. Each heterocycle consists of one or more carbon atoms and from one to four heteroatoms selected from the group consisting of nitrogen, oxygen and sulfur. "Heterocyclyl" or "heterocycle" include stable non-aromatic 3-7 membered monocyclic heterocyclic ring structures and 8-11 membered bicyclic heterocyclic ring structures. A heterocyclyl radical may be attached at any endocyclic carbon or nitrogen atom that results in the creation of a stable structure. Preferred heterocycles include 3-7 membered monocyclic heterocycles (more preferably 5-7-membered monocyclic heterocycles) and 8-10 membered bicyclic heterocycles. Examples of such groups include piperidinyl, piperazinyl, pyranyl, pyrrolidinyl, morpholinyl, thiomorpholinyl, oxopiperidinyl, oxopyrrolidinyl, oxoazepinyl, azepinyl, isoxozolyl, tetrahydropyranyl, tetrahydrofuranyl, dioxolyl, dioxinyl, oxathiolyl, dithiolyl, sulfolanyl, dioxanyl, dioxolanyl, tetrahydrofurodihydrofuranyl, tetrahydropyranodihydro-furanyl, dihydropyranyl, tetrahydrofurofuranyl, tetrahydropyranofuran, quinuclidinyl (1-azabicyclo[2.2.2]octanyl) and tropanyl (8-methyl-8-azabicyclo[3.2.1]octanyl).

All stereoisomers of the compounds of the instant invention are contemplated, either in a mixture or in pure or substantially pure form, including crystalline forms of racemic mixtures and crystalline forms of individual isomers. The definition of the compounds according to the invention embraces all possible stereoisomers (e.g., the R and S configurations for each asymmetric center) and their mixtures. It very particularly embraces the racemic forms and the isolated optical isomers having a specified activity. The racemic forms can be resolved by physical methods, such as, for example, fractional crystallization, separation or crystallization of diastereomeric derivatives, separation by chiral column chromatography or supercritical fluid chromatography. The individual optical isomers can be obtained from the racemates by conventional methods, such as, for example, salt formation with an optically active acid followed by crystallization. Furthermore, all geometric isomers, such as E- and Z-configurations at a double bond, are within the scope of the invention unless otherwise stated. Certain compounds of this invention may exist in tautomeric forms. All such tautomeric forms of the compounds are considered to be within the scope of this invention unless otherwise stated. The present invention also includes one or more regioisomeric mixtures of an analog or derivative.

As used herein, the term "salt" is a pharmaceutically acceptable salt and can include acid addition salts including hydrochlorides, hydrobromides, phosphates, sulphates, hydrogen sulphates, alkylsulphonates, arylsulphonates, acetates, benzoates, citrates, maleates, fumarates, succinates, lactates, and tartrates; alkali metal cations such as $Na^+$, $K^+$, $Li^+$, alkali earth metal salts such as $Mg^{2+}$ or $Ca^{2+}$, or organic amine salts.

As used herein, the term "metabolite" means a product of metabolism of a compound of the present invention, or a pharmaceutically acceptable salt, analog or derivative thereof, that exhibits a similar activity in vivo to said compound of the present invention.

As used herein, the term "prodrug" means a compound of the present invention covalently linked to one or more pro-moieties, such as an amino acid moiety or other water solubilizing moiety. A compound of the present invention may be released from the pro-moiety via hydrolytic, oxidative, and/or enzymatic release mechanisms. In an embodiment, a prodrug composition of the present invention exhibits the added benefit of increased aqueous solubility, improved stability, and improved pharmacokinetic profiles. The pro-moiety may be selected to obtain desired prodrug characteristics. For example, an amino acid moiety or other water solubilizing moiety such as phosphate within $R_4$, may be selected based on solubility, stability, bioavailability, and/or in vivo delivery or uptake.

In an embodiment of the present invention, the compound is a compound of formula I or formula II wherein $R_3$ and $R_4$ are hydrogen.

In another embodiment of the present invention, the compound is a compound of formula I or formula II wherein $R_1$ is 3-OH and $R_2$ is hydrogen.

In another embodiment of the present invention, the compound is a compound of formula I or formula II wherein $R_{13}$ is hydrogen.

In another embodiment of the present invention, the compound is a compound of formula II wherein m+n=4, m is not equal to n, and the configuration is R. As used herein, the configuration of a molecule is the permanent geometry that results from the spatial arrangement of its atoms. The configuration can be either R or S and is defined according to the UIPAC rules. When more than one stereogenic atoms are present in a molecule, each one will be defined as of configuration R or S.

In another embodiment of the present invention, the compound is a compound of formula I or formula II wherein Z is —S(O)$_2$— and $R_{12}$ is 4-chlorophenyl, 4-fluorophenyl or 4-cyanophenyl.

In an embodiment of the present invention, the compound is one of compounds #1-316 listed in table 2. In a further embodiment of the present invention, the compound is one of compounds #1-289 listed in table 2. In an embodiment of the present invention, the compound is one of compounds #290-316 listed in table 2. In an embodiment of the present invention, the compound is one of compounds #317-401 listed in table 2.

In an embodiment of the present invention, the compound is 3-{5-[2-({(3R)-1-[(4-chlorophenyl)sulfonyl]piperidin-3-yl}amino)pyrimidin-4-yl]imidazo[2,1-b][1,3]thiazol-6-yl}phenyl carbamate, 3-{5-[2-({(3R)-1-[(4-chlorophenyl)sulfonyl]piperidin-3-yl}amino)pyrimidin-4-yl]imidazo[2,1-b][1,3]thiazol-6-yl}phenyl sulfamate, 3-{5-[2-({(3R)-1-[(4-chlorophenyl)sulfonyl]piperidin-3-yl}amino)pyrimidin-4-yl]imidazo[2,1-b][1,3]oxazol-6-yl}phenyl sulfamate, 3-{5-[2-({(3R)-1-[(4-chlorophenyl)sulfonyl]piperidin-3-yl}amino)pyrimidin-4-yl]imidazo[2,1-b][1,3]oxazol-6-yl}phenyl carbamate, (1E)-1-(3-{5-[2-({(3R)-1-[(4-chlorophenyl)sulfonyl]piperidin-3-yl}amino)pyrimidin-4-yl]imidazo[2,1-b][1,3]thiazol-6-yl}phenyl)ethanone oxime, 2-chloro-5-{5-[2-({(3R)-1-[(4-chlorophenyl)sulfonyl]piperidin-3-yl}amino)pyrimidin-4-yl]imidazo[2,1-b][1,3]thiazol-6-yl}phenol, 3-{5-[2-({(3R)-1-[(4-chlorophenyl)sulfonyl]piperidin-3-yl}amino)pyrimidin-4-yl]imidazo[2,1-b][1,3]oxazol-6-yl}phenol, 4-{[(3R)-3-({4-[6-(3-hydroxyphenyl)imidazo[2,1-b][1,3]thiazol-5-yl]pyrimidin-2-yl}amino)piperidin-1-yl]sulfonyl}benzonitrile, 4-{[(3R)-3-({4-[6-(3-hydroxyphenyl)imidazo[2,1-b][1,3]thiazol-5-yl]pyrimidin-2-yl}amino)piperidin-1-yl]sulfonyl}benzoic acid, 3-{[(3R)-3-({4-[6-(3-hydroxyphenyl)imidazo[2,1-b][1,3]thiazol-5-yl]pyrimidin-2-yl}amino)piperidin-1-yl]sulfonyl}phenol, 2-{5-[2-({(3R)-1-[(4-chlorophenyl)sulfonyl]piperidin-3-yl}amino)pyrimidin-4-yl]imidazo[2,1-b][1,3]thiazol-6-yl}benzene-1,4-diol, 3-[5-(2-{[(3R)-1-(methylsulfonyl)piperidin-3-yl]amino}pyrimidin-4-yl)imidazo[2,1-b][1,3]thiazol-6-yl]phenol, 3-{5-[2-({1-[(4-fluorophenyl)sulfonyl]piperidin-4-yl}amino)pyrimidin-4-yl]imidazo[2,1-b][1,3]thiazol-6-yl}phenol, 3-{5-[2-({1-[(4-chlorophenyl)sulfonyl]piperidin-4-yl}amino)pyrimidin-4-yl]imidazo[2,1-b][1,3]thiazol-6-yl}phenol, N-ethyl-4-({4-[6-(3-hydroxyphenyl)imidazo[2,1-b][1,3]thiazol-5-yl]pyrimidin-2-yl}amino)piperidine-1-carboxamide, 3-{5-[2-({(3R)-1-[(4-chlorophenyl)sulfonyl]piperidin-3-yl}amino)pyrimidin-4-yl]imidazo[2,1-b][1,3]thiazol-6-yl}phenol, 4-{[4-({4-[6-(3-hydroxyphenyl)imidazo[2,1-b][1,3]oxazol-5-yl]pyrimidin-2-yl}amino)piperidin-1-yl]sulfonyl}benzonitrile, 4-{[4-({4-[6-(3-hydroxyphenyl)imidazo[2,1-b][1,3]oxazol-5-yl]pyrimidin-2-yl}amino)piperidin-1-yl]sulfonyl}benzamide, 4-{[(3R)-3-({4-[6-(3-hydroxyphenyl)imidazo[2,1-b][1,3]oxazol-5-yl]pyrimidin-2-yl}amino)piperidin-1-yl]sulfonyl}benzonitrile, 3-{5-[2-({1-[(4-chlorophenyl)sulfonyl]piperidin-4-yl}amino)pyrimidin-4-yl]imidazo[2,1-b][1,3]oxazol-6-yl}phenol, 3-{5-[2-({1-[(4-fluorophenyl)sulfonyl]piperidin-4-yl}amino)pyrimidin-4-yl]imidazo[2,1-b][1,3]oxazol-6-yl}phenol, 5-{5-[2-({(3R)-1-[(4-chlorophenyl)sulfonyl]piperidin-3-yl}amino)pyrimidin-4-yl]imidazo[2,1-b][1,3]thiazol-6-yl}-2-fluorophenol, 3-{5-[2-({(3R)-1-[(1-methyl- 1H-imidazol-4-yl)sulfonyl]piperidin-3-yl}amino) pyrimidin-4-yl]imidazo[2,1-b][1,3]thiazol-6-yl}phenol, 3-[5-(2-{[(3R )-1-(3-thienylsulfonyl)piperidin-3-yl] amino}pyrimidin-4-yl)imidazo[2,1-b][1,3]thiazol-6-yl]phenol, 3-[5-(2-{[(3R)-1-(2-thienylsulfonyl)piperidin-3-yl] amino}pyrimidin-4-yl)imidazo[2,1-b][1,3]thiazol-6-yl] phenol, 3-[5-(2-{[(3R)-1-(phenylsulfonyl)piperidin-3-yl] amino}pyrimidin-4-yl)imidazo[2,1-b][1,3]thiazol-6-yl] phenol, 3-{5-[2-({(3R)-1-[(1-methyl-1H-pyrazol-3-yl) sulfonyl]piperidin-3-yl}amino)pyrimidin-4-yl]imidazo[2,1-b][1,3]thiazol-6-yl}phenol, 3-[5-(2-{[(3R)-1-(4H-1,2,4-triazol-3-ylsulfonyl)piperidin-3-yl]amino}pyrimidin-4-yl) imidazo[2,1-b][1,3]thiazol-6-yl]phenol, 3-[5-(2-{[(3R)-1-(2-thienylsulfonyl)piperidin-3-yl]amino}pyrimidin-4-yl) imidazo[2,1-b][1,3]oxazol-6-yl]phenol, 3-[5-(2-{[(3R)-1-(phenylsulfonyl)piperidin-3-yl]amino}pyrimidin-4-yl) imidazo[2,1-b][1,3]oxazol-6-yl]phenol, 3-[5-(2-{[1-(cyclopropylsulfonyl)piperidin-4-yl]amino}pyrimidin-4-yl) imidazo[2,1-b][1,3]thiazol-6-yl]phenol, 3-[5-(2-{[1-(methylsulfonyl)piperidin-4-yl]amino}pyrimidin-4-yl) imidazo[2,1-b][1,3]thiazol-6-yl]phenol, 3-[5-(2-{[1-(cyclopropylsulfonyl)piperidin-4-yl]amino}pyrimidin-4-yl) imidazo[2,1-b][1,3]oxazol-6-yl]phenol, 3-[5-(2-{[1-(methylsulfonyl)piperidin-4-yl]amino}pyrimidin-4-yl) imidazo[2,1-b][1,3]oxazol-6-yl]phenol, 5-[5-(2-{[1-(cyclopropylsulfonyl)piperidin-4-yl]amino}pyrimidin-4-yl) imidazo[2,1-b][1,3]thiazol-6-yl]-2-fluorophenol, or 3-[5-(2-{[(3R)-1-(cyclopropylsulfonyl)piperidin-3-yl] amino}pyrimidin-4-yl)imidazo[2,1-b][1,3]oxazol-6-yl] phenol.

In a further embodiment of the present invention, the compound is 3-{5-[2-({(3R)-1-[(4-chlorophenyl)sulfonyl]piperidin-3-yl}amino)pyrimidin-4-yl]imidazo[2,1-b][1,3]thiazol-6-yl}phenyl carbamate, 3-{5-[2-({(3R)-1-[(4-chlorophenyl) sulfonyl]piperidin-3-yl}amino)pyrimidin-4-yl]imidazo[2,1-b][1,3]thiazol-6-yl}phenyl sulfamate, 3-{5-[2-({(3R)-1-[(4-chlorophenyl)sulfonyl]piperidin-3-yl}amino)pyrimidin-4-yl]imidazo[2,1-b][1,3]oxazol-6-yl}phenyl sulfamate, 3-{5-[2-({(3R)-1-[(4-chlorophenyl)sulfonyl]piperidin-3-yl}amino)pyrimidin-4-yl]imidazo[2,1-b][1,3]oxazol-6-yl}phenyl carbamate, or (1E)-1-(3-{5-[2-({(3R)-1-[(4-chlorophenyl)sulfonyl]piperidin-3-yl}amino)pyrimidin-4-yl]imidazo[2,1-b][1,3]thiazol-6-yl}phenyl)ethanone oxime.

In an alternative embodiment of the present invention, the compound is 3-[5-(2-{[1-(cyclopropylsulfonyl)piperidin-4-yl]amino}pyrimidin-4-yl)imidazo[2,1-b][1,3]thiazol-6-yl] phenol, 3-[5-(2-{[1-(methylsulfonyl)piperidin-4-yl] amino}pyrimidin-4-yl)imidazo[2,1-b][1,3]thiazol-6-yl] phenol, 3-[5-(2-{[1-(cyclopropylsulfonyl)piperidin-4-yl] amino}pyrimidin-4-yl)imidazo[2,1-b][1,3]oxazol-6-yl] phenol, 3-[5-(2-{[1-(methylsulfonyl)piperidin-4-yl] amino}pyrimidin-4-yl)imidazo[2,1-b][1,3]oxazol-6-yl] phenol, 5-[5-(2-{[1-(cyclopropylsulfonyl)piperidin-4-yl] amino}pyrimidin-4-yl)imidazo[2,1-b][1,3]thiazol-6-yl]-2-fluorophenol, or 3-[5-(2-{[(3R)-1-(cyclopropylsulfonyl) piperidin-3-yl]amino}pyrimidin-4-yl)imidazo[2,1-b][1,3] oxazol-6-yl]phenol.

2. Methods and Intermediates for Preparing Compounds of the Invention

Standard synthetic methods and procedures for the preparation of organic molecules and functional group transformations and manipulations including the use of protective groups can be obtained from the relevant scientific literature or from standard reference textbooks in the field. Although not limited to any one or several sources, recognized reference textbooks of organic synthesis include: Smith, M. B.; March, J. March's Advanced Organic Chemistry: Reactions, Mechanisms, and Structure, 5$^{th}$ ed.; John Wiley & Sons: New York, 2001; and Greene, T. W.; Wuts, P. G. M. Protective Groups in Organic Synthesis, 3R$^d$; John Wiley & Sons: New York, 1999. The following descriptions of synthetic methods are designed to illustrate, but not limit, general procedures for the preparation of compounds of the invention.

Compounds of the invention can be prepared in a variety of ways, some of which are known in the art. In general, the compounds of the present invention can be prepared from commercially available starting materials, compounds known in the literature, or from readily-prepared intermediates, by employing standard synthetic methods and procedures known to those skilled in the art, or which will be apparent to the skilled artisan in light of the teachings herein. Standard synthetic methods and procedures for the preparation of organic molecules and functional group transformations and manipulations can be obtained from the relevant scientific literature or from standard textbooks in the field. The description of the synthesis of some compounds of the present invention can also be found in PCT patent publications WO 2004/110990, and WO 2006/010082, and WO 2006/044869.

A method for preparing imidazooxazole and imidazothiazole compounds of the invention is described in the Examples below and illustrated in FIG. 1. In FIG. 1, step a, a suitably substituted α-haloketone III is reacted with an optionally substituted 2-aminooxazole IV. This reaction is typically conducted in inert organic solvent such as acetonitrile or similar at room temperature. The product (not shown) is typically isolated from the reaction mixture as a solid hydrogen bromide salt by filtration. The cyclization of the hydrogen bromide intermediate to yield the imidazooxazole compound V is conveniently performed by the addition of a dehydrating reagent, such as titanium tetrachloride. This reaction, following appropriate pH modification of the resulting reaction mixture, provides V. In the case of the imidazothiazole compounds, step b, a suitably substituted α-haloketone III is reacted with an optionally substituted 2-aminothiazole IV. This reaction is typically conducted in a solvent such as ethanol at reflux to yield compound V directly. The compounds V are purified by chromatography or by trituration in an inert solvent such as diethylether. Acetylation of compounds V (step c) is typically done in acetic anhydride, using concentrated sulfuric acid in catalytic amount, providing compounds VI. The compounds VI are typically purified by chromatography. The ketones VI are converted to the enaminones VIII by reaction with DMF-DME at high temperature or by mean of microwave activation (step d). Typically, the solid enaminones VIII can be purified by chromatography or by trituration in an inert solvent such as diethylether. The enaminones VIII are cyclized to intermediate X (step f) by reaction with the guanidinium salt IX in a suitable solvent such as ethanol, at elevated temperature, typically reflux and using a base such as sodium ethoxide. The compounds X can be purified by chromatography or by trituration in an inert solvent such as diethylether. The BOC protective group is suitably removed using HCl solution, typically 4N in dioxane, to yield the compounds XI (step g). Compounds XI are typically hydrogen chloride salts and can be used without purification.

Figure 2:
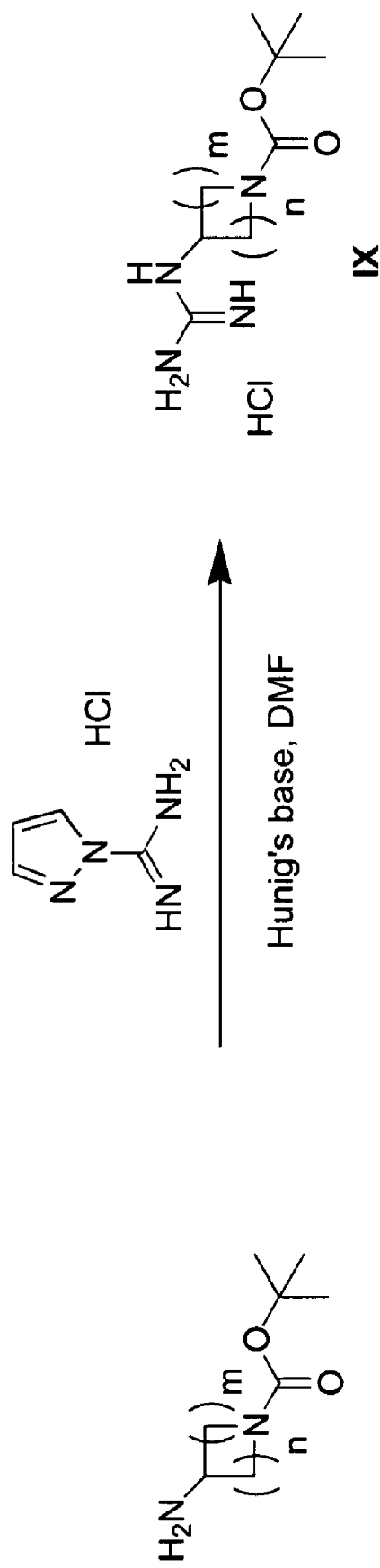
FIG. 2: Preparation of the guanidinium salts of formula IX.

The preparation of the guanidinium hydrochloride is illustrated in FIG. 2. Typically, an amine such as tert-butyl 4-aminopiperidine-1-carboxylate is reacted with pyrazole carboxamidine hydrochloride in an appropriate solvent such as DMF at elevated temperature, in the presence of a tertiary amine such as Hunig's base. The product IX is purified by repetitive trituration in an inert solvent such as diethylether.

Figure 3:
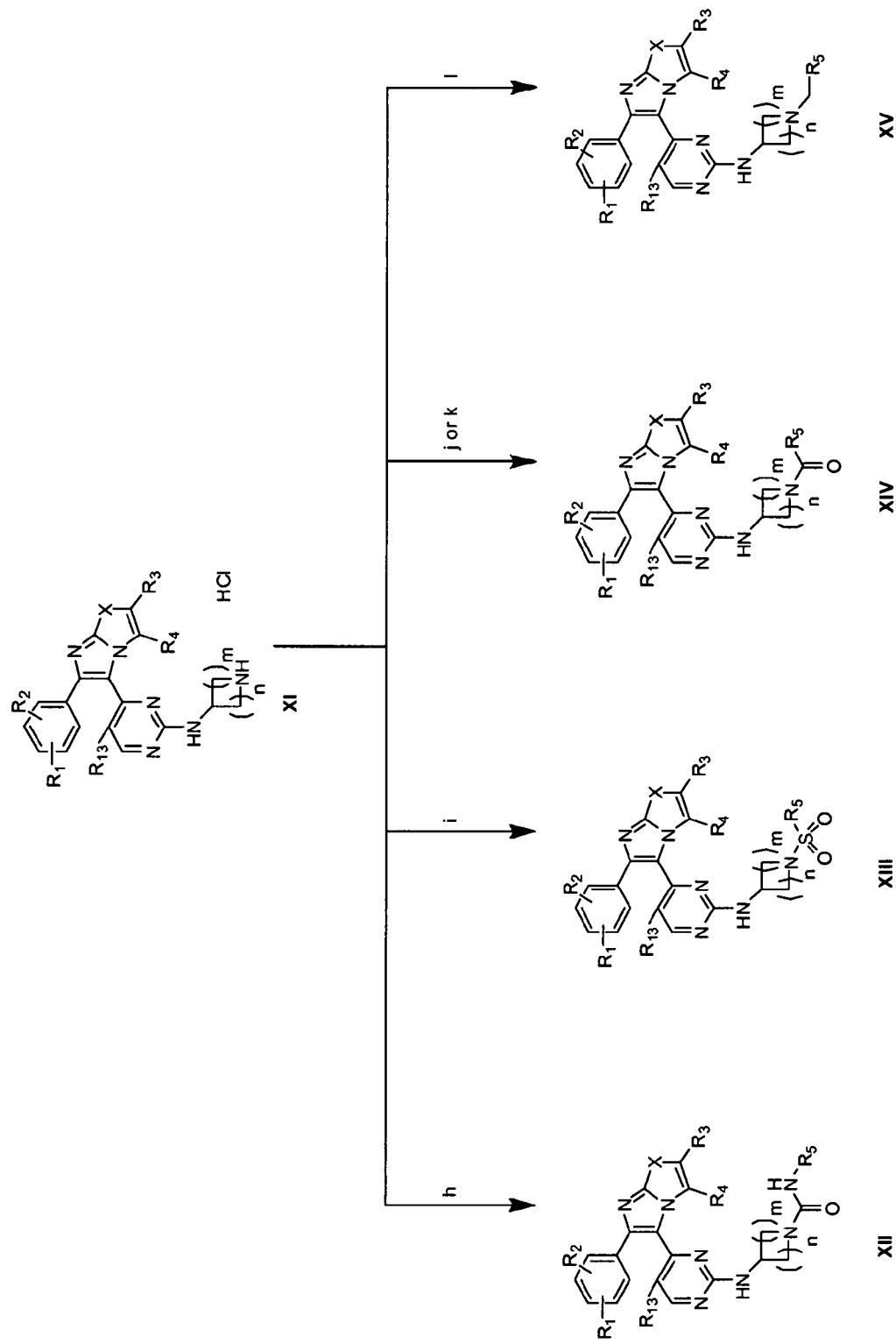
FIG. 3: Transformation of intermediate XI to compounds of formulas XII to XV.

The functionalization of the amine XI is illustrated in FIG. 3. Typically, compounds XI are reacted with an appropriately substituted isocyanate (step h) in an inert solvent such as tetrahydrofuran, in the presence of a tertiary amine such as triethylamine, at room temperature or at an elevated temperature. The compounds XII are purified by chromatography or by trituration in an inert solvent such as diethylether. Sulfonamides XIII are prepared by reacting compounds XI with an appropriately substituted sulfonyl chloride in an inert solvent such as methylene chloride, in the presence of a tertiary amine such as Hunig's base, at room temperature or at elevated temperature (step i). Compounds XIII are purified by chromatography or by trituration in an inert solvent such as diethylether. Compounds XIV can be prepared using any coupling reagent and a carboxylic acid or by using an acyl halide. For example, compounds XI are reacted with a suitably substituted acid chloride in the presence of a tertiary amine such as triethylamine, in an inert solvent such as methylene chloride, at room temperature or elevated temperature (step j). Compounds XIV are purified by chromatography or by trituration in an inert solvent such as diethylether. In another example, compounds XI are reacted with a suitably substituted carboxylic acid using HBTU as a coupling reagent in the presence of DMAP and triethylamine, in an inert solvent such as DMF, at room temperature or elevated temperature (step k). Compounds XIV are purified by chromatography or by trituration in an inert solvent such as diethylether. Compounds XV are prepared by reacting compounds XI with an appropriately substituted aldehyde in the presence of a reducing agent such as $Me_4NBH(OAc)_3$ in an inert solvent such as DCE, at room temperature or elevated temperature (step l). Compounds XV are purified by chromatography or by trituration in an inert solvent such as diethylether.

Figure 4:
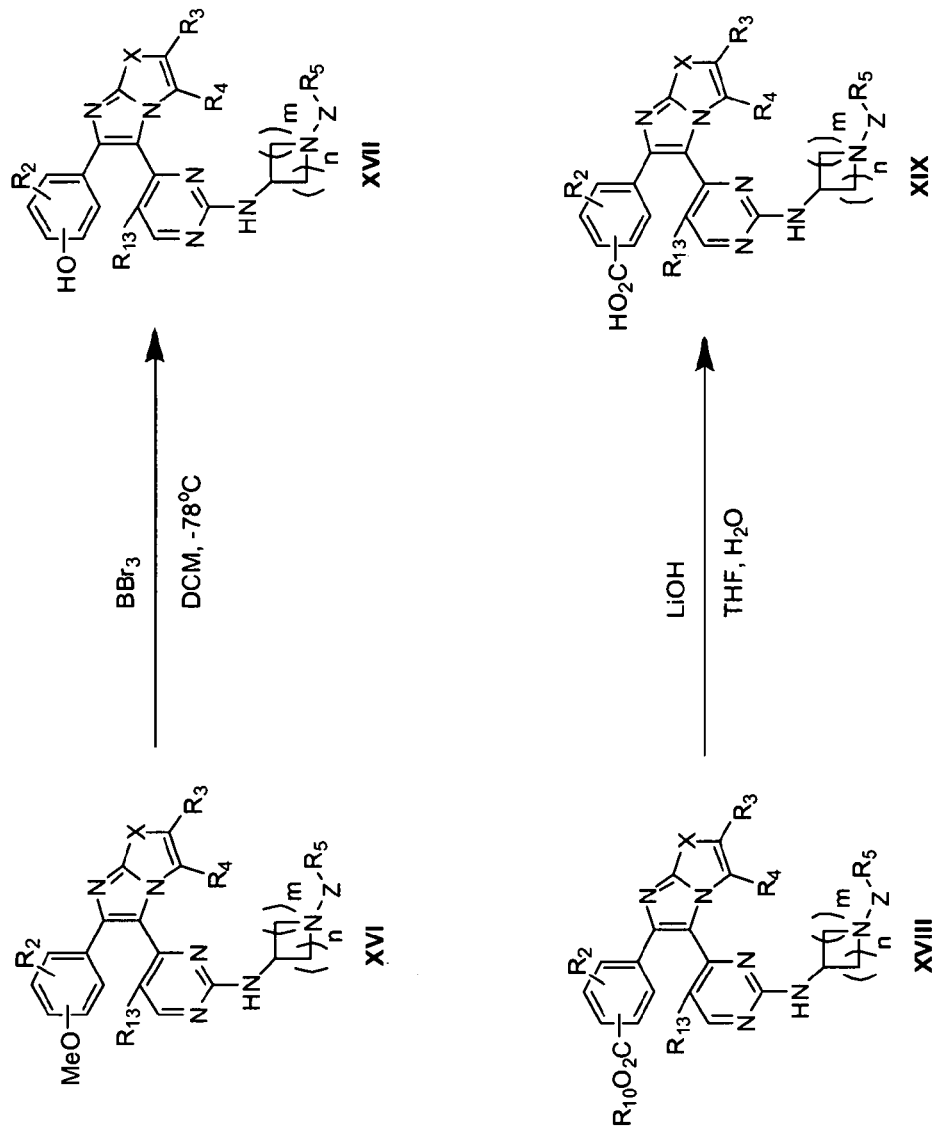
FIG. 4: Preparation of phenols of formula XVII and carboxylic acids of formula XIX.

The preparation of compounds XVIII and XIX is illustrated in FIG. 4. Compounds XVI are reacted with excess boron tribromide in an inert solvent such as methylene chloride, at low temperature, typically −78° C. After all starting material has been consumed, the reaction is carefully quench with an alcohol, typically methanol, at low temperature (from −78° C. to 0° C.). The product XVII is purified by chromatography or by trituration in an inert solvent such as diethylether. Compounds XIX are prepared by reacting compounds XVIII with an hydroxide, typically lithium hydroxide, in an appropriate solvent such as tetrahydrofuran, at room temperature or elevated temperature. Compounds XIX are purified by chromatography or by trituration in an inert solvent such as diethylether.

3. Methods of Treatment

The compounds of the present invention can be used for the treatment and/or prevention of cell proliferative disorder such as cancer. The compounds of the present invention are capable of inhibiting the RAF protein kinases. Thus, the compounds can be used for the treatment of cell proliferative disorder characterized by aberrant RAS-RAF signaling. In an embodiment, the cells of cell proliferative disorder such as cancer harbor a mutated B-RAF. In a further embodiment, the mutated B-RAF is a B-RAF with the V600E mutation (B-RAF$^{V600E}$). The cell proliferative disorder can be melanomas, papillary thyroid cancers, colon cancers.

The present invention also provides a method of treating any other conditions characterized by a B-RAF$^{V600E}$, e.g., Congenital Nevi (commonly known as moles or freckles) possessing the B-RAF$^{V600E}$, with the imidazooxazole and/or imidazothiazole compounds. In a further embodiment, the present invention may be used prophylactically (e.g., topically applied to the skin) to prevent such nevi to develop into malignant melanomas.

As used herein, a "subject" can be any mammal, e.g., a human, a primate, mouse, rat, dog, cat, cow, horse, pig, sheep, goat, camel. In a preferred aspect, the subject is a human.

As used herein, a "subject in need thereof" is a subject having a cell proliferative disorder, or a subject having an increased risk of developing a cell proliferative disorder relative to the population at large. In one aspect, a subject in need thereof has a precancerous condition. In a preferred aspect, a subject in need thereof has cancer.

As used herein, the term "cell proliferative disorder" refers to conditions in which unregulated or abnormal growth, or both, of cells can lead to the development of an unwanted condition or disease, which may or may not be cancerous. In one aspect, a cell proliferative disorder includes a non-cancerous condition, e.g., rheumatoid arthritis; inflammation; autoimmune disease; lymphoproliferative conditions; acromegaly; rheumatoid spondylitis; osteoarthritis; gout, other arthritic conditions; sepsis; septic shock; endotoxic shock; gram-negative sepsis; toxic shock syndrome; asthma; adult respiratory distress syndrome; chronic obstructive pulmonary disease; chronic pulmonary inflammation; inflammatory bowel disease; Crohn's disease; psoriasis; eczema; ulcerative colitis; pancreatic fibrosis; hepatic fibrosis; acute and chronic renal disease; irritable bowel syndrome; pyresis; restenosis; cerebral malaria; stroke and ischemic injury; neural trauma; Alzheimer's disease; Huntington's disease; Parkinson's disease; acute and chronic pain; allergic rhinitis; allergic conjunctivitis; chronic heart failure; acute coronary syndrome; cachexia; malaria; leprosy; leishmaniasis; Lyme disease; Reiter's syndrome; acute synovitis; muscle degeneration, bursitis; tendonitis; tenosynovitis; herniated, ruptures, or prolapsed intervertebral disk syndrome; osteopetrosis; thrombosis; restenosis; silicosis; pulmonary sarcosis; bone resorption diseases, such as osteoporosis; graft-versus-host reaction; Multiple Sclerosis; lupus; fibromyalgia; AIDS and other viral diseases such as Herpes Zoster, Herpes Simplex I or II, influenza virus and cytomegalovirus; and diabetes mellitus. In another aspect, a cell proliferative disorder includes a precancer or a precancerous condition. In another aspect, a cell proliferative disorder includes cancer. Various cancers to be treated include but are not limited to breast cancer, lung cancer, colorectal cancer, pancreatic cancer, ovarian cancer, prostate cancer, renal carcinoma, hepatoma, brain cancer, melanoma, multiple myeloma, chronic myelogenous leukemia, hematologic tumor, and lymphoid tumor, including metastatic lesions in other tissues or organs distant from the primary tumor site. Cancers to be treated include but are not limited to sarcoma, carcinoma, and adenocarcinoma. In one aspect, a "precancer cell" or "precancerous cell" is a cell manifesting a cell proliferative disorder that is a precancer or a precancerous condition. In another aspect, a "cancer cell" or "cancerous cell" is a cell manifesting a cell proliferative disorder that is a cancer. Any reproducible means of measurement may be used to identify cancer cells or precancerous cells. In a preferred aspect, cancer cells or precancerous cells are identified by histological typing or grading of a tissue sample (e.g., a biopsy sample). In another aspect, cancer cells or precancerous cells are identified through the use of appropriate molecular markers.

A "cell proliferative disorder of the colon" is a cell proliferative disorder involving cells of the colon. In a preferred aspect, the cell proliferative disorder of the colon is colon cancer. In a preferred aspect, compositions of the present invention may be used to treat colon cancer or cell proliferative disorders of the colon. In one aspect, colon cancer includes all forms of cancer of the colon. In another aspect, colon cancer includes sporadic and hereditary colon cancers. In another aspect, colon cancer includes malignant colon neoplasms, carcinoma in situ, typical carcinoid tumors, and atypical carcinoid tumors. In another aspect, colon cancer includes adenocarcinoma, squamous cell carcinoma, and adenosquamous cell carcinoma. In another aspect, colon cancer is associated with a hereditary syndrome selected from the group consisting of hereditary nonpolyposis colorectal cancer, familial adenomatous polyposis, Gardner's syndrome, Peutz-Jeghers syndrome, Turcot's syndrome and juvenile polyposis. In another aspect, colon cancer is caused by a hereditary syndrome selected from the group consisting of hereditary nonpolyposis colorectal cancer, familial adenomatous polyposis, Gardner's syndrome, Peutz-Jeghers syndrome, Turcot's syndrome and juvenile polyposis.

In one aspect, cell proliferative disorders of the colon include all forms of cell proliferative disorders affecting colon cells. In one aspect, cell proliferative disorders of the colon include colon cancer, precancerous conditions of the colon, adenomatous polyps of the colon and metachronous lesions of the colon. In one aspect, a cell proliferative disorder of the colon includes adenoma. In one aspect, cell proliferative disorders of the colon are characterized by hyperplasia, metaplasia, and dysplasia of the colon. In another aspect, prior colon diseases that may predispose individuals to development of cell proliferative disorders of the colon include prior colon cancer. In another aspect, current disease that may predispose individuals to development of cell proliferative disorders of the colon include Crohn's disease and ulcerative colitis. In one aspect, a cell proliferative disorder of the colon is associated with a mutation in a gene selected from the group consisting of p53, ras, FAP and DCC. In another aspect, an individual has an elevated risk of developing a cell proliferative disorder of the colon due to the presence of a mutation in a gene selected from the group consisting of p53, ras, FAP and DCC.

A "cell proliferative disorder of the skin" is a cell proliferative disorder involving cells of the skin. In one aspect, cell proliferative disorders of the skin include all forms of cell proliferative disorders affecting skin cells. In one aspect, cell proliferative disorders of the skin include a precancer or precancerous condition of the skin, benign growths or lesions of the skin, melanoma, malignant melanoma and other malignant growths or lesions of the skin, and metastatic lesions in tissue and organs in the body other than the skin. In another aspect, cell proliferative disorders of the skin include hyperplasia, metaplasia, and dysplasia of the skin.

In one aspect, a cancer that is to be treated has been staged according to the American Joint Committee on Cancer (AJCC) TNM classification system, where the tumor (T) has been assigned a stage of TX, T1, T1mic, T1a, T1b, T1c, T2, T3, T4, T4a, T4b, T4c, or T4d; and where the regional lymph nodes (N) have been assigned a stage of NX, N0, N1, N2, N2a, N2b, N3, N3a, N3b, or N3c; and where distant metastasis (M) has been assigned a stage of MX, M0, or M1. In another aspect, a cancer that is to be treated has been staged according to an American Joint Committee on Cancer (AJCC) classification as Stage I, Stage IIA, Stage IIB, Stage IIIA, Stage IIIB, Stage IIIC, or Stage IV. In another aspect, a cancer that is to be treated has been assigned a grade according to an AJCC classification as Grade GX (e.g., grade cannot be assessed), Grade 1, Grade 2, Grade 3 or Grade 4. In another aspect, a cancer that is to be treated has been staged according to an AJCC pathologic classification (pN) of pNX, pN0, PN0 (I−), PN0 (I+), PN0 (mol−), PN0 (mol+), PN1, PN1(mi), PN1a, PN1b, PN1c, pN2, pN2a, pN2b, pN3, pN3a, pN3b, or pN3c.

In one aspect, a cancer that is to be treated includes a tumor that has been determined to be less than or equal to about 2 centimeters in diameter. In another aspect, a cancer that is to be treated includes a tumor that has been determined to be from about 2 to about 5 centimeters in diameter. In another aspect, a cancer that is to be treated includes a tumor that has been determined to be greater than or equal to about 3 centimeters in diameter. In another aspect, a cancer that is to be treated includes a tumor that has been determined to be greater than 5 centimeters in diameter. In another aspect, a cancer that is to be treated is classified by microscopic appearance as well differentiated, moderately differentiated, poorly differentiated, or undifferentiated. In another aspect, a cancer that is to be treated is classified by microscopic appearance with respect to mitosis count (e.g., amount of cell division) or nuclear pleiomorphism (e.g., change in cells). In another aspect, a cancer that is to be treated is classified by microscopic appearance as being associated with areas of necrosis (e.g., areas of dying or degenerating cells). In one aspect, a cancer that is to be treated is classified as having an abnormal karyotype, having an abnormal number of chromosomes, or having one or more chromosomes that are abnormal in appearance. In one aspect, a cancer that is to be treated is classified as being aneuploid, triploid, tetraploid, or as having an altered ploidy. In one aspect, a cancer that is to be treated is classified as having a chromosomal translocation, or a deletion or duplication of an entire chromosome, or a region of deletion, duplication or amplification of a portion of a chromosome.

In one aspect, a cancer that is to be treated is evaluated by DNA cytometry, flow cytometry, or image cytometry. In one aspect, a cancer that is to be treated has been typed as having 10%, 20%, 30%, 40%, 50%, 60%, 70%, 80%, or 90% of cells in the synthesis stage of cell division (e.g., in S phase of cell division). In one aspect, a cancer that is to be treated has been typed as having a low S-phase fraction or a high S-phase fraction.

As used herein, a "normal cell" is a cell that cannot be classified as part of a "cell proliferative disorder." In one aspect, a normal cell lacks unregulated or abnormal growth, or both, that can lead to the development of an unwanted condition or disease. Preferably, a normal cell possesses normally functioning cell cycle checkpoint control mechanisms.

As used herein, "contacting a cell" refers to a condition in which a compound or other composition of matter is in direct contact with a cell, or is close enough to induce a desired biological effect in a cell.

As used herein, "candidate compound" refers to a compound of the present invention that has been or will be tested in one or more in vitro or in vivo biological assays, in order to determine if that compound is likely to elicit a desired biological or medical response in a cell, tissue, system, animal or human that is being sought by a researcher or clinician. In one aspect, a candidate compound is a compound of formula II; in another aspect, a candidate compound is a compound of formula I. In a preferred aspect, the biological or medical response is treatment of cancer. In another aspect, the biological or medical response is treatment or prevention of a cell proliferative disorder. In one aspect, in vitro or in vivo biological assays include, but are not limited to, enzymatic activity assays, electrophoretic mobility shift assays, reporter gene assays, in vitro cell viability assays.

As used herein, "monotherapy" refers to administration of a single active or therapeutic compound to a subject in need thereof. Preferably, monotherapy will involve administration of a therapeutically effective amount of an active compound. For example, cancer monotherapy with 3-{5-[2-({(3R)-1-[(4-chlorophenyl)sulfonyl]piperidin-3-yl}amino)pyrimidin-4-yl]imidazo[2,1-b][1,3]thiazol-6-yl}phenol comprises administration of a therapeutically effective amount of 3-{5-[2-({(3R)-1-[(4-chlorophenyl)sulfonyl]piperidin-3-yl}amino)pyrimidin-4-yl]imidazo[2,1-b][1,3]thiazol-6-yl}phenol, or a pharmaceutically acceptable salt, prodrug, metabolite, analog or derivative thereof, to a subject in need of treatment of cancer. Monotherapy may be contrasted with combination therapy, in which a combination of multiple active compounds is administered, preferably with each component of the combination present in a therapeutically effective amount. In one aspect, montherapy with a compound of the present invention is more effective than combination therapy in inducing a desired biological effect.

As used herein, "treating" describes the management and care of a patient for the purpose of combating a disease, condition, or disorder and includes the administration of a compound of the present invention to prevent the onset of the symptoms or complications, alleviating the symptoms or complications, or eliminating the disease, condition or disorder.

In one aspect, treating cancer results in a reduction in size of a tumor. A reduction in size of a tumor may also be referred to as "tumor regression." Preferably, after treatment, tumor size is reduced by 5% or greater relative to its size prior to treatment; more preferably, tumor size is reduced by 10% or greater; more preferably, reduced by 20% or greater; more preferably, reduced by 30% or greater; more preferably, reduced by 40% or greater; even more preferably, reduced by 50% or greater; and most preferably, reduced by greater than 75% or greater. Size of a tumor may be measured by any reproducible means of measurement. In a preferred aspect, size of a tumor may be measured as a diameter of the tumor.

In another aspect, treating cancer results in a reduction in tumor volume. Preferably, after treatment, tumor volume is reduced by 5% or greater relative to its size prior to treatment; more preferably, tumor volume is reduced by 10% or greater; more preferably, reduced by 20% or greater; more preferably, reduced by 30% or greater; more preferably, reduced by 40% or greater; even more preferably, reduced by 50% or greater; and most preferably, reduced by greater than 75% or greater. Tumor volume may be measured by any reproducible means of measurement.

In another aspect, treating cancer results in a decrease in number of tumors. Preferably, after treatment, tumor number is reduced by 5% or greater relative to number prior to treatment; more preferably, tumor number is reduced by 10% or greater; more preferably, reduced by 20% or greater; more preferably, reduced by 30% or greater; more preferably, reduced by 40% or greater; even more preferably, reduced by 50% or greater; and most preferably, reduced by greater than 75%. Number of tumors may be measured by any reproducible means of measurement. In a preferred aspect, number of tumors may be measured by counting tumors visible to the naked eye or at a specified magnification. In a preferred aspect, the specified magnification is 2×, 3×, 4×, 5×, 10×, or 50×.

In another aspect, treating cancer results in a decrease in number of metastatic lesions in other tissues or organs distant from the primary tumor site. Preferably, after treatment, the number of metastatic lesions is reduced by 5% or greater relative to number prior to treatment; more preferably, the number of metastatic lesions is reduced by 10% or greater; more preferably, reduced by 20% or greater; more preferably, reduced by 30% or greater; more preferably, reduced by 40% or greater; even more preferably, reduced by 50% or greater; and most preferably, reduced by greater than 75%. The number of metastatic lesions may be measured by any reproducible means of measurement. In a preferred aspect, the number of metastatic lesions may be measured by counting metastatic lesions visible to the naked eye or at a specified magnification. In a preferred aspect, the specified magnification is 2×, 3×, 4×, 5×, 10×, or 50×.

In another aspect, treating cancer results in an increase in average survival time of a population of treated subjects in comparison to a population receiving carrier alone. Preferably, the average survival time is increased by more than 30 days; more preferably, by more than 60 days; more preferably, by more than 90 days; and most preferably, by more than 120 days. An increase in average survival time of a population may be measured by any reproducible means. In a preferred aspect, an increase in average survival time of a population may be measured, for example, by calculating for a population the average length of survival following initiation of treatment with an active compound. In another preferred aspect, an increase in average survival time of a population may also be measured, for example, by calculating for a population the average length of survival following completion of a first round of treatment with an active compound.

In another aspect, treating cancer results in an increase in average survival time of a population of treated subjects in comparison to a population of untreated subjects. Preferably, the average survival time is increased by more than 30 days; more preferably, by more than 60 days; more preferably, by more than 90 days; and most preferably, by more than 120 days. An increase in average survival time of a population may be measured by any reproducible means. In a preferred aspect, an increase in average survival time of a population may be measured, for example, by calculating for a population the average length of survival following initiation of treatment with an active compound. In another preferred aspect, an increase in average survival time of a population may also be measured, for example, by calculating for a population the average length of survival following completion of a first round of treatment with an active compound.

In another aspect, treating cancer results in increase in average survival time of a population of treated subjects in comparison to a population receiving monotherapy with a drug that is not a compound of the present invention, or a pharmaceutically acceptable salt, prodrug, metabolite, analog or derivative thereof. Preferably, the average survival time is increased by more than 30 days; more preferably, by more than 60 days; more preferably, by more than 90 days; and most preferably, by more than 120 days. An increase in average survival time of a population may be measured by any reproducible means. In a preferred aspect, an increase in average survival time of a population may be measured, for example, by calculating for a population the average length of survival following initiation of treatment with an active compound. In another preferred aspect, an increase in average survival time of a population may also be measured, for example, by calculating for a population the average length of survival following completion of a first round of treatment with an active compound.

In another aspect, treating cancer results in a decrease in the mortality rate of a population of treated subjects in comparison to a population receiving carrier alone. In another aspect, treating cancer results in a decrease in the mortality rate of a population of treated subjects in comparison to an untreated population. In a further aspect, treating cancer results a decrease in the mortality rate of a population of treated subjects in comparison to a population receiving monotherapy with a drug that is not a compound of the present invention, or a pharmaceutically acceptable salt, prodrug, metabolite, analog or derivative thereof. Preferably, the mortality rate is decreased by more than 2%; more preferably, by more than 5%; more preferably, by more than 10%; and most preferably, by more than 25%. In a preferred aspect, a decrease in the mortality rate of a population of treated subjects may be measured by any reproducible means. In another preferred aspect, a decrease in the mortality rate of a population may be measured, for example, by calculating for a population the average number of disease-related deaths per unit time following initiation of treatment with an active compound. In another preferred aspect, a decrease in the mortality rate of a population may also be measured, for example, by calculating for a population the average number of disease-related deaths per unit time following completion of a first round of treatment with an active compound.

In another aspect, treating cancer results in a decrease in tumor growth rate. Preferably, after treatment, tumor growth rate is reduced by at least 5% relative to number prior to treatment; more preferably, tumor growth rate is reduced by at least 10%; more preferably, reduced by at least 20%; more preferably, reduced by at least 30%; more preferably, reduced by at least 40%; more preferably, reduced by at least 50%; even more preferably, reduced by at least 50%; and most preferably, reduced by at least 75%. Tumor growth rate may be measured by any reproducible means of measurement. In a preferred aspect, tumor growth rate is measured according to a change in tumor diameter per unit time.

In another aspect, treating cancer results in a decrease in tumor regrowth. Preferably, after treatment, tumor regrowth is less than 5%; more preferably, tumor regrowth is less than 10%; more preferably, less than 20%; more preferably, less than 30%; more preferably, less than 40%; more preferably, less than 50%; even more preferably, less than 50%; and most preferably, less than 75%. Tumor regrowth may be measured by any reproducible means of measurement. In a preferred aspect, tumor regrowth is measured, for example, by measuring an increase in the diameter of a tumor after a prior tumor shrinkage that followed treatment. In another preferred aspect, a decrease in tumor regrowth is indicated by failure of tumors to reoccur after treatment has stopped.

In another aspect, treating or preventing a cell proliferative disorder results in a reduction in the rate of cellular proliferation. Preferably, after treatment, the rate of cellular proliferation is reduced by at least 5%; more preferably, by at least 10%; more preferably, by at least 20%; more preferably, by at least 30%; more preferably, by at least 40%; more preferably, by at least 50%; even more preferably, by at least 50%; and most preferably, by at least 75%. The rate of cellular proliferation may be measured by any reproducible means of measurement. In a preferred aspect, the rate of cellular proliferation is measured, for example, by measuring the number of dividing cells in a tissue sample per unit time.

In another aspect, treating or preventing a cell proliferative disorder results in a reduction in the proportion of proliferating cells. Preferably, after treatment, the proportion of proliferating cells is reduced by at least 5%; more preferably, by at least 10%; more preferably, by at least 20%; more preferably, by at least 30%; more preferably, by at least 40%; more preferably, by at least 50%; even more preferably, by at least 50%; and most preferably, by at least 75%. The proportion of proliferating cells may be measured by any reproducible means of measurement. In a preferred aspect, the proportion of proliferating cells is measured, for example, by quantifying the number of dividing cells relative to the number of nondividing cells in a tissue sample. In another preferred aspect, the proportion of proliferating cells is equivalent to the mitotic index.

In another aspect, treating or preventing a cell proliferative disorder results in a decrease in size of an area or zone of cellular proliferation. Preferably, after treatment, size of an area or zone of cellular proliferation is reduced by at least 5% relative to its size prior to treatment; more preferably, reduced by at least 10%; more preferably, reduced by at least 20%; more preferably, reduced by at least 30%; more preferably, reduced by at least 40%; more preferably, reduced by at least 50%; even more preferably, reduced by at least 50%; and most preferably, reduced by at least 75%. Size of an area or zone of cellular proliferation may be measured by any reproducible means of measurement. In a preferred aspect, size of an area or zone of cellular proliferation may be measured as a diameter or width of an area or zone of cellular proliferation.

In another aspect, treating or preventing a cell proliferative disorder results in a decrease in the number or proportion of cells having an abnormal appearance or morphology. Preferably, after treatment, the number of cells having an abnormal morphology is reduced by at least 5% relative to its size prior to treatment; more preferably, reduced by at least 10%; more preferably, reduced by at least 20%; more preferably, reduced by at least 30%; more preferably, reduced by at least 40%; more preferably, reduced by at least 50%; even more preferably, reduced by at least 50%; and most preferably, reduced by at least 75%. An abnormal cellular appearance or morphology may be measured by any reproducible means of measurement. In one aspect, an abnormal cellular morphology is measured by microscopy, e.g., using an inverted tissue culture microscope. In one aspect, an abnormal cellular morphology takes the form of nuclear pleiomorphism.

As used herein, the term "selectively" means tending to occur at a higher frequency in one population than in another population. In one aspect, the compared populations are cell populations. In a preferred aspect, a compound of the present invention, or a pharmaceutically acceptable salt, prodrug, metabolite, analog or derivative thereof, acts selectively on a cancer or precancerous cell but not on a normal cell. In another preferred aspect, a compound of the present invention, or a pharmaceutically acceptable salt, prodrug, metabolite, analog or derivative thereof, acts selectively to modulate one molecular target (e.g., B-RAF). In another preferred aspect, the invention provides a method for selectively inhibiting the activity of an enzyme, such as a kinase. Preferably, an event occurs selectively in population A relative to population B if it occurs greater than two times more frequently in population A as compared to population B. More preferably, an event occurs selectively if it occurs greater than five times more frequently in population A. More preferably, an event occurs selectively if it occurs greater than ten times more frequently in population A; more preferably, greater than fifty times; even more preferably, greater than 100 times; and most preferably, greater than 1000 times more frequently in population A as compared to population B. For example, cell death would be said to occur selectively in cancer cells if it occurred greater than twice as frequently in cancer cells as compared to normal cells.

In a preferred aspect, a compound of the present invention or a pharmaceutically acceptable salt, prodrug, metabolite, analog or derivative thereof, modulates the activity of a molecular target (e.g., B-RAF). In one aspect, modulating refers to stimulating or inhibiting an activity of a molecular target. Preferably, a compound of the present invention modulates the activity of a molecular target if it stimulates or inhibits the activity of the molecular target by at least 2-fold relative to the activity of the molecular target under the same conditions but lacking only the presence of said compound. More preferably, a compound of the present invention modulates the activity of a molecular target if it stimulates or inhibits the activity of the molecular target by at least 5-fold, at least 10-fold, at least 20-fold, at least 50-fold, at least 100-fold relative to the activity of the molecular target under the same conditions but lacking only the presence of said compound. The activity of a molecular target may be measured by any reproducible means. The activity of a molecular target may be measured in vitro or in vivo. For example, the activity of a molecular target may be measured in vitro by an enzymatic activity assay or a DNA binding assay, or the activity of a molecular target may be measured in vivo by assaying for expression of a reporter gene.

In one aspect, a compound of the present invention, or a pharmaceutically acceptable salt, prodrug, metabolite, analog or derivative thereof, does not significantly modulate the activity of a molecular target if the addition of the compound does not stimulate or inhibit the activity of the molecular target by greater than 10% relative to the activity of the molecular target under the same conditions but lacking only the presence of said compound.

As used herein, the term "isozyme selective" means preferential inhibition or stimulation of a first isoform of an enzyme in comparison to a second isoform of an enzyme (e.g., preferential inhibition or stimulation of a kinase isozyme alpha in comparison to a kinase isozyme beta). Preferably, a compound of the present invention demonstrates a minimum of a four-fold differential, preferably a ten fold differential, more preferably a fifty fold differential, in the dosage required to achieve a biological effect. Preferably, a compound of the present invention demonstrates this differential across the range of inhibition, and the differential is exemplified at the $IC_{50}$, i.e., a 50% inhibition, for a molecular target of interest.

In a preferred embodiment, administering a compound of the present invention, or a pharmaceutically acceptable salt, prodrug, metabolite, analog or derivative thereof, to a cell or a subject in need thereof results in modulation (i.e., stimulation or inhibition) of an activity of RAF. As used herein, an activity of RAF refers to any biological function or activity that is carried out by RAF. For example, a function of RAF includes phosphorylation of downstream target proteins.

In a preferred embodiment, administering a compound of the present invention, or a pharmaceutically acceptable salt, prodrug, metabolite, analog or derivative thereof, to a cell or a subject in need thereof results in modulation (i.e., stimulation or inhibition) of an activity of ERK 1 or ERK 2, or both. As used herein, an activity of ERK 1 or ERK 2 refers to any biological function or activity that is carried out by ERK 1 or ERK 2. For example, a function of ERK 1 or ERK 2 includes phosphorylation of downstream target proteins.

In one aspect, activating refers to placing a composition of matter (e.g., protein or nucleic acid) in a state suitable for carrying out a desired biological function. In one aspect, a composition of matter capable of being activated also has an unactivated state. In one aspect, an activated composition of matter may have an inhibitory or stimulatory biological function, or both.

In one aspect, elevation refers to an increase in a desired biological activity of a composition of matter (e.g., a protein or a nucleic acid). In one aspect, elevation may occur through an increase in concentration of a composition of matter.

As used herein, "a cell cycle checkpoint pathway" refers to a biochemical pathway that is involved in modulation of a cell cycle checkpoint. A cell cycle checkpoint pathway may have stimulatory or inhibitory effects, or both, on one or more functions comprising a cell cycle checkpoint. A cell cycle checkpoint pathway is comprised of at least two compositions of matter, preferably proteins, both of which contribute to modulation of a cell cycle checkpoint. A cell cycle checkpoint pathway may be activated through an activation of one or more members of the cell cycle checkpoint pathway. Preferably, a cell cycle checkpoint pathway is a biochemical signaling pathway.

As used herein, "cell cycle checkpoint regulator" refers to a composition of matter that can function, at least in part, in modulation of a cell cycle checkpoint. A cell cycle checkpoint regulator may have stimulatory or inhibitory effects, or both, on one or more functions comprising a cell cycle checkpoint. In one aspect, a cell cycle checkpoint regulator is a protein. In another aspect, a cell cycle checkpoint regulator is not a protein.

In one aspect, treating cancer or a cell proliferative disorder results in cell death, and preferably, cell death results in a decrease of at least 10% in number of cells in a population. More preferably, cell death means a decrease of at least 20%; more preferably, a decrease of at least 30%; more preferably, a decrease of at least 40%; more preferably, a decrease of at least 50%; most preferably, a decrease of at least 75%. Number of cells in a population may be measured by any reproducible means. In one aspect, number of cells in a population is measured by fluorescence activated cell sorting (FACS). In another aspect, number of cells in a population is measured by immunofluorescence microscopy. In another aspect, number of cells in a population is measured by light microscopy. In another aspect, methods of measuring cell death are as shown in Li et al., (2003) *Proc Natl Acad Sci USA*. 100(5): 2674-8. In an aspect, cell death occurs by apoptosis.

In a preferred aspect, an effective amount of a compound of the present invention, or a pharmaceutically acceptable salt, prodrug, metabolite, analog or derivative thereof is not significantly cytotoxic to normal cells. A therapeutically effective amount of a compound is not significantly cytotoxic to normal cells if administration of the compound in a therapeutically effective amount does not induce cell death in greater than 10% of normal cells. A therapeutically effective amount of a compound does not significantly affect the viability of normal cells if administration of the compound in a therapeutically effective amount does not induce cell death in greater than 10% of normal cells. In an aspect, cell death occurs by apoptosis.

In one aspect, contacting a cell with a compound of the present invention, or a pharmaceutically acceptable salt, prodrug, metabolite, analog or derivative thereof, induces or activates cell death selectively in cancer cells. Preferably, administering to a subject in need thereof a compound of the present invention, or a pharmaceutically acceptable salt, prodrug, metabolite, analog or derivative thereof, induces or activates cell death selectively in cancer cells. In another aspect, contacting a cell with a compound of the present invention, or a pharmaceutically acceptable salt, prodrug, metabolite, analog or derivative thereof, induces cell death selectively in one or more cells affected by a cell proliferative disorder. Preferably, administering to a subject in need thereof a compound of the present invention, or a pharmaceutically acceptable salt, prodrug, metabolite, analog or derivative thereof, induces cell death selectively in one or more cells affected by a cell proliferative disorder. In a preferred aspect, the present invention relates to a method of treating or preventing cancer by administering a compound of the present invention, or a pharmaceutically acceptable salt, prodrug, metabolite, analog or derivative thereof to a subject in need thereof, where administration of the compound of the present invention, or a pharmaceutically acceptable salt, prodrug, metabolite, analog or derivative thereof results in one or more of the following: accumulation of cells in G1 and/or S phase of the cell cycle, cytotoxicity via cell death in cancer cells without a significant amount of cell death in normal cells, antitumor activity in animals with a therapeutic index of at least 2, and activation of a cell cycle checkpoint. As used herein, "therapeutic index" is the maximum tolerated dose divided by the efficacious dose.

One skilled in the art may refer to general reference texts for detailed descriptions of known techniques discussed herein or equivalent techniques. These texts include Ausubel et al., *Current Protocols in Molecular Biology*, John Wiley and Sons, Inc. (2005); Sambrook et al., *Molecular Cloning, A Laboratory Manual* (3d ed.), Cold Spring Harbor Press, Cold Spring Harbor, N.Y. (2000); Coligan et al., *Current Protocols in Immunology*, John Wiley & Sons, N.Y.; Enna et al., *Current Protocols in Pharmacology*, John Wiley & Sons, N.Y.; Fingl et al., *The Pharmacological Basis of Therapeutics* (1975), *Remington's Pharmaceutical Sciences*, Mack Publishing Co., Easton, Pa., 18th edition (1990). These texts can, of course, also be referred to in making or using an aspect of the invention.

In additional aspects, a compound of the present invention, or a pharmaceutically acceptable salt, prodrug, metabolite, analog or derivative thereof, may be administered in combination with a second chemotherapeutic agent. The second chemotherapeutic agent can be a taxane, an aromatase inhibitor, an anthracycline, a microtubule targeting drug, a. topoisomerase poison drug, a targeted monoclonal or polyconal antibody, an inhibitor of a molecular target or enzyme (e.g., a kinase inhibitor), or a cytidine analogue drug. In preferred aspects, the chemotherapeutic agent can be, but not restricted to, tamoxifen, raloxifene, anastrozole, exemestane, letrozole, HERCEPTIN® (trastuzumab), GLEEVEC® (imatanib), TAXOL® (paclitaxel), cyclophosphamide, lovastatin, minosine, araC, 5-fluorouracil (5-FU), methotrexate (MTX), TAXOTERE® (docetaxel), ZOLADEX® (goserelin), vincristin, vinblastin, nocodazole, teniposide, etoposide, GEMZAR® (gemcitabine), epothilone, navelbine, camptothecin, daunonibicin, dactinomycin, mitoxantrone, amsacrine, doxorubicin (adriamycin), epirubicin or idarubicin or agents listed in www.cancer.org/docroot/cdg/cdg_0.asp. In another aspect, the second chemotherapeutic agent can be a cytokine such as G-CSF (granulocyte colony stimulating factor). In another aspect, a compound of the present invention, or a pharmaceutically acceptable salt, prodrug, metabolite, analog or derivative thereof, may be administered in combination with radiation therapy. In yet another aspect, a compound of the present invention, or a pharmaceutically acceptable salt, prodrug, metabolite, analog or derivative thereof, may be administered in combination with standard chemotherapy combinations such as, but not restricted to, CMF (cyclophosphamide, methotrexate and 5-fluorouracil), CAF (cyclophosphamide, adriamycin and 5-fluorouracil), AC (adriamycin and cyclophosphamide), FEC (5-fluorouracil, epirubicin, and cyclophosphamide), ACT or ATC (adriamycin, cyclophosphamide, and paclitaxel), or CMFP (cyclophosphamide, methotrexate, 5-fluorouracil and prednisone).

A compound of the present invention, or a pharmaceutically acceptable salt, prodrug, metabolite, analog or derivative thereof, can be incorporated into pharmaceutical compositions suitable for administration. Such compositions typically comprise the compound (i.e. including the active compound), and a pharmaceutically acceptable excipient or carrier. As used herein, "pharmaceutically acceptable excipient" or "pharmaceutically acceptable carrier" is intended to include any and all solvents, dispersion media, coatings, antibacterial and antifungal agents, isotonic and absorption delaying agents, and the like, compatible with pharmaceutical administration. Suitable carriers are described in the most recent edition of Remington's Pharmaceutical Sciences, a standard reference text in the field. Preferred examples of such carriers or diluents include, but are not limited to, water, saline, ringer's solutions, dextrose solution, and 5% human serum albumin. Pharmaceutically acceptable carriers include solid carriers such as lactose, terra alba, sucrose, talc, gelatin, agar, pectin, acacia, magnesium stearate, stearic acid and the like. Exemplary liquid carriers include syrup, peanut oil, olive oil, water and the like. Similarly, the carrier or diluent may include time-delay material known in the art, such as glyceryl monostearate or glyceryl distearate, alone or with a wax, ethylcellulose, hydroxypropylmethylcellulose, methylmethacrylate or the like. Other fillers, excipients, flavorants, and other additives such as are known in the art may also be included in a pharmaceutical composition according to this invention. Liposomes and non-aqueous vehicles such as fixed oils may also be used. The use of such media and agents for pharmaceutically active substances is well known in the art. Except insofar as any conventional media or agent is incompatible with the active compound, use thereof in the compositions is contemplated. Supplementary active compounds can also be. incorporated into the compositions.

In one aspect, a compound of the present invention, or a pharmaceutically acceptable salt, prodrug, metabolite, analog or derivative thereof, is administered in a suitable dosage form prepared by combining a therapeutically effective amount (e.g., an efficacious level sufficient to achieve the desired therapeutic effect through inhibition of tumor growth, killing of tumor cells, treatment or prevention of cell proliferative disorders, etc.) of a compound of the present invention, or a pharmaceutically acceptable salt, prodrug, metabolite, analog or derivative thereof, (as an active ingredient) with standard pharmaceutical carriers or diluents according to conventional procedures (i.e., by producing a pharmaceutical composition of the invention). These procedures may involve mixing, granulating, and compressing or dissolving the ingredients as appropriate to attain the desired preparation.

4. The Pharmaceutical Compositions and Formulations

A pharmaceutical composition of the invention is formulated to be compatible with its intended route of administration. Examples of routes of administration include parenteral, e.g., intravenous, intradermal, subcutaneous, oral (e.g., inhalation), transdermal (topical), and transmucosal administration. Solutions or suspensions used for parenteral, intradermal, or subcutaneous application can include the following components: a sterile diluent such as water for injection, saline solution, fixed oils, polyethylene glycols, glycerine, propylene glycol or other synthetic solvents; antibacterial agents such as benzyl alcohol or methyl parabens; antioxidants such as ascorbic acid or sodium bisulfite; chelating agents such as ethylenediaminetetraacetic acid; buffers such as acetates, citrates or phosphates, and agents for the adjustment of tonicity such as sodium chloride or dextrose. The pH can be adjusted with acids or bases, such as hydrochloric acid or sodium hydroxide. The parenteral preparation can be enclosed in ampoules, disposable syringes or multiple dose vials made of glass or plastic.

A compound or pharmaceutical composition of the invention can be administered to a subject in many of the well-known methods currently used for chemotherapeutic treatment. For example, for treatment of cancers, a compound of the invention may be injected directly into tumors, injected into the blood stream or body cavities or taken orally or applied through the skin with patches. The dose chosen should be sufficient to constitute effective treatment but not so high as to cause unacceptable side effects. The state of the disease condition (e.g., cancer, precancer, and the like) and the health of the patient should preferably be closely monitored during and for a reasonable period after treatment.

The term "therapeutically effective amount," as used herein, refers to an amount of a pharmaceutical agent to treat, ameliorate, or prevent an identified disease or condition, or to exhibit a detectable therapeutic or inhibitory effect. The effect can be detected by any assay method known in the art. The precise effective amount for a subject will depend upon the subject's body weight, size, and health; the nature and extent of the condition; and the therapeutic or combination of therapeutics selected for administration. Therapeutically effective amounts for a given situation can be determined by routine experimentation that is within the skill and judgment of the clinician. In a preferred aspect, the disease or condition to be treated is cancer. In another aspect, the disease or condition to be treated is a cell proliferative disorder.

For any compound, the therapeutically effective amount can be estimated initially either in cell culture assays, e.g., of neoplastic cells, or in animal models, usually rats, mice, rabbits, dogs, or pigs. The animal model may also be used to determine the appropriate concentration range and route of administration. Such information can then be used to determine useful doses and routes for administration in humans. Therapeutic/prophylactic efficacy and toxicity may be determined by standard pharmaceutical procedures in cell cultures or experimental animals, e.g., $ED_{50}$ (the dose therapeutically effective in 50% of the population) and $LD_{50}$ (the dose lethal to 50% of the population). The dose ratio between toxic and therapeutic effects is the therapeutic index, and it can be expressed as the ratio, $LD_{50}/ED_{50}$. Pharmaceutical compositions that exhibit large therapeutic indices are preferred. The dosage may vary within this range depending upon the dosage form employed, sensitivity of the patient, and the route of administration.

Dosage and administration are adjusted to provide sufficient levels of the active agent(s) or to maintain the desired effect. Factors which may be taken into account include the severity of the disease state, general health of the subject, age, weight, and gender of the subject, diet, time and frequency of administration, drug combination(s), reaction sensitivities, and tolerance/response to therapy. Long-acting pharmaceutical compositions may be administered every 3 to 4 days, every week, or once every two weeks depending on half-life and clearance rate of the particular formulation.

The pharmaceutical compositions containing active compounds of the present invention may be manufactured in a manner that is generally known, e.g., by means of conventional mixing, dissolving, granulating, dragee-making, levigating, emulsifying, encapsulating, entrapping, or lyophilizing processes. Pharmaceutical compositions may be formulated in a conventional manner using one or more pharmaceutically acceptable carriers comprising excipients and/or auxiliaries that facilitate processing of the active compounds into preparations that can be used pharmaceutically. Of course, the appropriate formulation is dependent upon the route of administration chosen.

Pharmaceutical compositions suitable for injectable use include sterile aqueous solutions (where water soluble) or dispersions and sterile powders for the extemporaneous preparation of sterile injectable solutions or dispersion. For intravenous administration, suitable carriers include physiological saline, bacteriostatic water, Cremophor EL™ (BASF, Parsippany, N.J.) or phosphate buffered saline (PBS). In all cases, the composition must be sterile and should be fluid to the extent that easy syringeability exists. It must be stable under the conditions of manufacture and storage and must be preserved against the contaminating action of microorganisms, such as bacteria and fungi. The carrier can be a solvent or dispersion medium containing, for example, water, ethanol, polyol (for example, glycerol, propylene glycol, and liquid polyethylene glycol, and the like), and suitable mixtures thereof. The proper fluidity can be maintained, for example, by the use of a coating such as lecithin, by the maintenance of the required particle size in the case of dispersion and by the use of surfactants. Prevention of the action of microorganisms can be achieved by various antibacterial and antifungal agents, for example, parabens, chlorobutanol, phenol, ascorbic acid, thimerosal, and the like. In many cases, it will be preferable to include isotonic agents, for example, sugars, polyalcohols such as manitol, sorbitol, sodium chloride in the composition. Prolonged absorption of the injectable compositions can be brought about by including in the composition an agent which delays absorption, for example, aluminum monostearate and gelatin.

Sterile injectable solutions can be prepared by incorporating the active compound in the required amount in an appropriate solvent with one or a combination of ingredients enumerated above, as required, followed by filtered sterilization. Generally, dispersions are prepared by incorporating the active compound into a sterile vehicle that contains a basic dispersion medium and the required other ingredients from those enumerated above. In the case of sterile powders for the preparation of sterile injectable solutions, methods of preparation are vacuum drying and freeze-drying that yields a powder of the active ingredient plus any additional desired ingredient from a previously sterile-filtered solution thereof.

Oral compositions generally include an inert diluent or an edible pharmaceutically acceptable carrier. They can be enclosed in gelatin capsules or compressed into tablets. For the purpose of oral therapeutic administration, the active compound can be incorporated with excipients and used in the form of tablets, troches, or capsules. Oral compositions can also be prepared using a fluid carrier for use as a mouthwash, wherein the compound in the fluid carrier is applied orally and swished and expectorated or swallowed. Pharmaceutically compatible binding agents, and/or adjuvant materials can be included as part of the composition. The tablets, pills, capsules, troches and the like can contain any of the following ingredients, or compounds of a similar nature: a binder such as microcrystalline cellulose, gum tragacanth or gelatin; an excipient such as starch or lactose, a disintegrating agent such as alginic acid, Primogel, or corn starch; a lubricant such as magnesium stearate or Sterotes; a glidant such as colloidal silicon dioxide; a sweetening agent such as sucrose or saccharin; or a flavoring agent such as peppermint, methyl salicylate, or orange flavoring.

For administration by inhalation, the compounds are delivered in the form of an aerosol spray from pressured container or dispenser, which contains a suitable propellant, e.g., a gas such as carbon dioxide, or a nebulizer.

Systemic administration can also be by transmucosal or transdermal means. For transmucosal or transdermal administration, penetrants appropriate to the barrier to be permeated are used in the formulation. Such penetrants are generally known in the art, and include, for example, for transmucosal administration, detergents, bile salts, and fusidic acid derivatives. Transmucosal administration can be accomplished through the use of nasal sprays or suppositories. For transdermal administration, the active compounds are formulated into ointments, salves, gels, or creams as generally known in the art.

In one aspect, the active compounds are prepared with pharmaceutically acceptable carriers that will protect the compound against rapid elimination from the body, such as a controlled release formulation, including implants and microencapsulated delivery systems. Biodegradable, biocompatible polymers can be used, such as ethylene vinyl acetate, polyanhydrides, polyglycolic acid, collagen, polyorthoesters, and polylactic acid. Methods for preparation of such formulations will be apparent to those skilled in the art. The materials can also be obtained commercially from Alza Corporation and Nova Pharmaceuticals, Inc. Liposomal suspensions (including liposomes targeted to infected cells with monoclonal antibodies to viral antigens) can also be used as pharmaceutically acceptable carriers. These can be prepared according to methods known to those skilled in the art, for example, as described in U.S. Pat. No. 4,522,811.

It is especially advantageous to formulate oral or parenteral compositions in dosage unit form for ease of administration and uniformity of dosage. Dosage unit form as used herein refers to physically discrete units suited as unitary dosages for the subject to be treated; each unit containing a predetermined quantity of active compound calculated to produce the desired therapeutic effect in association with the required pharmaceutical carrier. The specification for the dosage unit forms of the invention are dictated by and directly dependent on the unique characteristics of the active compound and the particular therapeutic effect to be achieved.

In therapeutic applications, the dosages of the pharmaceutical compositions used in accordance with the invention vary depending on the agent, the age, weight, and clinical condition of the recipient patient, and the experience and judgment of the clinician or practitioner administering the therapy, among other factors affecting the selected dosage. Generally, the dose should be sufficient to result in slowing, and preferably regressing, the growth of the tumors and also preferably causing complete regression of the cancer. Dosages can range from about 0.01 mg/kg per day to about 3000 mg/kg per day. In preferred aspects, dosages can range from about 1 mg/kg per day to about 1000 mg/kg per day. In an aspect, the dose will be in the range of about 0.1 mg/day to about 50 g/day; about 0.1 mg/day to about 25 g/day; about 0.1 mg/day to about 10 g/day; about 0.1 mg to about 3 g/day; or about 0.1 mg to about 1 g/day, in single, divided, or continuous doses (which dose may be adjusted for the patient's weight in kg, body surface area in $m^2$, and age in years). An effective amount of a pharmaceutical agent is that which provides an objectively identifiable improvement as noted by the clinician or other qualified observer. For example, regression of a tumor in a patient may be measured with reference to the diameter of a tumor. Decrease in the diameter of a tumor indicates regression. Regression is also indicated by failure of tumors to reoccur after treatment has stopped. As used herein, the term "dosage effective manner" refers to amount of an active compound to produce the desired biological effect in a subject or cell.

The pharmaceutical compositions can be included in a container, pack, or dispenser together with instructions for administration.

All patents, patent applications and references cited herein are incorporated by reference herein in their entirety.

EXAMPLES

Examples are provided below to further illustrate different features of the present invention. The examples also illustrate useful methodology for practicing the invention. These examples do not limit the claimed invention.

Example 1

Preparation of 3-{5-[2-({(3R)-1-[(4-chlorophenyl) sulfonyl]piperidin-3yl}amino)pyrimidin-4-yl]imidazo[2,1-b][1,3]thiazol-6-yl}phenol 1a: Preparation of 6-(3-methoxyphenyl)-imidazo[2,1-b]thiazole.

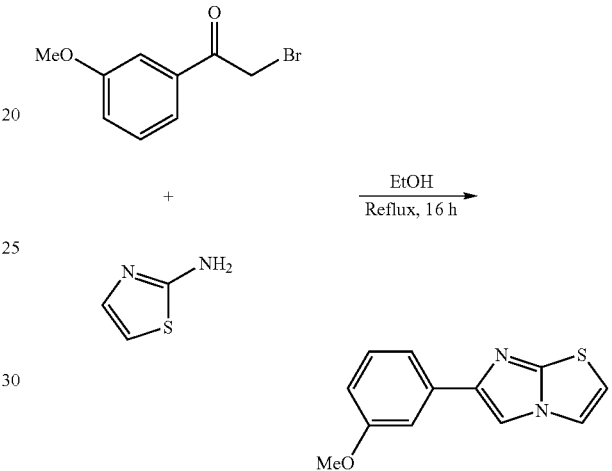

To a mixture of 2-aminothiazole (2.7 g, 26.7 mmol) and 2-bromo-3'-methoxyacetophenone (6.0 g, 0.0262 mol) was added absolute ethanol (100 ml). The reaction was allowed to reflux with vigorous stirring for 18 hours (checked by HPLC). The reaction mixture was reduced to half its original volume in vacuo. The remaining liquid was poured onto ice and the solution made basic by the addition of ammonium hydroxide solution (30%). The resulting fine solid was filtered and washed with water resulting in a dark yellow solid product. The solid product was dried in a vacuum oven at 50° C. to provide 6-(3-methoxyphenyl)-imidazo[2,1-b]thiazole (5.0 g, 81%). 400 MHz $^1$H NMR (DMSO-$d_6$) δ 8.18 (s, 1H), 7.88 (d, J=4.4 Hz, 1H), 7.36-7.42 (m, 2H), 7.28 (t, J=8.1 Hz, 1H), 7.22 (d, J=4.4 Hz, 1H), 6.82 (ddd, J=8.1, 2.6, 1.1 Hz, 1H), 3.80 (s, 3H). LCMS: 231 [M+H].

1b: Preparation of 1-[6-(3-methoxyphenyl)imidazo[2,1-b][1,3]thiazol-5-yl]ethanone

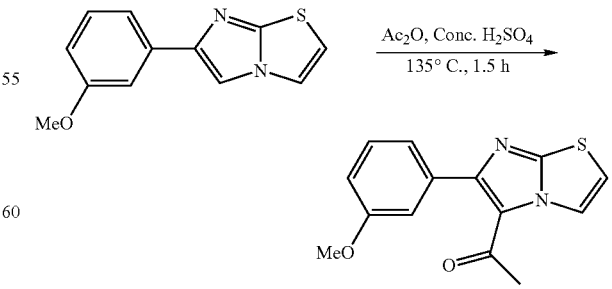

To a mixture of 6-(3-methoxyphenyl)-imidazo[2,1-b]thiazole (14.3 g, 62 mmol) and acetic anhydride (250 ml) was added 1 ml of concentrated sulfuric acid. The reaction mixture was heated at 140° C. for 4 hours. The reaction mixture was then poured onto 500 ml of ice, and diluted with 500 ml of water and the resulting mixture was extracted three times with 300 ml each of ethyl acetate. The combined extracts were washed with three portions of 100 ml of water and one portion of 200 ml of saturated aqueous sodium chloride solution. The organic phase was dried with magnesium sulfate, filtered and concentrated in vacuo, to give a brown oil (17.95 g). The product, -[6-(3-methoxyphenyl)imidazo[2,1-b][1,3]thiazol-5-yl]ethanone, was used directly in the next step. 400 MHz $^1$H NMR (DMSO-d$_6$) δ 8.43 (d, J=4.4 Hz, 1H), 7.55 (d, J=4.4 Hz, 1H), 7.42 (t, J=8.2 Hz, 1H), 7.16-7.2 (m, 2H), 7.04-7.1 (m, 1H), 3.81 (s, 3H), 2.13 (s, 3H). LCMS: 273 [M+H].

1c: Preparation of 3-(dimethylamino)-1-[6-(3-methoxyphenyl)imidazo[2,1-b][1,3]thiazol-5-yl]prop-2-en-1-one

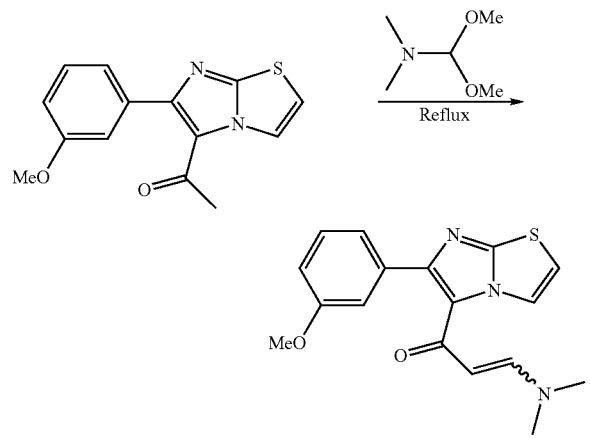

A 100 ml round bottom flask was charged with the 1-[6-(3-methoxyphenyl)imidazo [2,1-b][1,3]thiazol-5-yl]ethanone (17.95 g, 62 mmol) and dimethylformamide dimethylacetal (120 ml). The mixture was refluxed for 72 hours and then cooled to room temperature. The mixture was concentrated in vacuo and the residue was purified by flash chromatography (ethyl acetate), giving a pale yellow solid (16.82 g). 300 MHz $^1$H NMR (DMSO-d$_6$) δ: 8.40 (d, J=4.4 Hz, 1H), 7.59 (d, J=12.5 Hz, 1H), 7.41 (d, J=4.4 Hz, 1H), 7.37 (t, J=7.7 Hz, 1H), 7.17-7.21 (m, 2H), 6.99-7.03 (m, 1H), 5.15 (d, J=12.5 Hz, 1H), 3.79 (s, 3H), 3.04 (s, 3H), 2.44 (s, 3H).

1d: Preparation of tert-butyl (3R)-3-{[(Z)-amino(imino)methyl]amino}piperidine-1-carboxylate hydrochloride

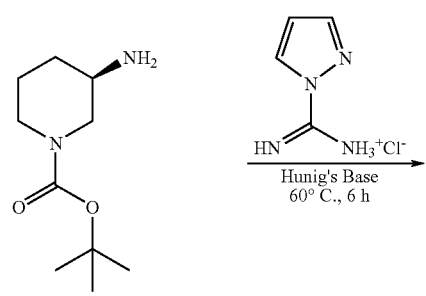

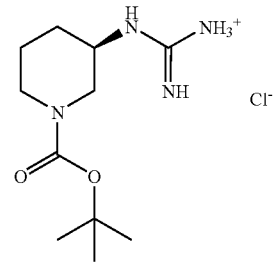

To a mixture of tert-butyl (3R)-3-aminopiperidine-1-carboxylate (10 g, 49.9 mmol) and pyrazole carboxamidine hydrochloride (7.31 g, 49.9 mmol) was added Hunig's base (8.72 ml, 49.9 mmol) and DMF (30 ml). The reaction was heated at 70° C. for 18 hours. The reaction was then cooled to room temperature and quenched by adding 700 ml of diethyl ether and stirring at room temperature for 24 hours. Product separated out as a white solid, which was filtered, washed, and dried (13 g, 94%). 400 MHz $^1$H NMR (DMSO-d$_6$) δ: 7.67 (d, J=8.8 HZ, 1H), 6.9-7.6 (br. s, 4H), 3.55 (br.s, 2H), 2.8-3.6 (m, 4H), 2.8-2.9 (m, 1H), 1.6-1.7 (m, 1H), 1.39 (s, 9H), 1.2-1.3 (m, 1H). LCMS: 243 [M+H].

1e: Preparation of tert-butyl (3R)-3-({4-[6-(3-methoxyphenyl)imidazo[2,1-b][1,3]thiazol-5-yl]pyrimidin-2-yl}amino)piperidine-1-carboxylate

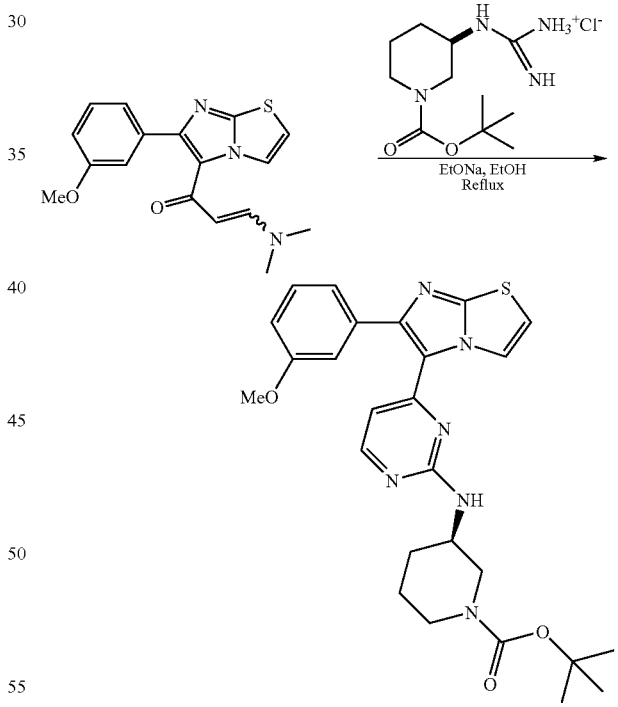

A mixture of 3-(dimethylamino)-1-[6-(3-methoxyphenyl)imidazo[2,1-b][1,3]thiazol-5-yl]prop-2-en-1-one (5.0 g, 15.3 mmol) and tert-butyl (3R)-3-{[(Z)-amino(imino)methyl]amino}piperidine-1-carboxylate hydrochloride (5.28 g, 18.95 mmol) was diluted with 60 ml of absolute ethanol and treated with 1.15 eq. of a 21% w/w solution of sodium ethoxide in ethanol (6.56 ml) to form a reaction mixture. The reaction mixture was heated to reflux for 24 hours. Volatiles were removed in vacuo and the residue was taken up in 250 ml of ethyl acetate and 250 ml of water. The phases were separated and the aqueous phase was extracted with 250 ml of ethyl acetate. The combined organic extracts were washed with 250 ml each of water, and then with a saturated sodium chloride solution (250 ml). The organic phase was dried with magnesium sulfate, filtered and concentrated in vacuo, to give a yellow oil. The product was purified by flash chromatography on silica gel (ethyl acetate/hexanes, 50%) to yield 7.2 g of a pale yellow solid (93%). 300 MHz $^1$H NMR (DMSO-$d_6$ at 80° C.) δ: 8.69 (d, J=3.5 Hz, 1H), 8.10 (d, J=5.3 Hz, 1H), 7.32-7.41 (m, 2H), 7.12-7.18 (m, 2H), 6.91-7.02 (m, 2H), 6.41 (d, J=5.3 Hz, 1H), 3.94 (br. d, J=7.0, 1H), 3.74-3.88 (m, 1H), 3.78 (s, 3H), 3.67 (br. d, J=13.2, 1H), 2.86-3.02 (m, 2H), 1.90-2.06 (m, 1H), 1.70-1.84 (m, 1H), 1.38-1.64 (m, 2H), 1.34 (s, 9H). LCMS: 507 [M+H].

1f: Preparation of 4-[6-(3-methoxyphenyl)imidazo[2,1-b][1,3]thiazol-5-yl]-N-[(3R)-piperidin-3-yl]pyrimidin-2-amine hydrochloride The tert-butyl (3R)-3-({4-[6-(3-methoxyphenyl)imidazo[2,1-b][1,3]thiazol-5-yl]pyrimidin-2-yl}amino)piperidine-1-carboxylate (21 g, 41.5 mmol) was dissolved in 250 ml of dioxane and treated with 75 ml of anhydrous a four molar HCl in dioxane at room temperature. The reaction mixture was stirred at room temperature for three hours. The mixture was then diluted with 350 ml of ether and stirred until product separated as a solid. Solid product was filtered and washed with ether. The solid was dissolved in MeOH (200 ml) and concentrated to dryness (this was done twice). The product was dried at high vacuum to yield 20.275 g of yellow solid (tris HCl salt) (90%). M.p.=220-225° C.; 300 MHz $^1$H NMR (DMSO-$d_6$ at 80° C.) δ: 9.6-9.3 (br. s, 2H), 8.9-8.4 (br. s, 2H), 8.82 (s, 1H), 8.11 (d, J=5.8 Hz, 1H), 7.50 (d, J=4.7 Hz, 1H), 7.39 (t, J=7.98 Hz, 1H), 7.2-7.1 (m, 2H), 7.08-7.0 (m, 1H), 6.49 (d, J=5.8 Hz, 1H), 4.4-4.3 (m, 1H), 3.79 (s, 3H), 3.39 (d, J=10.2 Hz, 1H), 3.16 (br. s, 1H), 3.05-2.7 (m, 2H), 2.2-1.6 (m, 3H), 1.55-1.2 (m, 1H). LCMS: 407 [M+H]; calc. for $C_{21}H_{22}N_6OS.3.3HCl.0.05$ dioxane.0.3 methanol: C, 47.75; H, 5.01; N, 15.54. Found C, 47.73; H, 5.26; N, 15.55.

1g: Preparation of N-{(3R)-1-[(4-chlorophenyl)sulfonyl]piperidin-3-yl}-4-[6-(3-methoxyphenyl)imidazo[2,1-b][1,3]thiazol-5-yl]pyrimidin-2-amine

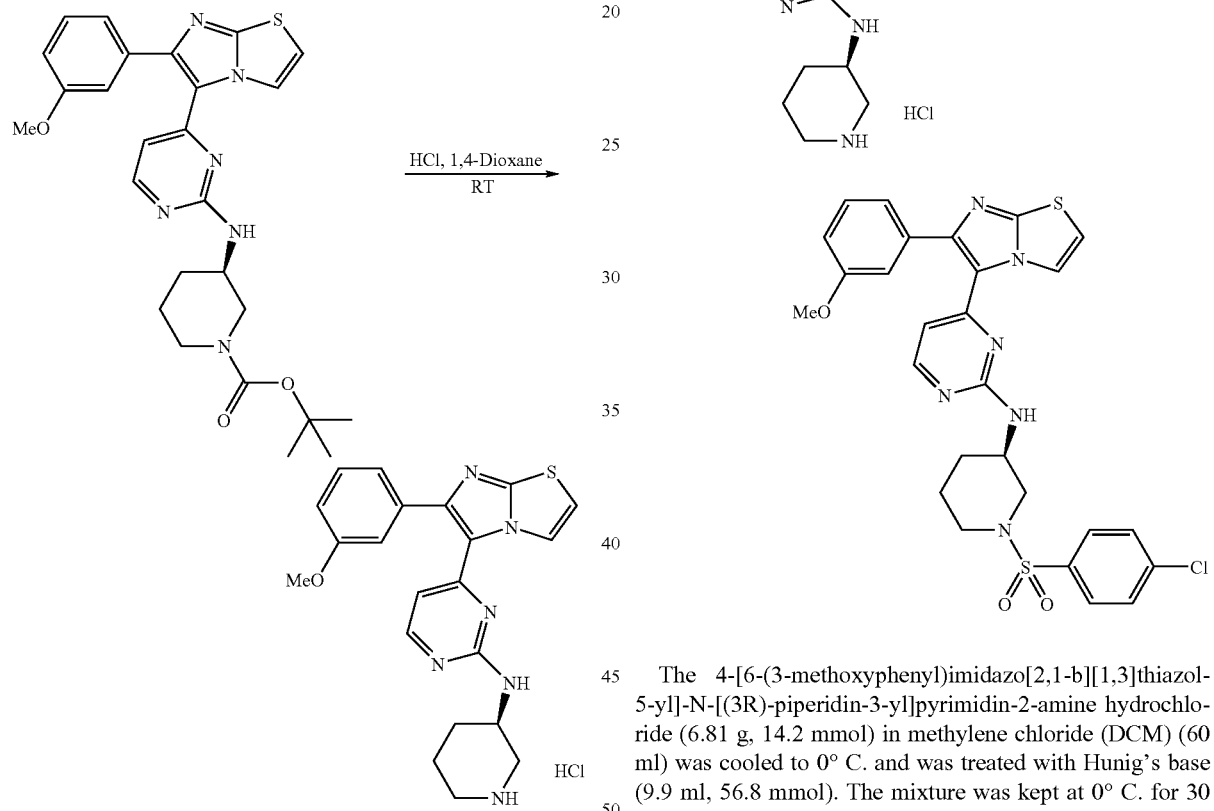

The 4-[6-(3-methoxyphenyl)imidazo[2,1-b][1,3]thiazol-5-yl]-N-[(3R)-piperidin-3-yl]pyrimidin-2-amine hydrochloride (6.81 g, 14.2 mmol) in methylene chloride (DCM) (60 ml) was cooled to 0° C. and was treated with Hunig's base (9.9 ml, 56.8 mmol). The mixture was kept at 0° C. for 30 minutes then the 4-chlorophenylsulfonyl chloride (3.3 g, 15.6 mmol) was added. The reaction mixture was stirred at room temperature overnight. The mixture was diluted with methylene chloride (100 ml) and was washed water (100 ml) and a saturated aqueous sodium chloride solution (100 ml). The organic phase was dried over sodium sulfate and concentrated in vacuo. The crude product was purified by flash chromatography using a gradient (ethyl acetate/hexanes, 40-100%), affording 6.98 g (85%) of the title compound as a pale yellow solid. 400 MHz $^1$H NMR (DMSO-$d_6$ at 60° C.) δ: 8.42 (br. s, 1H), 8.12 (d, J=5.1 Hz, 1H), 7.8-7.75 (m, 2H), 7.7-7.65 (m, 2H), 7.43-7.39 (m, 1H), 7.36 (d, J=7.8 Hz, 1H), 7.18-7.1 (m, 2H), 7.05-6.98 (m, 1H), 6.42 (d, J=5.1 Hz, 1H), 4.0-3.9 (m, 1H), 3.78 (s, 3H), 3.74 (d, J=11.7 Hz, 1H), 3.48 (d, J=11.7 Hz, 1H), 2.5-2.4 (m, 1H), 2.33 (t, J=5.3 Hz, 1H), 1.95-1.8 (m, 2H), 1.65-1.5 (m, 1H), 1.45-1.4 (m, 1H). LCMS: 581 [M+H].

1h: Preparation of 3-{5-[2-({(3R)-1-[(4-chlorophenyl)sulfonyl]piperidin-3-yl}amino)pyrimidin-4-yl]imidazo[2,1-b][1,3]thiazol-6-yl}phenol

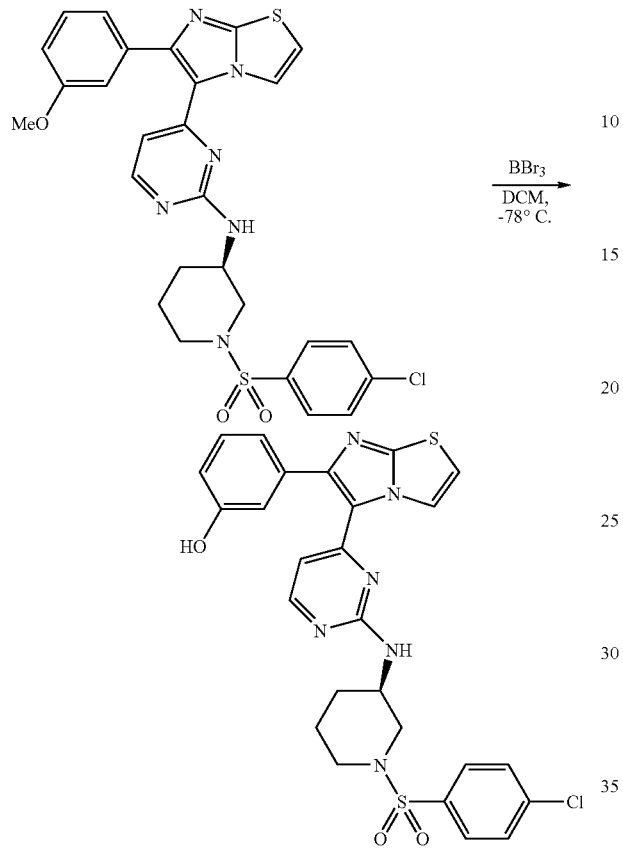

The N-{(3R)-1-[(4-chlorophenyl)sulfonyl]piperidin-3-yl}-4-[6-(3-methoxy-phenyl)imidazo[2,1-b][1,3]thiazol-5-yl]pyrimidin-2-amine (6.98 g, 12.03 mmol) in methylene chloride (100 ml) was cooled to −78° C. and slowly treated with 1 molar solution of boron tribromide in methylene chloride (65 ml). The reaction mixture was kept at −78° C. for one hour then was allowed to warm to room temperature for two hours. The mixture was quenched by the addition of methanol (25 ml) at 0° C. and was stirred at room temperature for an additional hour. The mixture was diluted with methylene chloride (500 ml) and washed with three portions of 100 ml of saturated sodium bicarbonate solution, two portions of 100 ml of water and two portions of 100 ml of saturated sodium chloride solution. The organic phase was dried over sodium sulfate and concentrated in vacuo, giving a yellow foam. The crude product was re-crystallized from methanol as a yellow solid (4.85 g, 71%). M.p.=174-177° C. 400 MHz $^1$H NMR (DMSO-d$_6$ at 60° C.) δ: 9.4 (br. s, 1H), 8.70 (br. s, 1H), 8.12 (d, J=5.5 Hz, 1H), 7.8-7.7 (m, 2H), 7.7-7.65 (m, 2H), 7.40 (d, J=4.7 Hz, 1H), 7.25 (t, J=8.0 Hz, 1H), 7.15 (d, J=7.4 Hz, 1H), 7.0-6.95 (m, 1H), 6.85-6.8 (m, 1H), 6.44 (d, J=5.5 Hz, 1H), 3.95 (br. s, 1H), 3.72 (dd, J=10.6 3.1 Hz, 1H), 3.40 (m, 1H), 2.5-2.4 (m, 1H), 2.35 (t, J=10.2 Hz, 1H), 2.0-1.8 (m, 2H), 1.65-1.5 (m, 1H), 1.46-1.32 (m, 1H). LCMS: 567 [M+H]. Calc. for C$_{26}$H$_{23}$N$_6$O$_3$S$_2$Cl.0.5 water.1.0 methanol: C, 53.33; H, 4.64; N, 13.82. Found C, 53.32; H, 4.64; N, 13.82.

Example 2

Preparation of 2-amino-oxazole

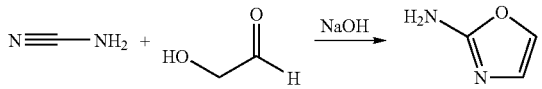

To a solution of cyanamide (19.8 ml of 50% w/w in water, 0.25 mol) in THF (60 ml) was added the hydroxyacetaldehyde (15 g, 0.25 mol) in 24 ml of water. The reaction mixture was treated at 0° C. with a solution of sodium hydroxide 2 M (25.2 ml, 0.05 mol). The mixture was allowed to warm to room temperature and stirred for 24 hrs. The volatiles were removed in vacuo (THF) and the remaining aqueous solution was extracted with four portions of 200 ml of ethyl acetate. The organic extracts were dried over sodium sulfate and concentrated in vacuo, yielding 14:968 g (71.3%) of a white solid. 400 MHz $^1$H NMR (CDCl$_3$) δ: 7.13 (s, 1H), 6.74 (s, 1H), 5.26 (br. s, 2H). Calc. for C$_3$H$_4$N$_2$O: C, 42.86; H, 4.80; N, 33.32. Found C, 43.01; H, 4.87; N, 33.11.

Example 3

Preparation of N-[4-(dimethylamino)phenyl]-4-({4-[6-(4-fluorophenyl)-imidazo[2,1-b][1,3]oxazol-5-yl]pyrimidin-2-yl}amino)piperidine-1-carboxamide 3a: Preparation of 1-(4-fluorophenyl)-2-(2-imino-1,3-oxazol-3(2H)-yl)ethanone hydrobromide A solution of 2-amino-oxazole (14.9 g, 0.179 mol) in acetonitrile (100 ml) was slowly added over a period of 20 minutes to a solution of 2-bromo-1-(4-fluorophenyl)ethanone (57.6 g, 0.36 mol) in THF (150 ml). The reaction mixture was stirred at room temperature for 24 hrs then cooled to 0° C. A precipitate formed and was filtered off. The solid was washed with three portions of 30 ml of cold acetonitrile and dried at 50° C. under vacuum, yielding 38.75 g (72%) of an off-white solid. M.p.=218-221° C.; 300 MHz $^1$H NMR (DMSO-d$_6$) δ: 9.80 (br. s, 1H), 8.16-8.11 (m, 2H), 8.00 (s, 1H), 7.62 (s, 1H), 7.52-7.46 (m, 2H), 5.80 (s, 2H); LCMS: 221 [M+H]. Calc. for C$_{11}$H$_9$N$_2$O$_2$F.1.05HBr.0.14ACN: C, 43.58; H, 3.39; N, 9.64. Found C, 43.63; H, 3.38; N, 9.65.

3b: Preparation of 6-(4-fluorophenyl)-imidazo[2,1-b]oxazole

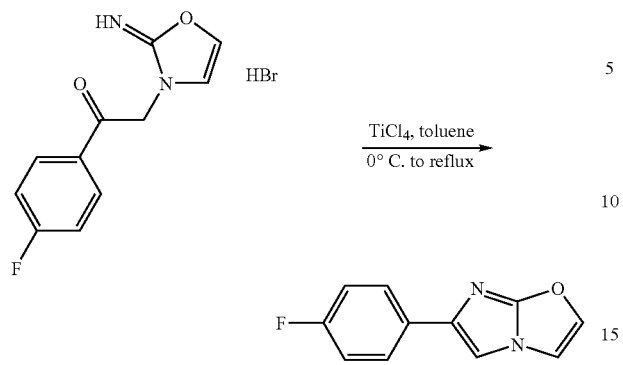

The 1-(4-fluorophenyl)-2-(2-iminooxazol-3-yl)-ethanone hydrobromide salt (10.0 g, 0.32 mol) was introduced in a two-neck flask, fitted with a condenser, and flushed with nitrogen. Anhydrous toluene (100 ml) was added and the mixture was cooled to −10° C. TiCl$_4$ (17.5 ml, 0.16 mol) was added over a period of 30 minutes. The reaction becomes deep red and a dark precipitate was formed. The reaction mixture was allowed to warm to room temperature. The mixture was then brought to reflux and kept a reflux for 5.5 hrs. The reaction mixture was cooled to room temperature overnight. The toluene was decanted and iced water (60 ml) was added to the residue (caution!), which turned from dark brown to beige. The resulting suspension was transferred to a large beaker and treated with saturated aqueous sodium carbonate solution until pH 8. A saturated aqueous sodium chloride solution was added (200 ml), followed by 600 ml of ethyl acetate and the mixture was stirred vigorously for one hour. The organic phase was separated and the aqueous phase was further extracted with two portions of 600 ml of ethyl acetate. The organic extracts were dried over sodium sulfate and concentrated in vacuo, yielding 6.84 g of a pale yellow solid. 400 MHz $^1$H NMR (CDCl$_3$) δ: 7.78-7.72 (m, 2H), 7.37 (d, J=1.8 Hz, 1), 7.31 (d, J=1.8 Hz, 1), 7.24 (s, 1H), 7.10-7.00 (m, 2H).

3c: Preparation of 1-[6-(4-fluorophenyl)imidazo[2,1-b][1,3]oxazol-5-yl]ethanone

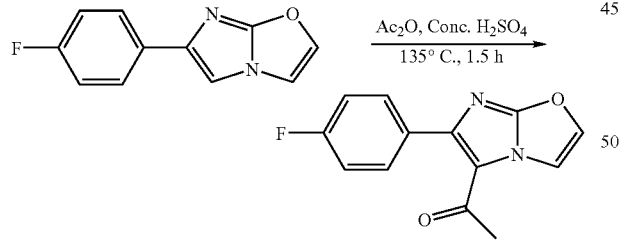

A solution of 6-(4-fluorophenyl)-imidazo[2,1-b]oxazole (2.5 g, 0.0124 mol) in acetic anhydride (60 ml) was heated to 140° C. and then treated with concentrated sulfuric acid (5 drops). After 15 minute at that temperature, HPLC showed clean conversion and the reaction mixture was quenched by the addition of ice cold water (150 ml). The mixture was extracted with ethyl acetate (3×150 ml). The combined extracts were washed with a saturated aqueous sodium chloride solution (300 ml), dried over magnesium sulfate and concentrated in vacuo as a brown solid. Trituration from a mixture of hexanes/ethyl acetate (1:1) provided 2.2 g (72.6%) of a pale yellow solid. M.p.=173° C.; 300 MHz $^1$H NMR (DMSO-d$_6$) δ 8.25-8.19 (m, 2H), 7.75-7.68 (m, 2H), 7.35-7.25 (m, 2H), 2.15 (s, 3H). LCMS: 245 [M+H].

3d: Preparation of 3-(dimethylamino)-1-[6-(4-fluorophenyl)imidazo[2,1-b][1,3]oxazol-5-yl]prop-2-en-1-one

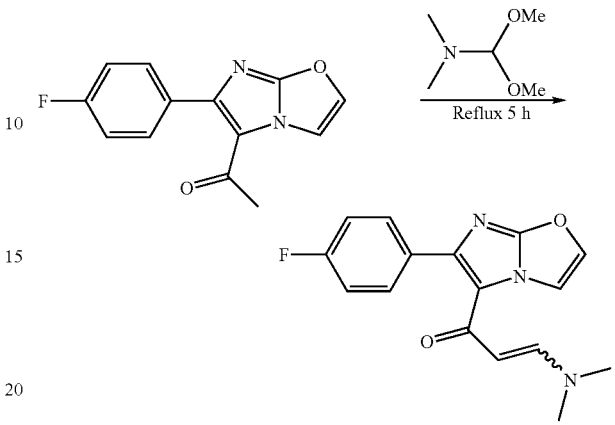

A solution of 1-[6-(4-fluorophenyl)imidazo[2,1-b][1,3]oxazol-5-yl]ethanone (0.0374 g, 0.000153 mol) in N,N-dimethylformamide dimethyl acetal (3.0 ml) was heated to 100° C. for 24 hrs. HPLC showed complete consumption of the starting material. The volatiles were removed in vacuo, yielding a brown solid (0.046 g, quantitative). M.p.=187-189° C.; 300 MHz $^1$H NMR (CDCl$_3$) δ 8.03 (s, 1H), 7.72-7.64 (m, 3H), 7.46 (s, 1H), 7.13-7.10 (m, 2H), 5.19 (d, J=12.5 Hz, 1H), 3.07 (bs, 3H), 2.55 (bs, 3H). LCMS: 300 [M+H]. Calc. for C$_{16}$H$_{14}$FN$_3$O$_2$: C, 64.21; H, 4.71; N, 14.04. Found C, 64.22; H, 4.31; N, 14.10.

3e: Preparation of tert-butyl 4-{[amino(imino)methyl]amino}piperidine-1-carboxylate hydrochloride

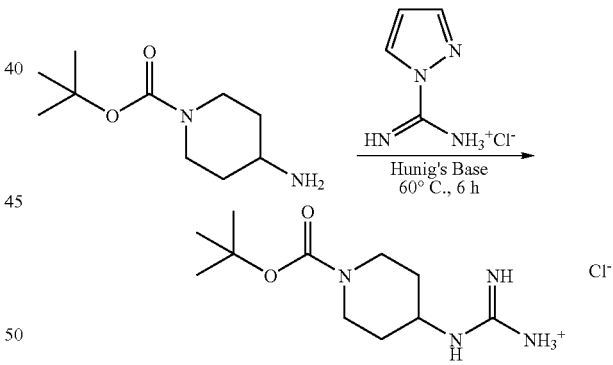

To a mixture of tert-butyl 4-aminopiperidine-1-carboxylate (8.93 g, 44.6 mmol) and pyrazole carbox-amidine hydrochloride (6.536 g, 44.6 mmol) was added Hunig's base (7.77 ml, 44.6 mmol) and DMF (25 ml). The reaction was heated at 60° C. for 15 hours. The reaction was then cooled to room temperature and quenched by adding 400 ml of diethyl ether and stirring at room temperature for 2 hours. Product separated out as a white solid, which was filtered, washed and dried (10.9 g, 88%). M.p.=169-172° C.; 400 MHz $^1$H NMR (DMSO-d$_6$) δ: 8.09 (d, J=8.8 HZ, 1H), 6.9-7.9 (br. s, 3H), 3.83 (d, J=13.6 Hz, 2H), 3.63 (m, 1H), 2.88 (m, 2H), 1.80 (m, 2H), 1.40 (s, 9H), 1.25 (m, 2H); LCMS: 243 [M+H]; calc. for C$_{11}$H$_{22}$N$_4$O$_2$.1.06HCl.0.2H$_2$O: C, 46.39; H, 8.31; N, 19.68. Found C, 46.43; H, 8.31; N, 20.68.

3f: Preparation of tert-butyl 4-({4-[6-(4-fluorophenyl)imidazo[2,1-b][1,3]oxazol-5-yl]pyrimidin-2-yl}amino)piperidine-1-carboxylate

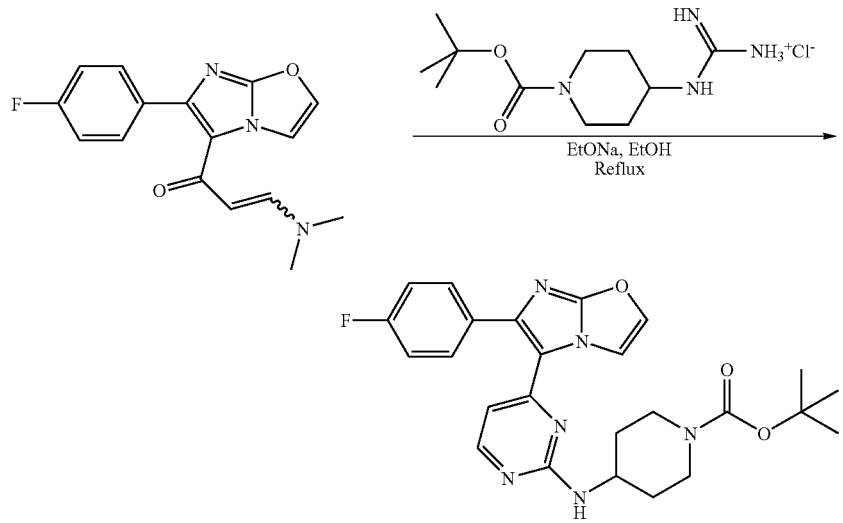

A mixture of 3-(dimethylamino)-1-[6-(4-fluorophenyl)imidazo[2,1-b][1,3]oxazol-5-yl]prop-2-en-1-one (4.24 g, 14.2 mmol) and tert-butyl 4-{[amino(imino)methyl]amino}-piperidine-1-carboxylate hydrochloride (5.92 g, 21.2 mmol) was diluted with 40 ml of absolute ethanol and treated with 1.35 eq. of a 21% w/w solution of sodium ethoxide in ethanol (7.2 ml) to form a reaction mixture. The reaction mixture was heated to reflux for 15 hours. Volatiles were removed in vacuo and the residue was taken up in 200 ml of ethyl acetate, washed twice with 100 ml each of water, and then with a saturated sodium chloride solution (100 ml). The organic phase was dried with magnesium sulfate, filtered and concentrated in vacuo, to give a brown solid. The product was purified by flash chromatography on silica gel (gradient 50%-75% ethyl acetate/hexanes) to yield 4.436 g of a tan solid (65%). M.p.=175° C.; 300 MHz $^1$H NMR (CDCl$_3$) δ: 8.06 (s, 1H), 8.04 (s, 1H), 7.65-7.60 (m, 2H), 7.48 (d, J=1.6 Hz, 1H), 7.17-7.13 (m, 2H), 6.52 (d, J=5.6 Hz, 1H), 5.1 (br. s, 1H), 4.2-3.9 (m, 3H), 2.2-2.0 9M, 2H), 16.-1.4 (m, 4H), 1.48 (s, 9H). LCMS: 479 [M+H]; calc. for C$_{25}$H$_{27}$FN$_6$O$_3$.0.25H$_2$O: C, 62.11; H, 5.74; N, 17.39. Found C, 62.43; H, 5.37; N, 17.35.

3g: Preparation of 4-[6-(4-fluorophenyl)imidazo[2,1-b][1,3]oxazol-5-yl]-N-piperidin-4-ylpyrimidin-2-amine hydrochloride -continued

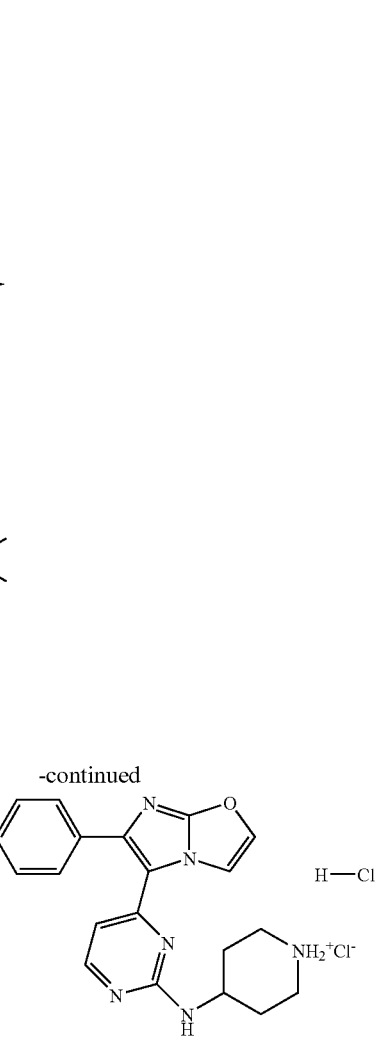

A solution of tert-butyl 4-({4-[6-(4-fluorophenyl)imidazo[2,1-b][1,3]oxazol-5-yl]pyrimidin-2-yl}amino)piperidine-1-carboxylate (3.2 g, 0.0067 mol) in dioxane (35 ml) was treated with HCl 4 M in dioxane (5 ml). The reaction mixture was stirred at room temperature for 4 hrs. The volatiles were removed in vacuo, giving 2.951 g (98%) of a yellow solid. M.p.=217-220° C.; 300 MHz $^1$H NMR (DMSO-d$_6$) δ: 9.55-9.25 (br. m, 2H), 9.03 (br. s, 1H), 8.31 (s, 1H), 8.06 (br. s, 1H), 7.67 (t, J=7.1 Hz, 2H), 7.38 (t, J=8.8 Hz, 2H), 6.50 (d, J=6.0 Hz, 1H), 4.22 (br. s, 1H), 3.5-3.3 (m, 2H), 3.25-2.9 (m, 2H), 2.16 (br. d, J=11.5 Hz, 2H), 2.0-1.8 (m, 2H). LCMS: 379 [M+H]; calc. for C$_{20}$H$_{19}$FN$_6$O.3.0HCl.0.3 dioxane: C, 49.47; H, 4.78; N, 16.34. Found C, 49.30; H, 4.77; N, 16.51.

3h: Preparation of N-[4-(dimethylamino)phenyl]-4-({4-[6-(4-fluorophenyl)-imidazo[2,1-b][1,3]oxazol-5-yl]pyrimidin-2-yl}amino)piperidine-1-carboxamide

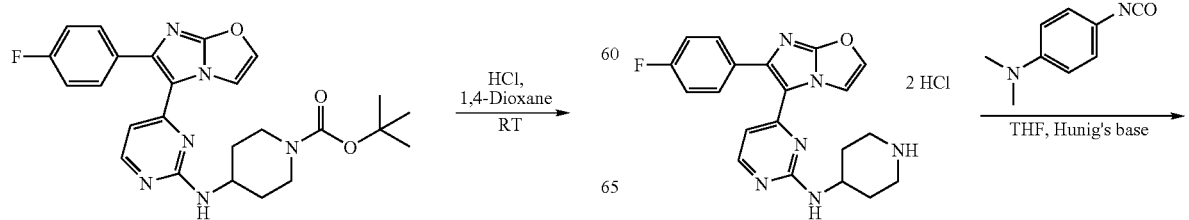

-continued

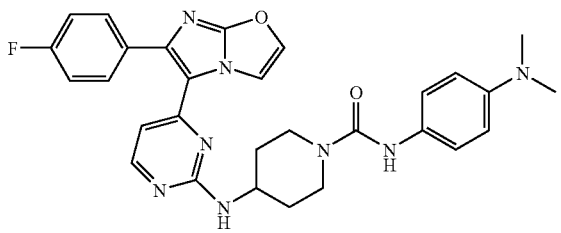

The 4-[6-(4-fluorophenyl)imidazo[2,1-b][1,3]oxazol-5-yl]-N-piperidin-4-ylpyrimidin-2-amine (bis HCl salt) (100 mg, 0.222 mmol) in tetrahydrofuran (5 ml) was treated with Hunig's base (240 ul), followed by 4-dimethylaminophenyl wasocyanate (44 mg). The reaction mixture was stirred at room temperature for 18 hours. The mixture was quenched by the addition of water (15 ml) and extracted with ethyl acetate (10 ml). The organic phase was washed with one portion of 10 ml of saturated sodium chloride solution, dried over sodium sulfate and concentrated in vacuo. The product was purified by trituration in ether, giving 116 mg of a pale yellow solid (97%). M.p.=225-227° C. 400 MHz $^1$H NMR (DMSO-d$_6$) δ: 8.73 (br. s, 1H), 8.24 (s, 1H), 8.18 (br. s, 1H), 8.10 (d, J=5.5 Hz, 1H), 7.67-7.61 (m, 2H), 7.38-7.29 (m, 2H), 7.26-7.19 (m, 2H), 6.70-6.61 (m, 2H), 6.35 (br. s, 1H), 4.08 (d, J=13.3 Hz, 2H), 4.00-3.90 (m, 1H), 2.93 (t, J=11.5 Hz, 2H), 2.82 (s, 6H), 1.93 (d, J=10.5 Hz, 2H), 1.50-1.35 (m, 2H). LCMS: 541 [M+H]. Calc. for $C_{29}H_{29}N_8O_2F$.0.35 ether: C, 64.45; H, 5.78; N, 19.78. Found C, 64.41; H, 5.58; N, 19.79.

Example 4

Preparation of 4-[6-(4-fluorophenyl)imidazo[2,1-b][1,3]oxazol-5-yl]-N-[1-(4-methoxybenzoyl)piperidin-4-yl]pyrimidin-2-amine

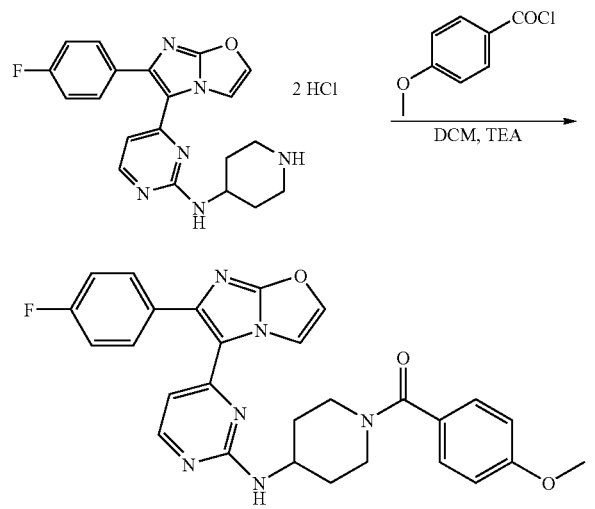

The 4-[6-(4-fluorophenyl)imidazo[2,1-b][1,3]oxazol-5-yl]-N-piperidin-4-ylpyrimidin-2-amine (bis HCl salt) (100 mg, 0.222 mmol) in dichloromethane (5 ml) was treated with triethylamine (500 ul). The mixture was cooled to 0° C. and treated with 4-methoxy benzoyl chloride (36 mg, 0.2 mmole). The reaction mixture was stirred at room temperature for 18 hours. The mixture was diluted with dichloromethane (10 ml) and washed with a soln. of sodium bicarbonate (3×15 ml) and water (15 ml). The organic phase was washed with one portion of 10 ml of saturated sodium chloride solution, dried over sodium sulfate and concentrated in vacuo. The product was purified by trituration in ether, giving 75 mg of a pale yellow solid (70%). M.p.=196-197° C. 400 MHz $^1$H NMR (CDCl$_3$) δ: 8.06-8.02 (m, 2H), 7.65-7.58 (m, 2H), 7.49 (d, J=1.6 Hz, 1H), 7.44-7.38 (m, 2H), 7.17-7.11 (m, 2H), 6.95-6.90 (m, 2H), 6.54 (d, J=5.5 Hz, 1H), 4.20-4.10 (m, 1H), 3.84 (s, 3H), 3.30-3.12 (m, 2H), 2.25-2.10 (m, 2H), 1.85-1.50 (m, 4H). LCMS: 513 [M+H]. Calc. for $C_{28}H_{25}N_6O_3F$.0.03 ether.0.52 water: C, 64.38; H, 5.07; N, 16.03. Found C, 64.43; H, 5.01; N, 16.04.

Example 5

Preparation of N-{2-[4-({4-[6-(4-fluorophenyl)imidazo[2,1-b][1,3]oxazol-5-yl]pyrimidin-2-yl}amino)piperidin-1-yl]-2-oxoethyl}acetamide

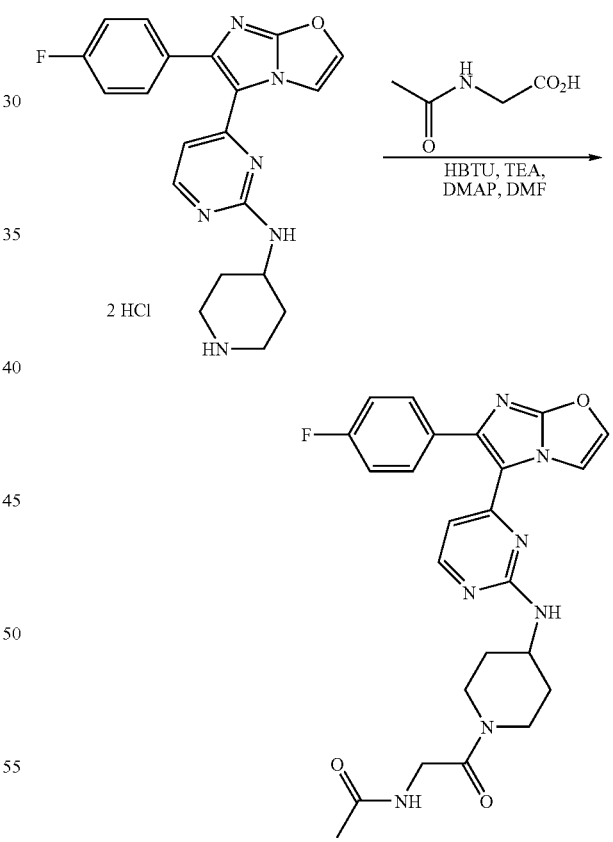

The 4-[6-(4-fluorophenyl)imidazo[2,1-b][1,3]oxazol-5-yl]-N-piperidin-4-ylpyrimidin-2-amine (bis HCl salt) (100 mg, 0.222 mmol) in dimethylformamide (4 ml) was treated with triethylamine (220 ul) and stirred until all solids dissolve. The mixture was treated sequentially with the acetamido glycine (26 mg), HBTU (84 mg) and DMAP (27 mg). The reaction mixture was stirred at room temperature for 15 hours. The mixture was partitioned into ethyl acetate (10 ml)

and water (10 ml). The phases were separated and the organic phase was washed with a saturated sodium carbonate solution (10 ml), water (10 ml) and a saturated sodium chloride solution (10 ml). The organic phase was dried over sodium sulfate and concentrated in vacuo. The crude product was purified by preparative chromatography plate (15% methanol/ethyl acetate), giving 78 mg of a pale yellow solid (74%). M.p.=235-237° C. 400 MHz $^1$H NMR (DMSO-$d_6$) δ: 8.73 (br. s, 1H), 8.18 (br. s, 1H), 8.10 (d, J=5.5 Hz, 1H), 7.98 (t, J=5.7 Hz, 1H), 7.66-7.6 (m, 2H), 7.38-7.28 (m, 3H), 6.36 (br. s, 1H), 4.26 (d, J=13.3 Hz, 1H), 4.05-3.87 (m, 3H), 3.82 (d, J=13.3 Hz, 1H), 3.15 (t, J=11.5 Hz, 1H), 2.83 (t, J=11.5 Hz, 1H), 2.0-1.9 (m, 2H), 1.87 (s, 3H), 1.5-1.2 (m, 2H). LCMS: 478 [M+H]. Calc. for $C_{24}H_{24}N_7O_3F.0.44$ water: C, 59.38; H, 5.17; N, 20.20. Found C, 59.38; H, 4.93; N, 20.47.

Example 6

Preparation of N-[1-(4-fluorobenzyl)piperidin-3-yl]-4-[6-(4-fluorophenyl)-imidazo[2,1-b][1,3]thiazol-5-yl]pyrimidin-2-amine

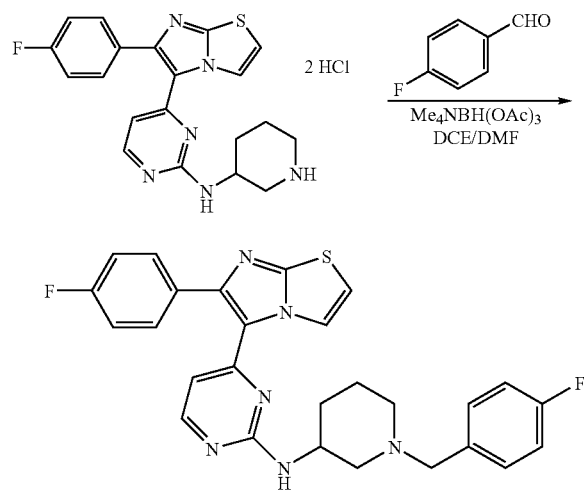

The racemic 4-[6-(4-fluorophenyl)imidazo[2,1-b][1,3]thiazol-5-yl]-N-[piperidin-3-yl]pyrimidin-2-amine hydrochloride (70 mg g, 0.15 mmol) was dissolved in a 80/20 mixture of DCE and DMF (1.2 ml) and treated with three equivalent of triethylamine (63 uL). The 4-fluorobenzaldehyde (19 mg, 0.15 mmol) was added, followed by a 0.2 M solution of Me$_4$NBH(OAc)$_3$ in 80/20 DCE/DMF (1.2 ml). The mixture was stirred at room temperature for 18 hours. The mixture was washed with a 1N sodium hydroxide solution (2 ml). Concentration in vacuo followed by purification on reverse phase HPLC provides the title compound as a pale yellow solid (42.4 mg, 56%). M.p.=131-133° C. 400 MHz $^1$H NMR (DMSO-$d_6$) δ: 8.73 (br. s, 1H), 8.06 (d, J=5.1 Hz, 1H), 7.64-7.58 (m, 2H), 7.44 (d, J=4.7 Hz, 1H), 7.35-7.31 (m, 2H), 7.30-7.23 (m, 2H), 7.07 (t, J=8.8 Hz, 2H), 7.00 (br. s, 1H), 6.29 (d, J=5.1 Hz, 1H), 4.00-3.90 (m, 1H), 3.49 (s, 2H), 2.96-2.90 (m, 1H), 2.69-2.62 (m, 1H), 2.08-1.94 (m, 2H), 1.93-1.85 (m, 1H), 1.76-1.67 (m, 1H), 1.61-1.48 (m, 1H), 1.42-1.30 (m, 1H). LCMS: 503 [M+H].

Example 7

Preparation of N~1~-(3-{5-[2-({(3R)-1-[(4-chlorophenyl)sulfonyl]piperidin-3-yl}amino)pyrimidin-4-yl]imidazo[2,1-b][1.3]thiazol-6-yl}phenyl)glycinamide 7a: Preparation of 4-[6-(3-aminophenyl)imidazo[2,1-b][1,3]thiazol-5-yl]-N-{(3R)-1-[(4-chlorophenyl)sulfonyl]piperidin-3-yl}pyrimidin-2-amine

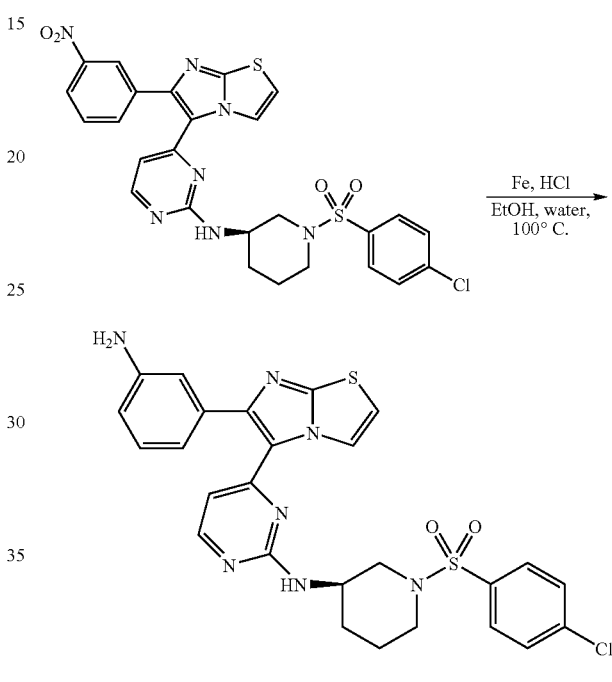

N-{(3R)-1-[(4-chlorophenyl)sulfonyl]piperidin-3-yl}-4-[6-(3-nitrophenyl)imidazo[2,1-b][1,3]thiazol-5-yl]pyrimidin-2-amine (1.05 g, 1.76 mmol) was dissolved in ethanol 95% (10 ml) and water (2.5 ml). The solution was treated with irn powder (1 g, 17.6 mmol) and concentrated HCl (200 uL). The reaction mixture was stirred at 100° C. for one hour. The mixture was cooled down and diluted with ethanol (100 ml). The heterogenous mixture was filtered over Celite and the volatiles were removed in vacuo. The residue was taken up in EtOAc (150 ml) and the organic phase was washed with a saturated aqueous NaHCO$_3$ solution (2×100 ml), water (100 ml) and a saturated aqueous NaCl solution (100 ml). After drying over sodium sulfate and concentration, the solid was triturated in ether, giving the title compound as a yellow powder, 0.835 g (84%). M.p.=226-228° C. 400 MHz $^1$H NMR (DMSO-$d_6$) δ: 8.73 (br. s, 1H), 8.10 (d, J=5.6 Hz, 1H), 7.77 (d, J=8.5 Hz, 2H), 7.67 (d, J=8.5 Hz, 2H), 7.36 (d, J=4.4 Hz, 1H), 7.09 (t, J=7.7 Hz, 1H), 7.02 (d, J=7.3 Hz, 1H), 6.81 (s, 1H), 6.69 (d, J=7.6 Hz, 1H), 6.65 (d, J=7.9 Hz, 1H), 6.49 (d, J=5.3 Hz, 1H), 5.01 (br. s, 2H), 4.02-3.88 (m, 1H), 3.73 (dd, J=11.1, 3.5 Hz, 1H), 3.47 (d, J=11.7 Hz, 1H), 2.60-2.46 (m, 1H), 2.39 (t, J=10.2 Hz, 1H), 1.98-1.80 (m, 2H), 1.68-1.51 (m, 1H), 1.47-1.32 (m, 1H). LCMS: 566 [M+H]. Calc. for $C_{26}H_{24}N_7O_2S_2Cl$: C, 55.16; H, 4.27; N, 17.32. Found C, 54.98; H, 3.85; N, 17.23.

7b: Preparation of tert-butyl{2-[(3-{5-[2-({(3R)-1-[(4-chlorophenyl)sulfonyl]piperidin-3-yl}amino)pyrimidin-4-yl]imidazo[2,1-b][1,3]thiazol-6-yl}phenyl)amino]-2-oxoethyl}carbamate

7c: Preparation of N-(3-{5-[2-({(3R)-1-[(4-chlorophenyl)sulfonyl]piperidin-3-yl}amino)-pyrimidin-4-yl]imidazo[2,1-b][1,3]thiazol-6-yl}phenyl)glycinamide hydrochloride

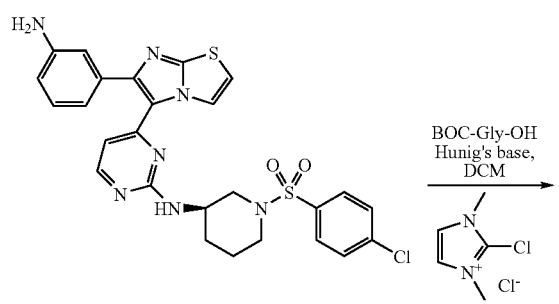

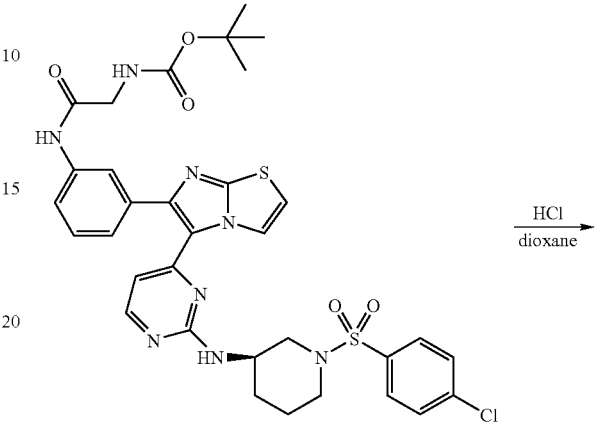

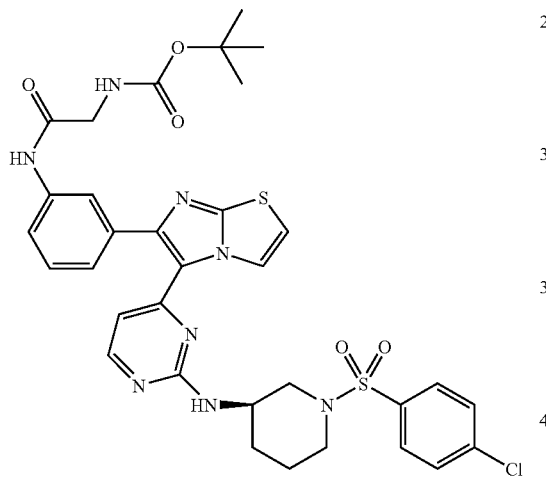

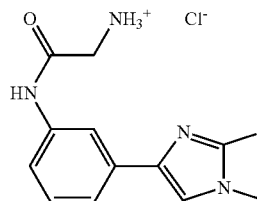

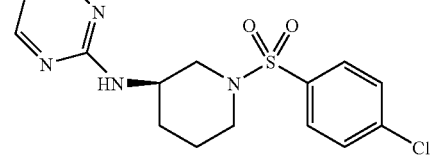

The 4-[6-(3-aminophenyl)imidazo[2,1-b][1,3]thiazol-5-yl]-N-{(3R)-1-[(4-chlorophenyl)-sulfonyl]piperidin-3-yl}pyrimidin-2-amine (0.1 g, 0.177 mmol) and N-(tert-butoxycarbonyl)glycine (34 mg, 0.194 mmol) were dissolved in DCM (5 ml) and treated with Hunig's base (92 uL, 0.53 mmol) and 2-chloro-1,3-dimethyl-1H-imidazol-3-ium chloride (33 mg, 0.194 mmol). The mixture was kept at room temperature for 90 minutes then was diluted with DCM (10 ml). The organic phase was washed with water (2×10 ml) and with an aqueous sodium chloride solution (10 ml). The organic phase was dried over sodium sulfate and concentrated in vacuo, giving a yellow oil. The product was purified by flash chromatography (gradient 70%-100% EtOAc/hexanes), affording the title compound as a pale yellow solid (71 mg). 400 MHz $^1$H NMR (DMSO-$d_6$) δ: 9.86 (s, 1H), 8.73 (br. s, 1H), 8.11 (d, J=5.5 Hz, 1H), 7.84 (s, 1H), 7.79-7.75 (m, 2H), 7.70-7.65 (m, 3H), 7.45-7.37 (m, 2H), 7.26 (d, J=7.4 Hz, 1H), 7.13 (d, J=8.2 Hz, 1H), 6.82 (br. s, 1H), 6.42 (d, J=6.9 Hz, 1H), 4.00-3.90 (m, 1H), 3.78-3.70 (m, 3H), 3.52-3.44 (m, 1H), 3.18 (s, 2H), 2.34 (t, J=10.2 Hz, 1H), 1.94-1.81 (m, 2H), 1.65-1.52 (m, 1H), 1.39 (s, 9H). LCMS: 723 [M+H].

The tert-butyl{2-[(3-{5-[2-({(3R)-1-[(4-chlorophenyl)sulfonyl]piperidin-3-yl}amino)-pyrimidin-4-yl]imidazo[2,1-b][1,3]thiazol-6-yl}phenyl)amino]-2-oxoethyl}carbamate (71 mg, 0.098 mmol) was dissolved in dioxane (3 ml) and treated with a 4N HCl solution in dioxane (1 ml). The mixture was stirred at room temperature for 3 hours. The volatiles were removed in vacuo and the residue was triturated in ether. Filtration afforded the title compound as a yellow solid (65 mg). M.p.=208-212° C. 400 MHz $^1$H NMR (DMSO-$d_6$) δ: 10.69 (s, 1H), 8.18 (br. s, 3H), 8.13 (d, J=5.9 Hz, 1H), 7.88 (t, J=1.6 Hz, 1H), 7.79-7.75 (m, 2H), 7.71-7.66 (m, 3H), 7.48-7.43 (m, 2H), 7.34 (d, J=7.8 Hz, 1H), 6.45 (d, J=5.9 Hz, 1H), 5.15 (br. s, 3H), 4.04-3.95 (m, 1H), 3.79 (d, J=5.5 Hz, 2H), 3.70 (dd, J=11.3, 4.3 Hz, 1H), 3.48-3.41 (m, 1H), 2.57-2.48 (m, 1H), 2.42 (t, J=10.6 Hz, 1H), 1.95-1.82 (m, 2H), 1.67-1.54 (m, 1H), 1.48-1.37 (m, 1H). LCMS: 623 [M+H]. Calc. for $C_{28}H_{27}N_8O_3S_2Cl.2.52HCl$: C, 47.03; H, 4.16; N, 15.67. Found C, 47.04; H, 3.97; N, 15.46.

Example 8

Preparation of N-(3-{5-[2-({(3R)-1-[(4-chlorophenyl)sulfonyl]piperidin-3-yl}amino)pyrimidin-4-yl]imidazo[2,1-b][1,3]thiazol-6-yl}phenyl)acetamide

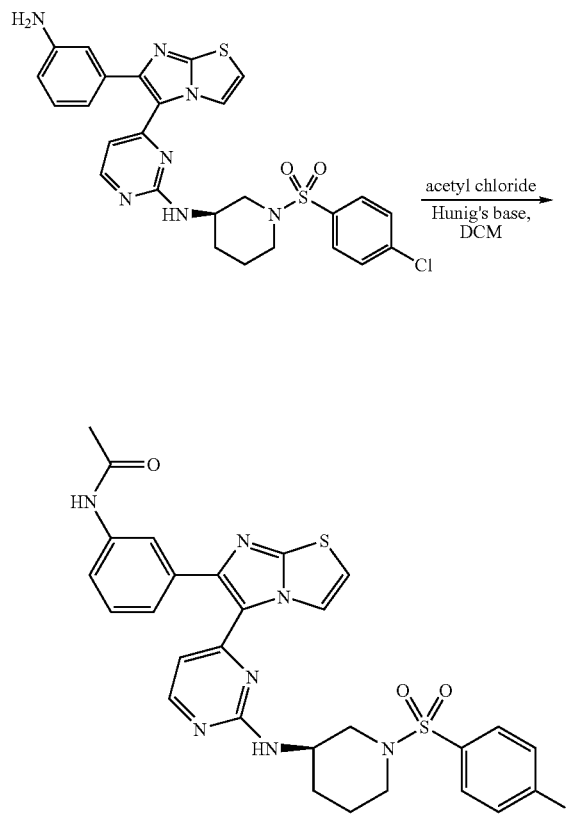

The 4-[6-(3-aminophenyl)imidazo[2,1-b][1,3]thiazol-5-yl]-N-{(3R)-1-[(4-chlorophenyl)-sulfonyl]piperidin-3-yl}pyrimidin-2-amine (0.1 g, 0.177 mmol) was dissolved in DCM (5 ml) and treated sequentially with Hunig's base (46 uL, 0.265 mmol) and acetyl chloride (15 uL, 0.212 mmol). The mixture was kept at room temperature for two hours then was diluted with DCM (10 ml). The organic phase was washed with water (2×10 ml) and with an aqueous sodium chloride solution (10 ml). The organic phase was dried over sodium sulfate and concentrated in vacuo, giving a yellow foam. The product was triturated in ether and filtered off, giving the title compound as a yellow solid (97 mg). M.p.=169-174° C. 400 MHz $^1$H NMR (DMSO-$d_6$) δ: 9.89 (s, 1H), 8.72 (br. s, 1H), 8.12 (d, J=5.1 Hz, 1H), 7.82 (s, 1H), 7.80-7.75 (m, 2H), 7.70-7.64 (m, 3H), 7.41 (d, J=4.3 Hz, 1H), 7.37 (t, J=7.8 Hz, 1H), 7.24 (d, J=7.8 Hz, 1H), 7.13 (d, J=7.4 Hz, 1H), 6.42 (d, J=5.5 Hz, 1H), 4.00-3.90 (m, 1H), 3.74 (d, J=8.6 Hz, 1H), 3.48 (d, J=11.7 Hz, 1H), 2.54-2.43 (m, 1H), 2.34 (t, J=10.2 Hz, 1H), 2.05 (s, 3H), 1.94-1.81 (m, 2H), 1.65-1.53 (m, 1H), 1.44-1.34 (m, 1H). LCMS: 608 [M+H]. Calc. for $C_{28}H_{26}N_7O_3S_2Cl$.0.38 water.0.41 dioxane: C, 54.68; H, 4.65; N, 15.06. Found C, 54.68; H, 4.32; N, 15.05.

Example 9

Preparation of (2R)-3-[(3R)-3-({4-[6-(3-hydroxyphenyl)imidazo[2,1-b][1,3]thiazol-5-yl]pyrimidin-2-yl}amino)piperidin-1-yl]propane-1,2-diol 9a: Preparation of N-((3R)-1-{[(4R)-2,2-dimethyl-1,3-dioxolan-4-yl]methyl}piperidin-3-yl)-4-[6-(3-methoxyphenyl)imidazo[2,1-b][1,3]thiazol-5-yl]pyrimidin-2-amine

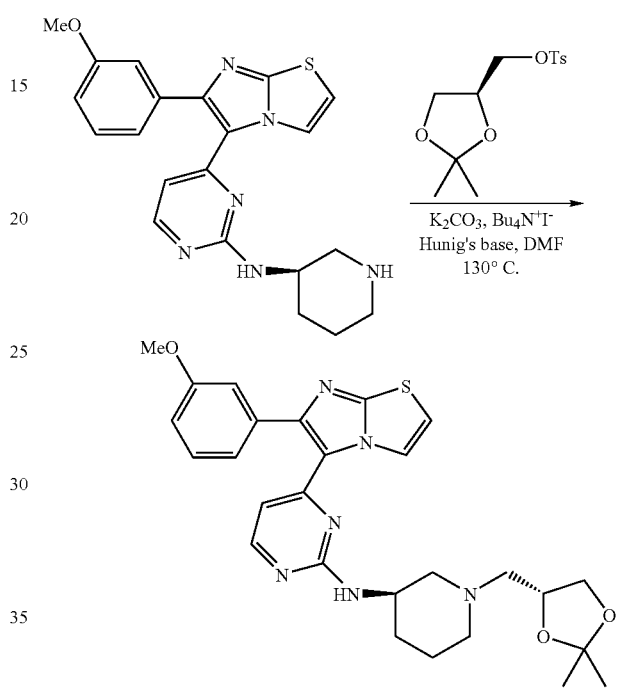

The 4-[6-(3-methoxyphenyl)imidazo[2,1-b][1,3]thiazol-5-yl]-N-[(3R)-piperidin-3-yl]-pyrimidin-2-amine hydrochloride (310 mg, 0.7 mmol) was dissolved in DMF (15 ml) and was treated successively with Hunig's base (240 uL, 1.4 mmol), potassium carbonate (192 mg, 0.7 mmol) and terabutylammonium iodide (26 mg, 0.07 mmol). The mixture was heated to 130° C. and the [(4S)-2,2-dimethyl-1,3-dioxolan-4-yl]methyl 4-methyl-benzenesulfonate (0.2 g, 0.7 mmol) was added in three portions. The mixture was kept at 130° C. for 5 hours, at which point no more starting material appears by HPLC. The volatiles were removed in vacuo and the residue was taken up in ether (100 ml). The organic phase was washed with water (2×20 ml) and with an aqueous sodium chloride solution (20 ml). The organic phase was dried over sodium sulfate and concentrated in vacuo, giving a yellow oil. The product was purified by flash chromatography (5:4:0.5 hexanes/EtOAc, MeOH), affording the title compound as an off-white solid (231 mg, 64%). M.p.=73-75° C. 400 MHz $^1$H NMR (DMSO-$d_6$) δ: 8.71 (br. s, 1H), 8.07 (d, J=5.1 Hz, 1H), 7.42 (d, J=4.4 Hz, 1H), 7.36 (t, J=7.9 Hz, 1H), 7.19-7.11 (m, 2H), 7.04-6.92 (m, 2H), 6.36 (d, J=5.1 Hz, 1H), 4.19 (quintet, J=6.2 Hz, 1H), 3.99 (dd, J=8.1, 6.2 Hz, 1H), 3.96-3.87 (m, 1H), 3.77 (s, 3H), 3.52 (t, J=7.5 Hz, 1H), 3.15 (s, 2H), 3.05 (d, J=9.9 Hz, 1H), 2.69 (d, J=10.3 Hz, 1H), 2.15 (t, J=9.4 Hz, 1H), 2.04 (t, J=9.5 Hz, 1H), 1.90-1.82 (m, 1H), 1.75-1.65 (m, 1H), 1.59-1.48 (m, 1H), 1.40-1.25 (m, 1H), 1.29 (s, 3H), 1.21 (s, 3H). LCMS: 521 [M+H].

9b: Preparation of (2R)-3-[(3R)-3-({4-[6-(3-methoxyphenyl)imidazo[2,1-b][1,3]thiazol-5-yl]pyrimidin-2-yl}amino)piperidin-1-yl]propane-1,2-diol

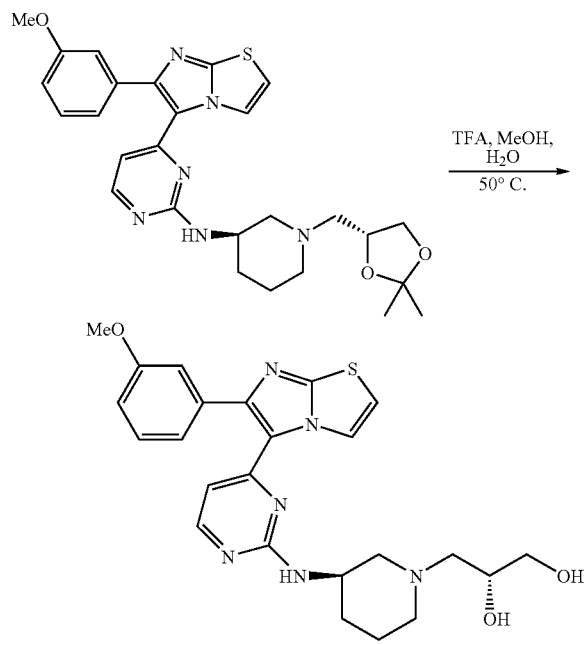

The N-((3R)-1-{[(4R)-2,2-dimethyl-1,3-dioxolan-4-yl]methyl}piperidin-3-yl)-4-[6-(3-methoxyphenyl)imidazo[2,1-b][1,3]thiazol-5-yl]pyrimidin-2-amine (150 mg, 0.288 mmol) was dissolved in MeOH (10 ml) and water (1.2 ml) and treated with trifluoroacetic acid (90 uL). The mixture was stirred at 50° C. overnight (18 hours). The mixture was neutralized with potassium carbonate (160 mg) and the volatiles were removed in vacuo. The product was purified by flash chromatography (6:1 EtOAc/MeOH), affording the title compound as an off-white solid (120 mg, 87%). M.p.=106-108° C. 400 MHz $^1$H NMR (DMSO-$d_6$) δ: 8.72 (br. s, 1H), 8.08 (d, J=5.5 Hz, 1H), 7.44 (d, J=4.4 Hz, 1H), 7.36 (t, J=7.9 Hz, 1H), 7.16-7.10 (m, 2H), 7.06-6.97 (m, 2H), 6.36 (d, J=5.5 Hz, 1H), 4.40-4.15 (m, 1H), 4.02-3.90 (m, 1H), 3.77 (s, 3H), 3.68-3.56 (m, 2H), 3.40-3.28 (m, 2H), 3.05-2.95 (m, 1H), 2.80-2.64 (m, 1H), 2.42 (br. s, 1H), 2.32 (br. s, 1H), 2.14 (br. s, 1H), 1.90-1.80 (m, 1H), 1.75-1.65 (m, 1H), 1.60-1.45 (m, 1H), 1.45-1.30 (m, 1H). LCMS: 481 [M+H].

9c: Preparation of (2R)-3-[(3R)-3-({4-[6-(3-hydroxyphenyl)imidazo[2,1-b][1,3]thiazol-5-yl]pyrimidin-2-yl}amino)piperidin-1-yl]propane-1,2-diol

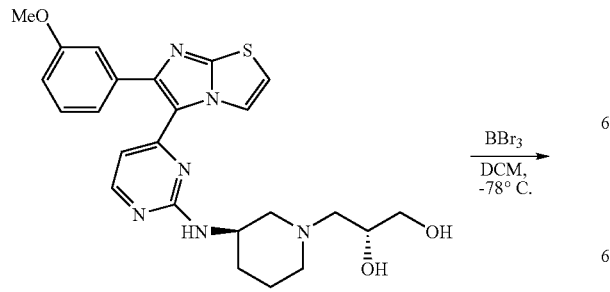

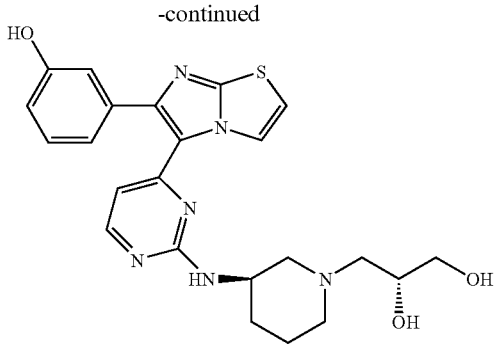

The (2R)-3-[(3R)-3-({4-[6-(3-methoxyphenyl)imidazo[2,1-b][1,3]thiazol-5-yl]pyrimidin-2-yl}amino)piperidin-1-yl]propane-1,2-diol (150 mg, 0.312 mmol) in methylene chloride (10 ml) was cooled to −78° C. and slowly treated with 1 molar solution of boron tribromide in methylene chloride (2.5 ml). The reaction mixture was kept at −78° C. for one hour then was allowed to warm to room temperature for 18 hours. The mixture was quenched by the addition of methanol (5 ml) at −78° C. and was stirred at room temperature for an additional hour. The mixture was concentrated in vacuo and the crude product was purified by flash chromatography (6:1 EtOAc/MeOH+drops of aq. NH$_4$OH), affording the title compound as a pale yellow solid (71 mg, 49%). M.p.=185-187° C. 400 MHz $^1$H NMR (DMSO-$d_6$) δ: 9.39 (s, 1H), 8.72 (br. s, 1H), 8.12 (d, J=5.1 Hz, 1H), 7.43 (d, J=4.4 Hz, 1H), 7.32 (br. s, 1H), 7.26-7.20 (m, 1H), 7.00-6.95 (m, 2H), 6.84-6.81 (m, 1H), 6.45 (d, J=5.5 Hz, 1H), 5.28-5.03 (br. s, 1H), 4.90-4.65 (br. s, 1H), 4.34-4.22 (m, 1H), 3.98-3.84 (m, 1H), 3.47-3.38 (m, 1H), 3.35-3.25 (m, 1H), 3.15-2.65 (m, 4H), 2.10-1.88 (m, 2H), 1.87-1.72 (m, 2H), 1.65-1.40 (m, 2H). LCMS: 467 [M+H].

In addition to those examples of compounds prepared by the methods of this invention set forth above, the following non-limiting list of compounds prepared by the methods of this invention is set forth in Table I.

Example 10

Preparation of 4-[6-(4-fluorophenyl)imidazo[2,1-b][1,3]oxazol-5-yl]-N-[(3R)-1-(morpholin-4-ylcarbonyl)piperidin-3-yl]pyrimidin-2-amine

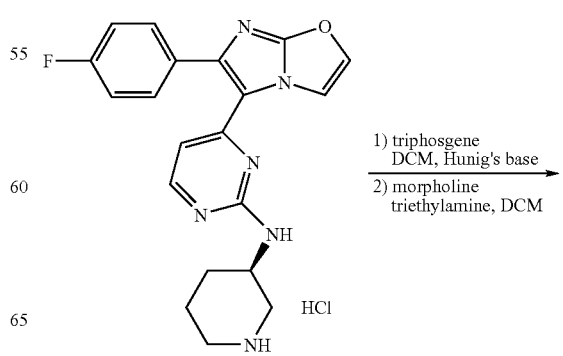

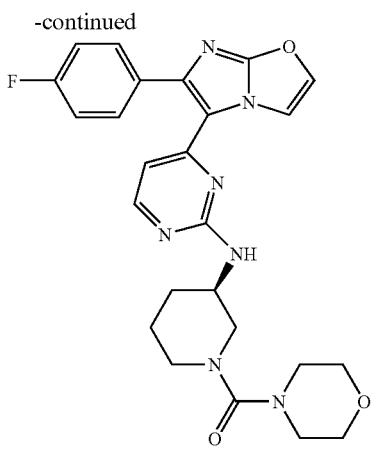

To a solution of 4-[6-(4-fluorophenyl)imidazo[2,1-b][1,3]oxazol-5-yl]-N-[(3R)-piperidin-3-yl]pyrimidin-2-amine (200 mg, 0.45 mmol) and Hunig's base (145 μL, 0.90 mmol) in 10 mL DCM was added a solution of triphosgene (660 mg; 2.25 mmol) in 10 mL DCM dropwise over 10 min with stirring. The mixture was allowed to stir at ambient temperature for 1.5 hr. The reaction mixture was then concentrated under reduced pressure. The residue was diluted with 20 mL ether and concentrated under reduced pressure yielding (3R)-3-({4-[6-(4-fluorophenyl)imidazo[2,1-b][1,3]oxazol-5-yl]pyrimidin-2-yl}amino)piperidine-1-carbonyl chloride as an off-white solid (190 mg). The solid was diluted in 10 mL DCM. To the resulting solution was added morpholine (60 μL, 0.67 mmol) and triethylamine (70 μL, 0.50 mmol). The mixture was allowed to stir at ambient temperature for 20 hr. The reaction mixture was then concentrated under reduced pressure and the residue purified by flash chromatography on silica gel (1:4, ethyl acetate:hexanes) to yield 4-[6-(4-fluorophenyl)imidazo[2,1-b][1,3]oxazol-5-yl]-N-[(3R)-1-(morpholin-4-ylcarbonyl)piperidin-3-yl]pyrimidin-2-amine as an off-white solid (50.2 mg, 23%). 400 MHz $^1$H NMR (DMSO-$d_6$) δ: 8.75 (s, 1H), 8.20 (s, 1H), 8.11 (d, J=5.2 Hz, 1H), 7.62-7.66 (m, 2H), 7.30-7.34 (m, 2H), 6.37 (s, 1H), 3.76 (m, 2H), 3.53 (m, 4H), 3.15 (m, 2H), 3.09 (m, 2H), 2.75 (m, 2H), 2.62 (m, 1H), 1.99 (s, 1H), 1.78 (br.s, 1H), 1.50-1.54 (m, 2H). LCMS: 492 [M+H].

Example 11

Preparation of 5-{5-[2-({(3R)-1-[(4-chlorophenyl)sulfonyl]piperidin-3-yl}amino)pyrimidin-4-yl]imidazo[2,1-b][1,3]thiazol-6-yl}-2-fluorophenol 11a Preparation of 2-bromo-1-(4-fluoro-3-methoxy-phenyl)-ethanone

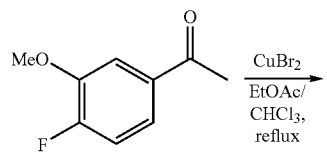

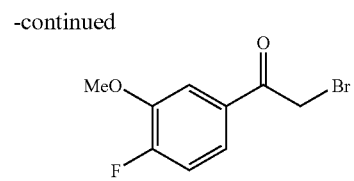

To a mixture of copper (II) bromide (5.31 g, 23.8 mmol) in ethyl acetate (20 ml), heated to 60° C. was added in a dropwise fashion, a solution of 3-fluoro-4-methoxyacetophenone (2.0 g, 11.9 mmol) in chloroform (20 ml). The reaction mixture was kept at reflux for 4.5 hours. The mixture was allowed to cool to room temperature and filtered. The volatiles were removed in vacuo, providing a brown oil which was purified by flash chromatography (gradient 5% to 10% ethyl acetate in hexanes). The title compound was obtained as an off-white solid (2.4 g, 82%). 400 MHz $^1$H NMR (DMSO-$d_6$) δ 7.72-7.66 (m, 2H), 7.42 (dd, J=11.0, 8.2 Hz, 1H), 4.97 (s, 2H), 3.93 (s, 3H). LCMS: 248 [M+H].

11b Preparation of 6-(4-fluoro-3-methoxy-phenyl)-imidazo[2,1-b]thiazole.

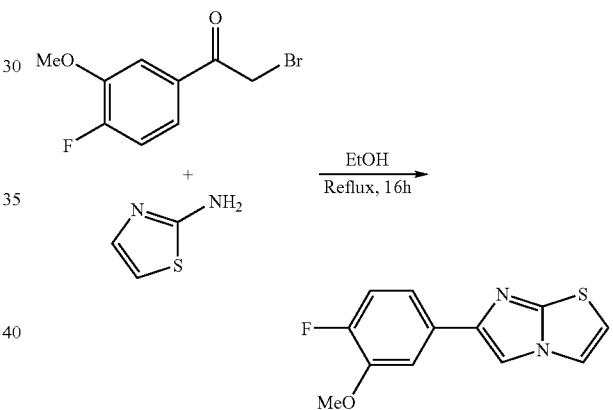

To a mixture of 2-aminothiazole (0.976 g, 9.74 mmol) and 2-bromo-1-(4-fluoro-3-methoxy-phenyl)-ethanone (2.4 g, 9.74 mmol) was added absolute ethanol (100 ml). The reaction was allowed to reflux with vigorous stirring for 18 hours (checked by HPLC). The reaction mixture was reduced to half its original volume in vacuo. The remaining liquid was poured onto ice and the solution made basic by the addition of ammonium hydroxide solution (30%), until pH is 8. The mixture was extracted with ethyl acetate (2×100 ml). The combined extracts were washed with water (100 ml) and saturated aqueous sodium chloride solution (100 ml). The organic phase was dried with sodium sulfate, filtered and concentrated in vacuo, to give an orange solid. Purification by flash chromatography (gradient 25%-50% ethyl actetate in hexanes) afforded the title product as a pale yellow solid (1.59 g, 66%). 400 MHz $^1$H NMR (DMSO-$d_6$) δ 8.26 (s, 1H), 7.95 (d, J=2.3 Hz, 1H), 7.61 (dd, J=8.6, 2.0 Hz, 1H), 7.39 (ddd, J=8.2, 4.3, 2.0 Hz, 1H); 7.28 (d, J=4.7 Hz, 1H), 7.22 (dd, J=11.3, 8.2 Hz, 1H), 3.91 (s, 3H). LCMS: 249 [M+H].

11c: Preparation of 1-[6-(4-fluoro-3-methoxyphenyl)imidazo[2,1-b][1,3]thiazol-5-yl]ethanone

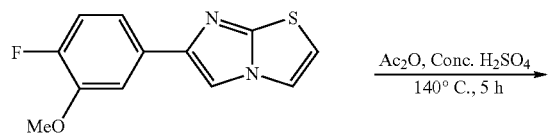

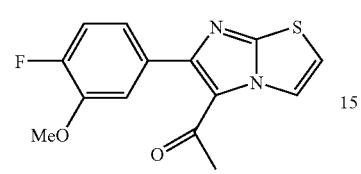

To a mixture of 6-(4-fluoro-3-methoxyphenyl)-imidazo[2,1-b]thiazole (1.0 g, 4.03 mmol) and acetic anhydride (25 ml), heated to 140° C., was added 43 µl of concentrated sulfuric acid. The reaction mixture was heated at 140° C. for 1 hour. The reaction was monitored by HPLC. After one hour, only 10% product was observed. Another 43 µl of concentrated sulfuric acid was added and the mixture was kept at 140° C. for 4 hours. The reaction mixture was then poured onto 50 ml of ice, and diluted with 50 ml of water and the resulting mixture was extracted two times with 100 ml each of ethyl acetate. The combined extracts were washed with two portions of 50 ml of water and two portions of 50 ml of saturated aqueous sodium chloride solution. The organic phase was dried with sodium sulfate, filtered and concentrated in vacuo, to give a brown solid. The product, -[6-(4-fluoro-3-methoxyphenyl)imidazo[2,1-b][1,3]thiazol-5-yl]ethanone, was purified by flash chromatography (gradient 25%-50% ethyl acetate in hexanes) and obtained as a pale yellow solid (1.12 g, 96%). 400 MHz $^1$H NMR (DMSO-$d_6$) δ 8.44 (d, J=4.3 Hz, 1H), 7.56 (d, J=4.3 Hz, 1H), 7.43 (dd, J=8.2, 2.0 Hz, 1H), 7.34 (dd, J=11.7, 8.6 Hz, 1H), 7.21 (ddd, J=8.2, 4.3, 2.0 Hz, 1H), 3.89 (s, 3H), 2.14 (s, 3H). LCMS: 291 [M+H].

11d: Preparation of 3-(dimethylamino)-1-[6-(4-fluoro-3-methoxyphenyl)imidazo[2,1-b][1,3]thiazol-5-yl]prop-2-en-1-one

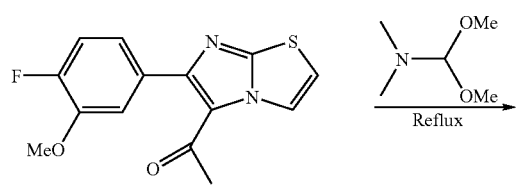

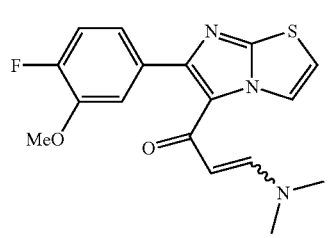

A 100 ml round bottom flask was charged with the 1-[6-(4-fluoro-3-methoxyphenyl)imidazo[2,1-b][1,3]thiazol-5-yl]ethanone (1.12 g, 3.86 mmol) and dimethylformamide dimethylacetal (25 ml). The mixture was refluxed for 20 hours and then cooled to room temperature. The mixture was concentrated in vacuo and the residue was purified by flash chromatography (ethyl acetate), giving a pale yellow solid (1.138 g, 85%). 400 MHz $^1$H NMR (DMSO-$d_6$) δ: 8.39 (d, J=4.7 Hz, 1H), 7.62 (d, J=12.5 Hz, 1H), 7.45-7.40 (m, 2H), 7.31 (dd, J=11.3, 8.2 Hz, 1H), 7.20 (ddd, J=8.2, 4.3, 2.0 Hz, 1H), 5.10 (d, J=12.5 Hz, 1H), 3.87 (s, 3H), 3.06 (br. s, 3H), 2.49 (br. s, 3H). LCMS: 346 [M+H].

11e: Preparation of tert-butyl (3R)-3-({4-[6-(4-fluoro-3-methoxyphenyl)imidazo[2,1-b][1,3]thiazol-5-yl]pyrimidin-2-yl}amino)piperidine-1-carboxylate

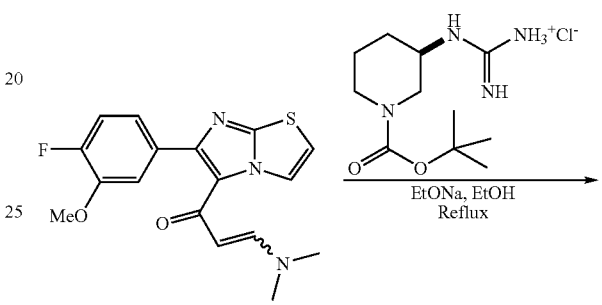

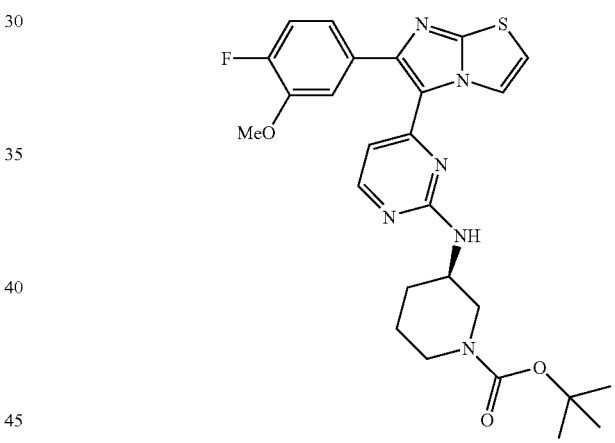

A mixture of 3-(dimethylamino)-1-[6-(4-fluoro-3-methoxyphenyl)imidazo[2,1-b][1,3]thiazol-5-yl]prop-2-en-1-one (0.6 g, 1.74 mmol) and tert-butyl (3R)-3-{[(Z)-amino (imino) methyl]amino}piperidine-1-carboxylate hydrochloride (0.726 g, 2.61 mmol) was diluted with 13 ml of absolute ethanol and treated with 1.35 eq. of a 21% w/w solution of sodium ethoxide in ethanol (875 µl) to form a reaction mixture. The reaction mixture was heated to reflux for 24 hours. HPLC revealed remaining starting enaminone. More tert-butyl (3R)-3-{[(Z)-amino(imino)methyl]amino}piperidine-1-carboxylate hydrochloride (0.243 g, 0.87 mmol) was added followed by a 21% w/w solution of sodium ethoxide in ethanol (270 µl). The mixture was kept at reflux for an additional 15 hours. Volatiles were removed in vacuo and the residue was taken up in 50 ml of ethyl acetate and 50 ml of water. The phases were separated and the aqueous phase was extracted with 50 ml of ethyl acetate. The combined organic extracts were washed with 100 ml of water, and then with a saturated sodium chloride solution (100 ml). The organic phase was dried with sodium sulfate, filtered and concentrated in vacuo, to give a brown oil. The product was purified by flash chromatography on silica gel (gradient 50% to 75% ethyl acetate in hexanes) to yield 0.785 g of a pale yellow solid (86%). 400 MHz $^1$H NMR (DMSO-$d_6$ at 60° C.) δ: 8.72 (br. s, 1H), 8.13 (d, J=5.5 Hz, 1H), 7.41 (d, J=4.7 Hz, 1H), 7.35 (dd, J=8.6, 2.0 Hz, 1H), 7.26 (dd, J=11.7, 8.6 Hz, 1H), 7.18-7.08 (m, 2H), 6.41 (d, J=5.5 Hz, 1H), 4.00-3.90 (m, 1H), 3.84 (s, 3H), 3.85-3.75 (m, 1H), 3.72-3.63 (m, 1H), 3.00-2.88 (m, 2H), 2.04-1.94 (m, 1H), 1.82-1.73 (m, 1H), 1.62-1.50 (m, 1H), 1.50-1.38 (m, 1H), 1.34 (s, 9H). LCMS: 525 [M+H].

11f: Preparation of 4-[6-(4-fluoro-3-methoxyphenyl)imidazo[2,1-b][1,3]thiazol-5-yl]-N-[(3R)-piperidin-3-yl]pyrimidin-2-amine hydrochloride

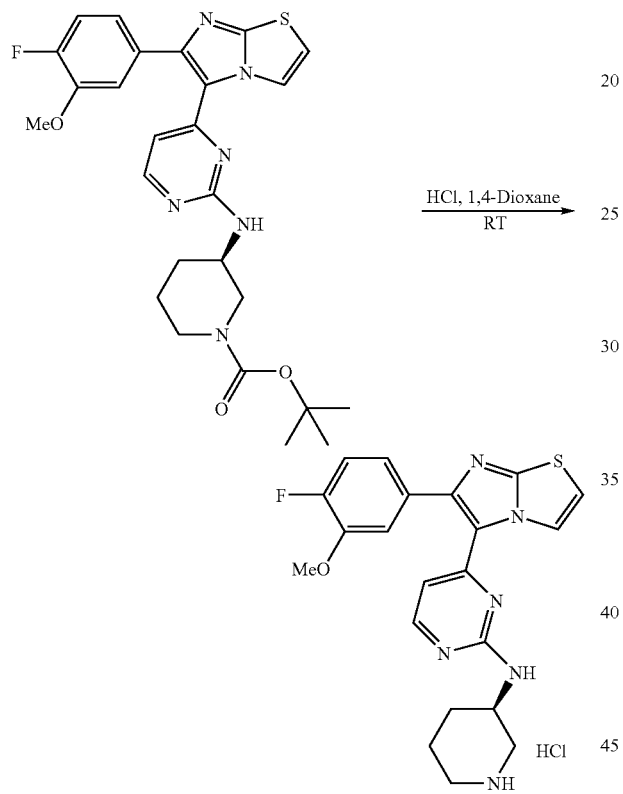

The tert-butyl (3R)-3-({4-[6-(4-fluoro-3-methoxyphenyl) imidazo[2,1-b][1,3]thiazol-5-yl]pyrimidin-2-yl}amino)piperidine-1-carboxylate (0.785 g, 1.50 mmol) was dissolved in 15 ml of dioxane and treated with 7.5 ml of anhydrous 4N HCl in dioxane at room temperature. The reaction mixture was stirred at room temperature for two hours. The mixture was then diluted with 25 ml of ether and stirred until product separated as a solid. Solid product was filtered and washed with ether. The solid was dissolved in MeOH (20 ml) and concentrated to dryness twice. The product was dried at high vacuum to yield 0.709 g of yellow solid (bis HCl salt) (95%). 400 MHz $^1$H NMR (DMSO-$d_6$ at 60° C.) δ: 11.65 (br. s, 2H), 9.60 (br. s, 1H), 8.90 (br. s, 1H), 8.14 (d, J=6.3 Hz, 1H), 7.61 (m, 1H), 7.40 (dd, J=8.6, 2.0 Hz, 1H), 7.33 (dd, J=11.7, 8.6 Hz, 1H), 7.20 (ddd, J=8.2, 4.3, 2.0 Hz, 1H), 6.55 (d, J=6.3 Hz, 1H), 4.50-4.40 (m, 1H), 3.86 (s, 3H), 3.48-3.38 (m, 1H), 3.22-3.10 (m, 1H), 3.06-2.88 (m, 2H), 2.12-2.02 (m, 1H), 2.00-1.84 (m, 2H), 1.78-1.64 (m, 1H). LCMS: 425 [M+H].

11g: Preparation of N-{(3R)-1-[(4-chlorophenyl)sulfonyl]piperidin-3-yl}-4-[6-(4-fluoro-3-methoxyphenyl)imidazo[2,1-b][1,3]thiazol-5-yl]pyrimidin-2-amine

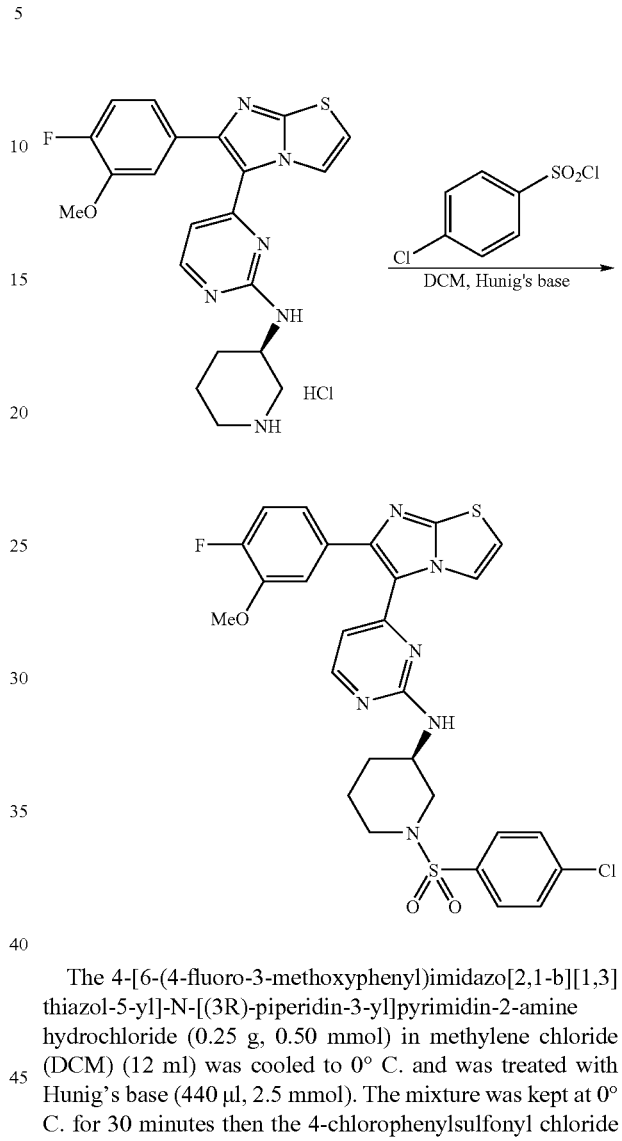

The 4-[6-(4-fluoro-3-methoxyphenyl)imidazo[2,1-b][1,3] thiazol-5-yl]-N-[(3R)-piperidin-3-yl]pyrimidin-2-amine hydrochloride (0.25 g, 0.50 mmol) in methylene chloride (DCM) (12 ml) was cooled to 0° C. and was treated with Hunig's base (440 μl, 2.5 mmol). The mixture was kept at 0° C. for 30 minutes then the 4-chlorophenylsulfonyl chloride (0.128 g, 0.60 mmol) was added. The reaction mixture was stirred at room temperature for one hour. The mixture was diluted with methylene chloride (10 ml) and was washed water (2×10 ml) and a saturated aqueous sodium chloride solution (10 ml). The organic phase was dried over sodium sulfate and concentrated in vacuo. The crude product was purified by flash chromatography using a gradient (ethyl acetate/hexanes, 50-75%), affording 0.281 g (94%) of the title compound as a pale yellow solid. M.p.: 142-143° C. 400 MHz $^1$H NMR (DMSO-$d_6$ at 60° C.) δ: 8.71 (br. s, 1H), 8.15 (d, J=5.5 Hz, 1H), 7.80-7.74 (m, 2H), 7.70-7.64 (m, 2H), 7.42 (d, J=4.5 Hz, 1H), 7.36 (dd, J=8.6, 2.3 Hz, 1H), 7.27 (dd, J=11.3, 8.2 Hz, 1H), 7.19-7.12 (m, 2H), 6.43 (d, J=5.5 Hz, 1H), 4.00-3.90 (m, 1H), 3.84 (s, 3H), 3.77-3.70 (m, 1H), 3.52-3.44 (m, 1H), 2.56-2.42 (m, 1H), 2.34 (t, J=10.0 Hz, 1H), 1.95-1.80 (m, 2H), 1.66-1.52 (m, 1H), 1.45-1.33 (m, 1H). LCMS: 599 [M+H]. Calc. for $C_{27}H_{24}N_6O_3S_2FCl.0.16$ water.0.74 diethyl ether: C, 53.94; H, 4.57; N, 12.60. Found C, 53.94; H, 4.19; N, 12.59.

11h: Preparation of 3-{5-[2-({(3R)-1-[(4-chlorophenyl)sulfonyl]piperidin-3-yl}amino)pyrimidin-4-yl]imidazo[2,1-b][1,3]thiazol-6-yl}-2-fluorophenol

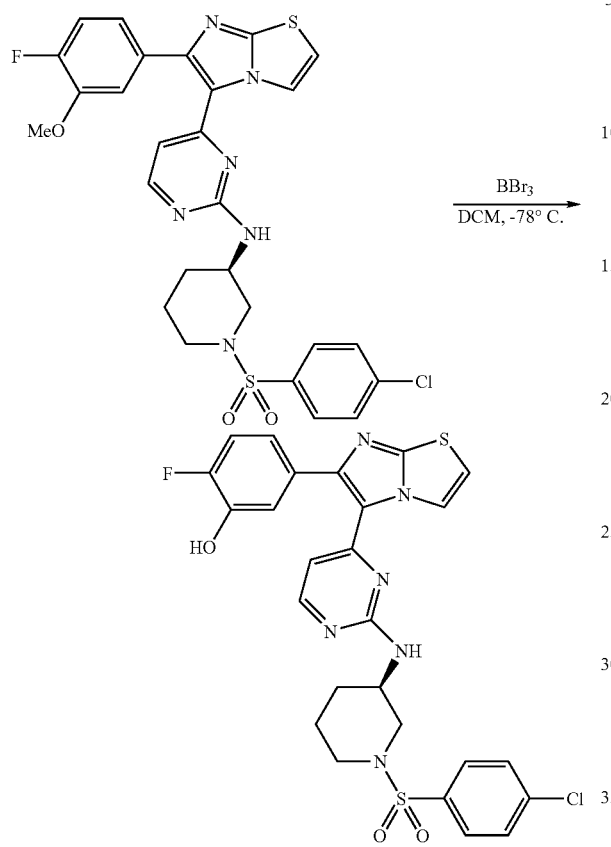

The N-{(3R)-1-[(4-chlorophenyl)sulfonyl]piperidin-3-yl}-4-[6-(4-fluoro-3-methoxy-phenyl)imidazo[2,1-b][1,3]thiazol-5-yl]pyrimidin-2-amine (0.251 g, 0.42 mmol) in methylene chloride (8 ml) was cooled to −78° C. and slowly treated with 1 molar solution of boron tribromide in methylene chloride (3.4 ml). The reaction mixture was kept at −78° C. for one hour then was allowed to warm to room temperature for two hours. The mixture was quenched by the addition of methanol (900 µl) at −78° C. and was stirred at room temperature for an additional hour. The mixture was diluted with methylene chloride (100 ml) and washed with three portions of 25 ml of saturated sodium bicarbonate solution, two portions of 25 ml of water and two portions of 25 ml of saturated sodium chloride solution. The organic phase was dried over sodium sulfate and concentrated in vacuo, giving a yellow solid. The crude product was purified by flash chromatography using a gradient (ethyl acetate/hexanes, 50-75%), affording 0.063 g of the title compound as a pale yellow solid. M.p.=172-175° C. 400 MHz $^1$H NMR (DMSO-$d_6$ at 60° C.) δ: 9.84 (s, 1H), 8.70 (br. s, 1H), 8.15 (d, J=5.5 Hz, 1H), 7.80-7.74 (m, 2H), 7.70-7.64 (m, 2H), 7.40 (d, J=4.3 Hz, 1H), 7.19 (dd, J=13.3, 8.6 Hz, 1H), 7.18 (d, J=8.2 Hz, 1H), 7.13 (br. d, J=7.8 Hz, 1H), 6.99 (ddd, J=8.2, 4.3, 2.0 Hz, 1H), 6.42 (d, J=5.1 Hz, 1H), 4.00-3.90 (m, 1H), 3.76-3.69 (m, 1H), 3.51-3.43 (m, 1H), 2.58-2.42 (m, 1H), 2.35 (t, J=10.6 Hz, 1H), 1.94-1.80 (m, 2H), 1.66-1.50 (m, 1H), 1.45-1.32 (m, 1H). LCMS: 585 [M+H]. Calc. for $C_{26}H_{22}N_6O_3S_2FCl$·0.89 diethyl ether: C, 53.51; H, 4.42; N, 12.67. Found C, 53.76; H, 12.66.

Example 12

Preparation of 5-[5-(2-{[1-(cyclopropylsulfonyl)piperidin-4-yl]amino}pyrimidin-4-yl)imidazo[2,1-b][1,3]thiazol-6-yl]-2-fluorophenol 12a: Preparation of tert-butyl 4-({4-[6-(4-fluoro-3-methoxyphenyl)imidazo[2,1-b][1,3]thiazol-5-yl]pyrimidin-2-yl}amino)piperidine-1-carboxylate

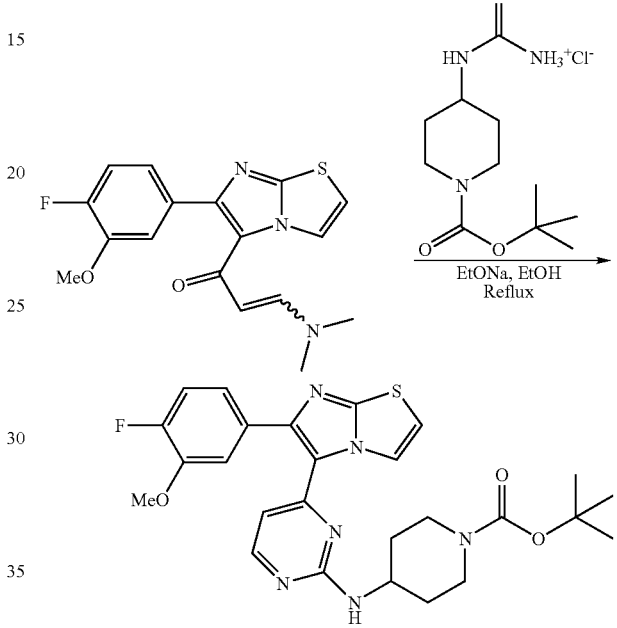

A mixture of 3-(dimethylamino)-1-[6-(4-fluoro-3-methoxyphenyl)imidazo[2,1-b][1,3]thiazol-5-yl]prop-2-en-1-one (0.537 g, 1.55 mmol) and tert-butyl 4-{[(Z)-amino(imino)methyl]amino}piperidine-1-carboxylate hydrochloride (0.650 g, 2.33 mmol) was diluted with 13 ml of absolute ethanol and treated with 1.35 eq. of a 21% w/w solution of sodium ethoxide in ethanol (780 µl) to form a reaction mixture. The reaction mixture was heated to reflux for 24 hours. Volatiles were removed in vacuo and the residue was taken up in 50 ml of ethyl acetate and 50 ml of water. The phases were separated and the aqueous phase was extracted with 50 ml of ethyl acetate. The combined organic extracts were washed with 100 ml of water, and then with a saturated sodium chloride solution (100 ml). The organic phase was dried with sodium sulfate, filtered and concentrated in vacuo, to give a brown oil. The product was purified by flash chromatography on silica gel (gradient 50% to 75% ethyl acetate in hexanes) to yield 0.713 g of a pale yellow solid (88%). 400 MHz $^1$H NMR (DMSO-$d_6$ at 60° C.) δ: 8.71 (br. s, 1H), 8.11 (d, J=5.5 Hz, 1H), 7.45 (d, J=4.3 Hz, 1H), 7.35 (dd, J=8.2, 2.0 Hz, 1H), 7.26 (dd, J=11.3, 8.2 Hz, 1H), 7.19-7.12 (m, 2H), 6.39 (d, J=5.1 Hz, 1H), 3.98-3.87 (m, 3H), 3.83 (s, 3H), 2.91 (t, J=11.5 Hz, 2H), 1.94-1.87 (m, 2H), 1.47-1.35 (m, 2H), 1.42 (s, 9H). LCMS: 525 [M+H].

12b: Preparation of 4-[6-(4-fluoro-3-methoxyphenyl)imidazo[2,1-b][1,3]thiazol-5-yl]-N-[piperidin-4-yl]pyrimidin-2-amine hydrochloride

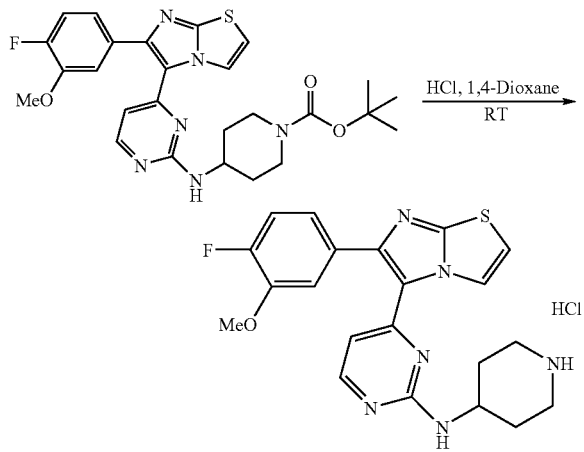

The tert-butyl 4-({4-[6-(4-fluoro-3-methoxyphenyl)imidazo[2,1-b][1,3]thiazol-5-yl]pyrimidin-2-yl}amino)piperidine-1-carboxylate (0.713 g, 1.36 mmol) was dissolved in 15 ml of dioxane and treated with 7.5 ml of anhydrous 4N HCl in dioxane at room temperature (RT). The reaction mixture was stirred at room temperature for two hours. The mixture was then diluted with 25 ml of ether and stirred until product separated as a solid. Solid product was filtered and washed with ether. The solid was dissolved in MeOH (20 ml) and concentrated to dryness twice. The product was dried at high vacuum to yield 0.652g of yellow solid (bis HCl salt) (96%). 400 MHz $^1$H NMR (DMSO-$d_6$ at 60° C.) δ: 9.32 (br. s, 1H), 8.10 (d, J=4.7 Hz, 1H), 7.61 (d, J=4.3 Hz, 1H), 7.39 (dd, J=8.2, 2.0 Hz, 1H), 7.33 (dd, J=11.3, 8.2 Hz, 1H), 7.19 (ddd, J=8.2, 4.3, 2.0 Hz, 1H), 6.56 (d, J=6.7 Hz, 1H), 4.30-4.20 (m, 1H), 3.86 (s, 3H), 3.40-3.32 (m, 2H), 3.12-2.96 (m, 2H), 2.22-2.12 (m, 2H), 1.99-1.86(m, 2H). LCMS: 425 [M+H].

12c: Preparation of N-[1-(cyclopropylsulfonyl)piperidin-4-yl]-4-[6-(4-fluoro-3-methoxyphenyl)imidazo[2,1-b][1,3]thiazol-5-yl]pyrimidin-2-amine

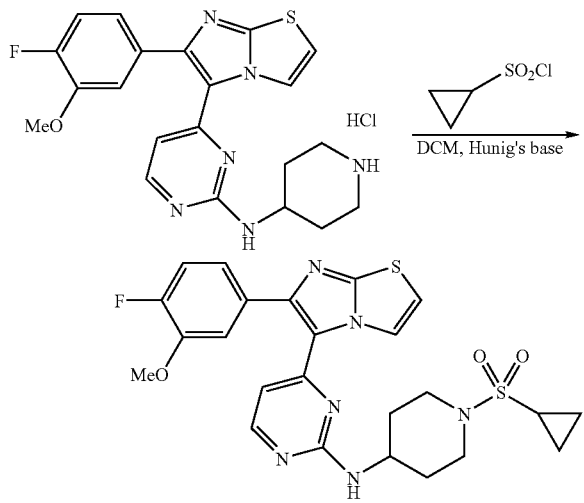

The 4-[6-(4-fluoro-3-methoxyphenyl)imidazo[2,1-b][1,3]thiazol-5-yl]-N-[piperidin-4-yl]pyrimidin-2-amine hydrochloride (0.25 g, 0.50 mmol) in methylene chloride (DCM) (12 ml) was cooled to 0° C. and was treated with Hunig's base (440 µl, 2.5 mmol). The mixture was kept at 0° C. for 30 minutes then the cyclopropyl-sulfonyl chloride (72 µl, 0.60 mmol) was added. The reaction mixture was stirred at room temperature for one hour. The mixture was diluted with methylene chloride (10 ml) and was washed water (2×10 ml) and a saturated aqueous sodium chloride solution (10 ml). The organic phase was dried over sodium sulfate and concentrated in vacuo. The crude product was purified by flash chromatography using a gradient (ethyl acetate/hexanes, 30-75%), affording 0.253 g (96%) of the title compound as a pale yellow solid. M.p.: 146-148° C. 400 MHz $^1$H NMR (DMSO-$d_6$ at 60° C.) δ: 8.72 (br. s, 1H), 8.13 (d, J=5.1 Hz, 1H), 7.45 (d, J=4.3 Hz, 1H), 7.35 (dd, J=8.6, 2.0 Hz, 1H), 7.26 (dd, J=11.3, 8.2 Hz, 1H), 7.25 (br. S, 1H), 7.15 (ddd, J=8.2, 4.7, 2.0 Hz, 1H), 6.41 (d, J=5.1 Hz, 1H), 3.95-3.86 (m, 1H), 3.83 (s, 3H), 3.68-3.61 (m, 2H), 3.06-2.96 (m, 2H), 2.60-2.52 (m, 1H), 2.08-1.96 (m, 2H), 1.66-1.54(m, 2H), 1.04-0.94 (m, 4H). LCMS: 529 [M+H]. Calc. for $C_{24}H_{25}N_6O_3S_2F$.0.13water.0.7 diethyl ether: C, 54.31; H, 5.25; N, 14.18. Found C, 54.32; H, 4.89; N, 14.19.

12d: Preparation of 5-[5-(2-{[1-(cyclopropylsulfonyl)piperidin-4-yl]amino}pyrimidin-4-yl)imidazo[2,1-b][1,3]thiazol-6-yl]-2-fluorophenol

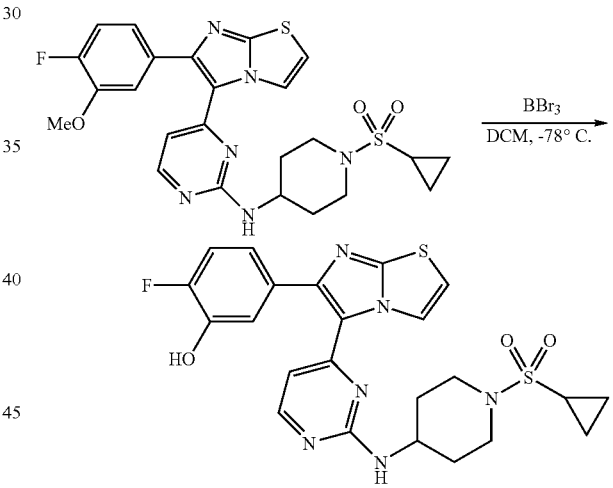

The N-[1-(cyclopropylsulfonyl)piperidin-4-yl]-4-[6-(4-fluoro-3-methoxyphenyl)imidazo[2,1-b][1,3]thiazol-5-yl]pyrimidin-2-amine (0.226 g, 0.43 mmol) in methylene chloride (8 ml) was cooled to −78° C. and slowly treated with 1 molar solution of boron tribromide in methylene chloride (3.4 ml). The reaction mixture was kept at −78° C. for one hour then was allowed to warm to room temperature for two hours. The mixture was quenched by the addition of methanol (900 µl) at −78° C. and was stirred at room temperature for an additional hour. The mixture was diluted with methylene chloride (100 ml) and washed with three portions of 25 ml of saturated sodium bicarbonate solution, two portions of 25 ml of water and two portions of 25 ml of saturated sodium chloride solution. The organic phase was dried over sodium sulfate and concentrated in vacuo, giving a yellow solid. The crude product was purified by flash chromatography (ethyl acetate), affording 0.19 g (86%) of the title compound as a beige solid. M.p.=224-225° C. 400 MHz $^1$H NMR (DMSO-d₆ at 60° C.) δ: 9.82 (s, 1H), 8.67 (br. s, 1H), 8.12 (d, J=5.5 Hz, 1H), 7.43 (d, J=4.3 Hz, 1H), 7.25-7.14 (m, 3H), 6.99 (ddd, J=8.2, 4.3, 2.0 Hz, 1H), 6.41 (d, J=5.1 Hz, 1H), 3.95-3.84 (m, 1H), 3.68-3.60 (m, 2H), 3.00 (td, J=11.9, 2.7 Hz, 2H), 2.59-2.52 (m, 1H), 2.06-1.98 (m, 2H), 1.66-1.54 (m, 2H), 1.04-0.92 (m, 4H). LCMS: 515 [M+H]. Calc. for C₂₃H₂₃N₆O₃S₂F.0.53 diethyl ether.0.17 water: C, 53.46; H, 4.93; N, 14.89. Found C, 53.46; H, 4.60; N, 14.88.

Example 13

Preparation of N-{(3R)-1-[(4-chlorophenyl)sulfonyl]piperidin-3-yl}-4-[6-(3-cyanophenyl)imidazo[2,1-b][1,3]thiazol-5-yl]pyrimidin-2-amine 13a: Preparation of 6-(3-cyanophenyl)-imidazo[2,1-b]thiazole.

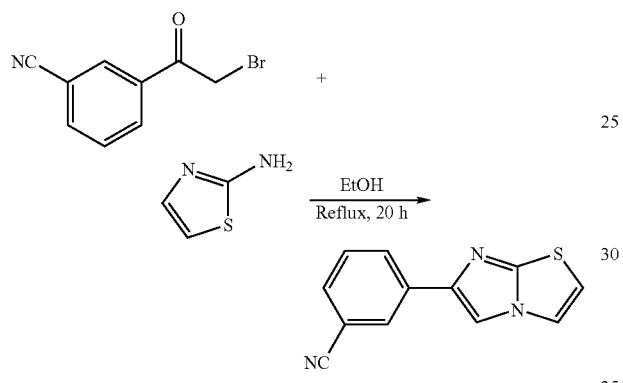

To a mixture of 2-aminothiazole (3.29 g, 32.9 mmol) and 2-bromo-3'-cyano-acetophenone (7.37 g, 32.9 mmol) was added absolute ethanol (250 mL). The reaction was allowed to reflux with vigorous stirring for 20 hours. The reaction mixture was reduced to half its original volume in vacuo. The remaining suspension was poured onto ice-water (200 mL) and the resulting mixture was basified by addition of ammonium hydroxide solution (30%, 100 mL). Product was collected by filtration and washed with water (50 mL), dried in a vacuum oven at 50° C. to provide 6-(3-cyanophenyl)-imidazo[2,1-b]thiazole (6.0 g, 81%). It was used with out further purification. LCMS: 226 [M+H].

13b: Preparation of 1-[6-(3-cyanophenyl)imidazo[2,1-b][1,3]thiazol-5-yl]ethanone

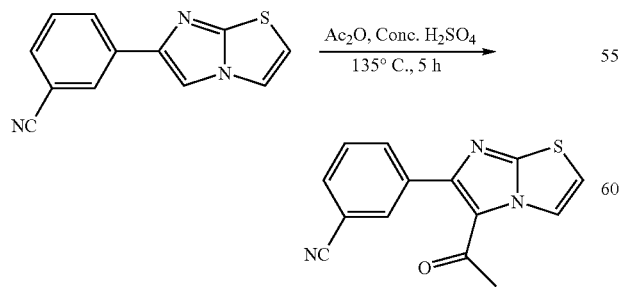

To a mixture of 6-(3-cyanophenyl)-imidazo[2,1-b]thiazole (5.50 g, 24.4 mmol) and acetic anhydride (50 mL) was added 0.6 mL of concentrated sulfuric acid. The reaction mixture was heated at 135° C. for 5 hours. After cooling to room temperature, the reaction mixture was diluted with dichloromethane (100 mL), washed with water (50 mL×2), saturated aqueous sodium bicarbonate solution (50 mL×2), water (50 mL), dried over sodium sulfate, filtered and concentrated in vacuo. Product was purified by flash chromatography on silica gel eluting with 40% ethyl acetate in hexane to yield 4.8 g (74%) of the title compound as a light yellow solid. LCMS: 268 [M+H].

13c: Preparation of 3-(dimethylamino)-1-[6-(3-cyanophenyl)imidazo[2,1-b][1,3]thiazol-5-yl]prop-2-en-1-one

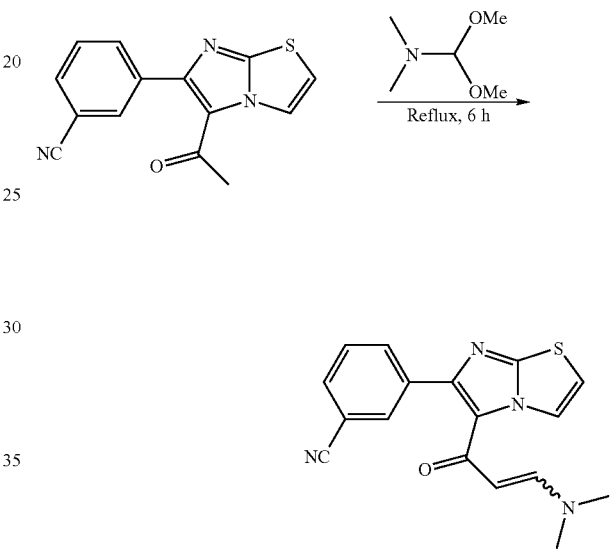

A 100 mL round bottom flask was charged with the 1-[6-(3-cyanophenyl)imidazo [2,1-b][1,3]thiazol-5-yl]ethanone (4.30 g, 16.1 mmol) and dimethylformamide dimethylacetal (40 mL). The mixture was refluxed for 6 hours and then concentrated in vacuo to provide a dark solid. LCMS: 323 [M+H]; purity: 90% by UV at 254 nm. This crude was used for next step reaction without further purification.

13d: Preparation of tert-butyl (3R)-3-({4-[6-(3-cyanophenyl)imidazo[2,1-b][1,3]thiazol-5-yl]pyrimidin-2-yl}amino)piperidine-1-carboxylate

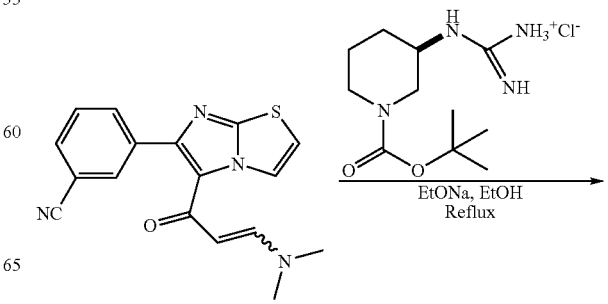

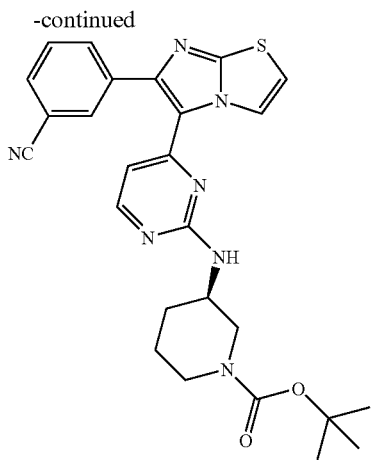

To a mixture of 3-(dimethylamino)-1-[6-(3-cyanoyphenyl) imidazo[2,1-b][1,3]thiazol-5-yl]prop-2-en-1-one (~16 mmol, crude) and tert-butyl (3R)-3-{[(Z)-amino(imino)methyl]amino}piperidine-1-carboxylate hydrochloride (6.71 g, 24.15 mmol) in 20 mL of absolute ethanol was added a solution of sodium ethoxide in ethanol (21% w/w, 6.8 mL). The mixture was heated to reflux for 24 hours. Then 3.0 mL of sodium ethoxide in ethanol (21% w/w ) was added and the mixture was stirred for further 18 hours. Volatiles were removed in vacuo and the residue was taken up in 200 mL of dichloridementhane, washed with water (100 mL×2), dried over sodium sulfate and concentrated. The product was purified by flash chromatography on silica gel (ethyl acetate/hexanes, 50%) to yield 4.7 g of a pale yellow solid (59%). M.p.=108-110° C.; 400 MHz $^1$H NMR (DMSO-d$_6$ at 60° C.) δ: 8.65 (bs, 1H), 8.15 (d, J=5.2 Hz, 1H), 8.00-7.99 (m, 1H), 7.93-7.90 (m, 1H), 7.86-7.83 (m, 1H), 7.64 (t, J=7.6 Hz, 1H), 7.43 (d, J=4.4 Hz, 1H), 7.16 (d, J=6.8 Hz, 1H), 6.34 (d, J=4.8 Hz, 1H), 3.93 (bs, 1H), 3.80-3.73 (m, 1H), 3.73 (bs, 1H), 2.92 (bs, 2H), 1.98-1.94 (m, 1H), 1.77-1.74 (m, 1H), 1.59-1.51 (m, 1H), 1.47-1.31 (m, 1H), 1.31 (s, 9H). LCMS: 502 [M+H].

13e: Preparation of 4-[6-(3-cyanophenyl)imidazo[2,1-b][1,3]thiazol-5-yl]-N-[(3R)-piperidin-3-yl]pyrimidin-2-amine hydrochloride

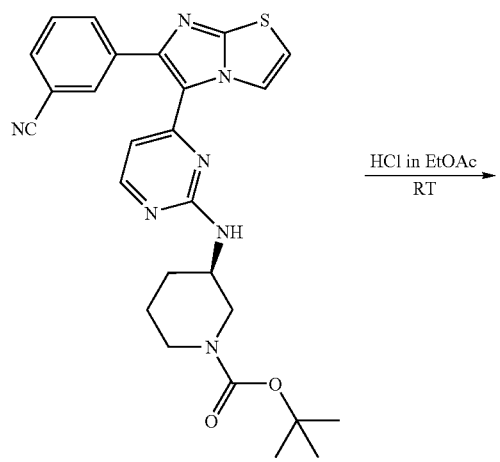

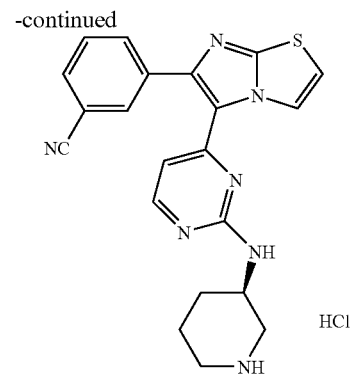

The tert-butyl (3R)-3-({4-[6-(3-cyanophenyl)imidazo[2,1-b][1,3]thiazol-5-yl]pyrimidin-2-yl}amino)piperidine-1-carboxylate (2.90 g, 5.79 mmol) was dissolved in 20 mL of ethyl acetate and treated with 30 mL of 3.0 M HCl in ethyl acetate at room temperature (RT) overnight. Solid product was filtered, washed with ethyl acetate and dried under vacuum overnight to provide the title compound as a yellow solid. It was used without further purification. LCMS: 402 [M+H].

13e: Preparation of N-{(3R)-1-[(4-chlorophenyl)sulfonyl]piperidin-3-yl}-4-[6-(3-cyanophenyl)imidazo[2,1-b][1,3]thiazol-5-yl]pyrimidin-2-amine

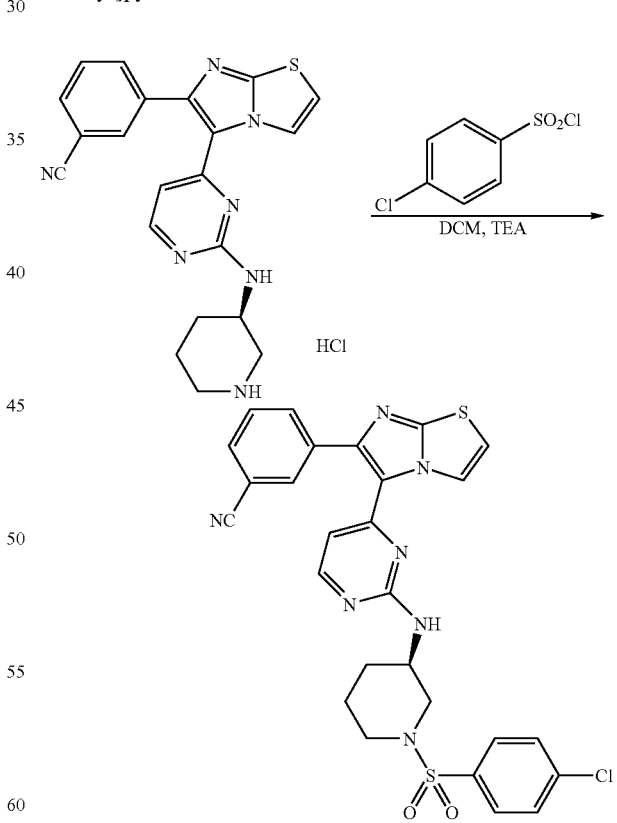

The 4-[6-(3-cyanophenyl)imidazo[2,1-b][1,3]thiazol-5-yl]-N-[(3R)-piperidin-3-yl]pyrimidin-2-amine hydrochloride (~5.79 mmol) in dichloromethane (DCM) (50 mL) was cooled to 0° C. and treated with triethylamine (4.0 mL, 28.9 mmol), then 4-chlorophenylsulfonyl chloride (1.34 g, 6.37 mmol) was added. The reaction mixture was stirred at room temperature for 1 hour, diluted with dichloromethane (100 mL), washed with water (50 mL×3), dried over sodium sulfate and concentrated in vacuo to provide 3.22 g (97%) of the title compound as a yellow solid. M.p.=144-146° C.; 400 MHz $^1$H NMR (DMSO-$d_6$ at 60° C.) δ: 8.65 (br. s, 1H), 8.17 (d, J=5.2 Hz, 1H), 8.01 (s, 1H), 7.94 (dd, J=0.8 and 7.6 Hz, 1H), 7.82-7.85 (m, 1H), 7.77-7.75 (m, 2H), 7.67-7.64 (m, 3H), 7.44 (d, J=4.4 Hz, 1H), 7.18 (d, J=7.2 Hz, 1H), 6.37 (d, J=4.8 Hz, 1H), 3.91 (bs, 1H), 3.72 (d, J=10.8 Hz, 1H), 3.48 (d, J=10.8 Hz, 1H), 2.48-2.45 (m, 1H), 2.32 (t, J=10 Hz, 1H), 1.89-1.82 (m, 2H), 1.60-1.56 (m, 1H), 1.41-1.36 (m, 1H). LCMS: 576 [M+H].

Example 14

Preparation of 3-{5-[2-({(3R)-1-[(4-chlorophenyl)sulfonyl]piperidin-3-yl}amino)pyrimidin-4-yl]imidazo[2,1-b][1,3]thiazol-6-yl}-N'-hydroxybenzenecarboximidamide

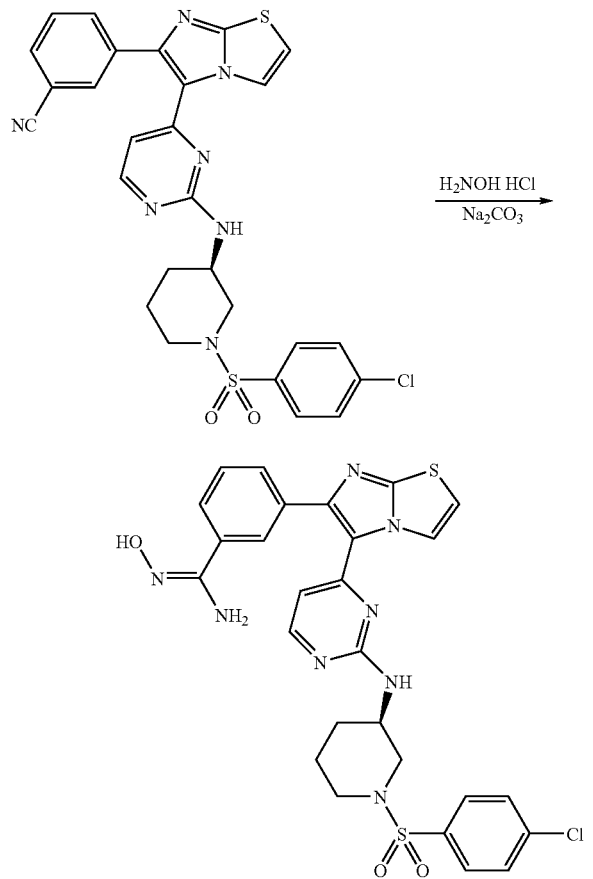

To a suspension of N-{(3R)-1-[(4-chlorophenyl)sulfonyl]piperidin-3-yl}-4-[6-(3-cyano-phenyl)imidazo[2,1-b][1,3]thiazol-5-yl]pyrimidin-2-amine (0.050 g, 0.086 mmol) in 80% ethanol-water (2.5 mL) was added an aqueous solution (0.50 mL) containing 6.65 mg of hydroxylamine hydrochloride (1.1 equivalents) and 4.61 mg of sodium carbonate (0.5 equivalents). The resulting solution was heated at 80° C. for 20 hours. Solid was collected by filtration and treated with hot (80° C.) 80% ethanol-water (2 mL×5). Solid was collected and dried under vacuum at 45° C. overnight to afford 25 mg (48%) of the title compound as a yellow solid. M.p.=272-273° C. 400 MHz $^1$H NMR (DMSO-$d_6$ at 60° C.) δ: 9.52 (s, 1H), 8.70 (bs, 1H), 8.11 (d, J=5.2 Hz, 1H), 7.93 (s, 1H), 7.77-7.73 (m, 3H), 7.67-7.66 (m, 2H), 7.59 (d, J=6.8 Hz, 1H), 7.47-7.40 (m, 2H), 7.11 (d, J=7.6 Hz, 1H), 6.38 (d, J=4.4 Hz, 1H), 5.68 (s, 2H), 3.94 (br. s, 1H), 3.73 (d, J=8.4 Hz, 1H), 3.48 (d, J=10.8 Hz, 1H), 2.49-2.48 (m, 1H), 2.35 (t, J=8.8 Hz, 1H), 1.95-1.84 (m, 2H), 1.60-1.5 (m, 1H), 1.46-1.30 (m, 1H). LCMS: 610 [M+H].

Example 15

Preparation of 3-(5-{2-[(R)-1-(4-chloro-benzenesulfonyl)-piperidin-3-ylamino]-pyrimidin-4-yl}-imidazo[2,1-b]thiazol-6-yl)-benzamide

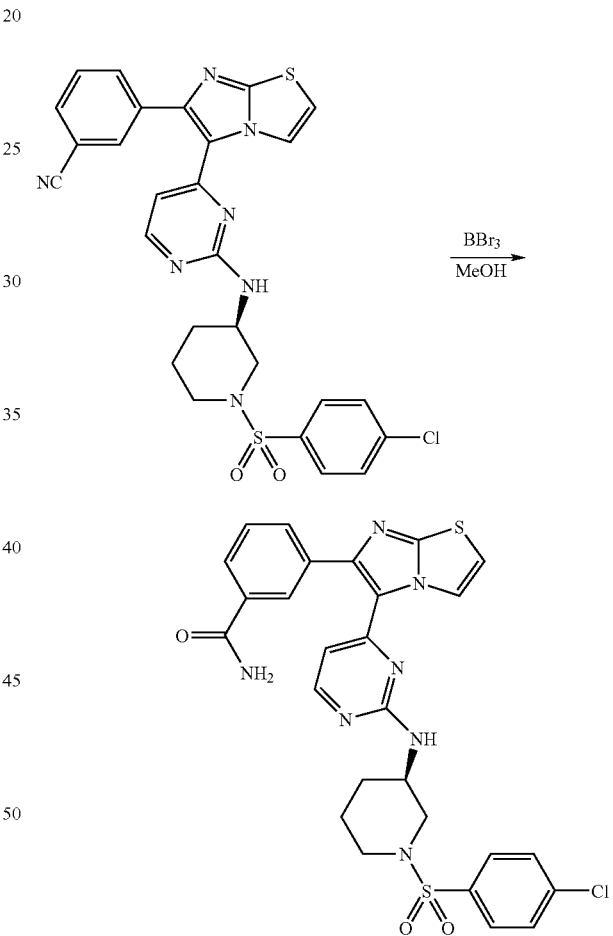

To a solution of N-{(3R)-1-[(4-chlorophenyl)sulfonyl]piperidin-3-yl}-4-[6-(3-cyano-phenyl)imidazo[2,1-b][1,3]thiazol-5-yl]pyrimidin-2-amine (0.50 g, 0.87 mmol) in dichloromethane (DCM) (10 mL) at −78° C. was added a solution of borane tribromide (BBr$_3$) (1.74 mL, 1.0 M in DCM). The mixture was stirred at −78° C. for 0.5 hour, then room temperature for one hour. The mixture was then cooled to −78° C. and methanol (1 mL) was added. The resulting mixture was stirred at room temperature overnight. Solvent was removed in vaco, the residue was treated with a 1:1 mixture of dichloromethane and water (50 mL). Organic layer was separated, dried over sodium sulfate and concentrated. Product was purified by flash chromatography on silica gel eluting with 5% methanol in dichloromethane to afford 0.019 g (4%) of the title compound as a yellow solid. M.p.=168-170° C. 400 MHz $^1$H NMR (DMSO-$d_6$ at 60° C.) δ: 8.70 (br. s, 1H), 8.10 (s, 1H), 8.10 (d, J=4.8 Hz, 1H), 7.94 (d, J=7.6 Hz, 1H), 7.94-7.80 (m, 1 H), 7.77-7.65 (m, 4H), 7.53 (t, J=8.0 Hz, 1H), 7.42 (d, J=4.4 Hz, 1H), 7.25-7.13 (m, 2H), 7.15 (d, J=7.2 Hz, 1H), 6.34 (d, J=5.6 Hz, 1H), 3.92 (bs, 1H), 3.73 (d, J=8.4 Hz, 1H), 3.48 (d, J=11.2 Hz, 1H), 2.48-2.43 (m, 1H), 2.35 (t, J=10.8 Hz, 1H), 1.90-1.82 (m, 2H), 1.59-1.56 (m, 1H), 1.39-1.34 (m, 1H). LCMS: 595 [M+H].

Example 16

Preparation of 3-(5-{2-[(3R)-piperidin-3-ylamino]pyrimidin-4-yl}imidazo[2,1-b][1,3]thiazol-6-yl)benzamide 16a: Preparation of (R)-3-{4-[6-(3-carbamoyl-phenyl)-imidazo[2,1-b]thiazol-5-yl]-pyrimidin-2-ylamino}-piperidine-1-carboxylic acid tert-butyl ester

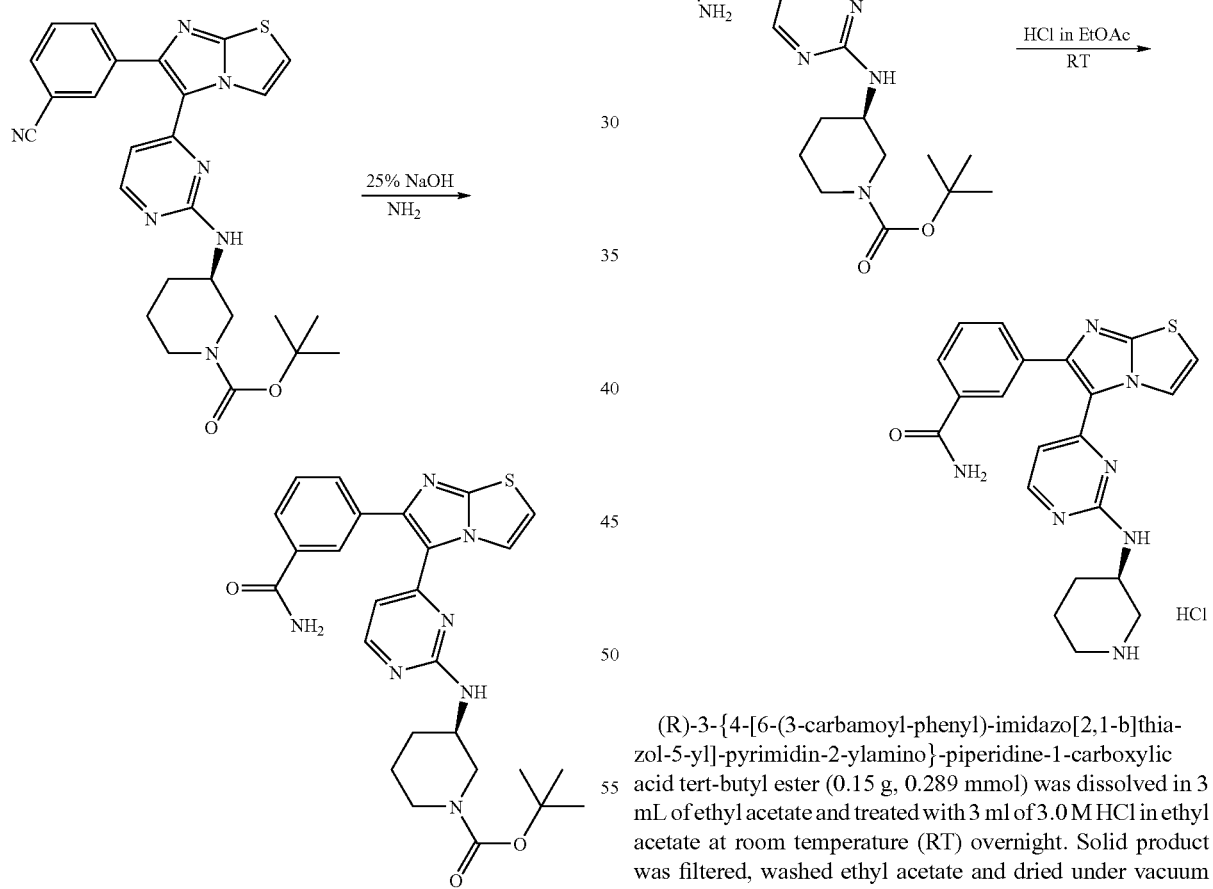

To a solution of tert-butyl (3R)-3-({4-[6-(3-cyanophenyl)imidazo[2,1-b][1,3]thiazol-5-yl]pyrimidin-2-yl}amino)piperidine-1-carboxylate (0.204 g, 0.407 mmol) in ethanol (5 mL) was added 25% aqueous sodium hydroxide (0.072 mL, 0.448 mmol). The mixture was heated at 75° C. for 20 hours. Solvent was removed to dryness. Residue was taken into dichloromethane (20 mL), washed with water (5 mL), dried over sodium sulfate and concentrated. Product was purified by flash chromatography on silica gel eluting with 5% methanol in dichloromethane to afford 0.175 g (83%) of the title compound as an off-white solid. M.p.=161-165° C. 400 MHz $^1$H NMR (DMSO-$d_6$ at 60° C.) δ: 8.70 (br. s, 1H), 8.14 (s, 1H), 8.10 (d, J=5.6 Hz, 1H), 7.94 (d, J=8.0 Hz, 1H), 7.72 (d, J=7.6 Hz, 1H). 7.54(t, J=7.6 Hz, 1H), 7.44 (d, J=4.4 Hz, 1H), 7.30-7.14 (bs, 2H), 7.15 (d, J=6.8 Hz, 1H), 6.33 (d, J=5.2 Hz, 1H), 3.96 (bs, 1H), 3.81-3.77 (m, 1H), 3.68 (bs, 1H), 2.94-2.90 (m, 2H), 2.00-1.97 (m, 1H), 1.80-1.77 (m, 1H), 1.59-1.53 (m, 1H), 1.46-1.40 (m, 1H), 1.34 (s, 9H); LCMS: 520 [M+H].

16b: Preparation of 3-(5-{2-[(3R)-piperidin-3-ylamino]pyrimidin-4-yl}imidazo[2,1-b][1,3]thiazol-6-yl)benzamide (R)-3-{4-[6-(3-carbamoyl-phenyl)-imidazo[2,1-b]thiazol-5-yl]-pyrimidin-2-ylamino}-piperidine-1-carboxylic acid tert-butyl ester (0.15 g, 0.289 mmol) was dissolved in 3 mL of ethyl acetate and treated with 3 ml of 3.0 M HCl in ethyl acetate at room temperature (RT) overnight. Solid product was filtered, washed ethyl acetate and dried under vacuum overnight to provide 0.130 g (97%) of the title compound as a yellow solid. M.p.=202-205° C. 400 MHz $^1$H NMR (DMSO-$d_6$ at 60° C.) δ: 9.35 (br. s, 1H), 9.20-8.25 (bs, 3H), 8.12-8.09 (m, 2H), 7.98-7.968.0 (m, 1H), 7.74-7.72 (m, 1H), 7.57-7.52 (m, 2H), 7.25 (bs, 1H), 6.40 (d, J=6.0 Hz, 1H), 4.31 (br. s, 1H), 3.40 (d, J=9.2 Hz, 1H), 3.16-3.13 (m, 1H), 2.94-2.90 (m, 2H), 2.03-1.97 (m, 1H), 1.96-1.89 (m, 1H), 1.89-1.80 (bs, 1 H), 1.66-1.60 (m, 1H); LCMS: 459 [M+H]. calc.

for $C_{21}H_{21}N_7OS \cdot 3.14(HCl) \cdot 0.25(EtOAc)$ C, 47.52; H, 4.74; N, 17.63. Found C, 47.57; H, 4.44; N, 17.52; LCMS: 420 [M+H].

Example 17

Preparation of 3-{5-[2-({(3R)-1-[(4-chlorophenyl)sulfonyl]piperidin-3-yl}amino)pyrimidin-4-yl]imidazo[2,1-b][1,3]thiazol-6-yl}benzoic acid 17a: Preparation of 3-(5-{2-[(R)-1-(4-Chloro-benzenesulfonyl)-piperidin-3-ylamino]-pyrimidin-4-yl}-imidazo[2,1-b]thiazol-6-yl)-N-methoxy-N-methyl-benzamide

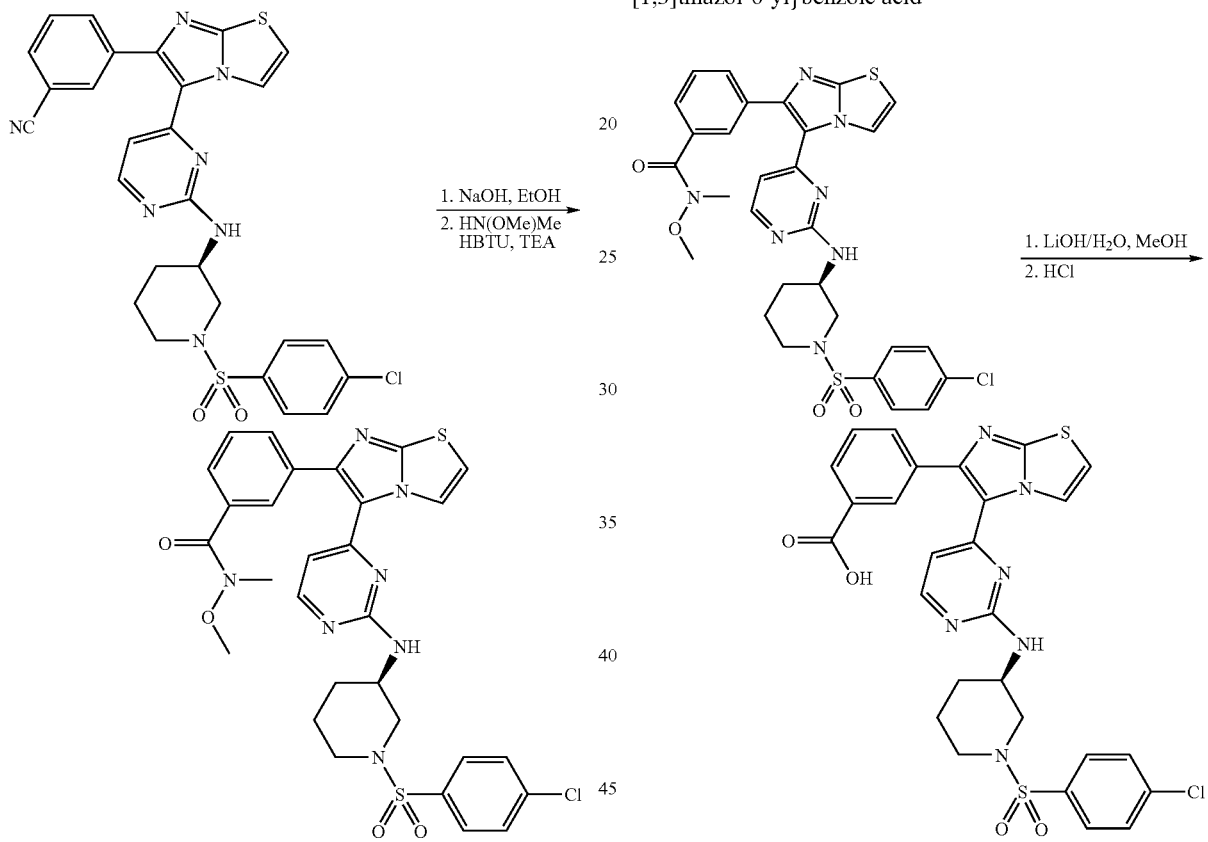

17b: Preparation of 3-{5-[2-({(3R)-1-[(4-chlorophenyl)sulfonyl]piperidin-3-yl}amino)pyrimidin-4-yl]imidazo[2,1-b][1,3]thiazol-6-yl}benzoic acid To a solution of N-{(3R)-1-[(4-chlorophenyl)sulfonyl]piperidin-3-yl}-4-[6-(3-cyano-phenyl)imidazo[2,1-b][1,3]thiazol-5-yl]pyrimidin-2-amine (1.43 g, 2.49 mmol) in ethanol (30 mL) was added 25% aqueous sodium hydroxide (1.5 mL, 15.5 mmol). The mixture was heated at 75° C. for 5 days. Solvent was removed to dryness. Residue was dissolved into a mixture of dichloromethane (100 mL) and 0.5 N HCl (40 mL). Organic layer was separated, dried over sodium sulfate and concentrated to dryness. The residue was dried further under high vacuum for 24 hours. It was used without further purification.

The crude product was dissolved in N,N-dimethylformamide (30 mL). To the resulting solution was added O-benzotriazole-1-yl-N,N,N',N'-tetramethyluronium hexafluorophosphate (HBTU) (1.42 g, 3.74 mmol), triethylamine (1.04 mL, 7.47 mmol), lastly, a solution of N,O-dimethyl hydroxylamine hydrochloride (0.365 g, 3.74 mmol). The mixture was stirred at room temperature for 1 hour, diluted with dichloromethane (100 mL), washed with water (50 mL×4), dried over sodium sulfate and concentrated. Product was purified by flash chromatography on silica gel (methanol:dichloromethane:ethylacetate=0.5:7:2) to afford the title compound 0.976 g (62%, two steps) as a pale yellow solid. M.p.=114-115° C. 400 MHz $^1$H NMR (DMSO-$d_6$ at 60° C.) δ: 8.70 (br. s, 1H), 8.11 (d, J=4.6 Hz, 1H), 7.77-7.74 (m, 3H), 7.71 (d, J=8.0 Hz, 1H), 7.68-7.62 (m, 3H), 7.53 (t, J=7.2 Hz, 1H), 7.41 (d, J=4.4 Hz, 1H), 7.14 (d, J=6.8 Hz, 1H), 6.40 (d, J=5.8 Hz, 1H), 3.93 (br. s, 1H), 3.73-3.71 (m, 1H), 3.54 (s, 3H), 3.48-3.45 (m, 1H), 3.25 (s, 3H), 2.48-2.43 (m, 1H), 2.33 (t, J=10.0 Hz, 1H), 1.89-1.82 (m, 2H), 1.59-1.56 (m, 1H), 1.41-1.32 (m, 1H). LCMS: 639 [M+H].

To a solution of 3-(5-{2-[(R)-1-(4-chloro-benzenesulfonyl)-piperidin-3-ylamino]-pyrimidin-4-yl}-imidazo[2,1-b]thiazol-6-yl)-N-methoxy-N-methyl-benzamide (0.57 g, 0.089 mmol) in a mixture of methanol (1.0 mL) and tetrahydrofuran (THF) (3.0 mL) was added a solution of lithium hydroxide (0.075 g, 0.179 mmoL) in water (1.0 mL). The mixture was stirred at room temperature for 48 hours. Solvent was removed to dryness. Residue was dissolved into a mixture of dichloromethane (20 mL) and 1.0 N HCl (1.0 mL). Organic layer was separated, washed with water (5 mL×4), dried over sodium sulfate and concentrated to dryness. The residue was dried further under high vacuum at 45° C. for 24 hours to provide 0.45 g (85%) as a yellow solid. M.p.=190-195° C. 400 MHz $^1$H NMR (DMSO-$d_6$ at 60° C.) δ: 8.70 (br. s, 1H), 8.16(bs, 1H), 8.12 (d, J=5.2 Hz, 1H), 7.99 (d, J=8.0 Hz, 1H), 7.78-7.83 (m, 1H), 7.77-7.74 (m, 2H), 7.68-7.65 (m, 2H), 7.58 (t, J=8.0 Hz, 1H), 7.41 (d, J=4.4 Hz, 1H), 7.17 (d, J=6.8 Hz, 1H), 6.37 (d, J=5.2 Hz, 1H), 3.92 (br. s, 1H), 3.75-3.71 (m, 1H), 3.48-3.45 (m, 1H), 2.49-2.43 (m, 1H), 2.32 (t, J=10.4 Hz, 1H), 1.90-1.82 (m, 2H), 1.59-1.56 (m, 1H), 1.39-1.32 (m, 1H). LCMS: 596 [M+H].

Example 18

Preparation of (1E)-1-(3-{5-[2-({(3R)-1-[(4-chlorophenyl)sulfonyl]piperidin-3-yl}amino)pyrimidin-4-yl]imidazo[2,1-b][1,3]thiazol-6-yl}phenyl)ethanone oxime 18a: Preparation of 1-(3-{5-[2-({(3R)-1-[(4-chlorophenyl)sulfonyl]piperidin-3-yl}amino)pyrimidin-4-yl]imidazo[2,1-b][1,3]thiazol-6-yl}phenyl)ethanone

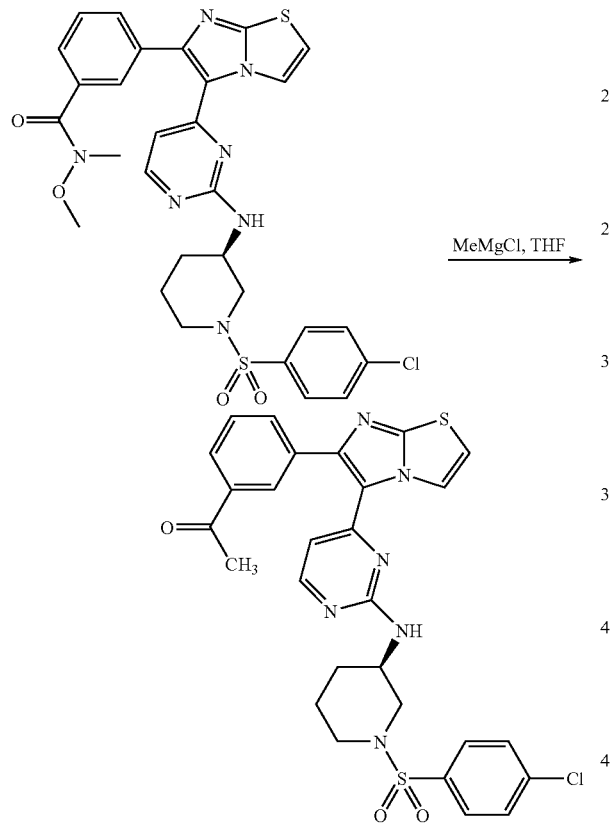

To a solution of 3-(5-{2-[(R)-1-(4-chloro-benzenesulfonyl)-piperidin-3-ylamino]-pyrimidin-4-yl}-imidazo[2,1-b]thiazol-6-yl)-N-methoxy-N-methyl-benzamide (0.10 g, 0.157 mmol) in anhydrous tetrahydrofuran (THF) (3.0 mL) at 0° C. was added a solution of methyl magnesium chloride (3.0 M in THF) (0.523 mL, 1.57 mmoL). The mixture was stirred for 3 hours, then quenched with saturated aqueous ammonium chloride solution (1 mL). Product was extracted with 10 mL of dichloromethane, washed with water (5 mL×2), dried over sodium sulfate and concentrated. Product was purified by flash chromatography on silica gel (40% dichloromethane in ethyl acetate) to afford 0.085 g (91%) of the title compound as a pale yellow solid. M.p.=124-127° C. 400 MHz $^1$H NMR (DMSO-d$_6$ at 60° C.) δ: 8.70 (br. s, 1H), 8.17 (m, 1H), 8.12 (d, J=5.6 Hz, 1H), 7.9 (d, J=7.6 Hz, 1H), 7.86-7.84 (m, 1H), 7.77-7.74 (m, 2H), 7.67-7.65 (m, 2H), 7.62 (t, J=8.0 Hz, 1H), 7.42 (d, J=4.8 Hz, 1H), 7.15 (d, J=7.6 Hz, 1H), 6.38 (d, J=5.2 Hz, 1H), 3.93 (bs, 1H), 3.74-3.72 (m, 1H), 3.48-3.45 (m, 1H), 2.57 (s, 3H), 2.49-2.45 (m, 1H), 2.32 (t, J=10.4 Hz, 1H), 1.90-1.82 (m, 2H), 1.59-1.56 (m, 1H), 1.39-1.32 (m, 1H); LCMS: 594 [M+H].

18b: Preparation of (1E)-1-(3-{5-[2-({(3R)-1-[(4-chlorophenyl)sulfonyl]piperidin-3-yl}amino)pyrimidin-4-yl]imidazo[2,1-b][1,3]thiazol-6-yl}phenyl)ethanone oxime

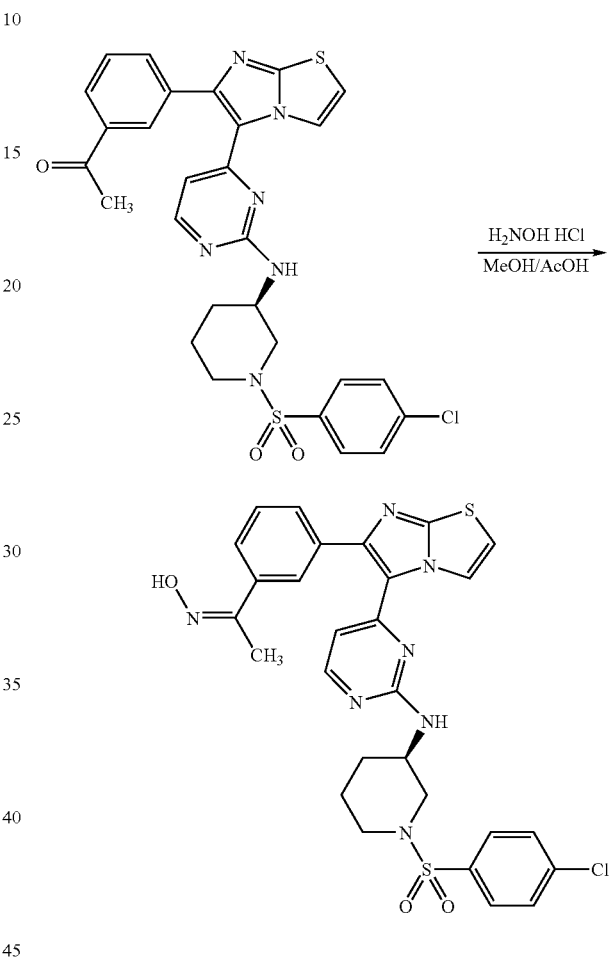

To a mixture of 1-(3-{5-[2-({(3R)-1-[(4-chlorophenyl)sulfonyl]piperidin-3-yl}amino)pyrimidin-4-yl]imidazo[2,1-b][1,3]thiazol-6-yl}phenyl)ethanone (0.10 g, 0.168 mmol) and hydroxylamine hydrochloride (0.0125 g, 0.188 mmoL) in methanol (2.0 mL) was added 0.2 mL of acetic acid. The mixture was heated at 50° C. for 3 hours. After cooled to room temperature, the mixture was diluted with dichloromethane (10 mL), washed with saturated aqueous sodium bicarbonate (5 mL×3), water (5 mL), dried over sodium sulfate and concentrated. Product was purified by flash chromatography on silica gel (methanol:dichloromethane:ethylacetate=0.5:7:2) to afford 0.069 g (67%) of the title compound as an off-white solid. M.p.=156-158° C. 400 MHz $^1$H NMR (DMSO-d$_6$ at 60° C.) δ: 11.08 (s, 1H), 8.70 (br. s, 1H), 8.11 (d, J=4.8 Hz, 1H), 7.87 (s, 1H), 7.77-7.74 (m, 2H), 7.71-7.59 (m, 3H), 7.59-7.56 (m, 1H), 7.46 (t, J=7.6 Hz, 1H), 7.41 (d, J=4.4 Hz, 1H), 7.13 (d, J=7.6 Hz, 1H), 6.40 (d, J=5.2 Hz, 1H), 3.93 (br. s, 1H), 3.74-3.71 (m, 1H), 3.48-3.45 (m, 1H), 2.48-2.45 (m, 1H), 2.33 (t, J=7.6 Hz, 1H), 2.15 (s, 3H), 1.89-1.82 (m, 2H), 1.59-1.56 (m, 1H), 1.39-1.34 (m, 1H); LCMS: 608 [M+H].

Example 19

Preparation of 3-{5-[2-({(3R)-1-[(4-chlorophenyl)sulfonyl]piperidin-3-yl}amino)pyrimidin-4-yl]imidazo[2,1-b][1,3]thiazol-6-yl}benzaldehyde oxime 19a: Preparation of 3-{5-[2-({(3R)-1-[(4-chlorophenyl)sulfonyl]piperidin-3-yl}amino)pyrimidin-4-yl]imidazo[2,1-b][1,3]thiazol-6-yl}benzaldehyde

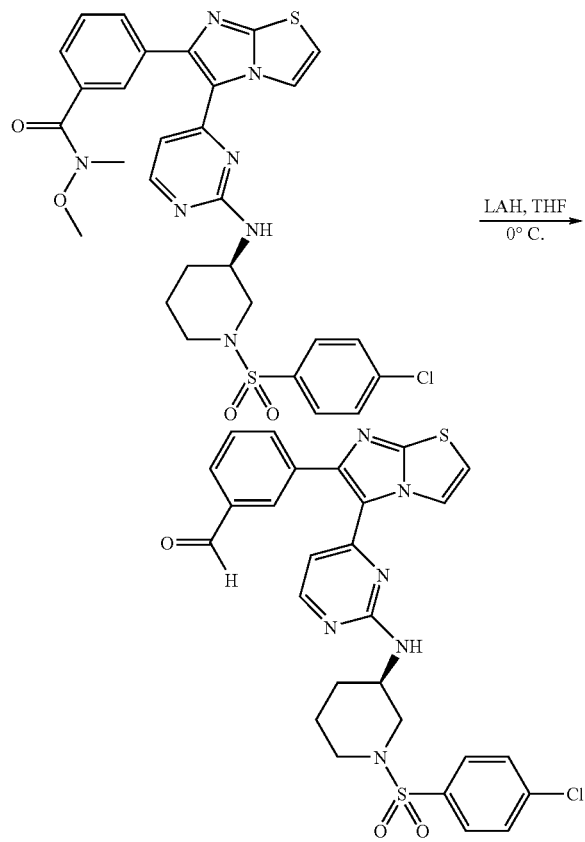

19b: Preparation of 3-{5-[2-({(3R)-1-[(4-chlorophenyl)sulfonyl]piperidin-3-yl}amino)pyrimidin-4-yl]imidazo[2,1-b][1,3]thiazol-6-yl}benzaldehyde oxime

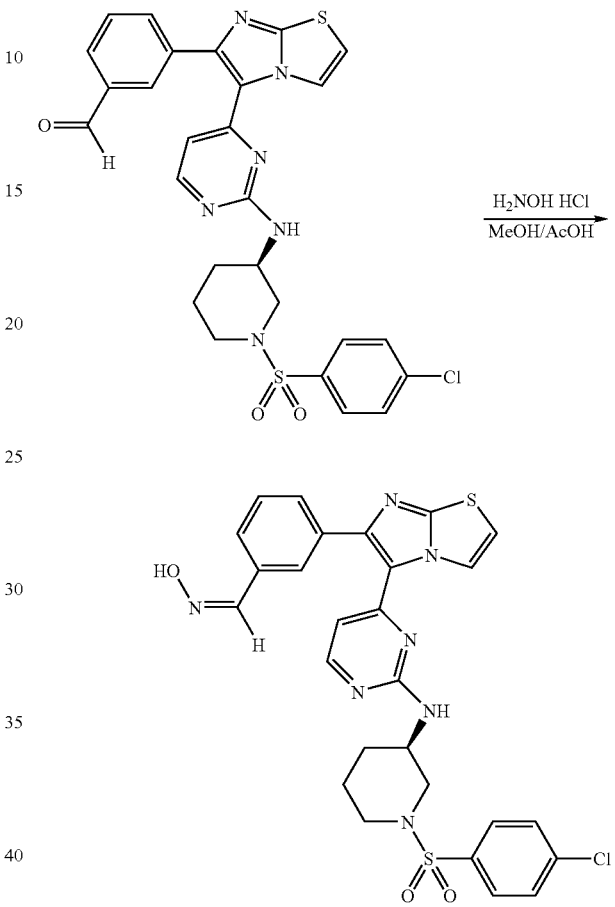

To a solution of 3-(5-{2-[(R)-1-(4-chloro-benzenesulfonyl)-piperidin-3-ylamino]-pyrimidin-4-yl}-imidazo[2,1-b]thiazol-6-yl)-N-methoxy-N-methyl-benzamide (0.05 g, 0.078 mmol) in anhydrous tetrahydrofuran (THF) (3.0 mL) at 0° C. was added a solution of lithium aluminum hydride (LAH) (2.0 M in THF) (0.078 mL, 0.15 mmol). The mixture was stirred at 0° C. for 30 minutes, then quenched with methanol (0.5 mL), diluted with dichloromethane (5 mL), washed with a solution of 10% aqueous potassium sodium tartrate (5 mL), water (5 mL), dried over sodium sulfate and concentrated. Product was purified by flash chromatography on silica gel (methanol:dichloromethane:ethylacetate=0.5:7:2) to afford 0.033 g (73%) of the title compound as a pale yellow solid. M.p.=124-126° C.; 400 MHz $^1$H NMR (DMSO-d$_6$ at 60° C.) δ: 10.06 (s, 1H), 8.70 (br. s, 1H), 8.14-8.12 (m, 2H), 7.96-7.91 (m, 2H), 7.77-7.74 (m, 2H), 7.70-7.64 (m, 3H), 7.43 (d, J=4.4 Hz, 1H), 7.15 (d, J=7.6 Hz, 1H), 6.39 (d, J=5.2 Hz, 1H), 3.93 (bs, 1H), 3.74-3.71 (m, 1H), 3.48-3.45 (m, 1H), 2.49-2.4 (m, 1H), 2.35 (t, J=10.8 Hz, 1H), 1.89-1.82 (m, 2H), 1.60-1.56 (m, 1H), 1.39-1.32 (m, 1H). LCMS: 580 [M+H].

To a mixture 3-{5-[2-({(3R)-1-[(4-chlorophenyl)sulfonyl]piperidin-3-yl}amino)pyrimidin-4-yl]imidazo[2,1-b][1,3]thiazol-6-yl}benzaldehyde (0.81 g, 0.14 mmol) and hydroxylamine hydrochloride (0.0107 g, 0.154 mmoL) in methanol (2.0 mL) was added 0.2 mL of acetic acid. The mixture was heated at 50° C. for 2 hours. After cooled to room temperature, the mixture was diluted with dichloromethane (10 mL), washed with saturated aqueous sodium bicarbonate (5 mL×3), water (5 mL), dried over sodium sulfate and concentrated. Product was purified by flash chromatography on silica gel (methanol:dichloromethane:ethylacetate=0.5:7:2) to afford 0.051 g (61%) of the title compound as an off-white solid. M.p.=238-240° C. 400 MHz $^1$H NMR (DMSO-d$_6$ at 60° C.) δ: 11.14 (s, 1H), 8.70 (bs, 1H), 8.17 (s, 1H), 8.11 (d, J=5.6 Hz, 1H), 7.8 (s, 1H), 7.77-7.74 (m, 2H), 7.68-7.64 (m, 3H), 7.60-7.57 (m, 1H), 7.47 (t, J=7.6 Hz, 1H), 7.41 (d, J=4.4 Hz, 1H), 7.14 (d, J=7.6 Hz, 1H), 6.40 (d, J=5.2 Hz, 1H), 3.93 (br. s, 1H), 3.74-3.71 (m, 1H), 3.48-3.45 (m, 1H), 2.5-2.4 (m, 1H), 2.33 (t, J=10.4 Hz, 1H), 1.89-1.82 (m, 2H), 1.59-1.56 (m, 1H), 1.40-1.32 (m, 1H). LCMS: 594 [M+H].

Example 20

Preparation of (3-{5-[2-({(3R)-1-[(4-chlorophenyl)sulfonyl]piperidin-3-yl}amino)pyrimidin-4-yl]imidazo[2,1-b][1,3]thiazol-6-yl}phenyl)methanol

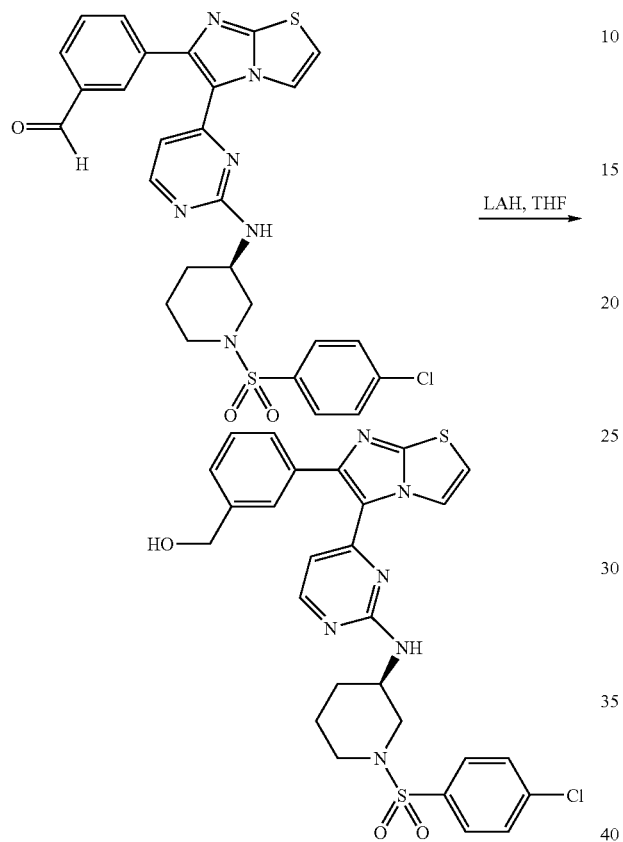

To a mixture 3-{5-[2-({(3R)-1-[(4-chlorophenyl)sulfonyl]piperidin-3-yl}amino)pyrimidin-4-yl]imidazo [2,1-b][1,3]thiazol-6-yl}benzaldehyde (0.20 g, 0.346 mmol) in anhydrous tetrahydrofuran (THF) (5.0 mL) at room temperature was added a solution of lithium aluminum hydride (LAH) (2.0 M in THF) (0.346 mL, 0.692 mmol). The mixture was stirred for one hour, then quenched with methanol (1.0 mL), diluted with dichloromethane (50 mL) and 30 mL of water. Organic layer was separated and the water layer was extracted with dichloromethane (50 mL×2). Organic layer was combined, dried over sodium sulfate and concentrated. Product was purified by flash chromatography on silica gel (methanol:dichloromethane:ethylacetate=0.5:7:2) to afford 0.142 g (71%) of the title compound as an off-white solid. M.p.=150-155° C. 400 MHz $^1$H NMR (DMSO-$d_6$ at 60° C.) δ: 8.75 (bs, 1H), 8.12 (d, J=5.6 Hz, 1H), 7.77-7.74 (m, 2H), 7.67-7.65 (m, 2H), 7.56 (s, 1H), 7.44-7.36 (m, 4H), 7.11 (d, J=7.2 Hz, 1H), 6.39 (d, J=5.6 Hz, 1H), 5.07 (t, J=5.6 Hz, 1H), 4.55 (d, J=6.0 Hz, 2H), 3.29 (br. s, 1H), 3.73 (d, J=7.2 Hz, 1H), 3.48 (d, J=11.2 Hz, 1H), 2.5-2.43 (m, 1H), 2.35 (t, J=10.0 Hz, 1H), 1.91-1.82 (m, 2H), 1.60-1.57 (m, 1H), 1.40-1.32 (m, 1H). LCMS: 581 [M+H].

Example 21

Preparation of 4-{6-[3-(5-methyl-1,2,4-oxadiazol-3-yl)phenyl]imidazo[2,1-b][1,3]thiazol-5-yl}-N-[(3R)-piperidin-3-yl]pyrimidin-2-amine 21a: Preparation of (R)-3-(4-{6-[3-(5-methyl-[1,2,4]oxadiazol-3-yl)-phenyl]-imidazo[2,1-b]thiazol-5-yl}-pyrimidin-2-ylamino)-piperidine-1-carboxylic acid tert-butyl ester

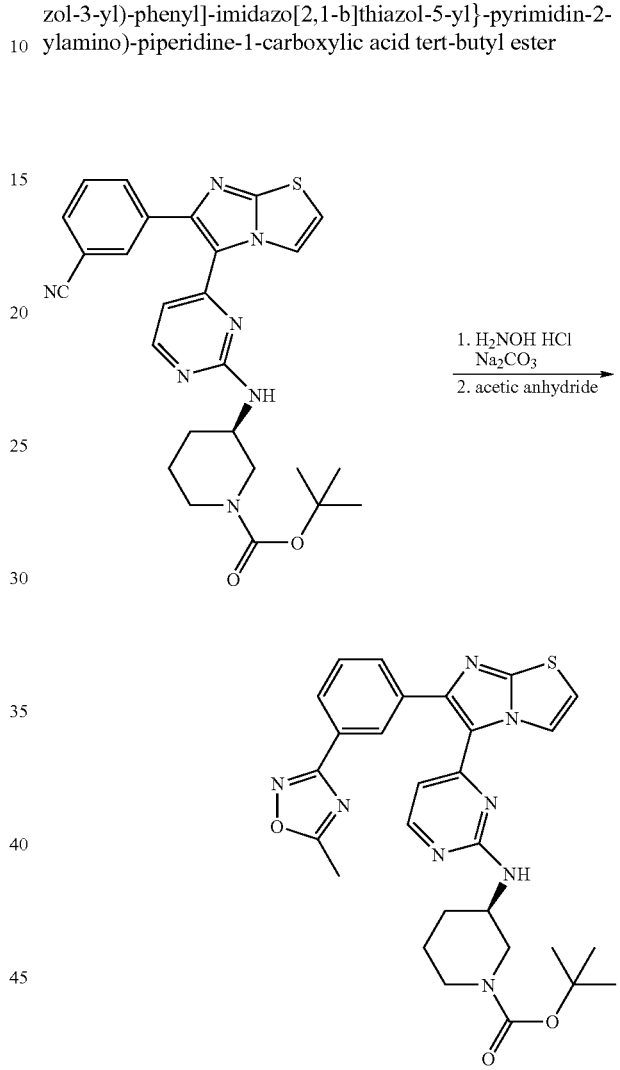

To mixture of hydroxylamine hydrochloride (0.030 g, 0.439 mmol) and sodium carbonate (0.021 g, 0.200 mmol) in water (0.40 mL) was added tert-butyl (3R)-3-({4-[6-(3-cyanophenyl)imidazo[2,1-b][1,3]thiazol-5-yl]pyrimidin-2-yl}amino)piperidine-1-carboxylate (0.200 g, 0.399 mmol) and ethanol (1.6 mL). The resulting mixture was heated at 80° C. for 4 hours and then solvent was removed. Residue was dried under vacuum at 45° C. overnight. It was used for next reaction without further purification.

The dried residue was dissolved in anhydrous N,N-demethylformamide (DMF) and acetic anhydride (0.041 mL, 0.419 mmol) was added. The resulting mixture was heated at 120° C. for 3 hours, cooled to room temperature, diluted with dichloromethane (10 mL), washed with water (5 mL×3), dried over sodium sulfate and concentrated. Product was purified by flash chromatography on silica gel eluting with 80% ethyl acetate in hexane to afford 0.169 g (76%) of the title compound as a yellow solid. M.p.=110-112° C. 400 MHz ¹H NMR (DMSO-d₆ at 60° C.) δ: 8.72 (bs, 1H), 8.25-8.24 (m, 1H), 8.12 (d, J=5.2 Hz, 1H), 8.06-8.03 (m, 1H), 7.83-7.80 (m, 1H), 7.66 (t, J=8.0 Hz, 1H), 7.44 (d, J=4.4 Hz, 1H), 7.17 (d, J=7.2 Hz, 1H), 6.44 (d, J=5.6 Hz, 1H), 3.95 (bs, 1H), 3.81-3.78 (m, 1H), 3.68 (bs, 1H), 2.96 (bs, 2H), 2.00-1.97 (m, 1H), 1.82-1.77 (m, 1H), 1.64-1.56 (m, 1H), 1.50-1.40 (m, 1H), 1.34 (s, 9H); LCMS: 559 [M+H].

21b: Preparation of 4-{6-[3-(5-methyl-1,2,4-oxadiazol-3-yl)phenyl]imidazo[2,1-b][1,3]thiazol-5-yl}-N-[(3R)-piperidin-3-yl]pyrimidin-2-amine

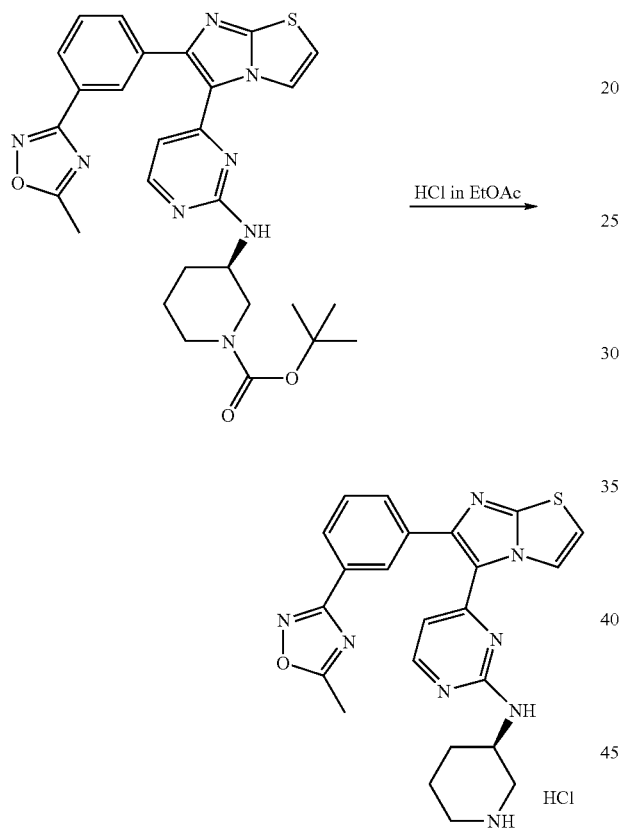

((R)-3-(4-{6-[3-(5-Methyl-[1,2,4]oxadiazol-3-yl)-phenyl]-imidazo[2,1-b]thiazol-5-yl}-pyrimidin-2-ylamino)-piperidine-1-carboxylic acid tert-butyl ester (0.15 g, 0.269 mmol) was dissolved in 2 mL of ethyl acetate and treated with 2 ml of 3.0 M HCl in ethyl acetate at room temperature (RT) overnight. Solid product was filtered, washed ethyl acetate and dried under vacuum overnight to provide 0.135 g (100%) of the title compound as a yellow solid. M.p.=203-207° C. 400 MHz ¹H NMR (DMSO-d₆ at 60° C.) δ: 9.35 (br. s, 1H), 8.21 (s, 1H), 8.12 (d, J=6.0 Hz, 1H), 8.0 (d, J=7.6 Hz, 1H), 7.82-7.80 (m, 1H), 7.67 (t, J=8.2 Hz, 1H), 7.54 (s, 1H), 6.90 (bs, 1H), 6.48 (d, J=5.6 Hz, 1H), 4.2 (br. s, 1H), 3.40 (d, J=10.8 Hz, 1H), 3.13 (d, 1H), 2.92-2.87 (m, 2H), 2.65 (s, 3H), 2.00-1.97 (m, 1H), 1.96-1.89 (m, 1H), 1.89-1.80 (bs, 1H), 1.64-1.57 (m, 1H); LCMS: 459 [M+H]. calc. for $C_{23}H_{22}N_8OS \cdot 2.3HCl$: C, 50.93; H, 4.52; N, 20.66. Found C, 50.93; H, 4.42; N, 19.30.

Example 22

Preparation of 3-{5-[2-({(3R)-1-[(4-chlorophenyl)sulfonyl]piperidin-3-yl}amino)pyrimidin-4-yl]imidazo[2,1-b][1,3]thiazol-6-yl}phenyl carbamate

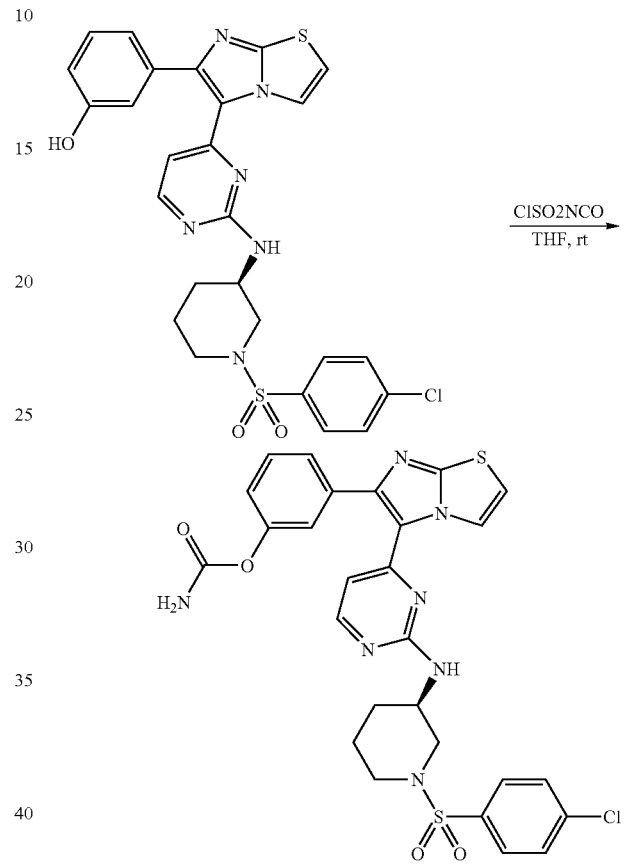

A solution of 3-{5-[2-({(3R)-1-[(4-chlorophenyl)sulfonyl]piperidin-3-yl}amino)pyrimidin-4-yl]imidazo[2,1-b][1,3]thiazol-6-yl}phenol (0.15 g, 0.26 mmol) in anhydrous tetrahydrofuran (10 ml, dissolved by slow warming) was treated with chlorosulfonyl isocyanate (34 ul, 1.5 eq) at room temperature. After 30 min the mixture was again treated with chlorosulfonyl isocyanate (34 ul, 1.5 eq) and stirred for 10 min. Solvent was removed under reduced pressure and the residue was purified by preparative HPLC (using TFA as modifier). Pure fractions were collected and dried to give product as TFA salt (0.03 g, 19%). M.p.=118-120° C. 400 MHz ¹H NMR (DMSO-d₆ at 60° C.) δ: 8.78 (br. s, 1H), 8.12 (d, J=5.6 Hz, 1H), 7.78-7.75 (m, 2H), 7.68-7.66 (m, 2H), 7.31 (m, 1H), 7.40 (m, 1H), 7.25 (m, 1H), 7.15 (tt, J=2.0 and 7.4 Hz, 1H), 6.9 (brm, 1H), 6.48 (d, J=5.6 Hz, 1H), 3.97 (br. s, 1H), 3.72 (dd, J=11.2 and 4.4 Hz, 1H), 3.46 (d, J=11.6 Hz, 1H), 2.51 (m, 1H), 2.36 (t, J=9.6 Hz, 1H), 1.91-1.83 (m, 2H), 1.65-1.5 (m, 1H), 1.44-1.38 (m, 1H). LCMS: 611 [M+H]. Calc. for $C_{27}H_{24}N_7O_4S_2Cl \cdot 1.84TFA$: C, 44.94; H, 3.18; N, 11.96. Found C, 44.93; H 3.3; N, 11.46.

Example 23

Preparation of 3-{5-[2-({(3R)-1-[(4-chlorophenyl)sulfonyl]piperidin-3-yl}amino)pyrimidin-4-yl]imidazo[2,1-b][1,3]thiazol-6-yl}phenyl sulfamate

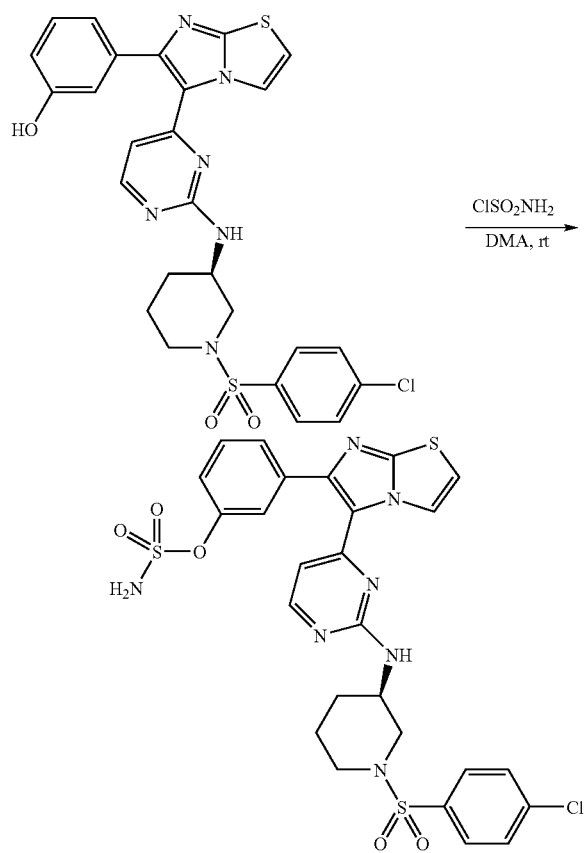

A solution of 3-{5-[2-({(3R)-1-[(4-chlorophenyl)sulfonyl]piperidin-3-yl}amino)pyrimidin-4-yl]imidazo[2,1-b][1,3]thiazol-6-yl}phenol (0.10 g, 0.176 mmol) in DMA (2.0 ml) was treated with sulfamoyl chloride (3-4 eq) in portions and monitor reaction for completion. After the reaction was complete dimethyl acetamide was removed under reduced pressure. Residue was taken in methanol (2.0 ml) and purified by preparative HPLC (using TFA as modifier). Pure fractions were collected and dried to give product as TFA salt (0.06 g, 53%). M.p.=133-35° C. 400 MHz $^1$H NMR (DMSO-$d_6$ at 60° C.) δ: 8.67 (br, 1H), 8.13 (d, J=5.2 Hz, 1H), 7.90 (brs, 2H), 7.77 (d, J=9.2 Hz 2H), 7.67 (d, J=9.2 Hz, 2H), 7.57 (m, 1H), 7.52 (m, 1H), 7.43 (d, J=4.4 Hz, 1H), 7.35-7.33 (m, 1H), 7.20 (m, 1H), 6.50 (d, J=5.2 Hz, 1H), 3.97 (br. s, 1H), 3.73 (m, 1H), 3.46 (d, J=10.8 Hz, 1H), 2.52 (m, 1H), 2.35 (t, J=10.8 Hz, 1H), 1.91-1.83 (m, 2H), 1.59 (m, 1H), 1.43-1.35 (m, 1H). LCMS: 647 [M+H]. Calc. for $C_{26}H_{24}N_7O_5S_3Cl.5.7TFA$: C 34.66; H, 2.31; N, 7.56. Found C, 35.08; H 1.78; N, 9.36.

Example 24

Measurement of RAF Activity

Materials: The RAF kinases and the anti-phospho MEK1/2 antibody were from Upstate (Charlottesville, Va.). The RAF substrate used was full length N-terminal GST-MEK-1, which was expressed in *E. coli* and purified in-house by HPLC. All proteins were aliquoted and stored at −80° C. Superblock™ in phosphate buffered saline (PBS) blocking reagent was form Pierce (cat. #37515). ATP was from Roche (cat. # 19035722). Alkaline Phosphatase-tagged goat anti-rabbit antibody was from Pierce (cat. # 31340).

Methods: All RAF biochemical assays were performed using an assay buffer containing 20 mM MOPS, 5 mM EGTA, 37.5 mM MgCl2, 1 mM DTT and 50 µM ATP. There was 6.25 ng/well mutant B-RAF and 7.5 ng/well MEK-1 in the final assay conditions. Compounds were serially diluted in assay buffer containing 1% DMSO and 20 µL of test compound at a concentration 3-fold more than the final concentration, and were added to a polypropylene V-well reaction plate. Vehicle control wells received buffer only with DMSO at equivalent concentrations to the test wells. In rapid succession, 20 µl of substrate was added (0.45 ng/µl MEK-1), followed by 20 µl of enzyme (0.375 ng/µl mutant B-RAF). These reaction plates were incubated at room temperature for 30 minutes. Capture of MEK-1 was initiated by transferring 50 µl of the reaction mixture to a Nunc Maxisorp™ microplate that is designed for non-specific protein capture. After 30 minute capture of MEK-1 at room temperature, this plate was washed with TBST (6×200 µL/well) to fully terminate the reaction. The plate was then blocked for 1 hour by the addition of 100 µl/well of Superblock™ in phosphate buffered saline (PBS) blocking reagent. Plate was again washed with TBST (6 times with 200 µL/well), followed by the addition of 70 µL/well of Upstate anti-phospho MEK 1/2 diluted 1:1000 in Pierce Superblock (PBS). After a 60 minute incubation, this plate was washed with TBST (6 times with 200 µL/well), and 70 µL of the secondary antibody (Pierce Alkaline Phosphatase tagged goat anti-rabbit) prepared at 1:4000 in Superblock, were added. After a 45 minute incubation at room temperature, the wells of the microplate were washed with TBST (6 times with 200 µL/well), and thereafter 100 µl/well of Attophos™ fluorescent alkaline phosphatase substrate was added according to the manufacturer's instructions (JBL Scientific). Fluorescence was read on a Perkin Elmer Envision multilabel reader, using the following filters: Excitation Filter: CFP430 nM, Emission Filter: Emission Filter 579 nM.

Example 25

Compounds of the present invention have been screened for their ability to inhibit all isoforms, both wild-type and mutant of RAF kinases (A-RAF, B-RAF and C-RAF) in general, and the mutant B-RAF (V600E) in particular in human cancer cells. A375 is a human melanoma cell line that harbors the most common B-RAF mutation-V600E found in human cancers. The ability of compounds to inhibit RAF kinases in this assay is correlated with the reduction of MEK and ERK phosphorylation, and is therefore a direct indicator of potential in vivo therapeutic activity.

Materials: A375 cells from ATCC were maintained at 37° C., 5% CO2 in DMEM media supplemented with 10% fetal bovine serum, penicillin/streptomycin and fungizone. (Invitrogen)

Methods: Test compounds were dissolved and diluted 1:1000 in DMSO. A375 cells were seeded in six-well tissue culture plates at 5-8×10$^5$ per well and cultured at 37° C. for 24 h. Cells were incubated with compounds for one hour before being lysed in EPage™ loading buffer (Invitrogen). Lysates were electrophoresed on 8% EPage™ gels and transferred to polyvinylidene difluoride membranes. After incubations with primary and secondary antibodies, the immunostained proteins were detected and quantitated by an Odyssey infrared imager (Li-cor). Analysis was performed by non-linear regression to generate a dose response curve. The calculated $IC_{50}$ value was the concentration of the test compound that causes a 50% decrease in phospho-MEK and phospho-ERK levels. The primary antibodies used were anti-MEK (Stressgen), anti-ERK (BD Biosciences), anti-phospho-ERK and anti-phospho-MEK (Cell Signaling). The secondary antibodies used were IRDYE800 anti-rabbit, IRDYE 800 anti-mouse (Rockland), AlexaFluor680 anti-mouse and AlexaFluro680 anti-rabbit (Invitrogen).

Figure 5:
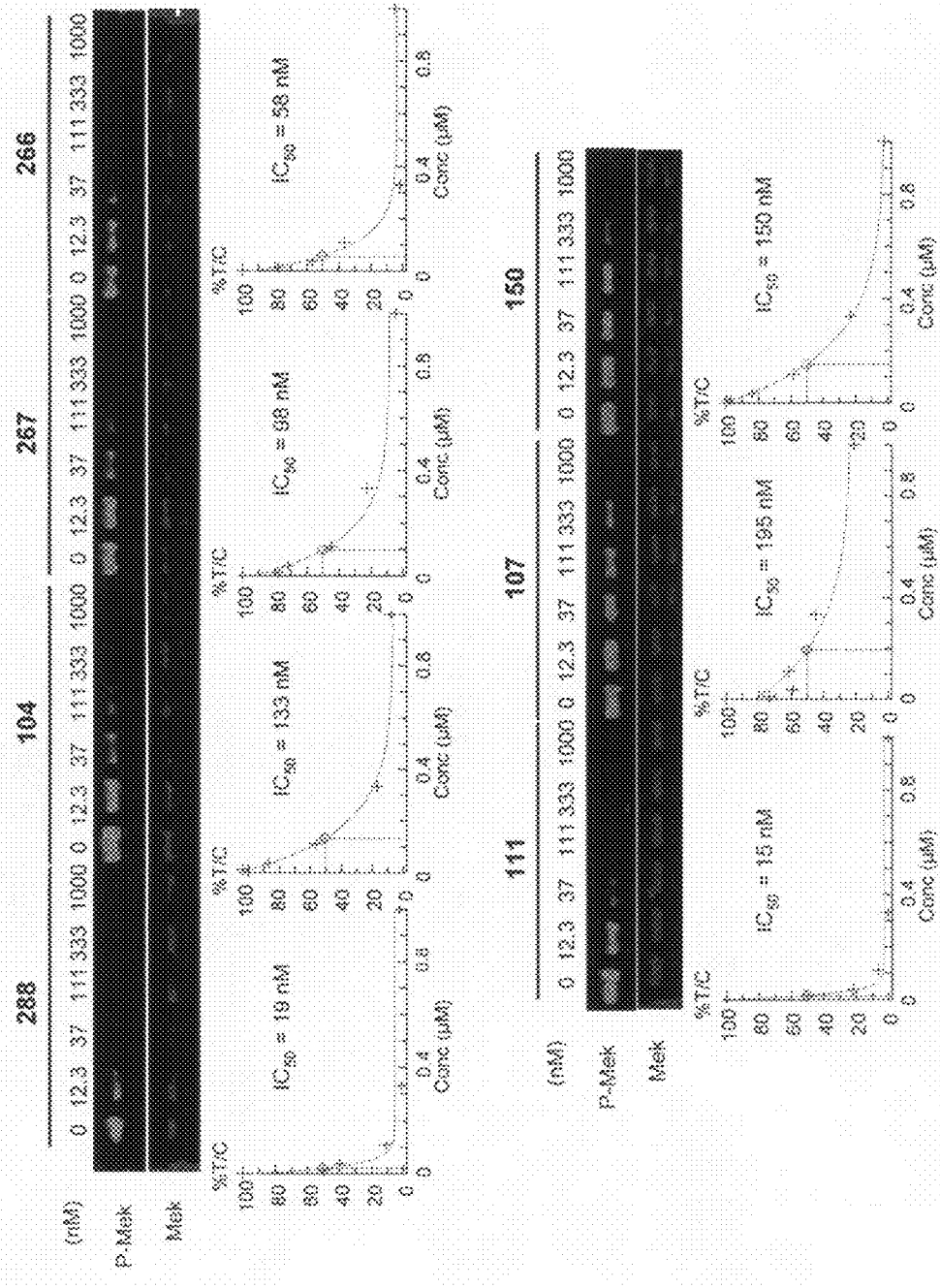
FIG. 5: Effects of compounds on Phospho-MEK in cancer cells. A375 cells were treated with 0, 12, 37, 111, 333 and 1000 nM of indicated compounds for 1 hr. The levels of Phospho-MEK and total-MEK were accessed by immunoblotting.
Figure 6:
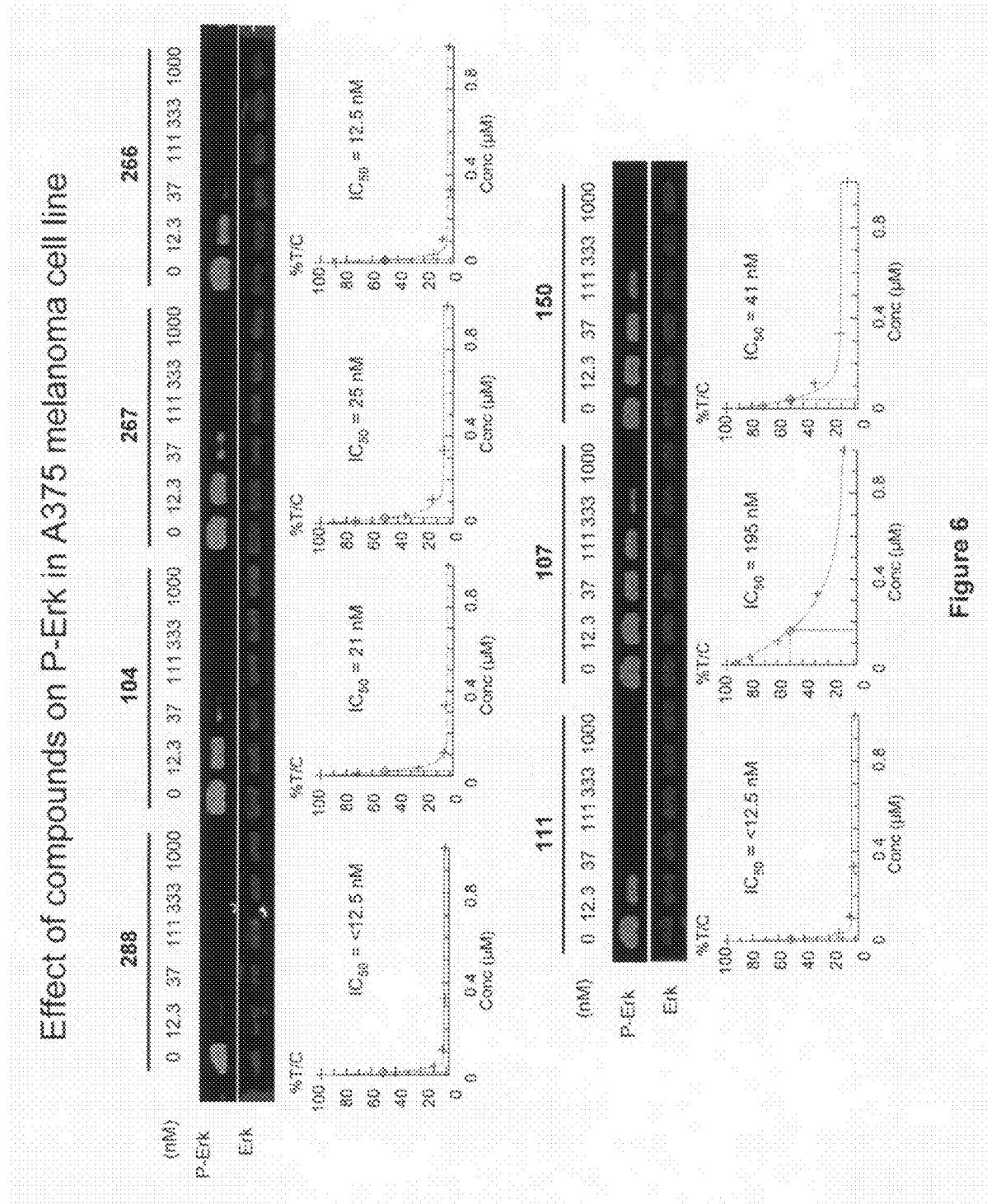
FIG. 6: Effects of compounds on Phospho-ERK in cancer cells. A375 cells were treated with 0, 12, 37, 111, 333 and 1000 nM of indicated compounds for 1 hr. The levels of Phospho-ERK and total-ERK were accessed by immunoblotting.

Compounds of the present invention reduce the levels of phospho-MEK and phospho-ERK through the inhibition of RAF kinases. The RAF/MEK/ERK pathway inhibition data for certain compounds of the present invention are shown in FIGS. 5 and 6.

Example 26

Compounds of the present invention have been tested for activity against a variety of cancer cell lines. The ability of compounds to inhibit cell growth in this assay is correlated with the reduction of dehydrogenase enzyme activity found in metabolically active cells.

Materials: A375 (a human melanoma cell line that harbors the B-RAF mutation V600E), Colo-205 (a human colon cancer cell line that harbors the B-RAF mutation V600E), DLD1 (a human colon cancer cell line that harbors the K-ras mutation G13D), SK-MEL-2 (a human melanoma cell line that harbors the N-ras mutation Q61R), SK-MEL-28 (a human melanoma cell line that harbors the B-RAF mutation V600E), and SW480 (a human colon cancer cell line that harbors the K-ras mutation G12V) cells from ATCC were maintained at 37° C., 5% $CO_2$ in DMEM media supplemented with 10% fetal bovine serum, penicillin/streptomycin and fungizone (Invitrogen). NCM460 (Incell), a normal colon epithelial cell line, and human mammary epithelial cells (Cambrex) were maintained at 37° C., 5% $CO_2$ in DMEM and HEBM media (Cambrex), respectively.

Methods: Test compounds were dissolved and diluted to 300× in DMSO then diluted 1:40 in DMEM. Cells were seeded into 96-well tissue culture plates at $2\text{-}5\times10^3$ per well and cultured at 37° C. for 24 h. Cells were incubated with test compounds for 72 hours followed by incubation with tetrazolium compound (3-(4,5-dimethylthiazol-2-yl)-5-(3-carboxymethoxyphenyl)-2-(4-sulfophenyl)-2H-tetrazolium, inner salt; MTS) and the electron coupling reagent, phenazine methosulfate (PMS) for 4 hr. MTS was chemically reduced by dehydrogenase in cells into formazan. The measurement of the absorbance of the formazan was assessed using an ENVISION™ (Perkin Elmer) microplate reader at 492 nm. The calculated $IC_{50}$ value is the concentration of the test compound that causes a 50% decrease in the absorbance.

Compounds of the present invention inhibit the growth of a variety of cancer cells. The data for certain compounds of the invention are shown in Table 1.

TABLE 1

| | $IC_{50}$ values of compound in various normal and cancer cell lines (units in µM) | | | | | | | |
|---|---|---|---|---|---|---|---|---|
| Compound # | HMEC Normal | NCM460 Normal | A375 B-RAF (V600E) | Colo205 B-RAF (V600E) | SKMEL28 B-RAF (V600E) | SKMEL2 NRAS (Q61R) | DLD1 KRAS (G13D) | SW480 KRAS (G12V) |
| 289 | 1.24 | 4.17 | 0.15 | 0.18 | 0.67 | 0.99 | 3.08 | 2.97 |
| 105 | 2.72 | 6.68 | 0.31 | 0.38 | 0.48 | 1.1 | 4.73 | 1.28 |
| 267 | 1.07 | 2.05 | 0.27 | 0.19 | 0.38 | 0.87 | 1.76 | 2.13 |
| 112 | 2.24 | 4.71 | 0.27 | 0.33 | 0.86 | 0.91 | 3.33 | 2.74 |
| 268 | 0.72 | 2.54 | 0.37 | 0.36 | 0.8 | 1.33 | 4.03 | 4.4 |

TABLE 2

Exemplary compounds of the invention

| Cmpd # | Structure | IUPAC name | Melting point (° C.) or LCMS | Mutant B-RAF $IC_{50}$ (uM) or % inhibition |
|---|---|---|---|---|
| 1 | 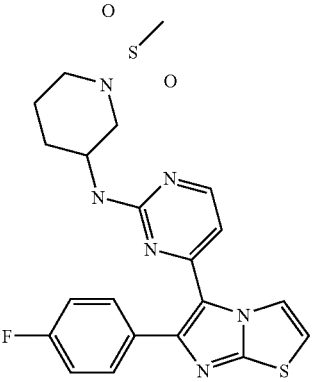 | 4-[6-(4-fluorophenyl)imidazo[2,1-b][1,3]thiazol-5-yl]-N-[1-(methylsulfonyl)piperidin-3-yl]pyrimidin-2-amine | 208-209 | 62 @ 10 uM |

TABLE 2-continued

Exemplary compounds of the invention

| Cmpd # | Structure | IUPAC name | Melting point (° C.) or LCMS | Mutant B-RAF IC$_{50}$ (uM) or % inhibition |
|---|---|---|---|---|
| 2 | 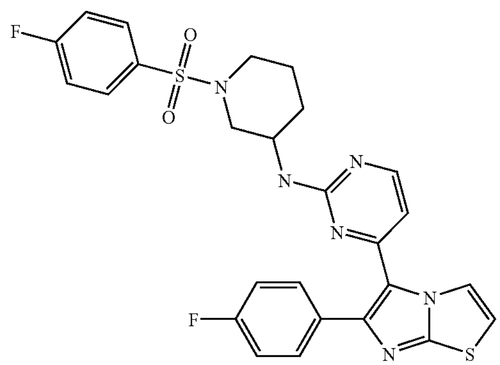 | 4-[6-(4-fluorophenyl)imidazo[2,1-b][1,3]thiazol-5-yl]-N-{1-[(4-fluorophenyl)sulfonyl]piperidin-3-yl}pyrimidin-2-amine | 196-197 | 0.458 |
| 3 | 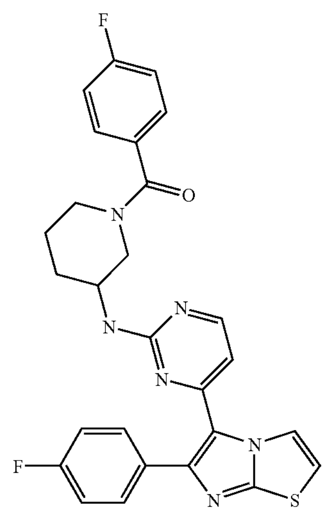 | N-[1-(4-fluorobenzoyl)piperidin-3-yl]-4-[6-(4-fluorophenyl)imidazo[2,1-b][1,3]thiazol-5-yl]pyrimidin-2-amine | 226-228 | 45 @ 10 uM |
| 4 | 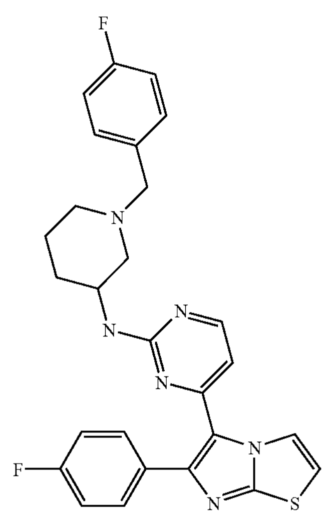 | N-[1-(4-fluorobenzyl)piperidin-3-yl]-4-[6-(4-fluorophenyl)imidazo[2,1-b][1,3]thiazol-5-yl]pyrimidin-2-amine | 131-133 | 55 @ 10 uM |

TABLE 2-continued

Exemplary compounds of the invention

| Cmpd # | Structure | IUPAC name | Melting point (° C.) or LCMS | Mutant B-RAF IC$_{50}$ (uM) or % inhibition |
|---|---|---|---|---|
| 5 | 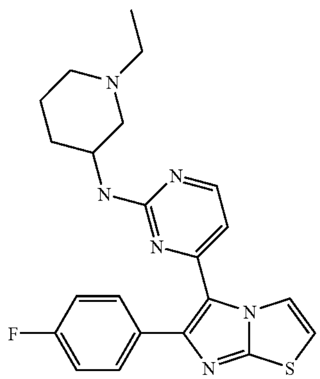 | N-(1-ethylpiperidin-3-yl)-4-[6-(4-fluorophenyl)imidazo[2,1-b][1,3]thiazol-5-yl]pyrimidin-2-amine | 115-117 | 54 @ 10 uM |
| 6 | 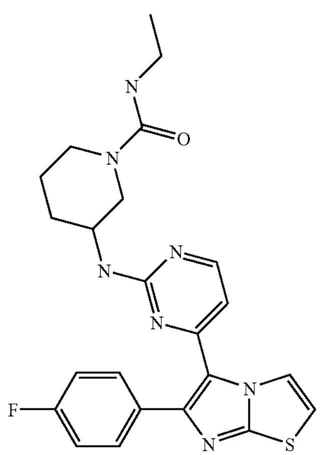 | N-ethyl-3-({4-[6-(4-fluorophenyl)imidazo[2,1-b][1,3]thiazol-5-yl]pyrimidin-2-yl}amino)piperidine-1-carboxamide | 128-130 | 54 @ 10 uM |
| 7 | 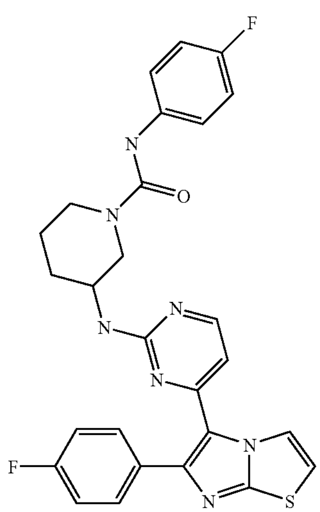 | N-(4-fluorophenyl)-3-({4-[6-(4-fluorophenyl)imidazo[2,1-b][1,3]thiazol-5-yl]pyrimidin-2-yl}amino)piperidine-1-carboxamide | 221-223 | 49 @ 10 uM |

TABLE 2-continued

Exemplary compounds of the invention

| Cmpd # | Structure | IUPAC name | Melting point (° C.) or LCMS | Mutant B-RAF IC$_{50}$ (uM) or % inhibition |
|---|---|---|---|---|
| 8 | Chiral | 4-[6-(4-fluorophenyl)imidazo[2,1-b][1,3]thiazol-5-yl]-N-{(3R)-1-[(4-fluorophenyl)sulfonyl]piperidin-3-yl}pyrimidin-2-amine | 145-148 | 0.023 |
| 9 | Chiral | 4-[6-(4-fluorophenyl)imidazo[2,1-b][1,3]thiazol-5-yl]-N-{(3S)-1-[(4-fluorophenyl)sulfonyl]piperidin-3-yl}pyrimidin-2-amine | 141-143 | 2.94 |
| 10 | Chiral | 4-[6-(4-fluorophenyl)imidazo[2,1-b][1,3]thiazol-5-yl]-N-[(3S)-piperidin-3-yl]pyrimidin-2-amine | 208-210 | 51 @ 10 uM |
| 11 | Chiral | 4-[6-(4-fluorophenyl)imidazo[2,1-b][1,3]oxazol-5-yl]-N-{(3R)-1-[(4-fluorophenyl)sulfonyl]piperidin-3-yl}pyrimidin-2-amine | 135-138 | 0.207 |

TABLE 2-continued

Exemplary compounds of the invention

| Cmpd # | Structure | IUPAC name | Melting point (° C.) or LCMS | Mutant B-RAF IC$_{50}$ (uM) or % inhibition |
|---|---|---|---|---|
| 12 | Chiral | 4-[6-(4-fluorophenyl)imidazo[2,1-b][1,3]oxazol-5-yl]-N-[(3R)-piperidin-3-yl]pyrimidin-2-amine | 184-186 | 46 @ 10 uM |
| 13 | Chiral | 4-[6-(4-fluorophenyl)imidazo[2,1-b][1,3]oxazol-5-yl]-N-[(3S)-piperidin-3-yl]pyrimidin-2-amine | 202-205 | 30 @ 10 uM |
| 14 | 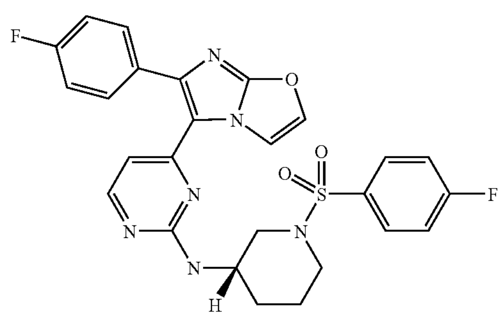 | 4-[6-(4-fluorophenyl)imidazo[2,1-b][1,3]oxazol-5-yl]-N-{(3S)-1-[(4-fluorophenyl)sulfonyl]piperidin-3-yl}pyrimidin-2-amine | 115-117 | >3.0 |
| 15 | 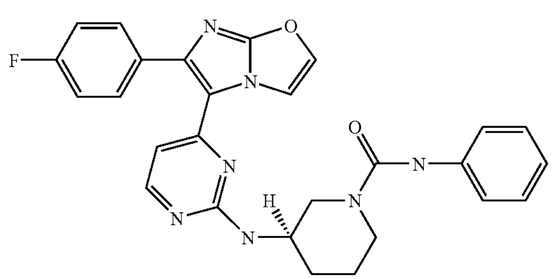 | (3R)-3-({4-[6-(4-fluorophenyl)imidazo[2,1-b][1,3]oxazol-5-yl]pyrimidin-2-yl}amino)-N-phenyl-piperidine-1-carboxamide | 141-144 | 28 @ 10 uM |

TABLE 2-continued

Exemplary compounds of the invention

| Cmpd # | Structure | IUPAC name | Melting point (° C.) or LCMS | Mutant B-RAF IC$_{50}$ (uM) or % inhibition |
|---|---|---|---|---|
| 16 | 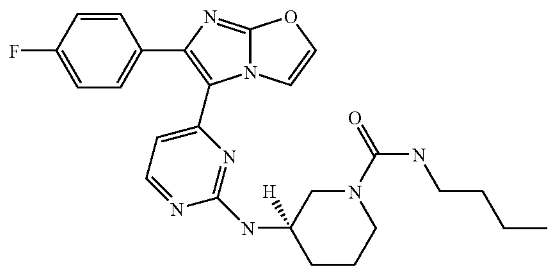 | (3R)-N-butyl-3-({4-[6-(4-fluorophenyl)imidazo[2,1-b][1,3]oxazol-5-yl]pyrimidin-2-yl}amino)piperidine-1-carboxamide | 108-111 | 44 @ 10 uM |
| 17 | 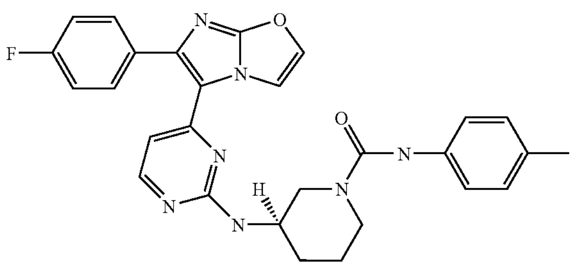 | (3R)-3-({4-[6-(4-fluorophenyl)imidazo[2,1-b][1,3]oxazol-5-yl]pyrimidin-2-yl}amino)-N-(4-methylphenyl)piperidine-1-carboxamide | 129-132 | 16 @ 10 uM |
| 18 | 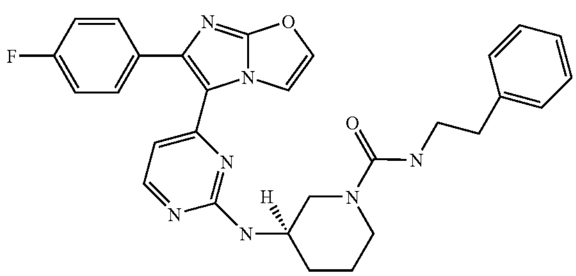 | (3R)-3-({4-[6-(4-fluorophenyl)imidazo[2,1-b][1,3]oxazol-5-yl]pyrimidin-2-yl}amino)-N-(2-phenylethyl)piperidine-1-carboxamide | 105-108 | 18 @ 10 uM |
| 19 | 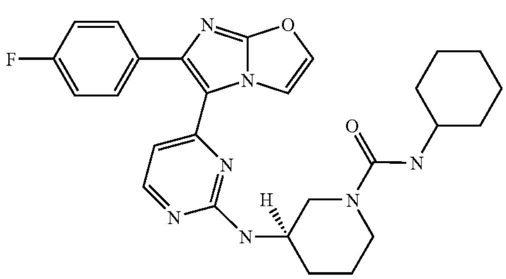 | (3R)-N-cyclohexyl-3-({4-[6-(4-fluorophenyl)imidazo[2,1-b][1,3]oxazol-5-yl]pyrimidin-2-yl}amino)piperidine-1-carboxamide | 130-132 | 46 @ 10 uM |
| 20 | 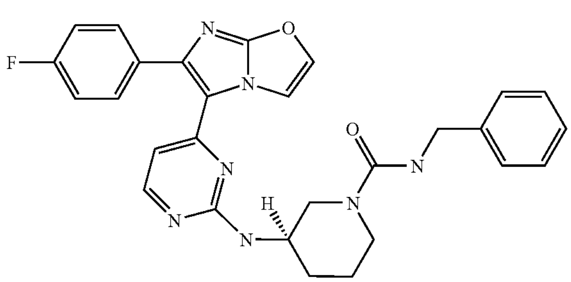 | (3R)-N-benzyl-3-({4-[6-(4-fluorophenyl)imidazo[2,1-b][1,3]oxazol-5-yl]pyrimidin-2-yl}amino)piperidine-1-carboxamide | 116-120 | 24 @ 10 uM |

TABLE 2-continued

Exemplary compounds of the invention

| Cmpd # | Structure | IUPAC name | Melting point (° C.) or LCMS | Mutant B-RAF IC$_{50}$ (uM) or % inhibition |
|---|---|---|---|---|
| 21 | 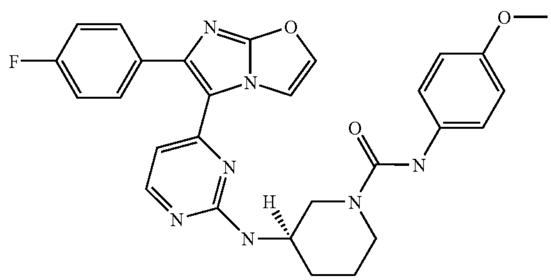 | (3R)-3-({4-[6-(4-fluorophenyl)imidazo[2,1-b][1,3]oxazol-5-yl]pyrimidin-2-yl}amino)-N-(4-methoxyphenyl)piperidine-1-carboxamide | 123-127 | 53 @ 10 uM |
| 22 | 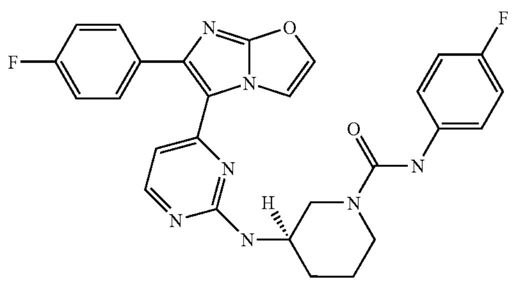 | (3R)-N-(4-fluorophenyl)-3-({4-[6-(4-fluorophenyl)imidazo[2,1-b][1,3]oxazol-5-yl]pyrimidin-2-yl}amino)piperidine-1-carboxamide | 134-137 | 35 @ 10 uM |
| 23 | 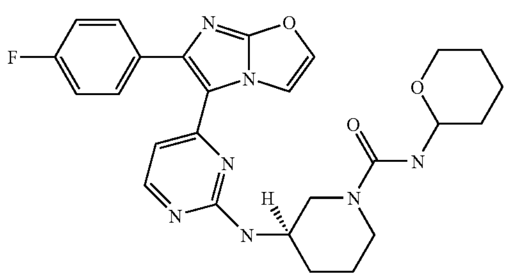 | (3R)-3-({4-[6-(4-fluorophenyl)imidazo[2,1-b][1,3]oxazol-5-yl]pyrimidin-2-yl}amino)-N-(tetrahydro-2H-pyran-2-yl)piperidine-1-carboxamide | 140-143 | 48 @ 10 uM |
| 24 | 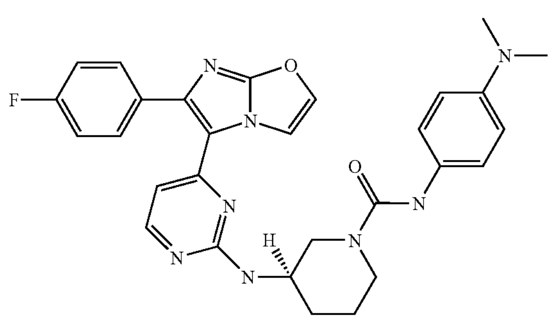 | (3R)-N-[4-(dimethylamino)phenyl]-3-({4-[6-(4-fluorophenyl)imidazo[2,1-b][1,3]oxazol-5-yl]pyrimidin-2-yl}amino)piperidine-1-carboxamide | 145-148 | 60 @ 10 uM |
| 25 | 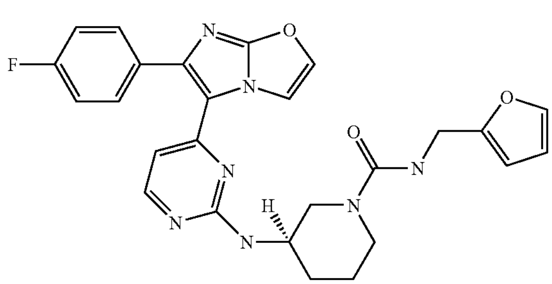 | (3R)-3-({4-[6-(4-fluorophenyl)imidazo[2,1-b][1,3]oxazol-5-yl]pyrimidin-2-yl}amino)-N-(2-furylmethyl)piperidine-1-carboxamide | 112-115 | 35 @ 10 uM |

TABLE 2-continued
Exemplary compounds of the invention
| Cmpd # | Structure | IUPAC name | Melting point (° C.) or LCMS | Mutant B-RAF IC$_{50}$ (uM) or % inhibition |
|---|---|---|---|---|
| 26 | Chiral 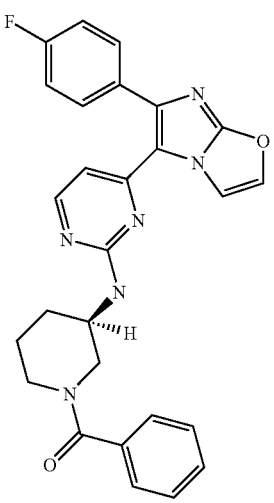 | N-[(3R)-1-benzoylpiperidin-3-yl]-4-[6-(4-fluorophenyl)imidazo[2,1-b][1,3]oxazol-5-yl]pyrimidin-2-amine | 131-133 | 0.195 |
| 27 | Chiral 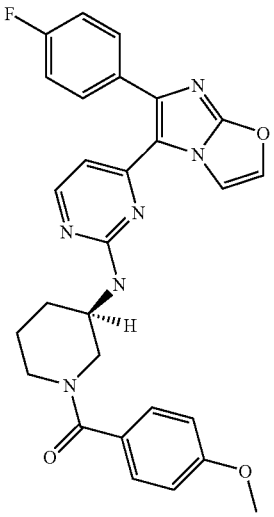 | 4-[6-(4-fluorophenyl)imidazo[2,1-b][1,3]oxazol-5-yl]-N-[(3R)-1-(4-methoxybenzoyl)piperidin-3-yl]pyrimidin-2-amine | 155-156 | 4.89 |

TABLE 2-continued

Exemplary compounds of the invention

| Cmpd # | Structure | IUPAC name | Melting point (° C.) or LCMS | Mutant B-RAF IC$_{50}$ (uM) or % inhibition |
|---|---|---|---|---|
| 28 | Chiral | N-[(3R)-1-(4-fluorobenzoyl)piperidin-3-yl]-4-[6-(4-fluorophenyl)imidazo[2,1-b][1,3]oxazol-5-yl]pyrimidin-2-amine | 184-185 | 0.184 |
| 29 | Chiral | N-{(3R)-1-[(4-chlorophenoxy)acetyl]piperidin-3-yl}-4-[6-(4-fluorophenyl)imidazo[2,1-b][1,3]oxazol-5-yl]pyrimidin-2-amine | 102-103 | 1.82 |

TABLE 2-continued
Exemplary compounds of the invention
| Cmpd # | Structure | IUPAC name | Melting point (° C.) or LCMS | Mutant B-RAF IC$_{50}$ (uM) or % inhibition |
|---|---|---|---|---|
| 30 | Chiral 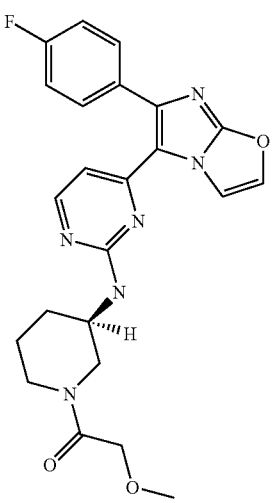 | 4-[6-(4-fluorophenyl)imidazo[2,1-b][1,3]oxazol-5-yl]-N-[(3R)-1-(methoxyacetyl)piperidin-3-yl]pyrimidin-2-amine | 161-162 | 0.711 |
| 31 | Chiral 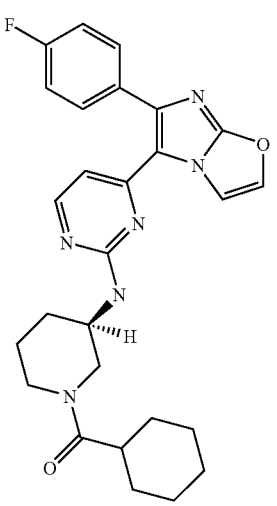 | N-[(3R)-1-(cyclohexylcarbonyl)piperidin-3-yl]-4-[6-(4-fluorophenyl)imidazo[2,1-b][1,3]oxazol-5-yl]pyrimidin-2-amine | 129-131 | 2.95 |

TABLE 2-continued

Exemplary compounds of the invention

| Cmpd # | Structure | IUPAC name | Melting point (° C.) or LCMS | Mutant B-RAF IC$_{50}$ (uM) or % inhibition |
|---|---|---|---|---|
| 32 | Chiral | 4-[6-(4-fluorophenyl)imidazo[2,1-b][1,3]oxazol-5-yl]-N-[(3R)-1-isonicotinoylpiperidin-3-yl]pyrimidin-2-amine | 196-198 | 0.362 |
| 33 | Chiral | 4-[6-(4-fluorophenyl)imidazo[2,1-b][1,3]oxazol-5-yl]-N-[(3R)-1-(2-furoyl)piperidin-3-yl]pyrimidin-2-amine | 110-112 | 2.17 |

TABLE 2-continued

Exemplary compounds of the invention

| Cmpd # | Structure | IUPAC name | Melting point (° C.) or LCMS | Mutant B-RAF IC$_{50}$ (uM) or % inhibition |
|---|---|---|---|---|
| 34 | Chiral | 4-[6-(4-fluorophenyl)imidazo[2,1-b][1,3]oxazol-5-yl]-N-[(3R)-1-propionylpiperidin-3-yl]pyrimidin-2-amine | 173-174 | 1.58 |
| 35 | Chiral | N-[(3R)-1-(aminoacetyl)piperidin-3-yl]-4-[6-(4-fluorophenyl)imidazo[2,1-b][1,3]oxazol-5-yl]pyrimidin-2-amine | 225-230 | 11 @ 10 um |
| 36 | Chiral | N-[(3R)-1-(2-amino-2-methylpropanoyl)piperidin-3-yl]-4-[6-(4-fluorophenyl)imidazo[2,1-b][1,3]oxazol-5-yl]pyrimidin-2-amine | 215-218 | 4.52 |

TABLE 2-continued

Exemplary compounds of the invention

| Cmpd # | Structure | IUPAC name | Melting point (° C.) or LCMS | Mutant B-RAF IC$_{50}$ (uM) or % inhibition |
|---|---|---|---|---|
| 37 | Chiral | 4-[6-(4-fluorophenyl)imidazo[2,1-b][1,3]oxazol-5-yl]-N-[(3R)-1-L-prolylpiperidin-3-yl]pyrimidin-2-amine | 210-212 | >5.0 |
| 38 | Chiral | 4-[6-(4-fluorophenyl)imidazo[2,1-b][1,3]oxazol-5-yl]-N-[(3R)-1-(3-phenylpropanoyl)piperidin-3-yl]pyrimidin-2-amine | 94-95 | 2.9 |
| 39 | Chiral | N-{(3R)-1-[4-(dimethylamino)benzoyl]piperidin-3-yl}-4-[6-(4-fluorophenyl)imidazo[2,1-b][1,3]oxazol-5-yl]pyrimidin-2-amine | 145-146 | 0.477 |
| 40 | Chiral | 4-[6-(4-fluorophenyl)imidazo[2,1-b][1,3]oxazol-5-yl]-N-[(3R)-1-(3-methylbutanoyl)piperidin-3-yl]pyrimidin-2-amine | 89-90 | 0.142 |

TABLE 2-continued

Exemplary compounds of the invention

| Cmpd # | Structure | IUPAC name | Melting point (° C.) or LCMS | Mutant B-RAF IC$_{50}$ (uM) or % inhibition |
|---|---|---|---|---|
| 41 | Chiral | 4-[6-(4-fluorophenyl)imidazo[2,1-b][1,3]oxazol-5-yl]-N-[(3R)-1-(morpholin-4-ylcarbonyl)piperidin-3-yl]pyrimidin-2-amine | 102-105 | 38 @ 10 uM |
| 42 | Chiral | 4-[6-(4-fluorophenyl)imidazo[2,1-b][1,3]oxazol-5-yl]-N-[(3R)-1-(phenylsulfonyl)piperidin-3-yl]pyrimidin-2-amine | 143-144 | 68 @ 10 uM |
| 43 | Chiral | N-{(3R)-1-[(4-chlorophenyl)sulfonyl]piperidin-3-yl}-4-[6-(4-fluorophenyl)imidazo[2,1-b][1,3]oxazol-5-yl]pyrimidin-2-amine | 146-147 | 0.143 |
| 44 | Chiral | 4-[6-(4-fluorophenyl)imidazo[2,1-b][1,3]oxazol-5-yl]-N-{(3R)-1-[(4-methoxyphenyl)sulfonyl]piperidin-3-yl}pyrimidin-2-amine | 233-234 | 45 @ 10 uM |

TABLE 2-continued

Exemplary compounds of the invention

| Cmpd # | Structure | IUPAC name | Melting point (° C.) or LCMS | Mutant B-RAF IC$_{50}$ (uM) or % inhibition |
|---|---|---|---|---|
| 45 | Chiral | 4-[6-(4-fluorophenyl)imidazo[2,1-b][1,3]oxazol-5-yl]-N-{(3R)-1-[(4-methylphenyl)sulfonyl]piperidin-3-yl}pyrimidin-2-amine | 194-195 | 0.59 |
| 46 | Chiral | 4-[6-(4-fluorophenyl)imidazo[2,1-b][1,3]oxazol-5-yl]-N-((3R)-1-{[3-(trifluoromethyl)phenyl]sulfonyl}piperidin-3-yl)pyrimidin-2-amine | 125-127 | 19 @ 10 uM |
| 47 | Chiral | N-{(3R)-1-[(3-chloro-4-fluorophenyl)sulfonyl]piperidin-3-yl}-4-[6-(4-fluorophenyl)imidazo[2,1-b][1,3]oxazol-5-yl]pyrimidin-2-amine | 135-136 | 0.963 |

TABLE 2-continued
Exemplary compounds of the invention
| Cmpd # | Structure | IUPAC name | Melting point (° C.) or LCMS | Mutant B-RAF IC$_{50}$ (uM) or % inhibition |
|---|---|---|---|---|
| 48 | 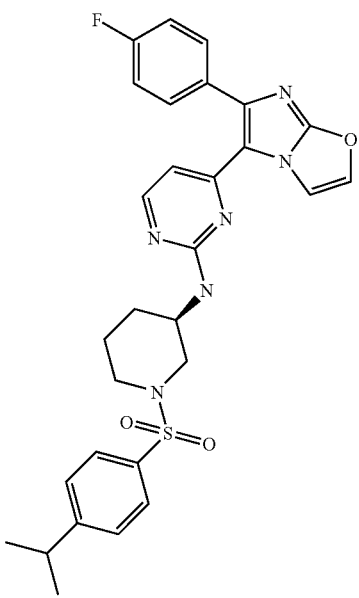 Chiral | 4-[6-(4-fluorophenyl)imidazo[2,1-b][1,3]oxazol-5-yl]-N-{(3R)-1-[(4-isopropylphenyl)sulfonyl]piperidin-3-yl}pyrimidin-2-amine | 199-200 | 3.02 |
| 49 | 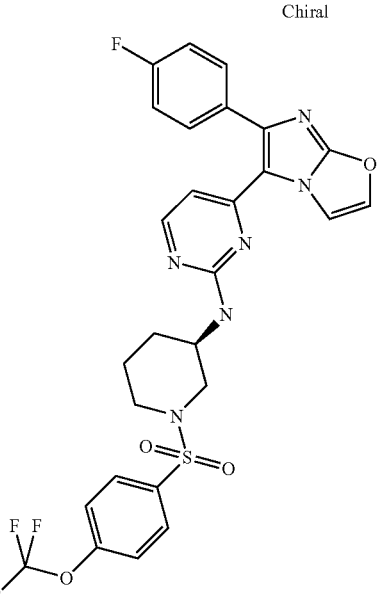 Chiral | 4-[6-(4-fluorophenyl)imidazo[2,1-b][1,3]oxazol-5-yl]-N-((3R)-1-{(4-(trifluoromethoxy)phenyl]sulfonyl}piperidin-3-yl)pyrimidin-2-amine | 164-165 | 32 @ 10 uM |

TABLE 2-continued
Exemplary compounds of the invention
| Cmpd # | Structure | IUPAC name | Melting point (° C.) or LCMS | Mutant B-RAF IC$_{50}$ (uM) or % inhibition |
|---|---|---|---|---|
| 50 | 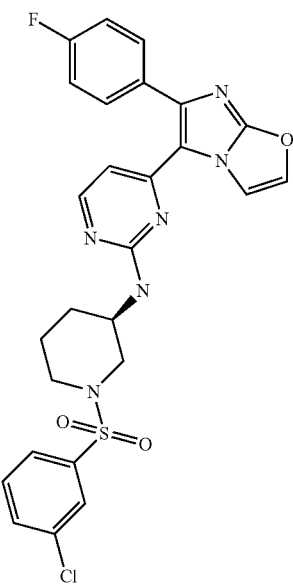 Chiral | N-{(3R)-1-[(3-chlorophenyl)sulfonyl]piperidin-3-yl}-4-[6-(4-fluorophenyl)imidazo[2,1-b][1,3]oxazol-5-yl]pyrimidin-2-amine | 165-166 | 35 @ 10 uM |
| 51 | 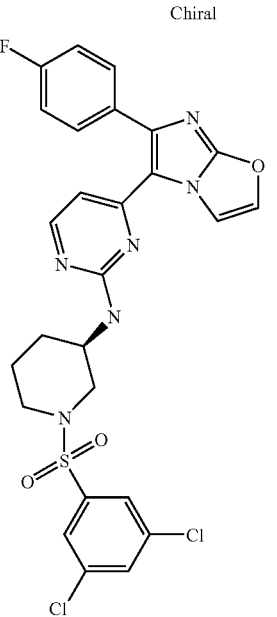 Chiral | N-{(3R)-1-[(3,5-dichlorophenyl)sulfonyl]piperidin-3-yl}-4-[6-(4-fluorophenyl)imidazo[2,1-b][1,3]oxazol-5-yl]pyrimidin-2-amine | 173-174 | 25 @ 10 uM |

TABLE 2-continued

Exemplary compounds of the invention

| Cmpd # | Structure | IUPAC name | Melting point (° C.) or LCMS | Mutant B-RAF IC$_{50}$ (uM) or % inhibition |
|---|---|---|---|---|
| 52 | Chiral | 4-[6-(4-fluorophenyl)imidazo[2,1-b][1,3]oxazol-5-yl]-N-{(3R)-1-[(3-fluorophenyl)sulfonyl]piperidin-3-yl}pyrimidin-2-amine | 134-135 | 55 @ 10 uM |
| 53 | Chiral | 4-(6-(4-fluorophenyl)imidazo[2,1-b][1,3]oxazol-5-yl]-N-{(3R)-1-[(2-methylphenyl)sulfonyl]piperidin-3-yl}pyrimidin-2-amine | 155-156 | 42 @ 10 uM |
| 54 | Chiral | N-{(3R)-1-[(2,6-difluorophenyl)sulfonyl]piperidin-3-yl}-4-[6-(4-fluorophenyl)imidazo[2,1-b][1,3]oxazol-5-yl]pyrimidin-2-amine | 192-193 | 47 @ 10 uM |

TABLE 2-continued
Exemplary compounds of the invention
| Cmpd # | Structure | IUPAC name | Melting point (° C.) or LCMS | Mutant B-RAF IC$_{50}$ (uM) or % inhibition |
|---|---|---|---|---|
| 55 | Chiral 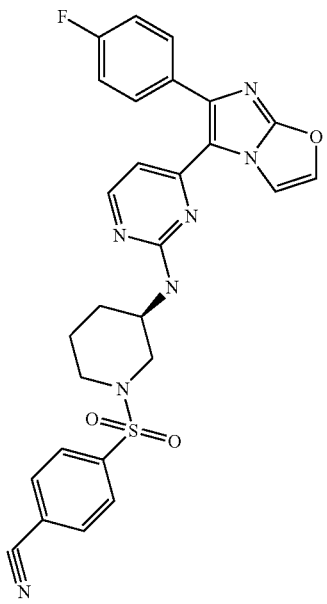 | 4-{[(3R)-3-({4-[6-(4-fluorophenyl)imidazo[2,1-b][1,3]oxazol-5-yl]pyrimidin-2-yl}amino)piperidin-1-yl]sulfonyl}benzonitrile | 144-145 | 0.63 |
| 56 | Chiral 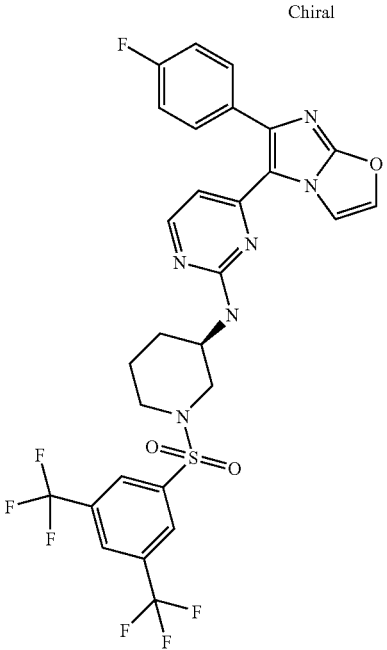 | N-((3R)-1-{[3,5-bis(trifluoromethyl)phenyl]sulfonyl}piperidin-3-yl)-4-[6-(4-fluorophenyl)imidazo[2,1-b][1,3]oxazol-5-yl]pyrimidin-2-amine | 185-186 | 57 @ 10 uM |

TABLE 2-continued

Exemplary compounds of the invention

| Cmpd # | Structure | IUPAC name | Melting point (° C.) or LCMS | Mutant B-RAF IC$_{50}$ (uM) or % inhibition |
|---|---|---|---|---|
| 57 | Chiral | 4-[6-(4-fluorophenyl)imidazo[2,1-b][1,3]oxazol-5-yl]-N-{(3R)-1-[(3-methoxyphenyl)sulfonyl]piperidin-3-yl}pyrimidin-2-amine | 188-190 | 34 @ 10 uM |
| 58 | Chiral | 4-[6-(4-fluorophenyl)imidazo[2,1-b][1,3]oxazol-5-yl]-N-((3R)-1-{[4-(trifluoromethyl)phenyl]sulfonyl}piperidin-3-yl)pyrimidin-2-amine | 153-154 | 0.403 |
| 59 | Chiral | 4-{[(3R)-3-({4-[6-(4-fluorophenyl)imidazo[2,1-b][1,3]oxazol-5-yl]pyrimidin-2-yl}amino)piperidin-1-yl]sulfonyl}benzoic acid | 300 | 0.576 |

TABLE 2-continued

Exemplary compounds of the invention

| Cmpd # | Structure | IUPAC name | Melting point (° C.) or LCMS | Mutant B-RAF IC$_{50}$ (uM) or % inhibition |
|---|---|---|---|---|
| 60 | Chiral | 4-[6-(4-fluorophenyl)imidazo[2,1-b][1,3]oxazol-5-yl]-N-{(3R)-1-[(4-phenoxyphenyl)sulfonyl]piperidin-3-yl}pyrimidin-2-amine | 279-280 | 15 @ 10 uM |
| 61 | Chiral | N-{(3R)-1-[(5-chloro-2-methoxyphenyl)sulfonyl]piperidin-3-yl}-4-[6-(4-fluorophenyl)imidazo[2,1-b][1,3]oxazol-5-yl]pyrimidin-2-amine | 173-174 | 37 @ 10 uM |
| 62 | Chiral | 4-[6-(4-fluorophenyl)imidazo[2,1-b][1,3]thiazol-5-yl]-N-[(3R)-piperidin-3-yl]pyrimidin-2-amine | 191-194 | 45 @ 10 uM |

TABLE 2-continued

Exemplary compounds of the invention

| Cmpd # | Structure | IUPAC name | Melting point (° C.) or LCMS | Mutant B-RAF IC$_{50}$ (uM) or % inhibition |
|---|---|---|---|---|
| 63 | Chiral | 3-(4-{[(3R)-3-({4-[6-(4-fluorophenyl)imidazo[2,1-b][1,3]oxazol-5-yl]pyrimidin-2-yl}amino)piperidin-1-yl]sulfonyl}phenyl)propanoic acid | 268-269 | 0.441 |
| 64 | Chiral | N-(5-{[(3R)-3-({4-[6-(4-fluorophenyl)imidazo[2,1-b][1,3]oxazol-5-yl]pyrimidin-2-yl}amino)piperidin-1-yl]sulfonyl}-4-methyl-1,3-thiazol-2-yl)acetamide | 176-177 | 58 @ 10 uM |
| 65 | Chiral | N-{(3R)-1-[(2,4-dimethyl-1,3-thiazol-5-yl)sulfonyl]piperidin-3-yl}-4-[6-(4-fluorophenyl)imidazo[2,1-b][1,3]oxazol-5-yl]pyrimidin-2-amine | 220-222 | 42 @ 10 uM |

TABLE 2-continued

Exemplary compounds of the invention

| Cmpd # | Structure | IUPAC name | Melting point (° C.) or LCMS | Mutant B-RAF IC$_{50}$ (uM) or % inhibition |
|---|---|---|---|---|
| 66 | Chiral | N-{(3R)-1-[(1,2-dimethyl-1H-imidazol-4-yl)sulfonyl]piperidin-3-yl}-4-[6-(4-fluorophenyl)imidazo[2,1-b][1,3]oxazol-5-yl]pyrimidin-2-amine | 141-143 | 70 @ 10 uM |
| 67 | Chiral | (3R)-3-({4-[6-(4-fluorophenyl)imidazo[2,1-b][1,3]oxazol-5-yl]pyrimidin-2-yl}amino)-N-[5-methyl-2-(trifluoromethyl)-3-furyl]piperidine-1-carboxamide | 120-122 | 29 @ 10 uM |
| 68 | Chiral | (3R)-N-(cyclohexylmethyl)-3-({4-[6-(4-fluorophenyl)imidazo[2,1-b][1,3]oxazol-5-yl]pyrimidin-2-yl}amino)piperidine-1-carboxamide | 118-120 | 42 @ 10 uM |

TABLE 2-continued

Exemplary compounds of the invention

| Cmpd # | Structure | IUPAC name | Melting point (° C.) or LCMS | Mutant B-RAF IC$_{50}$ (uM) or % inhibition |
|---|---|---|---|---|
| 69 | Chiral | (3R)-N-(2,4-dimethoxyphenyl)-3-({4-[6-(4-fluorophenyl)imidazo[2,1-b][1,3]oxazol-5-yl]pyrimidin-2-yl}amino)piperidine-1-carboxamide | 113-116 | 42 @ 10 uM |
| 70 | Chiral | (3R)-N-(5-chloro-2-methoxyphenyl)-3-({4-[6-(4-fluorophenyl)imidazo[2,1-b][1,3]oxazol-5-yl]pyrimidin-2-yl}amino)piperidine-1-carboxamide | 127-130 | 49 @ 10 uM |
| 71 | Chiral | (3R)-N-[2-(4-fluorophenyl)ethyl]-3-({4-[6-(4-fluorophenyl)imidazo[2,1-b][1,3]oxazol-5-yl]pyrimidin-2-yl}amino)piperidine-1-carboxamide | 114-116 | 16 @ 10 uM |

TABLE 2-continued

Exemplary compounds of the invention

| Cmpd # | Structure | IUPAC name | Melting point (° C.) or LCMS | Mutant B-RAF IC$_{50}$ (uM) or % inhibition |
|---|---|---|---|---|
| 72 | Chiral | (3R)-3-({4-[6-(4-fluorophenyl)imidazo[2,1-b][1,3]oxazol-5-yl]pyrimidin-2-yl}amino)-N-[(1R)-1-phenylethyl]piperidine-1-carboxamide | 121-122 | 53 @ 10 uM |
| 73 | Chiral | (3R)-N-(3,4-difluorophenyl)-3-({4-[6-(4-fluorophenyl)imidazo[2,1-b][1,3]oxazol-5-yl]pyrimidin-2-yl}amino)piperidine-1-carboxamide | 132-134 | 37 @ 10 uM |
| 74 | Chiral | (3R)-N-(2-fluorophenyl)-3-({4-[6-(4-fluorophenyl)imidazo[2,1-b][1,3]oxazol-5-yl]pyrimidin-2-yl}amino)piperidine-1-carboxamide | 112-115 | 35 @ 10 uM |

TABLE 2-continued

Exemplary compounds of the invention

| Cmpd # | Structure | IUPAC name | Melting point (° C.) or LCMS | Mutant B-RAF IC$_{50}$ (uM) or % inhibition |
|---|---|---|---|---|
| 75 | Chiral | (3R)-3-({4-[6-(4-fluorophenyl)imidazo[2,1-b][1,3]oxazol-5-yl]pyrimidin-2-yl}amino)-N-(2-methoxy-4-nitrophenyl)piperidine-1-carboxamide | 154-156 | >10 |
| 76 | Chiral | (3R)-N-(4-fluorobenzyl)-3-({4-[6-(4-fluorophenyl)imidazo[2,1-b][1,3]oxazol-5-yl]pyrimidin-2-yl}amino)piperidine-1-carboxamide | 111-113 | 36 @ 10 uM |
| 77 | Chiral | 4-[6-(3-methoxyphenyl)imidazo[2,1-b][1,3]thiazol-5-yl]-N-[(3R)-piperidin-3-yl]pyrimidin-2-amine | 220-225 | 1.81 |

TABLE 2-continued

Exemplary compounds of the invention

| Cmpd # | Structure | IUPAC name | Melting point (° C.) or LCMS | Mutant B-RAF IC$_{50}$ (uM) or % inhibition |
|---|---|---|---|---|
| 78 | Chiral 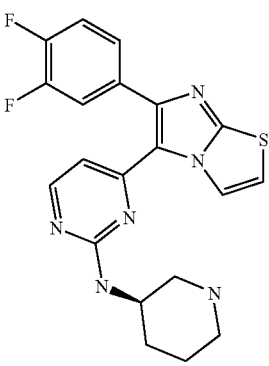 | 4-[6-(3,4-difluorophenyl)imidazo[2,1-b][1,3]thiazol-5-yl]-N-[(3R)-piperidin-3-yl]pyrimidin-2-amine | 195-198 | 1.26 |
| 79 | Chiral 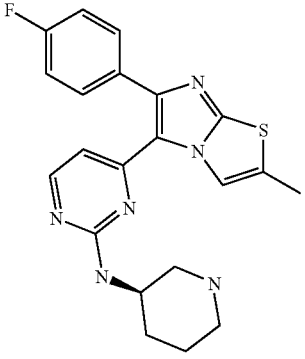 | 4-[6-(4-fluorophenyl)-2-methylimidazo[2,1-b][1,3]thiazol-5-yl]-N-((3R)-piperidin-3-yl]pyrimidin-2-amine | 206-208 | 67 @ 10 uM |
| 80 | Chiral 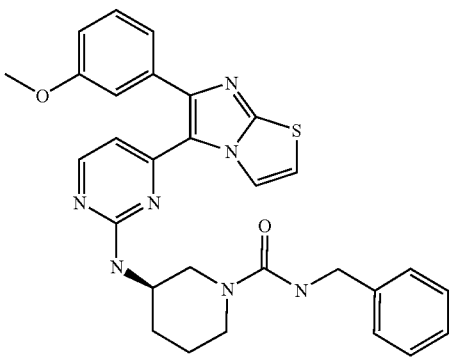 | (3R)-N-benzyl-3-({4-[6-(3-methoxyphenyl)imidazo[2,1-b][1,3]thiazol-5-yl]pyrimidin-2-yl}amino)piperidine-1-carboxamide | 108-110 | 40 @ 10 uM |

TABLE 2-continued

Exemplary compounds of the invention

| Cmpd # | Structure | IUPAC name | Melting point (° C.) or LCMS | Mutant B-RAF IC$_{50}$ (uM) or % inhibition |
|---|---|---|---|---|
| 81 | Chiral | (3R)-N-(2-furylmethyl)-3-({4-[6-(3-methoxyphenyl)imidazo[2,1-b][1,3]thiazol-5-yl]pyrimidin-2-yl}amino)piperidine-1-carboxamide | 119-121 | 50 @ 10 uM |
| 82 | Chiral | N-{(3R)-1-[(4-fluorophenyl)sulfonyl]piperidin-3-yl}-4-(6-(3-methoxyphenyl)imidazo[2,1-b][1,3]thiazot-5-yl]pyrimidin-2-amine | 143-144 | 0.192 |
| 83 | Chiral | N-[(3R)-1-(4-methoxybenzoyl)piperidin-3-yl]-4-[6-(3-methoxyphenyl)imidazo[2,1-b][1,3]thiazol-5-yl]pyrimidin-2-amine | 130-132 | >3.0 |

TABLE 2-continued

Exemplary compounds of the invention

| Cmpd # | Structure | IUPAC name | Melting point (° C.) or LCMS | Mutant B-RAF IC$_{50}$ (uM) or % inhibition |
|---|---|---|---|---|
| 84 | Chiral | (3R)-N-[4-(dimethylamino)phenyl]-3-({4-[6-(3-methoxyphenyl)imidazo[2,1-b][1,3]thiazol-5-yl]pyrimidin-2-yl}amino)piperidine-1-carboxamide | 127-129 | 19 @ 10 uM |
| 85 | Chiral | 4-[6-(3,4-difluorophenyl)imidazo[2,1-b][1,3]thiazol-5-yl]-N-{(3R)-1-[(4-fluorophenyl)sulfonyl]piperidin-3-yl}pyrimidin-2-amine | 128-131 | 0.058 |
| 86 | Chiral | (3R)-3-({4-[6-(3,4-difluorophenyl)imidazo[2,1-b][1,3]thiazol-5-yl]pyrimidin-2-yl}amino)-N-[4-(dimethylamino)phenyl]piperidine-1-carboxamide | 135-137 | 54 @ 10 uM |

TABLE 2-continued

Exemplary compounds of the invention

| Cmpd # | Structure | IUPAC name | Melting point (° C.) or LCMS | Mutant B-RAF IC$_{50}$ (uM) or % inhibition |
|---|---|---|---|---|
| 87 | Chiral | (3R)-N-benzyl-3-({4-[6-(3,4-difluorophenyl)imidazo[2,1-b][1,3]thiazol-5-yl]pyrimidin-2-yl}amino)piperidine-1-carboxamide | 107-110 | 53 @ 10 uM |
| 88 | Chiral | (3R)-3-({4-[6-(3,4-difluorophenyl)imidazo[2,1-b][1,3]thiazol-5-yl]pyrimidin-2-yl}amino)-N-(2-furylmethyl)piperidine-1-carboxamide | 101-102 | 54 @ 10 uM |

TABLE 2-continued

Exemplary compounds of the invention

| Cmpd # | Structure | IUPAC name | Melting point (° C.) or LCMS | Mutant B-RAF IC$_{50}$ (uM) or % inhibition |
|---|---|---|---|---|
| 89 | Chiral | 4-[6-(3,4-difluorophenyl)imidazo[2,1-b][1,3]thiazol-5-yl]-N-[(3R)-1-(4-methoxybenzoyl)piperidin-3-yl]pyrimidin-2-amine | 121-122 | 40 @ 10 uM |
| 90 | Chiral | (3R)-N-benzyl-3-({4-[6-(4-fluorophenyl)-2-methylimidazo[2,1-b][1,3]thiazol-5-yl]pyrimidin-2-yl}amino)piperidine-1-carboxamide | 135-137 | 34 @ 10 uM |

TABLE 2-continued
Exemplary compounds of the invention
| Cmpd # | Structure | IUPAC name | Melting point (° C.) or LCMS | Mutant B-RAF IC$_{50}$ (uM) or % inhibition |
|---|---|---|---|---|
| 91 | 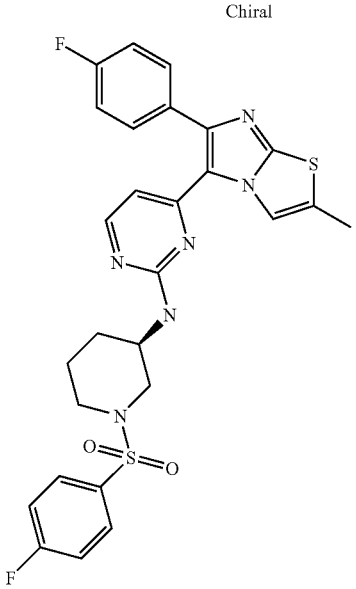 Chiral | 4-[6-(4-fluorophenyl)-2-methylimidazo[2,1-b][1,3]thiazol-5-yl]-N-{(3R)-1-[(4-fluorophenyl)sulfonyl]piperidin-3-yl}pyrimidin-2-amine | 245-246 | 0.352 |
| 92 | 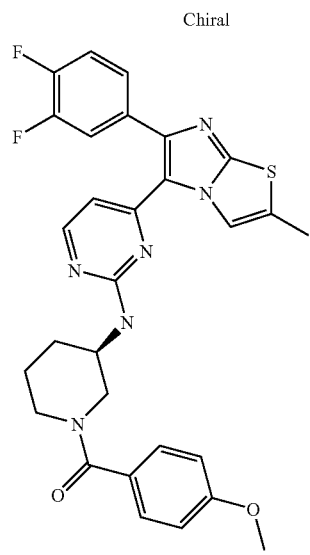 Chiral | 4-[6-(4-fluorophenyl)-2-methylimidazo[2,1-b][1,3]thiazol-5-yl]-N-[(3R)-1-(4-methoxybenzoyl)piperidin-3-yl]pyrimidin-2-amine | 200-201 | 5 @ 10 uM |

TABLE 2-continued

Exemplary compounds of the invention

| Cmpd # | Structure | IUPAC name | Melting point (° C.) or LCMS | Mutant B-RAF IC$_{50}$ (uM) or % inhibition |
|---|---|---|---|---|
| 93 | Chiral | (3R)-3-({4-[6-(4-fluoro-phenyl)-2-methylimidazo[2,1-b][1,3]thiazol-5-yl]pyrimidin-2-yl}amino)-N-(2-furylmethyl)piperidine-1-carboxamide | 113-115 | 61 @ 10 uM |
| 94 | Chiral | (3R)-N-[4-(dimethyl-amino)phenyl]-3-({4-[6-(4-fluorophenyl)-2-methylimidazo[2,1-b][1,3]thiazol-5-yl]pyrimidin-2-yl}amino)piperidine-1-carboxamide | 193-194 | >3.0 |
| 95 | Chiral | N-{(3R)-1-[(4-chlorophenyl)sulfonyl]piperidin-3-yl}-4-[6-(3-methoxyphenyl)imidazo[2,1-b][1,3]thiazol-5-yl]pyrimidin-2-amine | 127-128 | 0.147 |

TABLE 2-continued

Exemplary compounds of the invention

| Cmpd # | Structure | IUPAC name | Melting point (° C.) or LCMS | Mutant B-RAF IC$_{50}$ (uM) or % inhibition |
|---|---|---|---|---|
| 96 | Chiral | N-{(3R)-1-[(4-chlorophenyl)sulfonyl]piperidin-3-yl}-4-[6-(4-fluorophenyl)-2-methyl-imidazo[2,1-b][1,3]thiazol-5-yl]pyrimidin-2-amine | 273-274 | 0.026 |
| 97 | Chiral | 4-[6-(2-naphthyl)imidazo[2,1-b][1,3]thiazol-5-yl]-N-[(3R)-piperidin-3-yl]pyrimidin-2-amine | 202-205 | 0.314 |

TABLE 2-continued

Exemplary compounds of the invention

| Cmpd # | Structure | IUPAC name | Melting point (° C.) or LCMS | Mutant B-RAF IC$_{50}$ (uM) or % inhibition |
|---|---|---|---|---|
| 98 | Chiral | N-{(3R)-1-[(4-chlorophenyl)sulfonyl]piperidin-3-yl}-4-[6(4-fluorophenyl)imidazo[2,1-b][1,3]thiazol-5-yl]pyrimidin-2-amine | 154-155 | 0.036 |
| 99 | Chiral | 4-[6-(2,3-dihydro-1,4-benzodioxin-6-yl)imidazo[2,1-b][1,3]thiazol-5-yl]-N-[(3R)-piperidin-3-yl]pyrimidin-2-amine | 210-215 | 29 @ 10 uM |
| 100 | Chiral | 4-[6-(4-chloro-3-methoxyphenyl)imidazo[2,1-b][1,3]thiazol-5-yl]-N-{(3R)-1-[(4-chlorophenyl)sulfonyl]piperidin-3-yl}pyrimidin-2-amine | 149-151 | 40 @ 10 uM |

TABLE 2-continued

Exemplary compounds of the invention

| Cmpd # | Structure | IUPAC name | Melting point (° C.) or LCMS | Mutant B-RAF IC$_{50}$ (uM) or % inhibition |
|---|---|---|---|---|
| 101 | Chiral | 2-chloro-5-{5-[2-({(3R)-1-[(4-chlorophenyl)sulfonyl]piperidin-3-yl}amino)pyrimidin-4-yl]imidazo[2,1-b][1,3]thiazol-6-yl}phenol | 163-164 | 0.011 |
| 102 | Chiral | 4-[6-(2-methoxyphenyl)imidazo[2,1-b][1,3]thiazol-5-yl]-N-[(3R)-piperidin-3-yl]pyrimidin-2-amine | 237-239 | 1.28 |
| 103 | 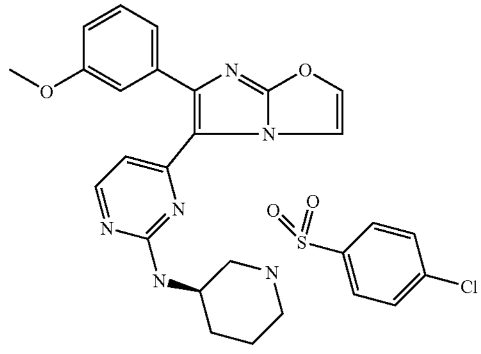 | N-{(3R)-1-[(4-chlorophenyl)sulfonyl]piperidin-3-yl}-4-[6-(3-methoxyphenyl)imidazo[2,1-b][1,3]oxazol-5-yl]pyrimidin-2-amine | 115-118 | 48 @ 10 uM |

TABLE 2-continued

Exemplary compounds of the invention

| Cmpd # | Structure | IUPAC name | Melting point (° C.) or LCMS | Mutant B-RAF IC$_{50}$ (uM) or % inhibition |
|---|---|---|---|---|
| 104 | Chiral | 3-{5-[2-({(3R)-1-[(4-chlorophenyl)sulfonyl]piperidin-3-yl}amino)pyrimidin-4-yl]imidazo[2,1-b][1,3]oxazol-6-yl}phenol | 205-210 | 0.038 |
| 105 | Chiral | N-{(3R)-1-[(4-chlorophenyl)sulfonyl]piperidin-3-yl}-4-[6-(2-methoxyphenyl)imidazo[2,1-b][1,3]thiazol-5-yl]pyrimidin-2-amine | 151-153 | 0.25 |
| 106 | Chiral | 4-[6-(4-methoxyphenyl)imidazo[2,1-b][1,3]thiazol-5-yl]-N-[(3R)-piperidin-3-yl]pyrimidin-2-amine | 189-191 | 27 @ 10 uM |

TABLE 2-continued

Exemplary compounds of the invention

| Cmpd # | Structure | IUPAC name | Melting point (° C.) or LCMS | Mutant B-RAF IC$_{50}$ (uM) or % inhibition |
|---|---|---|---|---|
| 107 | Chiral | 2-{5-[2-({(3R)-1-[(4-chlorophenyl)sulfonyl]piperidin-3-yl}amino)pyrimidin-4-yl]imidazo[2,1-b][1,3]thiazol-6-yl}phenol | 154-155 | 0.033 |
| 108 | Chiral | N-[(3R)-1-(4-fluorobenzoyl)piperidin-3-yl]-4-[6-(3-methoxyphenyl)imidazo[2,1-b][1,3]thiazol-5-yl]pyrimidin-2-amine | 88-90 | 73 @ 10 uM |
| 109 | Chiral | 4-[6-(3-methoxyphenyl)imidazo[2,1-b][1,3]thiazol-5-yl]-N-[(3R)-1-(3-methylbutanoyl)piperidin-3-yl]pyrimidin-2-amine | 85-87 | >3.0 |

TABLE 2-continued

Exemplary compounds of the invention

| Cmpd # | Structure | IUPAC name | Melting point (° C.) or LCMS | Mutant B-RAF IC$_{50}$ (uM) or % inhibition |
|---|---|---|---|---|
| 110 | 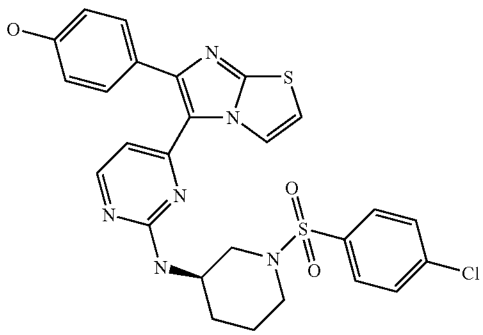 | 4-{5-[2-({(3R)-1-[(4-chlorophenyl)sulfonyl]piperidin-3-yl}amino)pyrimidin-4-yl]imidazo[2,1-b][1,3]thiazol-6-yl}phenol | 179-180 | >5.0 |
| 111 | Chiral | 4-{[(3R)-3-({4-[6-(3-hydroxyphenyl)imidazo[2,1-b][1,3]thiazol-5-yl]pyrimidin-2-yl}amino)piperidin-1-yl]sulfonyl}benzonitrile | 178-180 | 0.028 |
| 112 | Chiral | N-[(3R)-1-isonicotinoylpiperidin-3-yl]-4-[6-(3-methoxyphenyl)imidazo[2,1-b][1,3]thiazol-5-yl]pyrimidin-2-amine | 133-135 | >5.0 |

TABLE 2-continued

Exemplary compounds of the invention

| Cmpd # | Structure | IUPAC name | Melting point (° C.) or LCMS | Mutant B-RAF IC$_{50}$ (uM) or % inhibition |
|---|---|---|---|---|
| 113 | Chiral | 3-[5-(2-{[(3R)-1-(4-fluorobenzoyl)piperidin-3-yl]amino}pyrimidin-4-yl)imidazo[2,1-b][1,3]thiazol-6-yl}phenol | 155-157 | 3.84 |
| 114 | Chiral | N-{(3R)-1-[(4-chlorophenyl)sulfonyl]piperidin-3-yl}-4-[6-(3,4-difluorophenyl)imidazo[2,1-b][1,3]thiazol-5-yl]pyrimidin-2-amine | 111-113 | 48 @ 3 uM |
| 115 | Chiral | 4-[6-(3-methoxyphenyl)imidazo[2,1-b][1,3]oxazol-5-yl]-N-[(3R)-piperidin-3-yl]pyrimidin-2-amine | 172-175 | >10 |
| 116 | Chiral | 3-[5-(2-{[(3R)-1-(3-methylbutanoyl)piperidin-3-yl]amino}pyrimidin-4-yl)imidazo[2,1-b][1,3]thiazol-6-yl}phenol | 146-148 | 52 @ 10 uM |

TABLE 2-continued

Exemplary compounds of the invention

| Cmpd # | Structure | IUPAC name | Melting point (° C.) or LCMS | Mutant B-RAF IC$_{50}$ (uM) or % inhibition |
|---|---|---|---|---|
| 117 | Chiral | 3-[5-(2-{[(3R)-1-isonicotinoylpiperidin-3-yl]amino}pyrimidin-4-yl)imidazo[2,1-b][1,3]thiazol-6-yl]phenol | 162-164 | 0.328 |
| 118 | Chiral | 3-(4-{[(3R)-3-({4-[6-(3-methoxyphenyl)imidazo[2,1-b][1,3]thiazol-5-yl]pyrimidin-2-yl}amino)piperidin-1-yl]sulfonyl}phenyl)propanoic acid | 148-148 | 0.229 |
| 119 | Chiral | 4-{[(3R)-3-({4-[6-(3-methoxyphenyl)imidazo(2,1-b][1,3]thiazol-5-yl]pyrimidin-2-yl}amino)piperidin-1-yl]sulfonyl}benzoic acid | >300 | 0.092 |
| 120 | Chiral | N-{(3R)-1-[(4-chlorophenyl)sulfonyl]piperidin-3-yl}-4-[6-(3-nitrophenyl)imidazo[2,1-b][1,3]thiazol-5-yl]pyrimidin-2-amine | 185-187 | 55 @ 10 uM |

TABLE 2-continued

Exemplary compounds of the invention

| Cmpd # | Structure | IUPAC name | Melting point (° C.) or LCMS | Mutant B-RAF IC$_{50}$ (uM) or % inhibition |
|---|---|---|---|---|
| 121 | Chiral | 4-{[(3R)-3-({4-[6-(3-hydroxyphenyl)imidazo[2,1-b][1,3]thiazol-5-yl]pyrimidin-2-yl}amino)piperidin-1-yl]sulfonyl}benzoic acid | >300 | 0.002 |
| 122 | Chiral | 4-[6-(3-aminophenyl)imidazo[2,1-b][1,3]thiazol-5-yl]-N-{(3R)-1-[(4-chlorophenyl)sulfonyl]piperidin-3-yl}pyrimidin-2-amine | 226-228 | 0.429 |
| 123 | Chiral | N-(3-{5-[2-({(3R)-1-[(4-chlorophenyl)sulfonyl]piperidin-3-yl}amino)pyrimidin-4-yl]imidazo[2,1-b][1,3]thiazol-6-yl}phenyl)acetamide | 169-174 | 0.215 |

TABLE 2-continued

Exemplary compounds of the invention

| Cmpd # | Structure | IUPAC name | Melting point (° C.) or LCMS | Mutant B-RAF IC$_{50}$ (uM) or % inhibition |
|---|---|---|---|---|
| 124 | Chiral | N~1~-(3-{5-[2-({(3R)-1-[(4-chlorophenyl)sulfonyl]piperidin-3-yl}amino)pyrimidin-4-yl]imidazo[2,1-b][1,3]thiazol-6-yl}phenyl)glycinamide | 208-212 | 2.96 |
| 125 | Chiral | 3-(5-{2-[(3R)-piperidin-3-ylamino]pyrimidin-4-yl}imidazo[2,1-b][1,3]thiazol-6-yl)benzonitrile | 205-207 | 19 @ 10 uM |
| 126 | Chiral | 3-{5-[2-({(3R)-1-[(4-chlorophenyl)sulfonyl]piperidin-3-yl}amino)pyrimidin-4-yl]imidazo[2,1-b][1,3]thiazol-6-yl}benzonitrile | 144-146 | 0.71 | ns
TABLE 2-continued

Exemplary compounds of the invention

| Cmpd # | Structure | IUPAC name | Melting point (° C.) or LCMS | Mutant B-RAF IC$_{50}$ (uM) or % inhibition |
|---|---|---|---|---|
| 127 | Chiral | 4-{5-[2-({(3R)-1-[(4-chlorophenyl)sulfonyl]piperidin-3-yl}amino)pyrimidin-4-yl]imidazo[2,1-b][1,3]thiazol-6-yl}benzoic acid | 255-260 | >3.0 |
| 128 | Chiral | ethyl 2-ethoxy-4-(5-{2-[(3R)-piperidin-3-ylamino]pyrimidin-4-yl}imidazo[2,1-b][1,3]thiazol-6-yl)benzoate | 195-197 | 24 @ 10 uM |
| 129 | Chiral | 4-{[(3R)-3-({4-[6-(3-cyanophenyl)imidazo[2,1-b][1,3]thiazol-5-yl]pyrimidin-2-yl}sulfonyl}benzoic acid | 245-247 | >3.0 |

TABLE 2-continued

Exemplary compounds of the invention

| Cmpd # | Structure | IUPAC name | Melting point (° C.) or LCMS | Mutant B-RAF IC$_{50}$ (uM) or % inhibition |
|---|---|---|---|---|
| 130 | Chiral | ethyl 4-{5-[2-({(3R)-1-[(4-chlorophenyl)sulfonyl]piperidin-3-yl}amino)pyrimidin-4-yl]imidazo[2,1-b][1,3]thiazol-6-yl}-2-ethoxybenzoate | 138-140 | 1.09 |
| 131 | Chiral | N-{(3R)-1-[(4-chlorophenyl)sulfonyl]piperidin-3-yl}-4-[6-(2-nitrophenyl)imidazo[2,1-b][1,3]thiazol-5-yl]pyrimidin-2-amine | 155-156 | 0.025 |
| 132 | Chiral | 4-[6-(2-aminophenyl)imidazo[2,1-b][1,3]thiazol-5-yl]-N-{(3R)-1-[(4-chlorophenyl)sulfonyl]piperidin-3-yl}pyrimidin-2-amine | 155-157 | 0.444 |

TABLE 2-continued

Exemplary compounds of the invention

| Cmpd # | Structure | IUPAC name | Melting point (° C.) or LCMS | Mutant B-RAF IC$_{50}$ (uM) or % inhibition |
|---|---|---|---|---|
| 133 | Chiral | 4-{5-[2-({(3R)-1-[(4-chlorophenyl)sulfonyl]piperidin-3-yl}amino)pyrimidin-4-yl]imidazo[2,1-b][1,3]thiazol-6-yl}-2-hydroxybenzoic acid | 228-229 | 0.84 |
| 134 | Chiral | 4-{5-[2-({(3R)-1-[(4-chlorophenyl)sulfonyl]piperidin-3-yl}amino)pyrimidin-4-yl]imidazo[2,1-b][1,3]thiazol-6-yl}benzene-1,2-diol | 195-197 | 0.024 |
| 135 | Chiral | N-{(3R)-1-[(4-chlorophenyl)sulfonyl]piperidin-3-yl}-4-[6-(3,4-dimethoxyphenyl)imidazo[2,1-b][1,3]thiazol-5-yl]pyrimidin-2-amine | 168-170 | 0.696 |

TABLE 2-continued

Exemplary compounds of the invention

| Cmpd # | Structure | IUPAC name | Melting point (° C.) or LCMS | Mutant B-RAF IC$_{50}$ (uM) or % inhibition |
|---|---|---|---|---|
| 136 | 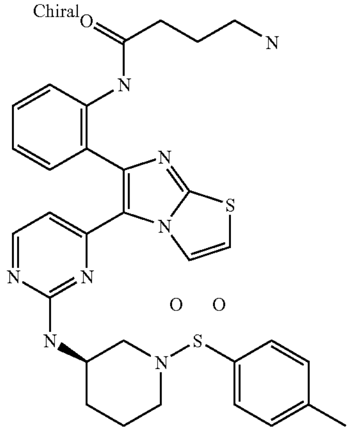 | 4-amino-N-(2-{5-[2-({(3R)-1-[(4-chlorophenyl)sulfonyl]piperidin-3-yl}amino)pyrimidin-4-yl]imidazo[2,1-b][1,3]thiazol-6-yl}phenyl)butanamide | 206-208 | >3.0 |
| 137 | 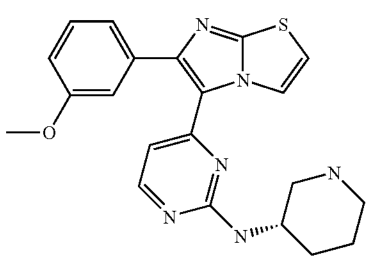 | 4-[6-(3-methoxyphenyl)imidazo[2,1-b][1,3]thiazol-5-yl]-N-[(3S)-piperidin-3-yl]pyrimidin-2-amine | 176-178 | 42 @ 10 uM |
| 138 | 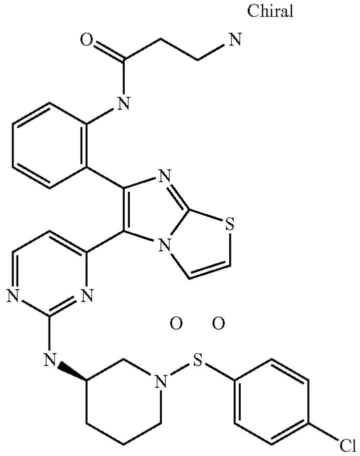 | N~1~-(2-{5-[2-({(3R)-1-[(4-chlorophenyl)sulfonyl]piperidin-3-yl}amino)pyrimidin-4-yl]imidazo[2,1-b][1,3]thiazol-6-yl}phenyl)-beta-alaninamide | 203-204 | 82 @ 10 uM |

TABLE 2-continued

Exemplary compounds of the invention

| Cmpd # | Structure | IUPAC name | Melting point (° C.) or LCMS | Mutant B-RAF IC$_{50}$ (uM) or % inhibition |
|---|---|---|---|---|
| 139 | Chiral | N-{(3S)-1-[(4-chlorophenyl)sulfonyl]piperidin-3-yl}-4-[6-(3-methoxyphenyl)imidazo[2,1-b][1,3]thiazol-5-yl]pyrimidin-2-amine | 125-127 | 41 @ 10 uM |
| 140 | Chiral | 3-{5-[2-({(3S)-1-[(4-chlorophenyl)sulfonyl]piperidin-3-yl}amino)pyrimidin-4-yl]imidazo[2,1-b][1,3]thiazol-6-yl}phenol | 158-160 | 0.953 |
| 141 | Chiral | N~1~-(2-{5-[2-({(3R)-1-[(4-chlorophenyl)sulfonyl]piperidin-3-yl}amino)pyrimidin-4-yl]imidazo[2,1-b][1,3]thiazol-6-yl}phenyl)glycinamide | 198-200 | 0.814 |
| 142 | Chiral | 4-[6-(3-methoxyphenyl)imidazo[2,1-b][1,3]thiazol-5-yl]-N-{(3R)-1-[(3-methoxyphenyl)sulfonyl]piperidin-3-yl}pyrimidin-2-amine | 105-106 | 56 @ 10 uM |

TABLE 2-continued

Exemplary compounds of the invention

| Cmpd # | Structure | IUPAC name | Melting point (° C.) or LCMS | Mutant B-RAF IC$_{50}$ (uM) or % inhibition |
|---|---|---|---|---|
| 143 | Chiral | 3-{[(3R)-3-({4-[6-(3-hydroxyphenyl)imidazo[2,1-b][1,3]thiazol-5-yl]pyrimidin-2-yl}amino)piperidin-1-yl]sulfonyl}phenol | 170-172 | 0.019 |
| 144 | Chiral | N-{(3R)-1-[(4-chlorophenyl)sulfonyl]piperidin-3-yl}-4-[6-(2,5-dimethoxyphenyl)imidazo[2,1-b][1,3]thiazol-5-yl]pyrimidin-2-amine | 128-131 | 69 @ 10 uM |
| 145 | Chiral | 2-{5-(2-({(3R)-1-[(4-chlorophenyl)sulfonyl]piperidin-3-yl}amino)pyrimidin-4-yl]imidazo[2,1-b][1,3]thiazol-6-yl}benzene-1,4-diol | 185-187 | 0.092 |
| 146 | Chiral | N-((3R)-1-{[(4R)-2,2-dimethyl-1,3-dioxolan-4-yl]methyl}piperidin-3-yl)-4-[6-(3-methoxyphenyl)imidazo[2,1-b][1,3]thiazol-5-yl]pyrimidin-2-amine | 73-75 | 43 @ 10 uM |

TABLE 2-continued

Exemplary compounds of the invention

| Cmpd # | Structure | IUPAC name | Melting point (° C.) or LCMS | Mutant B-RAF IC$_{50}$ (uM) or % inhibition |
|---|---|---|---|---|
| 147 | Chiral | (2R)-3-[(3R)-3-({4-[6-(3-methoxyphenyl)imidazo[2,1-b][1,3]thiazol-5-yl]pyrimidin-2-yl}amino)piperidin-1-yl]propane-1,2-diol | 106-108 | >3.0 |
| 148 | Chiral | (2R)-3-[(3R)-3-({4-[6-(3-hydroxyphenyl)imidazo[2,1-b][1,3]thiazol-5-yl]pyrimidin-2-yl}amino)piperidin-1-yl]propane-1,2-diol | 185-187 | >3.0 |
| 149 | Chiral | 4-[6-(3-methoxyphenyl)imidazo[2,1-b][1,3]thiazol-5-yl]-N-{(3R)-1-[(4-methoxyphenyl)sulfonyl]piperidin-3-yl}pyrimidin-2-amine | 105-107 | 0.188 |
| 150 | Chiral | 3-{5-[2-({(3R)-1-[(4-hydroxyphenyl)sulfonyl]piperidin-3-yl}amino)pyrimidin-4-yl]imidazo[2,1-b][1,3]thiazol-6-yl}phenol | 185-187 | 0.009 |

TABLE 2-continued

Exemplary compounds of the invention

| Cmpd # | Structure | IUPAC name | Melting point (° C.) or LCMS | Mutant B-RAF IC$_{50}$ (uM) or % inhibition |
|---|---|---|---|---|
| 151 | Chiral | 4-[6-(3-methoxyphenyl)imidazo[2,1-b][1,3]thiazol-5-yl]-N-[(3R)-1-(methylsulfonyl)piperidin-3-yl]pyrimidin-2-amine | 118-120 | 0.85 |
| 152 | Chiral | 3-[5-(2-{[(3R)-1-(methylsulfonyl)piperidin-3-yl]amino}pyrimidin-4-yl)imidazo[2,1-b][1,3]thiazol-6-yl]phenol | 172-175 | 0.116 |
| 153 | 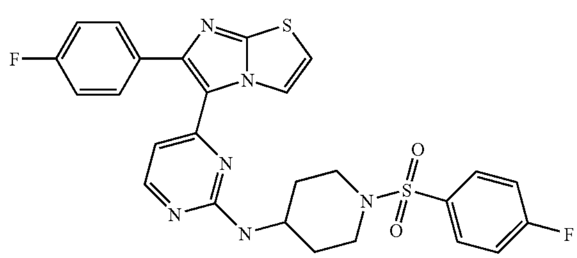 | 4-[6-(4-fluorophenyl)imidazo[2,1-b][1,3]thiazol-5-yl]-N-{1-[(4-fluorophenyl)sulfonyl]piperidin-4-yl}pyrimidin-2-amine | 259-260 | 0.078 |
| 154 | 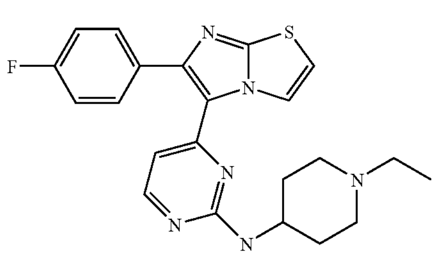 | N-(1-ethylpiperidin-4-yl)-4-[6-(4-fluorophenyl)imidazo[2,1-b][1,3]thiazol-5-yl]pyrimidin-2-amine | 173-175 | 36 @ 10 uM |

TABLE 2-continued

Exemplary compounds of the invention

| Cmpd # | Structure | IUPAC name | Melting point (° C.) or LCMS | Mutant B-RAF IC$_{50}$ (uM) or % inhibition |
|---|---|---|---|---|
| 155 | 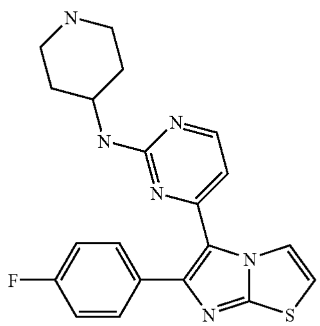 | 4-[6-(4-fluorophenyl)imidazo[2,1-b][1,3]thiazol-5-yl]-N-piperidin-4-ylpyrimidin-2-amine | 282-286 | 2.36 |
| 156 | 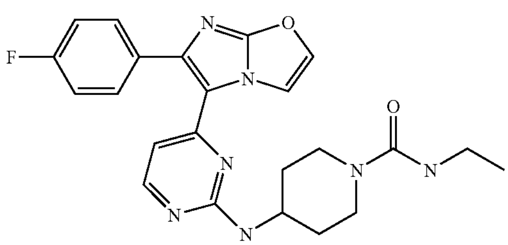 | N-ethyl-4-({4-[6-(4-fluorophenyl)imidazo[2,1-b][1,3]oxazol-5-yl]pyrimidin-2-yl}amino)piperidine-1-carboxamide | 110-112 | 0.428 |
| 157 | 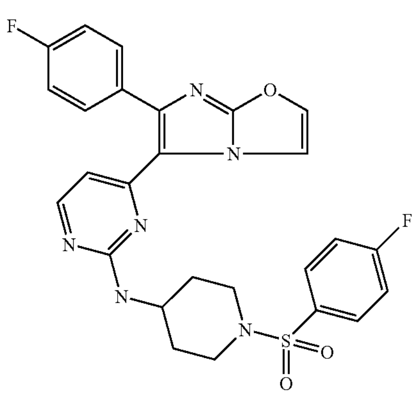 | 4-[6-(4-fluorophenyl)imidazo[2,1-b][1,3]oxazol-5-yl]-N-{1-[(4-fluorophenyl)sulfonyl]piperidin-4-yl}pyrimidin-2-amine | 222-223 | 0.675 |

TABLE 2-continued
Exemplary compounds of the invention
| Cmpd # | Structure | IUPAC name | Melting point (° C.) or LCMS | Mutant B-RAF IC$_{50}$ (uM) or % inhibition |
|---|---|---|---|---|
| 158 | 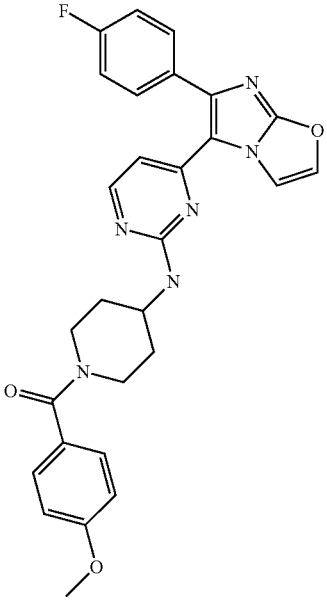 | 4-[6-(4-fluorophenyl)imidazo[2,1-b][1,3]oxazol-5-yl]-N-[1-(4-methoxybenzoyl)piperidin-4-yl]pyrimidin-2-amine | 196-197 | 0.465 |
| 159 | 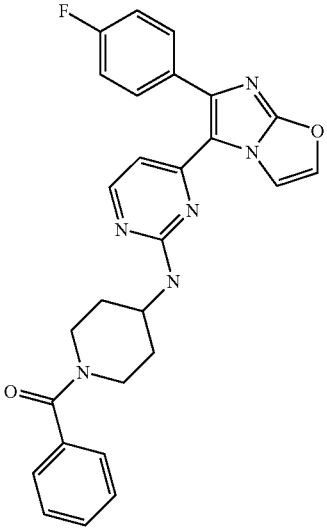 | N-(1-benzoylpiperidin-4-yl)-4-[6-(4-fluorophenyl)imidazo[2,1-b][1,3]oxazol-5-yl]pyrimidin-2-amine | 218-220 | 1.01 |

TABLE 2-continued

Exemplary compounds of the invention

| Cmpd # | Structure | IUPAC name | Melting point (° C.) or LCMS | Mutant B-RAF IC$_{50}$ (uM) or % inhibition |
|---|---|---|---|---|
| 160 | 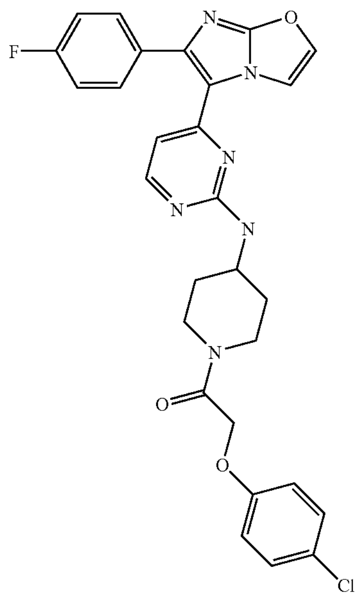 | N-{1-[(4-chlorophenoxy)acetyl]piperidin-4-yl}-4-[6-(4-fluorophenyl)imidazo[2,1-b][1,3]oxazol-5-yl]pyrimidin-2-amine | 209-210 | 3.85 |
| 161 | 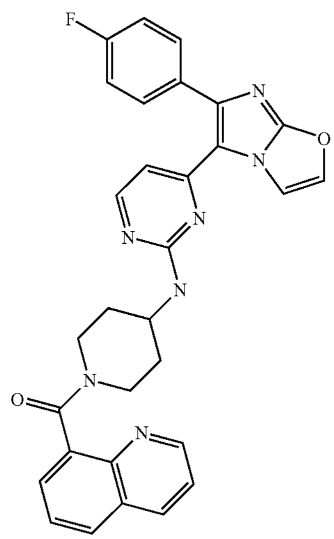 | 4-[6-(4-fluorophenyl)Imidazo[2,1-b][1,3]oxazol-5-yl]-N-[1-(quinolin-8-ylcarbonyl)piperidin-4-yl]pyrimidin-2-amine | 254-256 | 1.57 |

TABLE 2-continued

Exemplary compounds of the invention

| Cmpd # | Structure | IUPAC name | Melting point (° C.) or LCMS | Mutant B-RAF IC$_{50}$ (uM) or % inhibition |
|---|---|---|---|---|
| 162 | 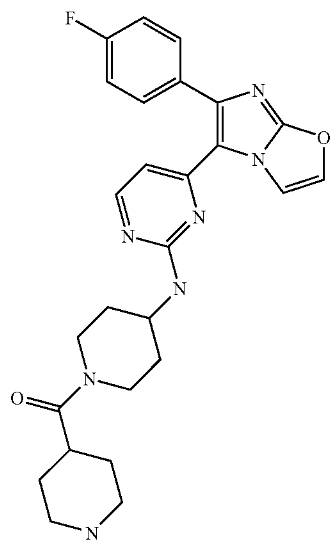 | 4-[6-(4-fluorophenyl)imidazo[2,1-b][1,3]oxazol-5-yl]-N-[1-(piperidin-4-ylcarbonyl)piperidin-4-yl]pyrimidin-2-amine | 209-212 | 1.32 |
| 163 | 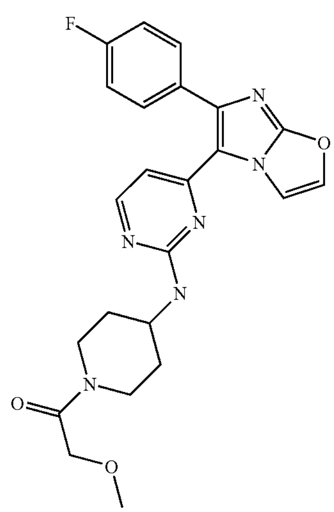 | 4-[6-(4-fluorophenyl)imidazo[2,1-b][1,3]oxazol-5-yl]-N-[1-(methoxyacetyl)piperidin-4-yl]pyrimidin-2-amine | 204-207 | 53 @ 10 uM |

TABLE 2-continued

Exemplary compounds of the invention

| Cmpd # | Structure | IUPAC name | Melting point (° C.) or LCMS | Mutant B-RAF IC$_{50}$ (uM) or % inhibition |
|---|---|---|---|---|
| 164 | 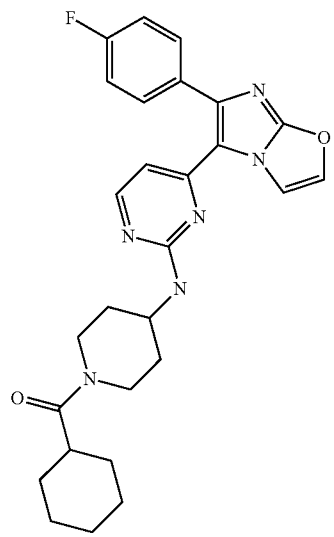 | N-[1-(cyclohexylcarbonyl)piperidin-4-yl]-4-[6-(4-fluorophenyl)imidazo[2,1-b][1,3]oxazol-5-yl]pyrimidin-2-amine | 135-136 | 38 @ 10 uM |
| 165 | 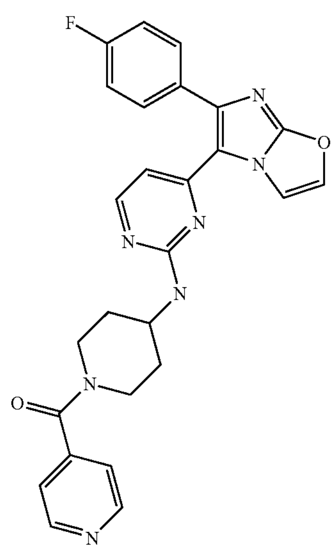 | 4-[6-(4-fluorophenyl)imidazo[2,1-b][1,3]oxazol-5-yl]-N-(1-isonicotinoylpiperidin-4-yl)pyrimidin-2-amine | 210-211 | 33 @ 10 uM |

TABLE 2-continued

Exemplary compounds of the invention

| Cmpd # | Structure | IUPAC name | Melting point (° C.) or LCMS | Mutant B-RAF IC$_{50}$ (uM) or % inhibition |
|---|---|---|---|---|
| 166 | 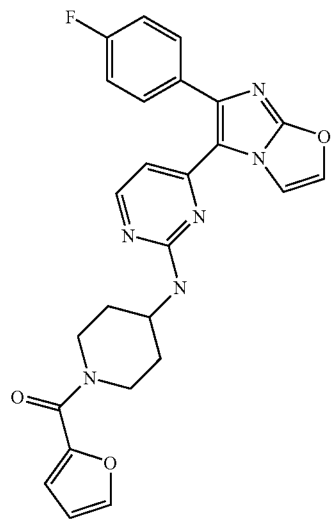 | 4-[6-(4-fluorophenyl)imidazo[2,1-b][1,3]oxazol-5-yl]-N-[1-(2-furoyl)piperidin-4-yl]pyrimidin-2-amine | 105-107 | 76 @ 10 uM |
| 167 | 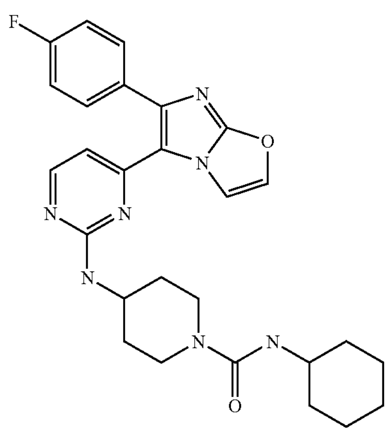 | N-cyclohexyl-4-({4-[6-(4-fluorophenyl)imidazo[2,1-b][1,3]oxazol-5-yl]pyrimidin-2-yl}amino)piperidine-1-carboxamide | 168-169 | 4.71 |
| 168 | 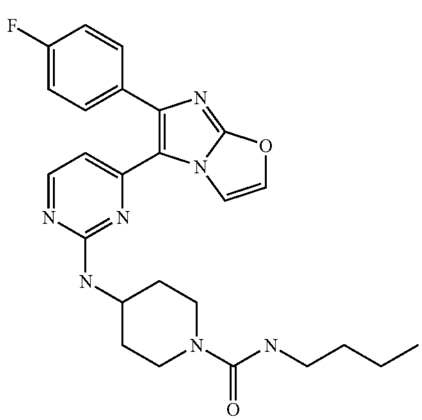 | N-butyl-4-({4-[6-(4-fluorophenyl)imidazo[2,1-b][1,3]oxazol-5-yl]pyrimidin-2-yl}amino)piperidine-1-carboxamide | 155-156 | 1.11 |

TABLE 2-continued

Exemplary compounds of the invention

| Cmpd # | Structure | IUPAC name | Melting point (° C.) or LCMS | Mutant B-RAF IC$_{50}$ (uM) or % inhibition |
|---|---|---|---|---|
| 169 | 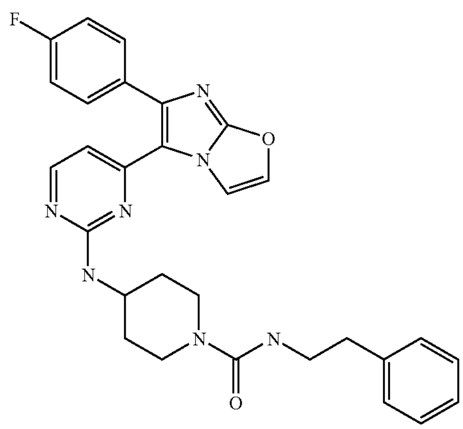 | 4-({4-[6-(4-fluorophenyl)imidazo[2,1-b][1,3]oxazol-5-yl]pyrimidin-2-yl}amino)-N-(2-phenylethyl)piperidine-1-carboxamide | 119-120 | 0.266 |
| 170 | 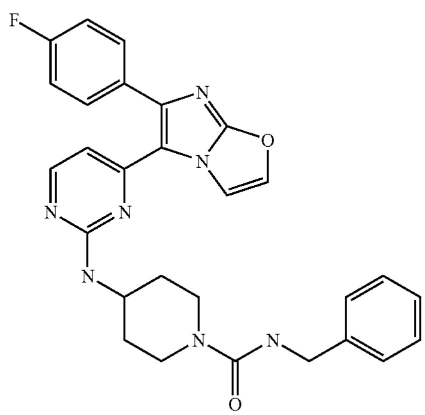 | N-benzyl-4-({4-[6-(4-fluorophenyl)imidazo[2,1-b][1,3]oxazol-5-yl]pyrimidin-2-yl}amino)piperidine-1-carboxamide | 124-126 | 0.189 |
| 171 | 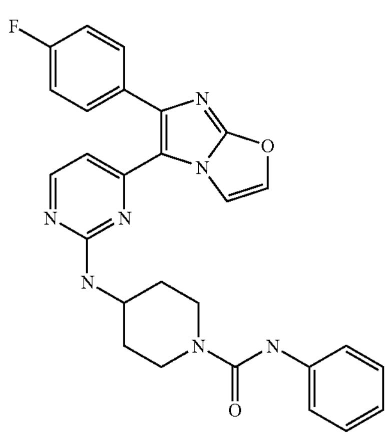 | 4-({4-[6-(4-fluorophenyl)imidazo[2,1-b][1,3]oxazol-5-yl]pyrimidin-2-yl}amino)-N-phenylpiperidine-1-carboxamide | 182-183 | 4.73 |

TABLE 2-continued

Exemplary compounds of the invention

| Cmpd # | Structure | IUPAC name | Melting point (° C.) or LCMS | Mutant B-RAF IC$_{50}$ (uM) or % inhibition |
| --- | --- | --- | --- | --- |
| 172 | 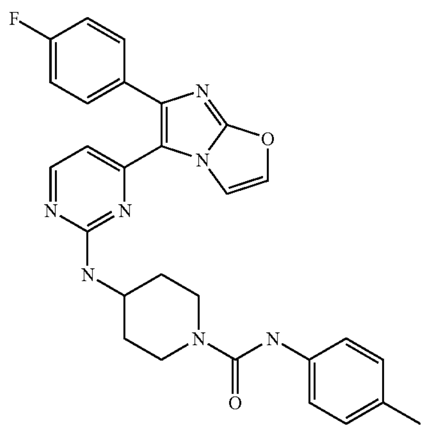 | 4-({4-[6-(4-fluorophenyl)imidazo[2,1-b][1,3]oxazol-5-yl]pyrimidin-2-yl}amino)-N-(4-methylphenyl)piperidine-1-carboxamide | 180-182 | 1.98 |
| 173 | 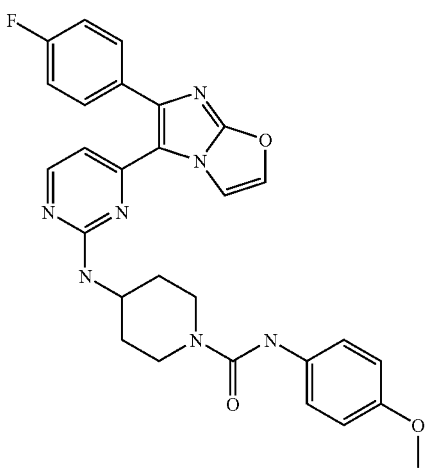 | 4-({4-[6-(4-fluorophenyl)imidazo[2,1-b][1,3]oxazol-5-yl]pyrimidin-2-yl}amino)-N-(4-methoxyphenyl)piperidine-1-carboxamide | 153-154 | 2.56 |
| 174 | 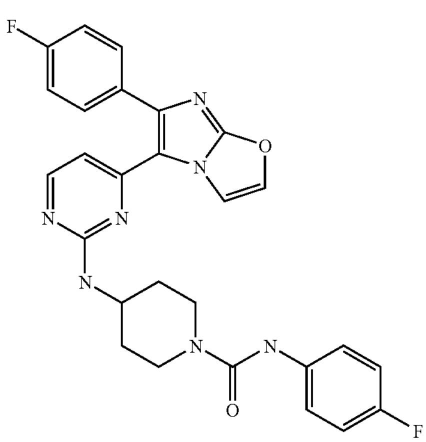 | N-(4-fluorophenyl)-4-({4-[6-(4-fluorophenyl)imidazo[2,1-b][1,3]oxazol-5-yl]pyrimidin-2-yl}amino)piperidine-1-carboxamide | 192-193 | 4.73 |

TABLE 2-continued

Exemplary compounds of the invention

| Cmpd # | Structure | IUPAC name | Melting point (° C.) or LCMS | Mutant B-RAF IC$_{50}$ (uM) or % inhibition |
|---|---|---|---|---|
| 175 | 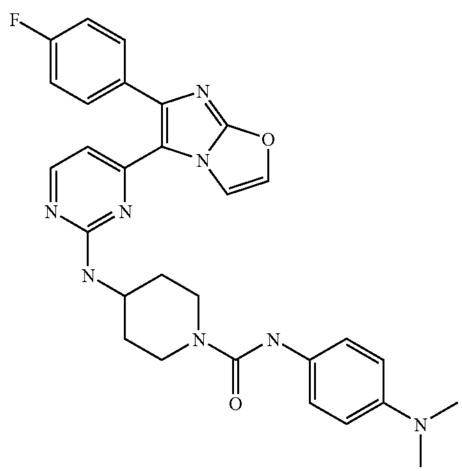 | N-[4-(dimethylamino)phenyl]-4-({4-[6-(4-fluorophenyl)imidazo[2,1-b][1,3]oxazol-5-yl]pyrimidin-2-yl}amino)piperidine-1-carboxamide | 225-227 | 0.066 |
| 176 | 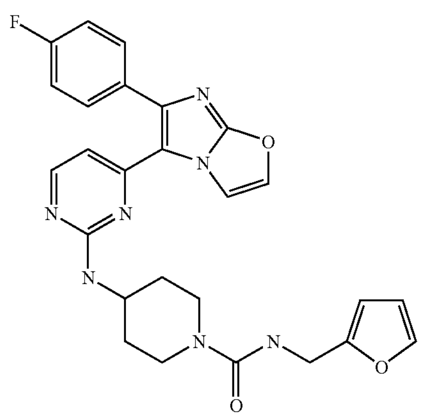 | 4-({4-[6-(4-fluorophenyl)imidazo[2,1-b][1,3]oxazol-5-yl]pyrimidin-2-yl}amino)-N-(2-furylmethyl)piperidine-1-carboxamide | 118-121 | 0.082 |
| 177 | 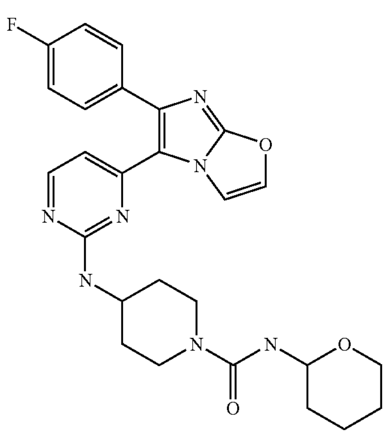 | 4-({4-[6-(4-fluorophenyl)imidazo[2,1-b][1,3]oxazol-5-yl]pyrimidin-2-yl}amino)-N-(tetrahydro-2H-pyran-2-yl)piperidine-1-carboxamide | 184-185 | 0.354 |

TABLE 2-continued

Exemplary compounds of the invention

| Cmpd # | Structure | IUPAC name | Melting point (° C.) or LCMS | Mutant B-RAF IC$_{50}$ (uM) or % inhibition |
|---|---|---|---|---|
| 178 | 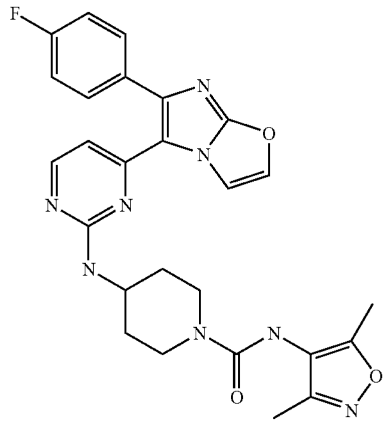 | N-(3,5-dimethylisoxazol-4-yl)-4-({4-[6-(4-fluorophenyl)imidazo[2,1-b][1,3]oxazol-5-yl]pyrimidin-2-yl}amino)piperidine-1-carboxamide | 208-210 | 19 @ 10 uM |
| 179 | 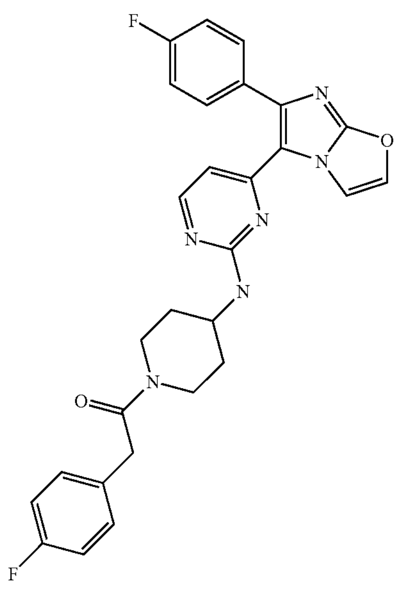 | N-{1-[(4-fluorophenyl)acetyl]piperidin-4-yl}-4-[6-(4-fluorophenyl)imidazo[2,1-b][1,3]oxazol-5-yl]pyrimidin-2-amine | 209-211 | 29 @ 10 uM |

TABLE 2-continued

Exemplary compounds of the invention

| Cmpd # | Structure | IUPAC name | Melting point (° C.) or LCMS | Mutant B-RAF IC$_{50}$ (uM) or % inhibition |
|---|---|---|---|---|
| 180 | 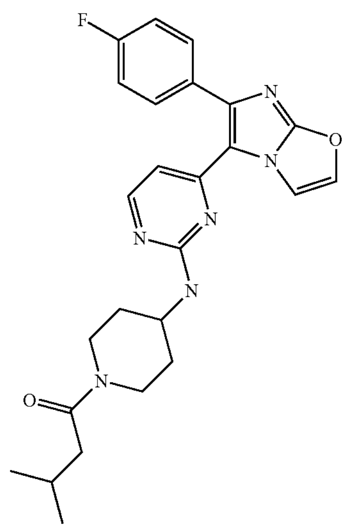 | 4-[6-(4-fluorophenyl)imidazo[2,1-b][1,3]oxazol-5-yl]-N-[1-(3-methylbutanoyl)piperidin-4-yl]pyrimidin-2-amine | 101-103 | 2.04 |
| 181 | 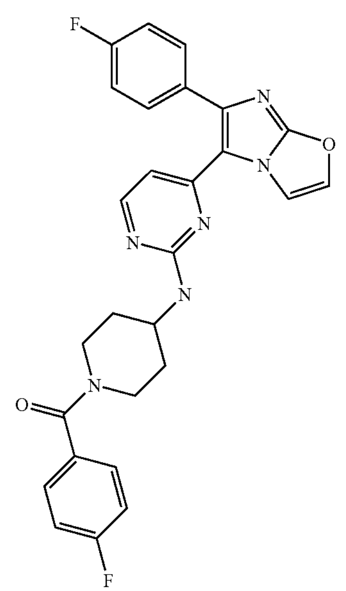 | N-[1-(4-fluorobenzoyl)piperidin-4-yl]-4-[6-(4-fluorophenyl)imidazo[2,1-b][1,3]oxazol-5-yl]pyrimidin-2-amine | 204-206 | 2.7 |

TABLE 2-continued

Exemplary compounds of the invention

| Cmpd # | Structure | IUPAC name | Melting point (° C.) or LCMS | Mutant B-RAF IC$_{50}$ (uM) or % inhibition |
|---|---|---|---|---|
| 182 | 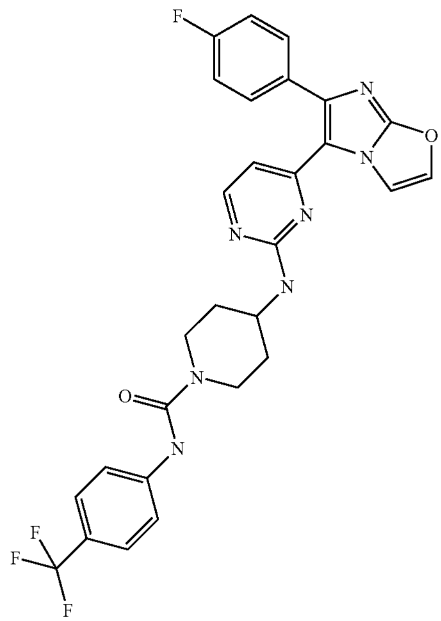 | 4-({4-[6-(4-fluorophenyl)imidazo[2,1-b][1,3]oxazol-5-yl]pyrimidin-2-yl}amino)-N-[4-(trifluoromethyl)phenyl]piperidine-1-carboxamide | 209-211 | 45 @ 10 uM |
| 183 | 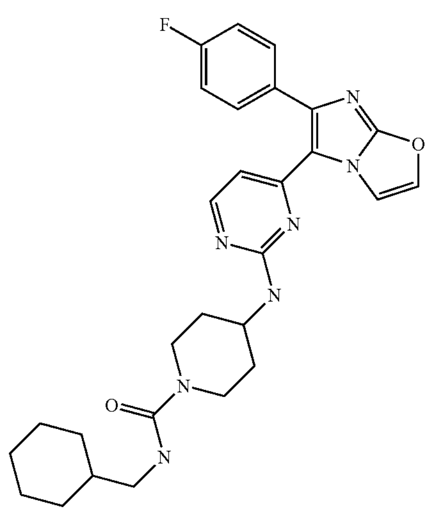 | N-(cyclohexylmethyl)-4-({4-[6-(4-fluorophenyl)imidazo[2,1-b][1,3]oxazol-5-yl]pyrimidin-2-yl}amino)piperidine-1-carboxamide | 127-130 | 3.61 |

TABLE 2-continued
Exemplary compounds of the invention
| Cmpd # | Structure | IUPAC name | Melting point (° C.) or LCMS | Mutant B-RAF IC$_{50}$ (uM) or % inhibition |
|---|---|---|---|---|
| 184 | 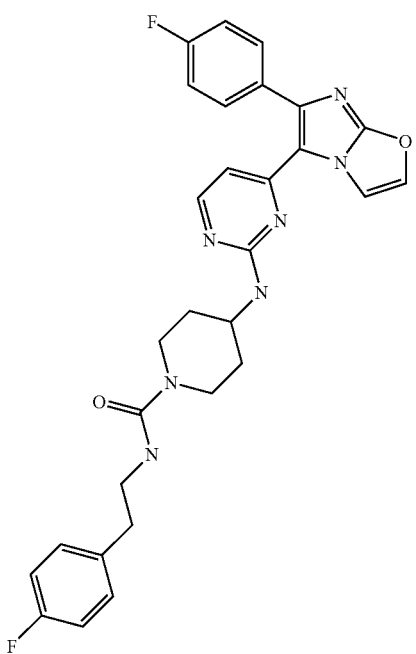 | N-[2-(4-fluorophenyl)ethyl]-4-({4-[6-(4-fluorophenyl)imidazo[2,1-b][1,3]oxazol-5-yl]pyrimidin-2-yl}amino)piperidine-1-carboxamide | 194-195 | 1.28 |
| 185 | 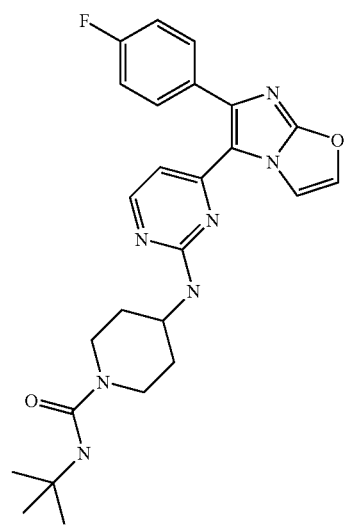 | N-(tert-butyl)-4-({4-[6-(4-fluorophenyl)imidazo[2,1-b][1,3]oxazol-5-yl]pyrimidin-2-yl}amino)piperidine-1-carboxamide | 134-138 | 1.58 |

TABLE 2-continued

Exemplary compounds of the invention

| Cmpd # | Structure | IUPAC name | Melting point (° C.) or LCMS | Mutant B-RAF IC$_{50}$ (uM) or % inhibition |
|---|---|---|---|---|
| 186 | 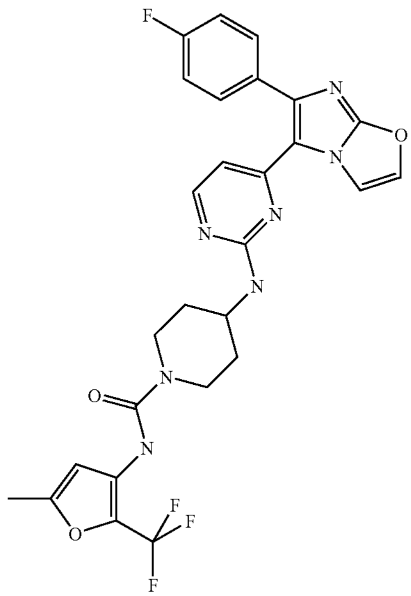 | 4-({4-[6-(4-fluorophenyl)imidazo[2,1-b][1,3]oxazol-5-yl]pyrimidin-2-yl}amino)-N-[5-methyl-2-(trifluoromethyl)-3-furyl]piperidine-1-carboxamide | 195-200 | 16 @ 10 uM |
| 187 | 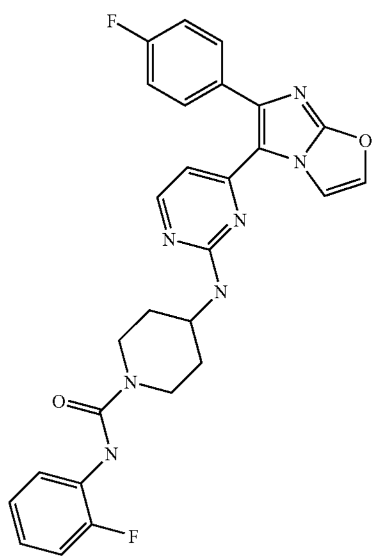 | N-(2-fluorophenyl)-4-({4-[6-(4-fluorophenyl)imidazo[2,1-b][1,3]oxazol-5-yl]pyrimidin-2-yl}amino)piperidine-1-carboxamide | 133-134 | 10 @ 10 uM |

TABLE 2-continued

Exemplary compounds of the invention

| Cmpd # | Structure | IUPAC name | Melting point (° C.) or LCMS | Mutant B-RAF IC$_{50}$ (uM) or % inhibition |
|---|---|---|---|---|
| 188 | 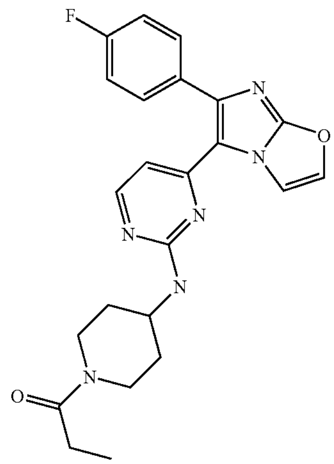 | 4-[6-(4-fluorophenyl)imidazo[2,1-b][1,3]oxazol-5-yl]-N-(1-propionylpiperidin-4-yl)pyrimidin-2-amine | 199-201 | 1.5 |
| 189 | 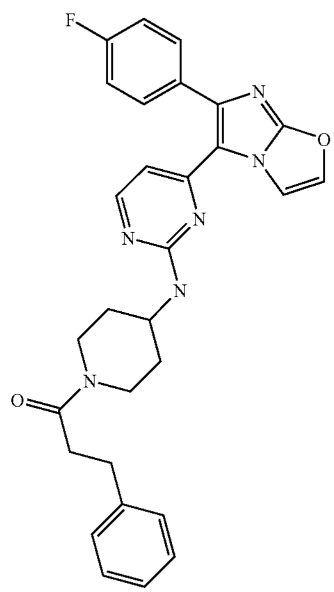 | 4-[6-(4-fluorophenyl)imidazo[2,1-b][1,3]oxazol-5-yl]-N-[1-(3-phenylpropanoyl)piperidin-4-yl]pyrimidin-2-amine | 144-146 | 1.94 |
| 190 | 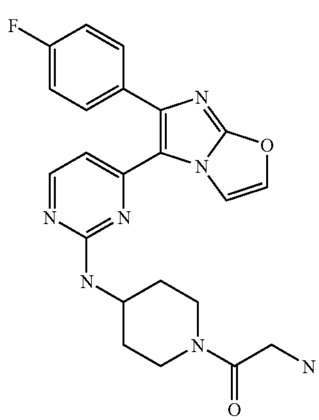 | N-[1-(aminoacetyl)piperidin-4-yl]-4-[6-(4-fluorophenyl)imidazo[2,1-b][1,3]oxazol-5-yl]pyrimidin-2-amine | 204-205 | 1.15 |

TABLE 2-continued

Exemplary compounds of the invention

| Cmpd # | Structure | IUPAC name | Melting point (° C.) or LCMS | Mutant B-RAF IC$_{50}$ (uM) or % inhibition |
|---|---|---|---|---|
| 191 | 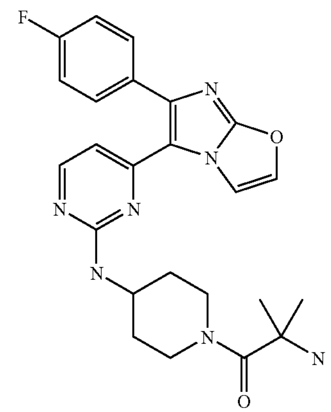 | N-[1-(2-amino-2-methylpropanoyl)piperidin-4-yl]-4-[6-(4-fluorophenyl)imidazo[2,1-b][1,3]oxazol-5-yl]pyrimidin-2-amine | 216-218 | 3.76 |
| 192 | Chiral | 4-[6-(4-fluorophenyl)imidazo[2,1-b][1,3]oxazol-5-yl]-N-(1-L-prolylpiperidin-4-yl)pyrimidin-2-amine | 198-202 | 1.45 |
| 193 | 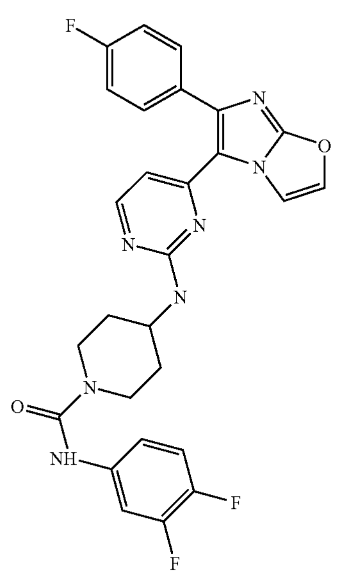 | N-(3,4-difluorophenyl)-4-({4-[6-(4-fluorophenyl)imidazo[2,1-b][1,3]oxazol-5-yl]pyrimidin-2-yl}amino)piperidine-1-carboxamide | 187-188 | 1.23 |

TABLE 2-continued

Exemplary compounds of the invention

| Cmpd # | Structure | IUPAC name | Melting point (° C.) or LCMS | Mutant B-RAF IC$_{50}$ (uM) or % inhibition |
|---|---|---|---|---|
| 194 | 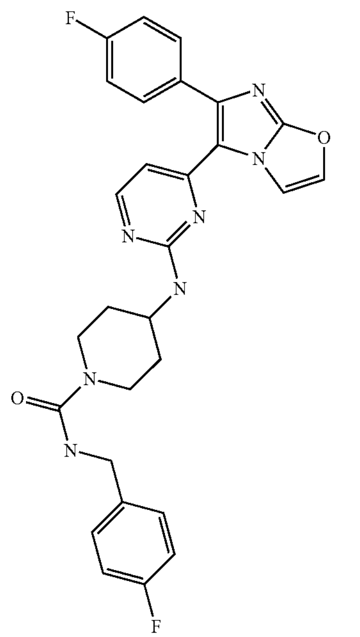 | N-(4-fluorobenzyl)-4-({4-[6-(4-fluorophenyl)imidazo[2,1-b][1,3]oxazol-5-yl]pyrimidin-2-yl}amino)piperidine-1-carboxamide | 115-118 | 55 @ 10 uM |
| 195 | Chiral | 4-({4-[6-(4-fluorophenyl)imidazo[2,1-b][1,3]oxazol-5-yl]pyrimidin-2-yl}amino)-N-[(1S)-1-phenylethyl]piperidine-1-carboxamide | 121-123 | 56 @ 10 uM |

TABLE 2-continued

Exemplary compounds of the invention

| Cmpd # | Structure | IUPAC name | Melting point (° C.) or LCMS | Mutant B-RAF IC$_{50}$ (uM) or % inhibition |
|---|---|---|---|---|
| 196 | Chiral | (4S)-4-amino-5-[4-({4-[6-(4-fluorophenyl)imidazo[2,1-b][1,3]oxazol-5-yl]pyrimidin-2-yl}amino)piperidin-1-yl]-5-oxopentanoic acid | 161-164 | 3.32 |
| 197 | 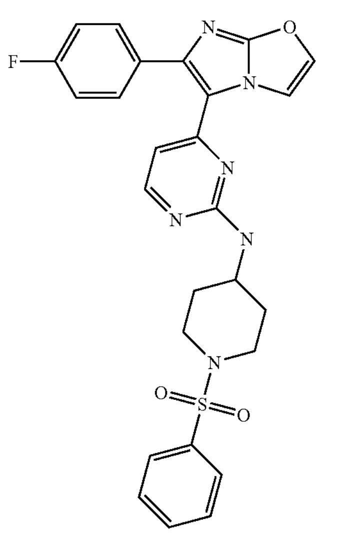 | 4-[6-(4-fluorophenyl)imidazo[2,1-b][1,3]oxazol-5-yl]-N-[1-(phenylsulfonyl)piperidin-4-yl]pyrimidin-2-amine | 266-268 | 0.168 |

TABLE 2-continued

Exemplary compounds of the invention

| Cmpd # | Structure | IUPAC name | Melting point (° C.) or LCMS | Mutant B-RAF IC$_{50}$ (uM) or % inhibition |
|---|---|---|---|---|
| 198 | 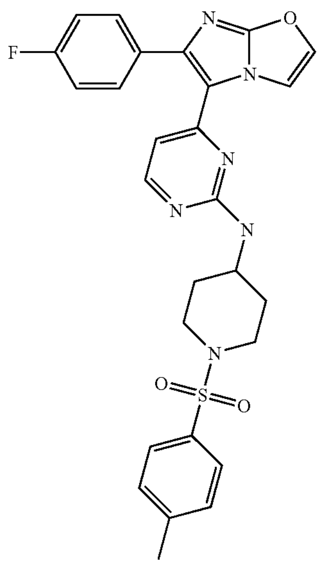 | 4-[6-(4-fluorophenyl)imidazo[2,1-b][1,3]oxazol-5-yl]-N-{1-[(4-methylphenyl)sulfonyl]piperidin-4-yl}pyrimidin-2-amine | 247-248 | 0.218 |
| 199 | 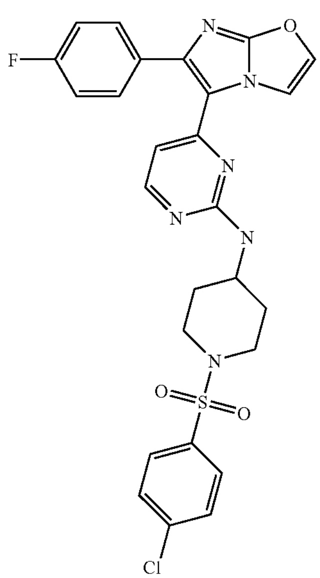 | N-{1-[(4-chlorophenyl)sulfonyl]piperidin-4-yl}-4-[6-(4-fluorophenyl)imidazo[2,1-b][1,3]oxazol-5-yl]pyrimidin-2-amine | 229-230 | 0.092 |

TABLE 2-continued

Exemplary compounds of the invention

| Cmpd # | Structure | IUPAC name | Melting point (° C.) or LCMS | Mutant B-RAF IC$_{50}$ (uM) or % inhibition |
|---|---|---|---|---|
| 200 | 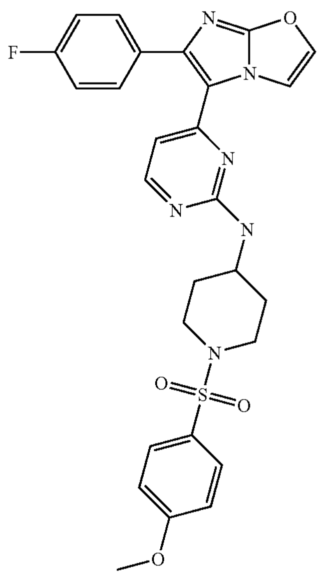 | 4-[6-(4-fluorophenyl)imidazo[2,1-b][1,3]oxazol-5-yl]-N-{1-[(4-methoxyphenyl)sulfonyl]piperidin-4-yl}pyrimidin-2-amine | 234-236 | 0.115 |
| 201 | 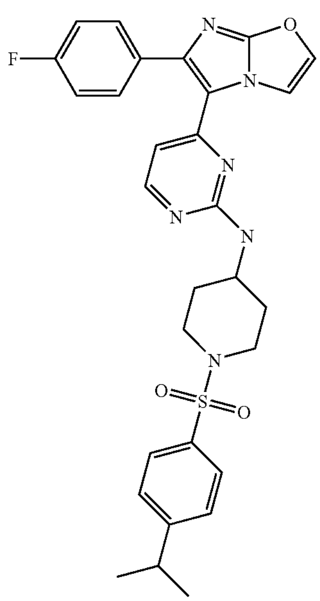 | 4-[6-(4-fluorophenyl)imidazo[2,1-b][1,3]oxazol-5-yl]-N-{1-[(4-isopropylphenyl)sulfonyl]piperidin-4-yl}pyrimidin-2-amine | 235-237 | 0.42 |

TABLE 2-continued

Exemplary compounds of the invention

| Cmpd # | Structure | IUPAC name | Melting point (° C.) or LCMS | Mutant B-RAF IC$_{50}$ (uM) or % inhibition |
|---|---|---|---|---|
| 202 | 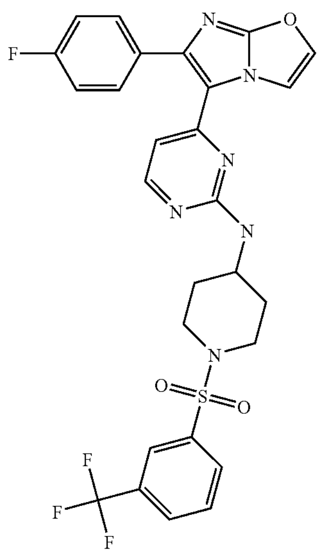 | 4-[6-(4-fluorophenyl)imidazo[2,1-b][1,3]oxazol-5-yl]-N-(1-{[3-(trifluoromethyl)phenyl]sulfonyl}piperidin-4-yl)pyrimidin-2-amine | 266-268 | 0.84 |
| 203 | 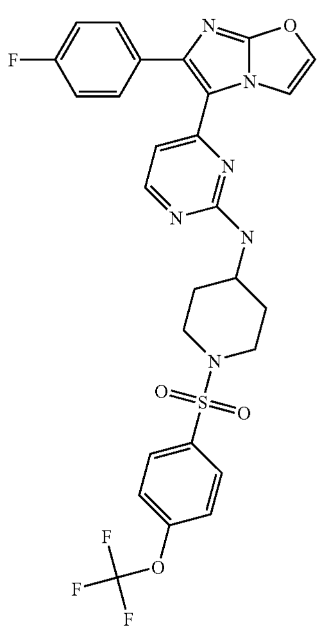 | 4-[6-(4-fluorophenyl)imidazo[2,1-b][1,3]oxazol-5-yl]-N-(1-{[4-(trifluoromethoxy)phenyl]sulfonyl}piperidin-4-yl)pyrimidin-2-amine | 230-232 | 0.521 |

TABLE 2-continued

Exemplary compounds of the invention

| Cmpd # | Structure | IUPAC name | Melting point (° C.) or LCMS | Mutant B-RAF IC$_{50}$ (uM) or % inhibition |
|---|---|---|---|---|
| 204 | 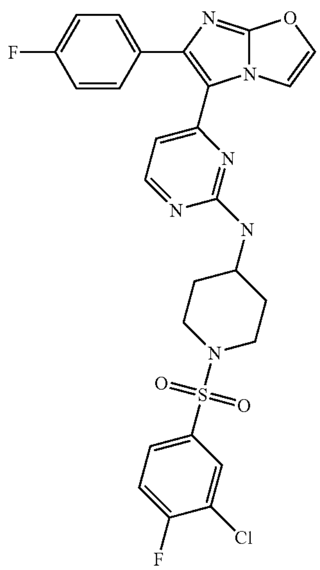 | N-{1-[(3-chloro-4-fluorophenyl)sulfonyl]piperidin-4-yl}-4-[-6-(4-fluorophenyl)imidazo[2,1-b][1,3]oxazol-5-yl]pyrimidin-2-amine | 218-220 | 0.541 |
| 205 | 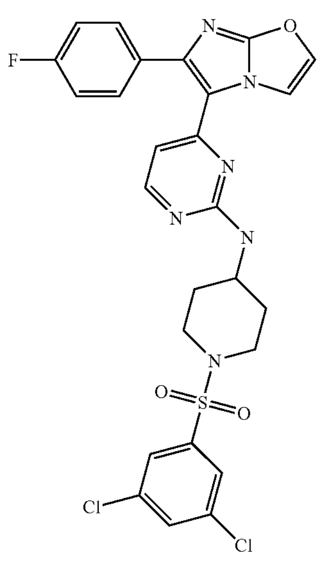 | N-{1-[(3,5-dichlorophenyl)sulfonyl]piperidin-4-yl}-4-[6-(4-fluorophenyl)imidazo[2,1-b][1,3]oxazol-5-yl]pyrimidin-2-amine | 218-220 | 0.981 |

TABLE 2-continued

Exemplary compounds of the invention

| Cmpd # | Structure | IUPAC name | Melting point (° C.) or LCMS | Mutant B-RAF IC$_{50}$ (uM) or % inhibition |
|---|---|---|---|---|
| 206 | 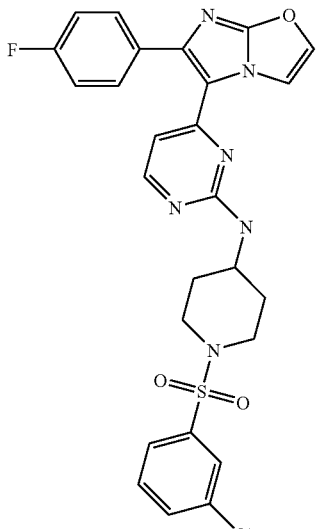 | N-{1-[(3-chlorophenyl)sulfonyl]piperidin-4-yl}-4-[6-(4-fluorophenyl)imidazo[2,1-b][1,3]oxazol-5-yl]pyrimidin-2-amine | 225-226 | 0.329 |
| 207 | 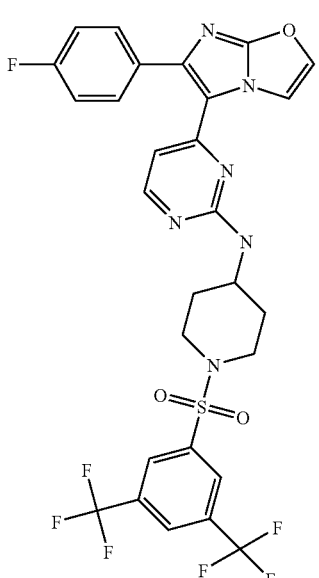 | N-(1-{[3,5-bis(trifluoromethyl)phenyl]sulfonyl}piperidin-4-yl)-4-[6-(4-fluorophenyl)imidazo[2,1-b][1,3]oxazol-5-yl]pyrimidin-2-amine | 225-227 | 0.027 |
| 208 | 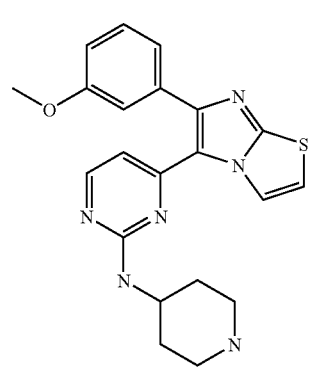 | 4-[6-(3-methoxyphenyl)imidazo[2,1-b][1,3]thiazol-5-yl]-N-piperidin-4-ylpyrimidin-2-amine | 255-260 | 2.93 |

TABLE 2-continued

Exemplary compounds of the invention

| Cmpd # | Structure | IUPAC name | Melting point (° C.) or LCMS | Mutant B-RAF IC$_{50}$ (uM) or % inhibition |
|---|---|---|---|---|
| 209 | 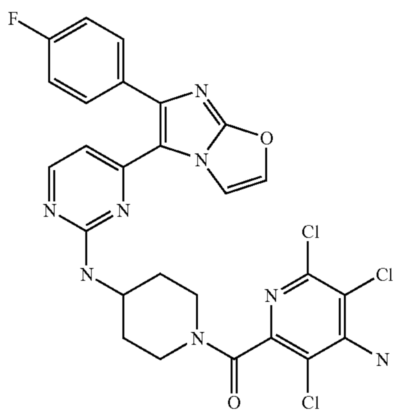 | N-{1-[(4-amino-3,5,6-trichloropyridin-2-yl)carbonyl]piperidin-4-yl}-4-[6-(4-fluorophenyl)imidazo[2,1-b][1,3]oxazol-5-yl]pyrimidin-2-amine | 275-276 | 49 @ 10 uM |
| 210 | 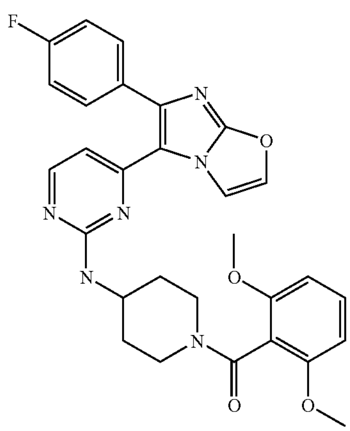 | N-[1-(2,6-dimethoxybenzoyl)piperidin-4-yl]-4-[6-(4-fluorophenyl)imidazo[2,1-b][1,3]oxazol-5-yl]pyrimidin-2-amine | 253-254 | 38 @ 10 uM |
| 211 | 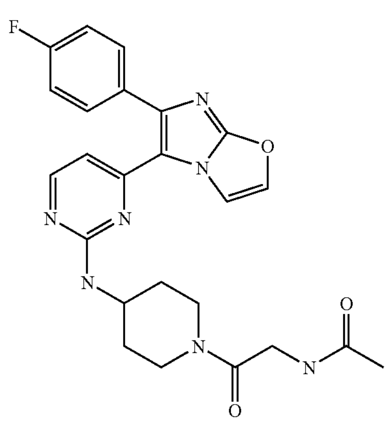 | N-{2-[4-({4-[6-(4-fluorophenyl)imidazo[2,1-b][1,3]oxazol-5-yl]pyrimidin-2-yl}amino)piperidin-1-yl]-2-oxoethyl}acetamide | 235-237 | 29 @ 10 uM |

TABLE 2-continued

Exemplary compounds of the invention

| Cmpd # | Structure | IUPAC name | Melting point (° C.) or LCMS | Mutant B-RAF IC$_{50}$ (uM) or % inhibition |
|---|---|---|---|---|
| 212 | 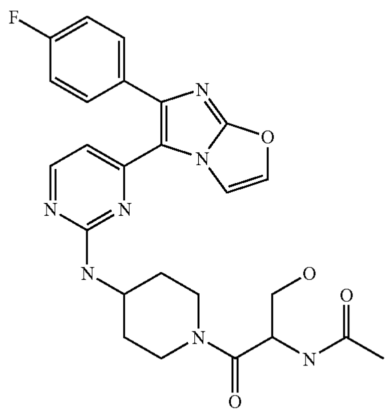 | N-[2-[4-({4-[6-(4-fluorophenyl)imidazo[2,1-b][1,3]oxazol-5-yl]pyrimidin-2-yl}amino)piperidin-1-yl]-1-(hydroxymethyl)-2-oxoethyl]acetamide | 155-157 | 43 @ 10 uM |
| 213 | 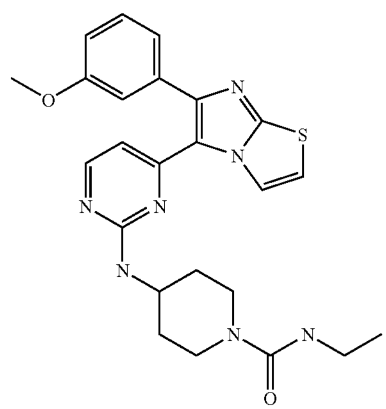 | N-ethyl-4-({4-[6-(3-methoxyphenyl)imidazo[2,1-b][1,3]thiazol-5-yl]pyrimidin-2-yl}amino)piperidine-1-carboxamide | 124-125 | 2.04 |
| 214 | 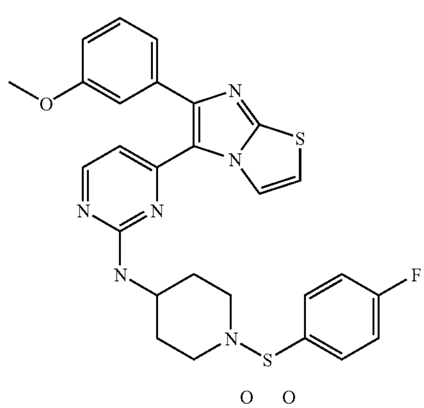 | N-{1-[(4-fluorophenyl)sulfonyl]piperidin-4-yl}-4-[6-(3-methoxyphenyl)imidazo[2,1-b][1,3]thiazol-5-yl]pyrimidin-2-amine | 208-209 | 0.392 |

TABLE 2-continued

Exemplary compounds of the invention

| Cmpd # | Structure | IUPAC name | Melting point (° C.) or LCMS | Mutant B-RAF IC$_{50}$ (uM) or % inhibition |
|---|---|---|---|---|
| 215 | 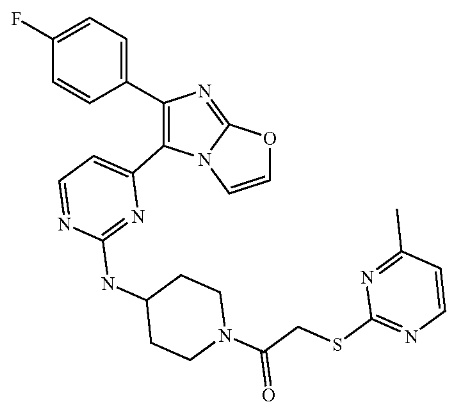 | 4-[6-(4-fluorophenyl)imidazo[2,1-b][1,3]oxazol-5-yl]-N-(1-{[(4-methylpyrimidin-2-yl)thio]acetyl}piperidin-4-yl)pyrimidin-2-amine | 219-220 | 40 @ 10 uM |
| 216 | 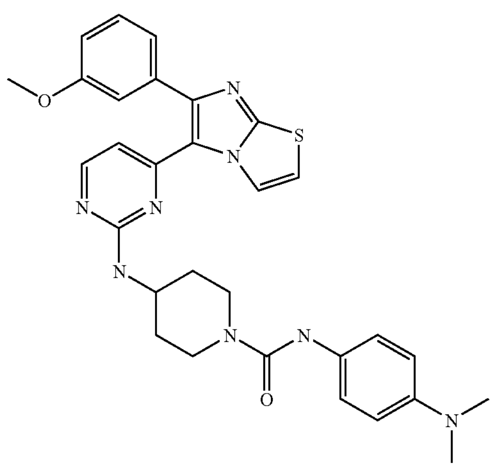 | N-[4-(dimethylamino)phenyl]-4-({4-[6-(3-methoxyphenyl)imidazo[2,1-b][1,3]thiazol-5-yl]pyrimidin-2-yl}amino)piperidine-1-carboxamide | 127-128 | 58 @ 10 uM |
| 217 | 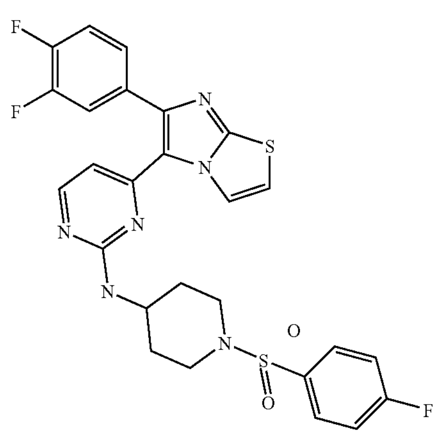 | 4-[6-(3,4-difluorophenyl)imidazo[2,1-b][1,3]thiazol-5-yl]-N-{1-[(4-fluorophenyl)sulfonyl]piperidin-4-yl}pyrimidin-2-amine | 258-259 | 48 @ 10 uM |

TABLE 2-continued

Exemplary compounds of the invention

| Cmpd # | Structure | IUPAC name | Melting point (° C.) or LCMS | Mutant B-RAF IC$_{50}$ (uM) or % inhibition |
|---|---|---|---|---|
| 218 | 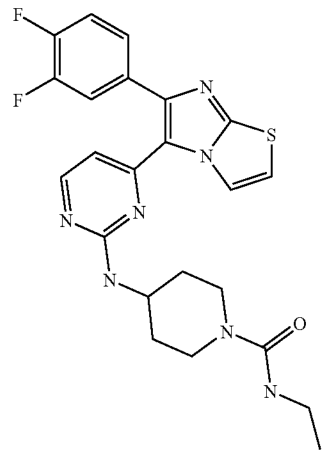 | 4-({4-[6-(3,4-difluorophenyl)imidazo[2,1-b][1,3]thiazol-5-yl]pyrimidin-2-yl}amino)-N-ethylpiperidine-1-carboxamide | 221-222 | 1.22 |
| 219 | 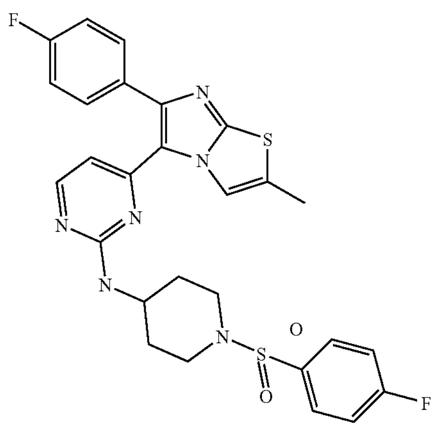 | 4-[6-(4-fluorophenyl)-2-methylimidazo[2,1-b][1,3]thiazol-5-yl]-N-{1-[(4-fluorophenyl)sulfonyl]piperidin-4-yl}pyrimidin-2-amine | 238-239 | 0.051 |
| 220 | 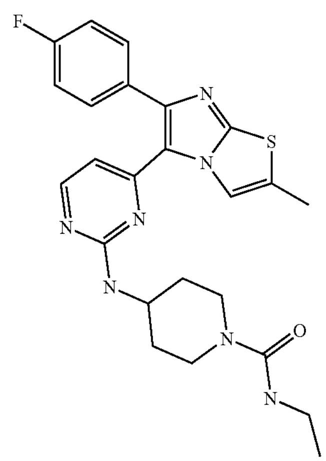 | N-ethyl-4-({4-[6-(4-fluorophenyl)-2-methylimidazo[2,1-b][1,3]thiazol-5-yl]pyrimidin-2-yl}amino)piperidine-1-carboxamide | 217-218 | 0.428 |

TABLE 2-continued

Exemplary compounds of the invention

| Cmpd # | Structure | IUPAC name | Melting point (° C.) or LCMS | Mutant B-RAF IC$_{50}$ (uM) or % inhibition |
|---|---|---|---|---|
| 221 | 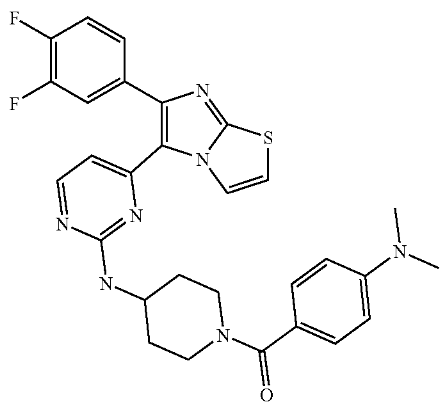 | 4-[6-(3,4-difluorophenyl)imidazo[2,1-b][1,3]thiazol-5-yl]-N-{1-[4-(dimethylamino)benzoyl]piperidin-4-yl}pyrimidin-2-amine | 148-149 | 42 @ 10 uM |
| 222 | 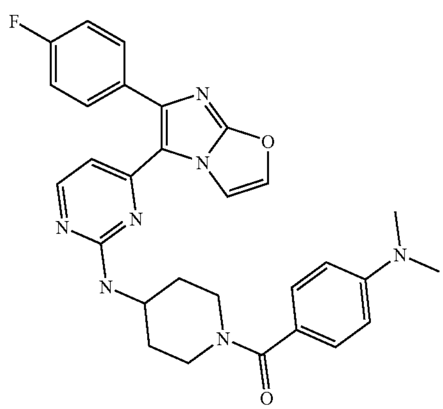 | N-{1-[4-(dimethylamino)benzoyl]piperidin-4-yl}-4-[6-(4-fluorophenyl)imidazo[2,1-b][1,3]oxazol-5-yl]pyrimidin-2-amine | 175-177 | 45 @ 10 uM |
| 223 | 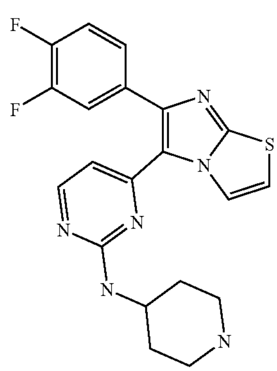 | 4-[6-(3,4-difluorophenyl)imidazo[2,1-b][1,3]thiazol-5-yl]-N-piperidin-4-ylpyrimidin-2-amine | 189-191 | 71 @ 10 uM |

TABLE 2-continued

Exemplary compounds of the invention

| Cmpd # | Structure | IUPAC name | Melting point (° C.) or LCMS | Mutant B-RAF IC$_{50}$ (uM) or % inhibition |
|---|---|---|---|---|
| 224 | 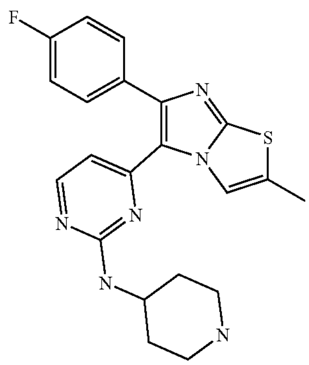 | 4-[6-(4-fluorophenyl)-2-methylimidazo[2,1-b][1,3]thiazol-5-yl]-N-piperidin-4-ylpyrimidin-2-amine | 267-268 | 70 @ 10 uM |
| 225 | 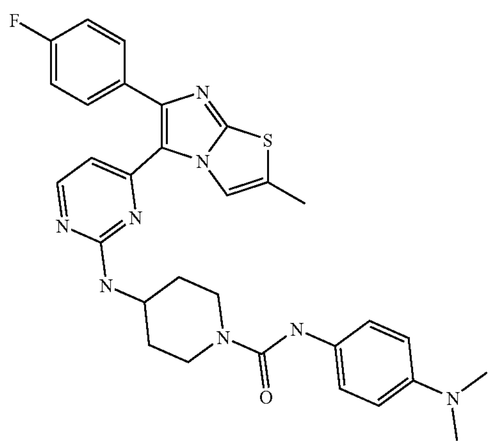 | N-[4-(dimethylamino)phenyl]-4-({4-[6-(4-fluorophenyl)-2-methylimidazo[2,1-b][1,3]thiazol-5-yl]pyrimidin-2-yl}amino)piperidine-1-carboxamide | 228-230 | 38 @ 10 uM |
| 226 | 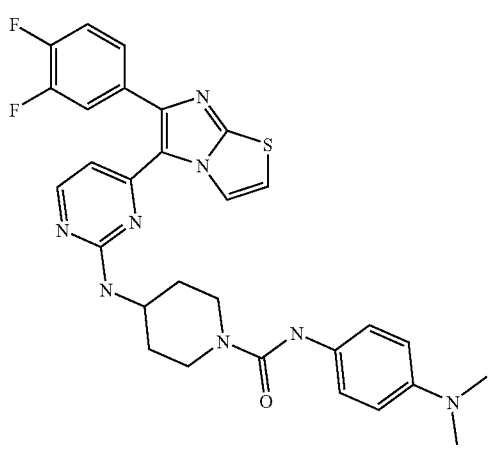 | 4-({4-[6-(3,4-difluorophenyl)imidazo[2,1-b][1,3]thiazol-5-yl]pyrimidin-2-yl}amino)-N-[4-(dimethylamino)phenyl]piperidine-1-carboxamide | 205-206 | 61 @ 10 uM |

TABLE 2-continued

Exemplary compounds of the invention

| Cmpd # | Structure | IUPAC name | Melting point (° C.) or LCMS | Mutant B-RAF IC$_{50}$ (uM) or % inhibition |
|---|---|---|---|---|
| 227 | 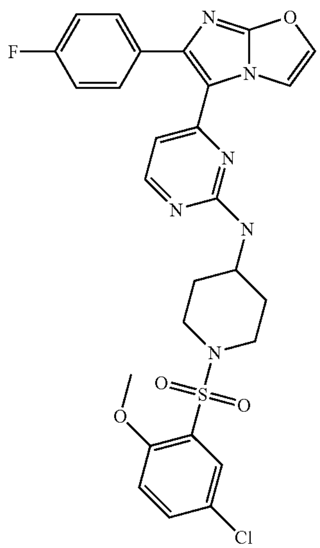 | N-{1-[(5-chloro-2-methoxyphenyl)sulfonyl]piperidin-4-yl}-4-[6-(4-fluorophenyl)imidazo[2,1-b][1,3]oxazol-5-yl]pyrimidin-2-amine | 156-158 | 27 @ 10 uM |
| 228 | 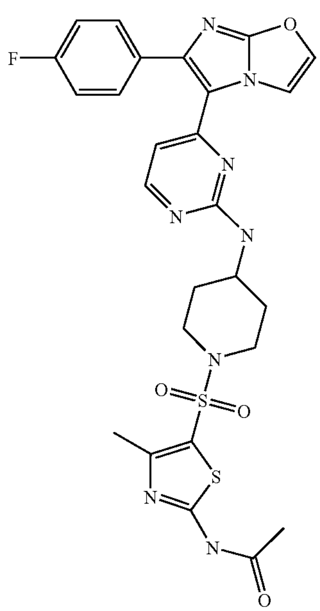 | N-(5-{(4-({4-[6-(4-fluorophenyl)imidazo[2,1-b][1,3]oxazol-5-yl]pyrimidin-2-yl}amino)piperidin-1-yl]sulfonyl}-4-methyl-1,3-thiazol-2-yl)acetamide | >300 | 40 @ 10 uM |

TABLE 2-continued

Exemplary compounds of the invention

| Cmpd # | Structure | IUPAC name | Melting point (° C.) or LCMS | Mutant B-RAF IC$_{50}$ (uM) or % inhibition |
|---|---|---|---|---|
| 229 | 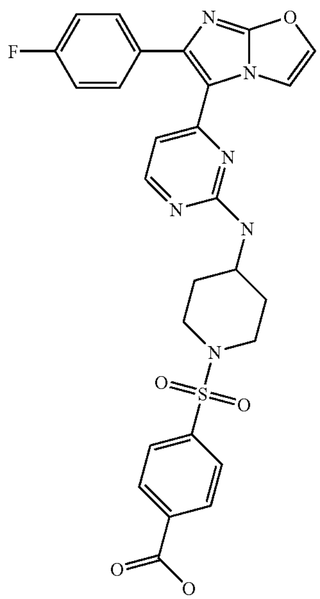 | 4-{[4-({4-[6-(4-fluorophenyl)imidazo[2,1-b][1,3]oxazol-5-yl]pyrimidin-2-yl}amino)piperidin-1-yl]sulfonyl)benzoic acid | 182-184 | 1.37 |
| 230 | 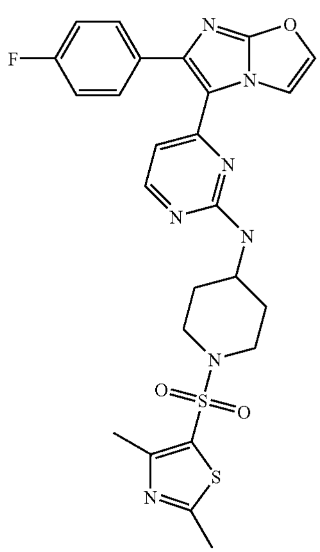 | N-{1-[(2,4-dimethyl-1,3-thiazol-5-yl)sulfonyl]piperidin-4-yl)-4-[6-(4-fluorophenyl)imidazo[2,1-b][1,3]oxazol-5-yl]pyrimidin-2-amine | 240-242 | 50 @ 10 uM |

TABLE 2-continued

Exemplary compounds of the invention

| Cmpd # | Structure | IUPAC name | Melting point (° C.) or LCMS | Mutant B-RAF IC$_{50}$ (uM) or % inhibition |
|---|---|---|---|---|
| 231 | 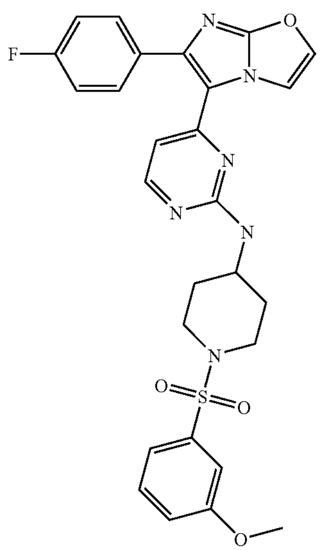 | 4-[6-(4-fluorophenyl)imidazo[2,1-b][1,3]oxazol-5-yl]-N-{1-[(3-methoxyphenyl)sulfonyl]piperidin-4-yl}pyrimidin-2-amine | 214-215 | 0.408 |
| 232 | 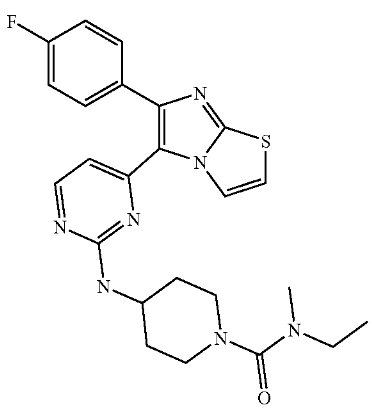 | N-ethyl-4-({4-[6-(4-fluorophenyl)imidazo[2,1-b][1,3]thiazol-5-yl]pyrimidin-2-yl}amino)-N-methylpiperidine-1-carboxamide | 104-107 | 56 @ 10 uM |
| 233 | 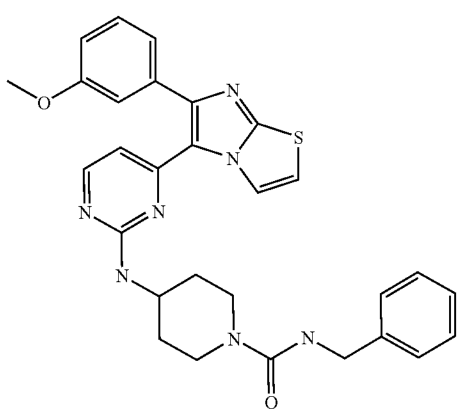 | N-benzyl-4-({4-[6-(3-methoxyphenyl)imidazo[2,1-b][1,3]thiazol-5-yl]pyrimidin-2-yl}amino)piperidine-1-carboxamide | 118-120 | 53 @ 10 uM |

TABLE 2-continued

Exemplary compounds of the invention

| Cmpd # | Structure | IUPAC name | Melting point (° C.) or LCMS | Mutant B-RAF IC$_{50}$ (uM) or % inhibition |
|---|---|---|---|---|
| 234 | 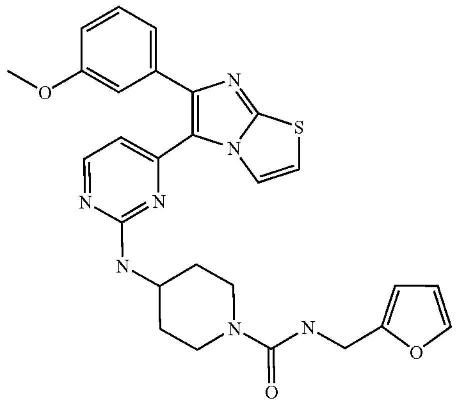 | N-(2-furylmethyl)-4-({4-[6-(3-methoxyphenyl)imidazo[2,1-b][1,3]thiazol-5-yl]pyrimidin-2-yl}amino)piperidine-1-carboxamide | 127-128 | 0.825 |
| 235 | 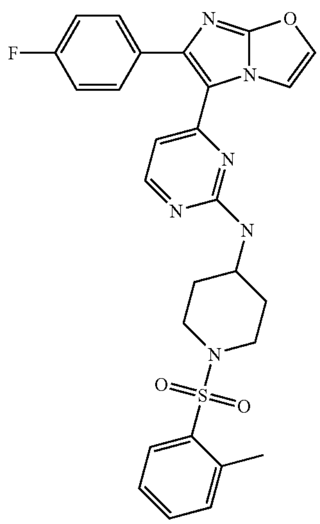 | 4-[6-(4-fluorophenyl)imidazo[2,1-b][1,3]oxazol-5-yl]-N-{1-[(2-methylphenyl)sulfonyl]piperidin-4-yl}pyrimidin-2-amine | 263-265 | 30 @ 10 uM |
| 236 | 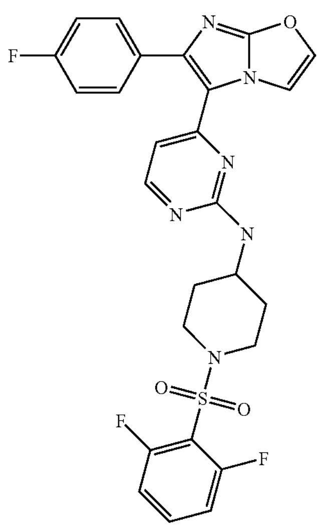 | N-{1-[(2,6-difluorophenyl)sulfonyl]piperidin-4-yl}-4-[6-(4-fluorophenyl)imidazo[2,1-b][1,3]oxazol-5-yl]pyrimidin-2-amine | 252-255 | 30 @ 10 uM |

TABLE 2-continued

Exemplary compounds of the invention

| Cmpd # | Structure | IUPAC name | Melting point (° C.) or LCMS | Mutant B-RAF IC$_{50}$ (uM) or % inhibition |
|---|---|---|---|---|
| 237 | 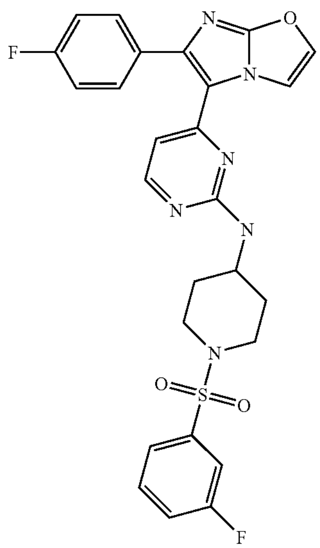 | 4-[6-(4-fluorophenyl)imidazo[2,1-b][1,3]oxazol-5-yl]-N-{1-[(3-fluorophenyl)sulfonyl]piperidin-4-yl}pyrimidin-2-amine | 215-218 | 85 @ 5 uM |
| 238 | 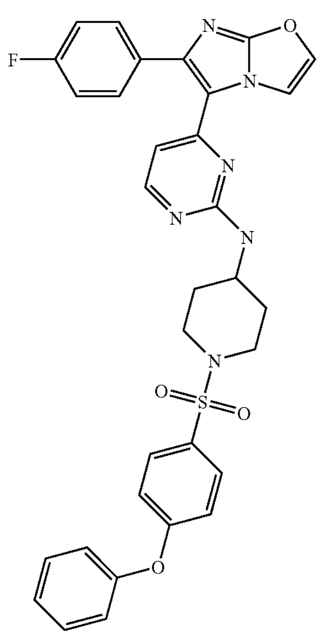 | 4-[6-(4-fluorophenyl)imidazo[2,1-b][1,3]oxazol-5-yl]-N-{1-[(4-phenoxyphenyl)sulfonyl]piperidin-4-yl}pyrimidin-2-amine | 213-215 | >10 |

TABLE 2-continued

Exemplary compounds of the invention

| Cmpd # | Structure | IUPAC name | Melting point (° C.) or LCMS | Mutant B-RAF IC$_{50}$ (uM) or % inhibition |
|---|---|---|---|---|
| 239 | 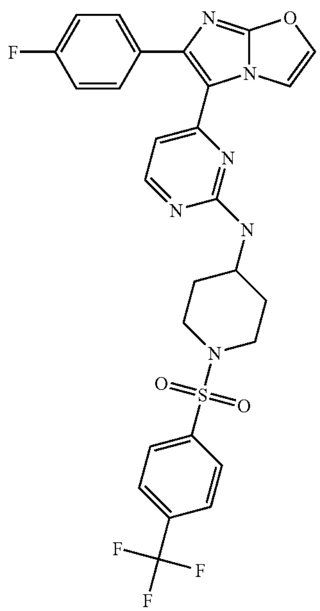 | 4-[6-(4-fluorophenyl)imidazo[2,1-b][1,3]oxazol-5-yl]-N-(1-{[4-(trifluoromethyl)phenyl]sulfonyl}piperidin-4-yl)pyrimidin-2-amine | 231-233 | 52 @ 3 uM |
| 240 | 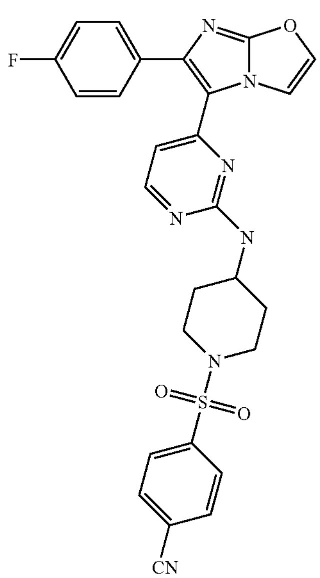 | 4-{[4-({4-[6-(4-fluorophenyl)imidazo[2,1-b][1,3]oxazol-5-yl]pyrimidin-2-yl}amino)piperidin-1-yl]sulfonyl}benzonitrile | 267-269 | 44 @ 10 uM |

TABLE 2-continued

Exemplary compounds of the invention

| Cmpd # | Structure | IUPAC name | Melting point (° C.) or LCMS | Mutant B-RAF IC$_{50}$ (uM) or % inhibition |
|---|---|---|---|---|
| 241 | 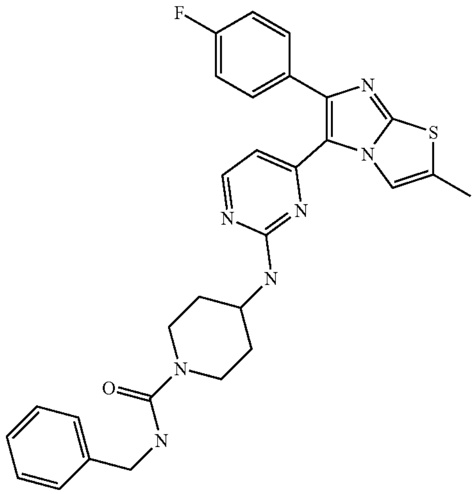 | N-benzyl-4-({4-[6-(4-fluorophenyl)-2-methylimidazo[2,1-b][1,3]thiazol-5-yl]pyrimidin-2-yl}amino)piperidine-1-carboxamide | 137-138 | 2.53 |
| 242 | 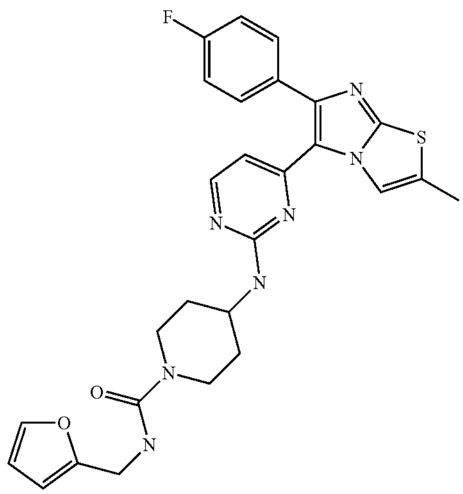 | 4-({4-[6-(4-fluorophenyl)-2-methylimidazo[2,1-b][1,3]thiazol-5-yl]pyrimidin-2-yl}amino)-N-(2-furylmethyl)piperidine-1-carboxamide | 178-179 | 67 @ 10 uM |
| 243 | 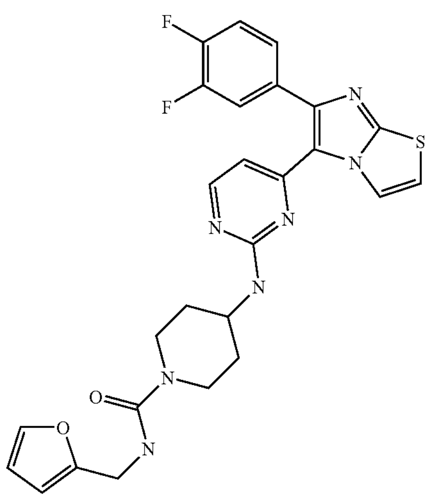 | 4-({4-[6-(3,4-difluorophenyl)imidazo[2,1-b][1,3]thiazol-5-yl]pyrimidin-2-yl}amino)-N-(2-furylmethyl)piperidine-1-carboxamide | 159-160 | 76 @ 10 uM |

TABLE 2-continued

Exemplary compounds of the invention

| Cmpd # | Structure | IUPAC name | Melting point (° C.) or LCMS | Mutant B-RAF IC$_{50}$ (uM) or % inhibition |
|---|---|---|---|---|
| 244 | 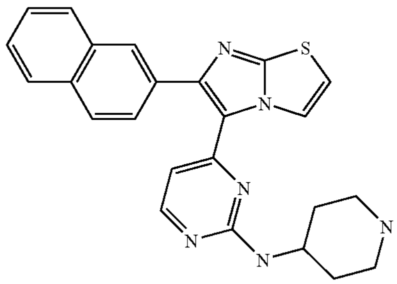 | 4-[6-(2-naphthyl)imidazo[2,1-b][1,3]thiazol-5-yl]-N-piperidin-4-ylpyrimidin-2-amine | 210-215 | 47 @ 10 uM |
| 245 | 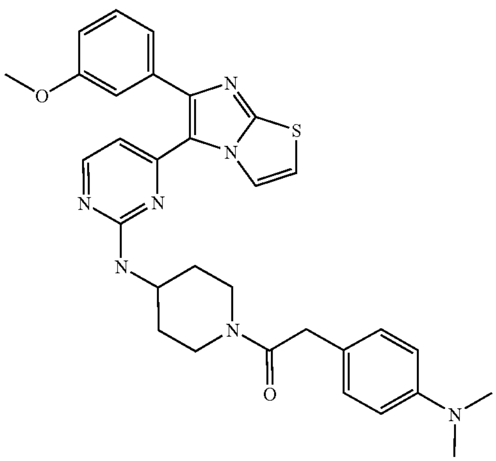 | N-(1-{[4-(dimethylamino)phenyl]acetyl}piperidin-4-yl)-4-[6-(3-methoxyphenyl)imidazo[2,1-b][1,3]thiazol-5-yl]pyrimidin-2-amine | 138-140 | 2.46 |
| 246 | 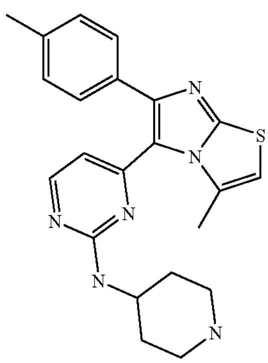 | 4-[3-methyl-6-(4-methylphenyl)imidazo[2,1-b][1,3]thiazol-5-yl]-N-piperidin-4-ylpyrimidin-2-amine | 185-189 | >10 |
| 247 | 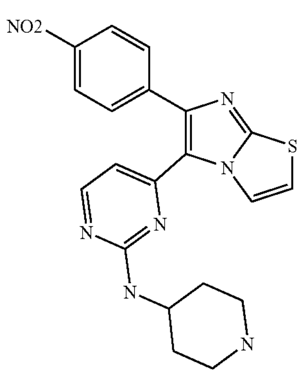 | 4-[6-(4-nitrophenyl)imidazo[2,1-b][1,3]thiazol-5-yl]-N-piperidin-4-ylpyrimidin-2-amine | 203-206 | 9 @ 2 uM |

TABLE 2-continued

Exemplary compounds of the invention

| Cmpd # | Structure | IUPAC name | Melting point (° C.) or LCMS | Mutant B-RAF IC$_{50}$ (uM) or % inhibition |
|---|---|---|---|---|
| 248 | 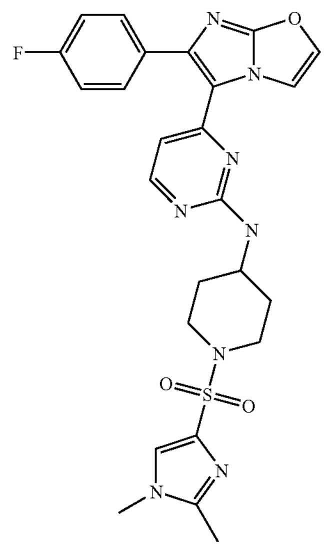 | N-{1-[(1,2-dimethyl-1H-imidazol-4-yl)sulfonyl]piperidin-4-yl}-4-[6-(4-fluorophenyl)imidazo[2,1-b][1,3]oxazol-5-yl]pyrimidin-2-amine | 148-152 | 0.931 |
| 249 | 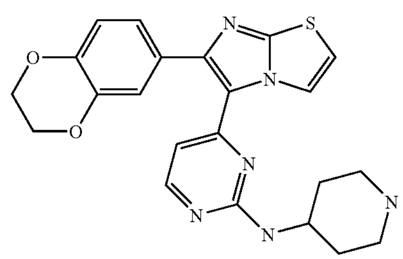 | 4-[6-(2,3-dihydro-1,4-benzodioxin-6-yl)imidazo[2,1-b][1,3]thiazol-5-yl]-N-piperidin-4-ylpyrimidin-2-amine | 231-235 | 58 @ 10 uM |
| 250 | 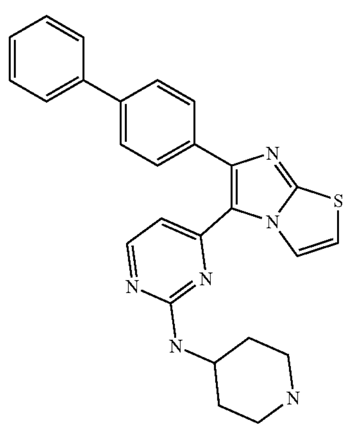 | 4-(6-biphenyl-4-ylimidazo[2,1-b][1,3]thiazol-5-yl)-N-piperidin-4-ylpyrimidin-2-amine | 195-198 | 2 @ 3 uM |

TABLE 2-continued

Exemplary compounds of the invention

| Cmpd # | Structure | IUPAC name | Melting point (° C.) or LCMS | Mutant B-RAF IC$_{50}$ (uM) or % inhibition |
|---|---|---|---|---|
| 251 | 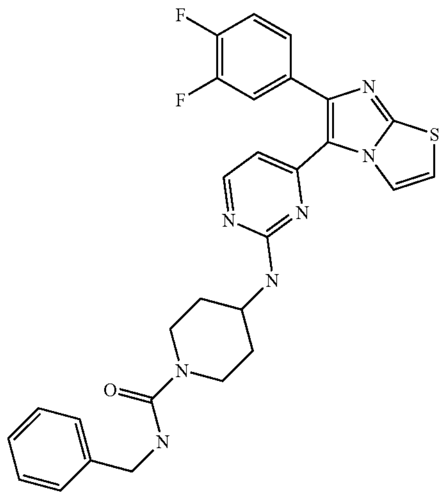 | N-benzyl-4-({4-[6-(3,4-difluorophenyl)imidazo[2,1-b][1,3]thiazol-5-yl]pyrimidin-2-yl}amino)piperidine-1-carboxamide | 187-188 | 63 @ 10 uM |
| 252 | 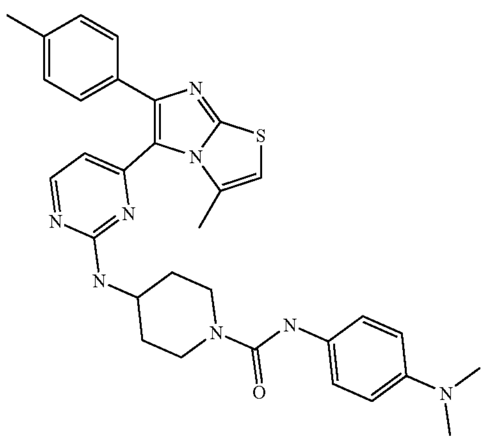 | N-[4-(dimethylamino)phenyl]-4-({4-[3-methyl-6-(4-methylphenyl)imidazo[2,1-b][1,3]thiazol-5-yl]pyrimidin-2-yl}amino)piperidine-1-carboxamide | 133-135 | >3.0 |
| 253 | 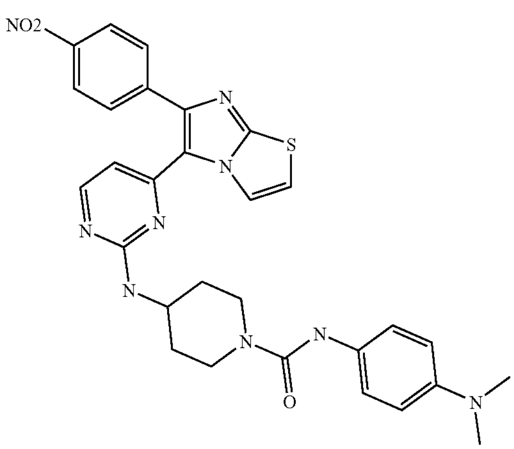 | N-[4-(dimethylamino)phenyl]-4-({4-[6-(4-nitrophenyl)imidazo[2,1-b][1,3]thiazol-5-yl]pyrimidin-2-yl}amino)piperidine-1-carboxamide | 185-188 | >3.0 |

TABLE 2-continued

Exemplary compounds of the invention

| Cmpd # | Structure | IUPAC name | Melting point (° C.) or LCMS | Mutant B-RAF IC$_{50}$ (uM) or % inhibition |
|---|---|---|---|---|
| 254 | 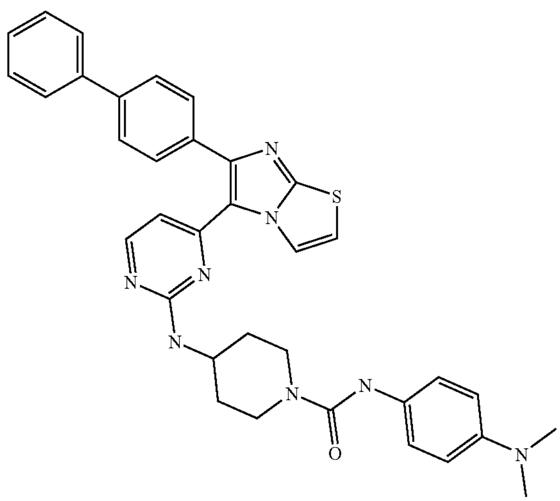 | 4-{[4-(6-biphenyl-4-ylimidazo[2,1-b][1,3]thiazol-5-yl)pyrimidin-2-yl]amino}-N-[4-(dimethylamino)phenyl]piperidine-1-carboxamide | 141-145 | >3.0 |
| 255 | 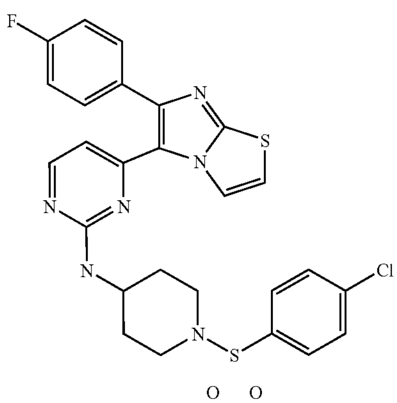 | N-{1-[(4-chlorophenyl)sulfonyl]piperidin-4-yl}-4-[6-(4-fluorophenyl)imidazo[2,1-b][1,3]thiazol-5-yl]pyrimidin-2-amine | 244-245 | 0.696 |
| 256 | 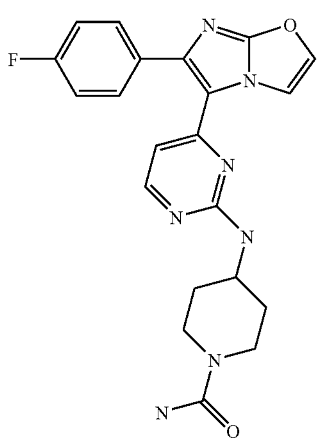 | 4-({4-[6-(4-fluorophenyl)imidazo[2,1-b][1,3]oxazol-5-yl]pyrimidin-2-yl}amino)piperidine-1-carboxamide | 185-190 | >1.0 |

TABLE 2-continued
Exemplary compounds of the invention
| Cmpd # | Structure | IUPAC name | Melting point (° C.) or LCMS | Mutant B-RAF IC$_{50}$ (uM) or % inhibition |
|---|---|---|---|---|
| 257 | 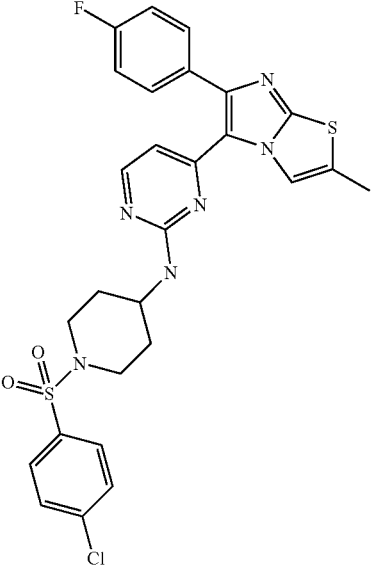 | N-{1-[(4-chlorophenyl)sulfonyl]piperidin-4-yl}-4-[6-(4-fluorophenyl)-2-methylimidazo[2,1-b][1,3]thiazol-5-yl]pyrimidin-2-amine | 148-149 | 0.073 |
| 258 | 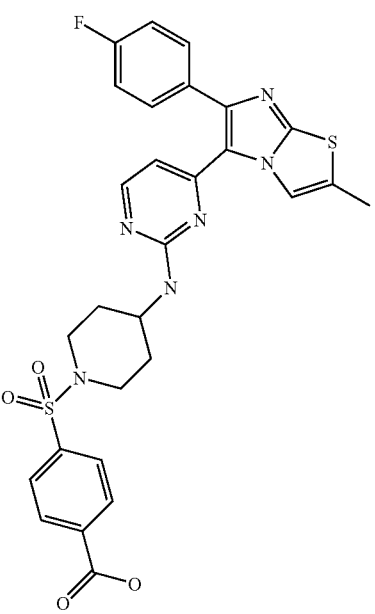 | 4-{[4-({4-[6-(4-fluorophenyl)-2-methylimidazo[2,1-b][1,3]thiazol-5-yl]pyrimidin-2-yl}amino)piperidin-1-yl]sulfonyl}benzoic acid | 195-196 | 0.322 |

TABLE 2-continued

Exemplary compounds of the invention

| Cmpd # | Structure | IUPAC name | Melting point (° C.) or LCMS | Mutant B-RAF IC$_{50}$ (uM) or % inhibition |
|---|---|---|---|---|
| 259 | 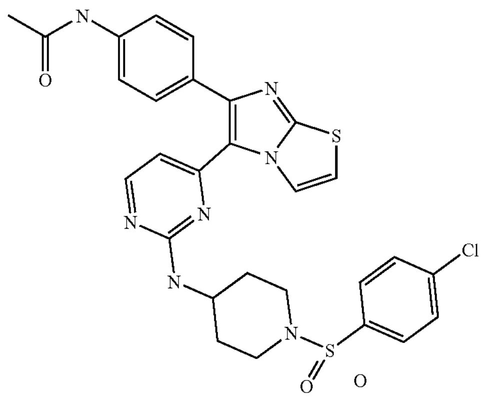 | N-(4-{5-[2-({1-[(4-chlorophenyl)sulfonyl]piperidin-4-yl}amino)pyrimidin-4-yl]imidazo[2,1-b][1,3]thiazol-6-yl}phenyl)acetamide | 175-178 | >3.0 |
| 260 | 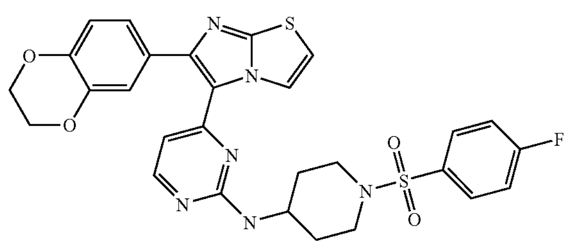 | 4-[6-(2,3-dihydro-1,4-benzodioxin-6-yl)imidazo[2,1-b][1,3]thiazol-5-yl]-N-{1-[(4-fluorophenyl)sulfonyl]piperidin-4-yl}pyrimidin-2-amine | 251-253 | 0.186 |
| 261 | 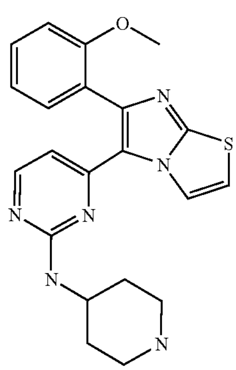 | 4-[6-(2-methoxyphenyl)imidazo[2,1-b][1,3]thiazol-5-yl]-N-piperidin-4-ylpyrimidin-2-amine | 235-237 | >3.0 |
| 262 | 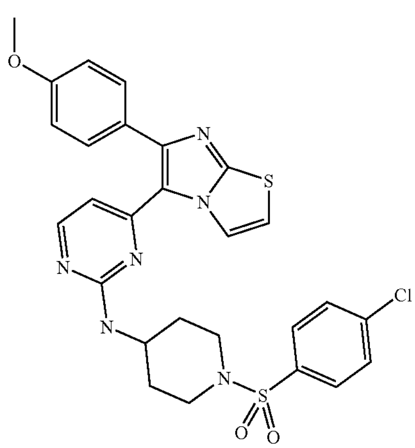 | N-{1-[(4-chlorophenyl)sulfonyl]piperidin-4-yl}-4-[6-(4-methoxyphenyl)imidazo[2,1-b][1,3]thiazol-5-yl]pyrimidin-2-amine | 127-129 | >3.0 |

TABLE 2-continued

Exemplary compounds of the invention

| Cmpd # | Structure | IUPAC name | Melting point (° C.) or LCMS | Mutant B-RAF IC$_{50}$ (uM) or % inhibition |
|---|---|---|---|---|
| 263 | 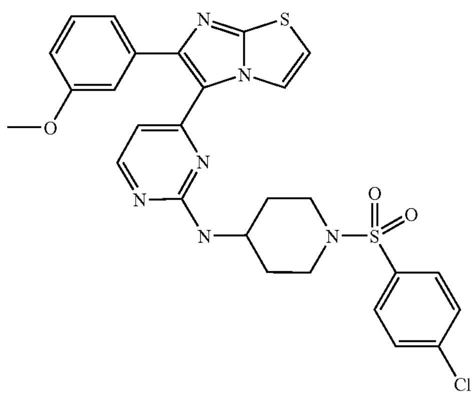 | N-{1-[(4-chlorophenyl)sulfonyl]piperidin-4-yl}-4-[6-(3-methoxyphenyl)imidazo[2,1-b][1,3]thiazol-5-yl]pyrimidin-2-amine | 215-216 | >5.0 |
| 264 | 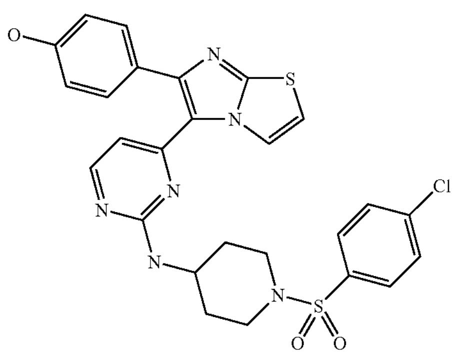 | 4-{5-[2-({1-[(4-chlorophenyl)sulfonyl]piperidin-4-yl}amino)pyrimidin-4-yl]imidazo[2,1-b][1,3]thiazol-6-yl}phenol | 188-190 | 5 @ 10 uM |
| 265 | 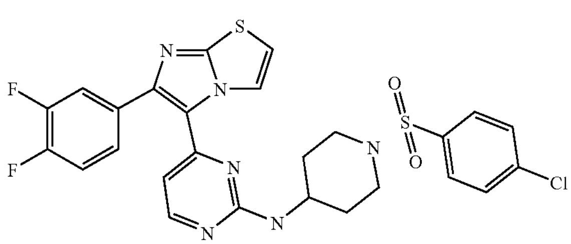 | N-{1-[(4-chlorophenyl)sulfonyl]piperidin-4-yl}-4-[6-(3,4-difluorophenyl)imidazo[2,1-b][1,3]thiazol-5-yl]pyrimidin-2-amine | 243-245 | >3.0 |
| 266 | 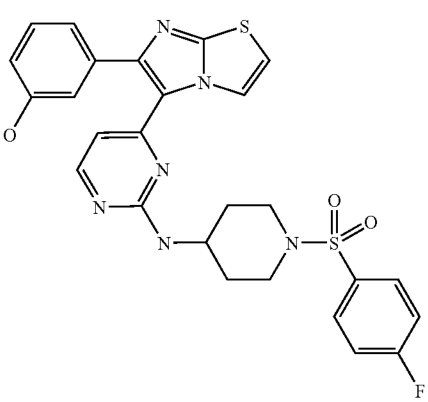 | 3-{5-[2-({1-[(4-fluorophenyl)sulfonyl]piperidin-4-yl}amino)pyrimidin-4-yl]imidazo[2,1-b][1,3]thiazol-6-yl}phenol | 175-179 | 0.029 |

TABLE 2-continued

Exemplary compounds of the invention

| Cmpd # | Structure | IUPAC name | Melting point (° C.) or LCMS | Mutant B-RAF IC$_{50}$ (uM) or % inhibition |
|---|---|---|---|---|
| 267 | 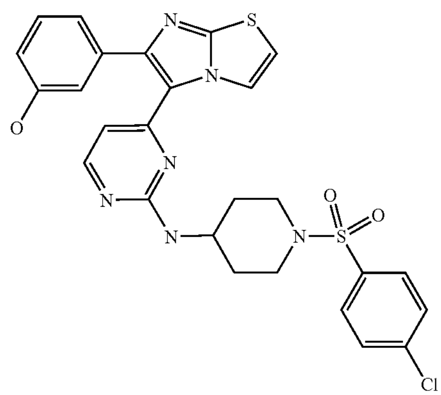 | 3-{5-[2-({1-[(4-chlorophenyl)sulfonyl]piperidin-4-yl}amino)pyrimidin-4-yl]imidazo[2,1-b][1,3]thiazol-6-yl}phenol | 160-170 | 0.031 |
| 268 | 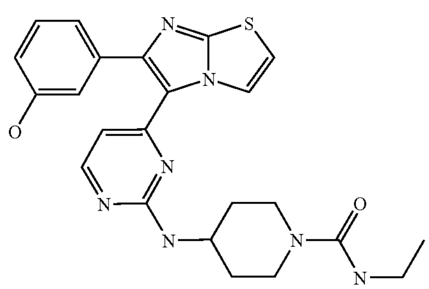 | N-ethyl-4-({4-[6-(3-hydroxyphenyl)imidazo[2,1-b][1,3]thiazol-5-yl]pyrimidin-2-yl}amino)piperidine-1-carboxamide | 170-172 | 0.009 |
| 269 | 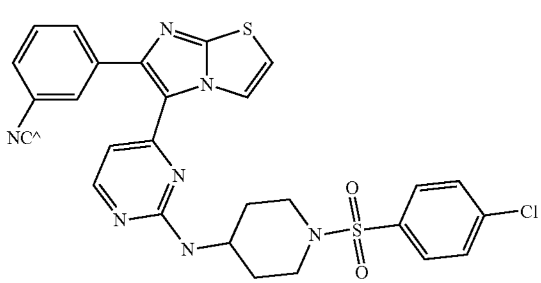 | 3-{5-[2-({1-[(4-chlorophenyl)sulfonyl]piperidin-4-yl}amino)pyrimidin-4-yl]imidazo[2,1-b][1,3]thiazol-6-yl}benzonitrile | 145-147 | 1.63 |

TABLE 2-continued
Exemplary compounds of the invention
| Cmpd # | Structure | IUPAC name | Melting point (° C.) or LCMS | Mutant B-RAF IC$_{50}$ (uM) or % inhibition |
|---|---|---|---|---|
| 270 | 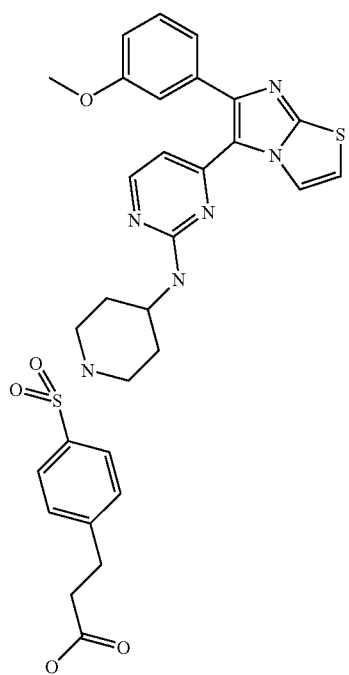 | 3-(4-{[4-({4-[6-(3-methoxyphenyl)imidazo[2,1-b][1,3]thiazol-5-yl]pyrimidin-2-yl}amino)piperidin-1-yl]sulfonyl}phenyl)propanoic acid | 159-160 | 0.316 |
| 271 | 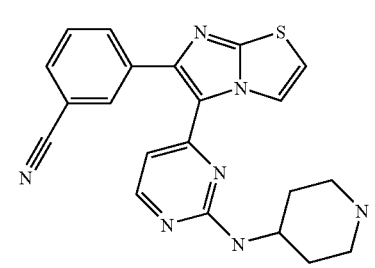 | 3-{5-[2-(piperidin-4-ylamino)pyrimidin-4-yl]imidazo[2,1-b][1,3]thiazol-6-yl}benzonitrile | 218-220 | 58 @ 10 uM |

TABLE 2-continued

Exemplary compounds of the invention

| Cmpd # | Structure | IUPAC name | Melting point (° C.) or LCMS | Mutant B-RAF IC$_{50}$ (uM) or % inhibition |
|---|---|---|---|---|
| 272 | 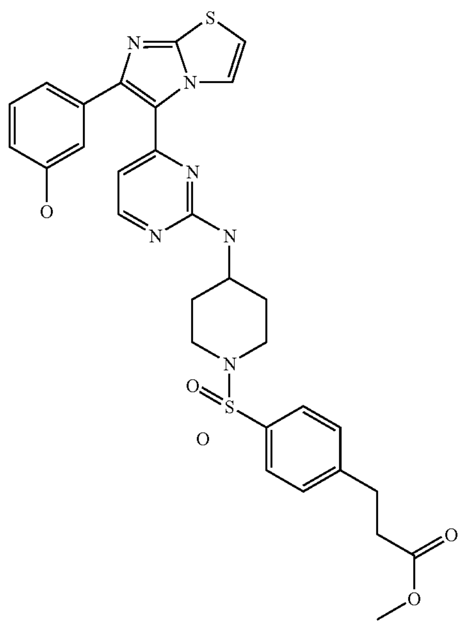 | methyl 3-(4-{[4-({4-[6-(3-hydroxyphenyl)imidazo[2,1-b][1,3]thiazol-5-yl]pyrimidin-2-yl}amino)piperidin-1-yl]sulfonyl}phenyl)propanoate | 155-157 | 0.01 |
| 273 | 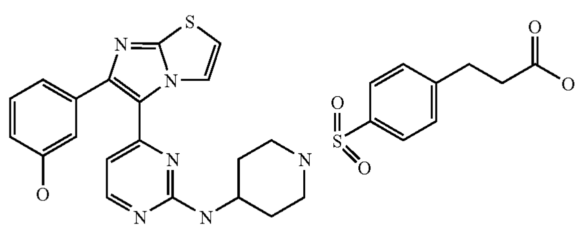 | 3-(4-{[4-({4-[6-(3-hydroxyphenyl)imidazo[2,1-b][1,3]thiazol-5-yl]pyrimidin-2-yl}amino)piperidin-1-yl]sulfonyl}phenyl)propanoic acid | 179-180 | 0.01 |
| 274 | 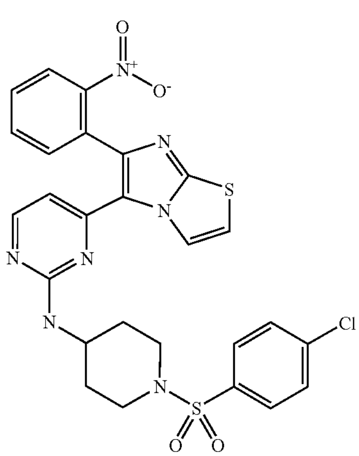 | N-{1-((4-chlorophenyl)sulfonyl]piperidin-4-yl}-4-[6-(2-nitrophenyl)imidazo[2,1-b][1,3]thiazol-5-yl]pyrimidin-2-amine | 258-260 | 0.722 |

TABLE 2-continued

Exemplary compounds of the invention

| Cmpd # | Structure | IUPAC name | Melting point (° C.) or LCMS | Mutant B-RAF IC$_{50}$ (uM) or % inhibition |
|---|---|---|---|---|
| 275 | Chiral | 4-[6-(4-fluorophenyl)imidazo[2,1-b][1,3]thiazol-5-yl]-N-[(3S)-pyrrolidin-3-yl]pyrimidin-2-amine | 230-232 | 30 @ 10 uM |
| 276 | Chiral | N-{(3S)-1-[(4-chlorophenyl)sulfonyl]pyrrolidin-3-yl}-4-[6-(4-fluorophenyl)imidazo[2,1-b][1,3]thiazol-5-yl]pyrimidin-2-amine | 190-191 | 95 @ 10 uM |
| 277 | Chiral | 4-[6-(4-fluorophenyl)imidazo[2,1-b][1,3]thiazol-5-yl]-N-[(3R)-pyrrolidin-3-yl]pyrimidin-2-amine | 175-179 | 0.044 |

TABLE 2-continued

Exemplary compounds of the invention

| Cmpd # | Structure | IUPAC name | Melting point (° C.) or LCMS | Mutant B-RAF IC$_{50}$ (uM) or % inhibition |
|---|---|---|---|---|
| 278 | Chiral | N-{(3R)-1-[(4-chlorophenyl)sulfonyl]pyrrolidin-3-yl}-4-[6-(4-fluorophenyl)imidazo[2,1-b][1,3]thiazol-5-yl]pyrimidin-2-amine | 191-192 | 10 @ 10 uM |
| 279 | Chiral | 4-[6-(3-methoxyphenyl)imidazo[2,1-b][1,3]thiazol-5-yl]-N-[(3R)-pyrrolidin-3-yl]pyrimidin-2-amine | 171-173 | 36 @ 10 uM |
| 280 | Chiral | N-{(3R)-1-[(4-chlorophenyl)sulfonyl]pyrrolidin-3-yl}-4-[6-(3-methoxyphenyl)imidazo[2,1-b][1,3]thiazol-5-yl]pyrimidin-2-amine | 180-182 | 37 @ 10 uM |
| 281 | Chiral | 4-{[(3R)-3-({4-[6-(3-methoxyphenyl)imidazo[2,1-b][1,3]thiazol-5-yl]pyrimidin-2-yl}amino)pyrrolidin-1-yl]sulfonyl)benzoic acid | 68-70 | >3.0 |

TABLE 2-continued

Exemplary compounds of the invention

| Cmpd # | Structure | IUPAC name | Melting point (° C.) or LCMS | Mutant B-RAF IC$_{50}$ (uM) or % inhibition |
|---|---|---|---|---|
| 282 | Chiral | 4-{[(3R)-3-({4-[6-(3-hydroxyphenyl)imidazo[2,1-b][1,3]thiazol-5-yl]pyrimidin-2-yl}amino)pyrrolidin-1-yl]sulfonyl}benzoic acid | 210-212 | 0.522 |
| 283 | Chiral | 3-{5-[2-({(3R)-1-[(4-chlorophenyl)sulfonyl]pyrrolidin-3-yl}amino)pyrimidin-4-yl]imidazo[2,1-b][1,3]thiazol-6-yl}phenol | 142-143 | 1.6 |
| 284 | Chiral | 3-(5-{2-[(3R)-pyrrolidin-3-ylamino]pyrimidin-4-yl}imidazo[2,1-b][1,3]thiazol-6-yl)benzonitrile | 186-188 | 61 @ 10 uM |
| 285 | Chiral | 3-{5-[2-({(3R)-1-[(4-chlorophenyl)sulfonyl]pyrrolidin-3-yl}amino)pyrimidin-4-yl]imidazo[2,1-b][1,3]thiazol-6-yl}benzonitrile | 165-167 | 35 @ 10 uM |

TABLE 2-continued

Exemplary compounds of the invention

| Cmpd # | Structure | IUPAC name | Melting point (° C.) or LCMS | Mutant B-RAF IC$_{50}$ (uM) or % inhibition |
|---|---|---|---|---|
| 286 | 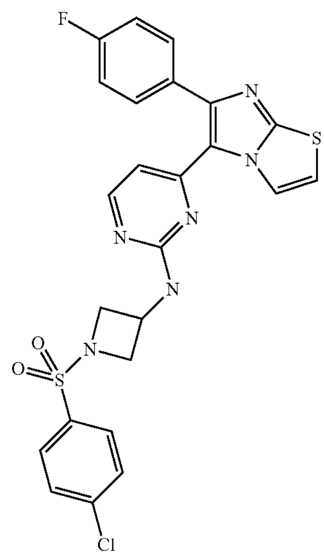 | N-{1-[(4-chlorophenyl)sulfonyl]azetidin-3-yl}-4-[6-(4-fluorophenyl)imidazo[2,1-b][1,3]thiazol-5-yl]pyrimidin-2-amine | 129-130 | 3 |
| 287 | 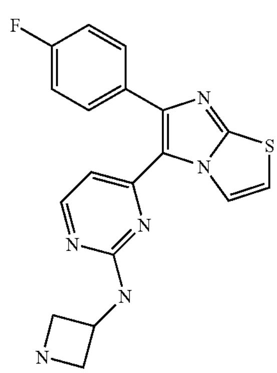 | N-azetidin-3-yl-4-[6-(4-fluorophenyl)imidazo[2,1-b][1,3]thiazol-5-yl]pyrimidin-2-amine | 223-225 | 2.49 |
| 288 | Chiral | 3-{5-[2-({(3R)-1-[(4-chlorophenyl)sulfonyl]piperidin-3-yl}amino)pyrimidin-4-yl]imidazo[2,1-b][1,3]thiazol-6-yl}phenol | 174-177 | 0.002 |

TABLE 2-continued

Exemplary compounds of the invention

| Cmpd # | Structure | IUPAC name | Melting point (° C.) or LCMS | Mutant B-RAF IC$_{50}$ (uM) or % inhibition |
|---|---|---|---|---|
| 289 | 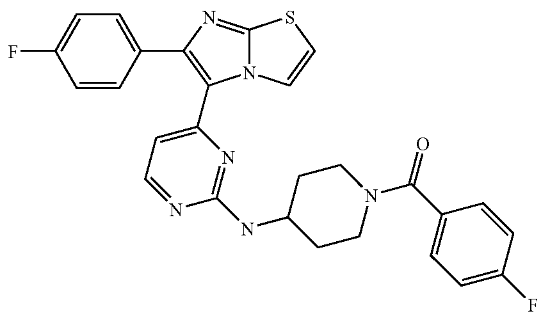 | N-[1-(4-fluorobenzoyl)piperidin-4-yl]-4-[6-(4-fluorophenyl)imidazo[2,1-b][1,3]thiazol-5-yl]pyrimidin-2-amine | 184-185 | >10 |
| 290 | 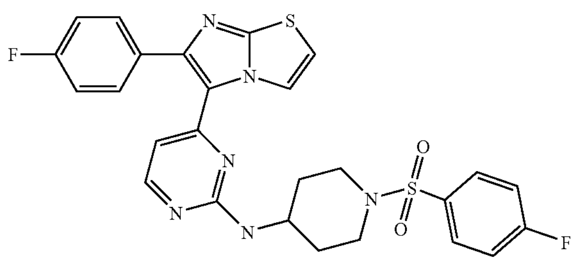 | 4-[6-(4-fluorophenyl)imidazo[2,1-b][1,3]thiazol-5-yl]-N-{1-[(4-fluorophenyl)sulfonyl]pipendin-4-yl}pyrimidin-2-amine | 256-257 | 0.078 |
| 291 | 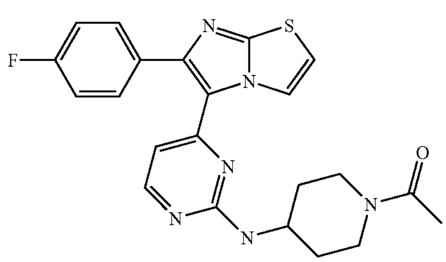 | N-(1-acetylpiperidin-4-yl)-4-[6-(4-fluorophenyl)imidazo[2,1-b][1,3]thiazol-5-yl]pyrimidin-2-amine | 201-203 | 41 @ 10 uM |
| 292 | 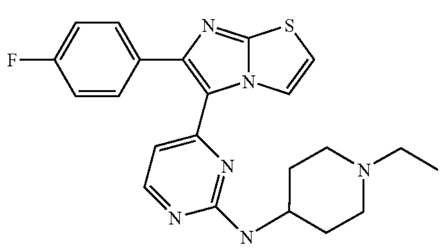 | N-(1-ethylpiperidin-4-yl)-4-[6-(4-fluorophenyl)imidazo[2,1-b][1,3]thiazol-5-yl]pyrimidin-2-amine | 173-175 | 36 @ 10 uM |
| 293 | 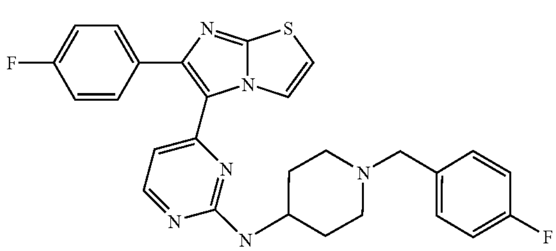 | N-[1-(4-fluorobenzyl)piperidin-4-yl]-4-[6-(4-fluorophenyl)imidazo[2,1-b][1,3]thiazol-5-yl]pyrimidin-2-amine | 503 [M + H] | 14 @ 10 uM |

TABLE 2-continued

Exemplary compounds of the invention

| Cmpd # | Structure | IUPAC name | Melting point (° C.) or LCMS | Mutant B-RAF IC$_{50}$ (uM) or % inhibition |
|---|---|---|---|---|
| 294 | 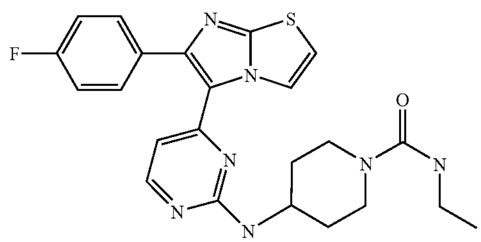 | N-ethyl-4-({4-[6-(4-fluorophenyl)imidazo[2,1-b][1,3]thiazol-5-yl]pyrimidin-2-yl}amino)piperidine-1-carboxamide | 210-212 | 0.041 |
| 295 | 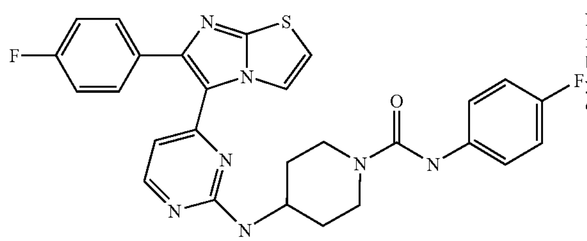 | N-(4-fluorophenyl)-4-({4-[6-(4-fluorophenyl)imidazo[2,1-b][1,3]thiazol-5-yl]pyrimidin-2-yl}amino)piperidine-1-carboxamide | 158-160 | 49 @ 10 uM |
| 296 | 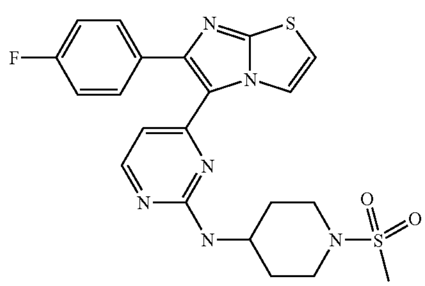 | 4-[6-(4-fluorophenyl)imidazo[2,1-b][1,3]thiazol-5-yl]-N-[1-(methylsulfonyl)piperidin-4-yl]pyrimidin-2-amine | 473 [M + H] | NT |
| 297 | 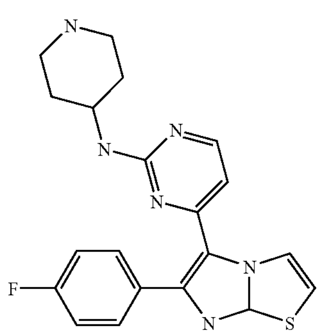 | 4-[6-(4-fluorophenyl)imidazo[2,1-b][1,3]thiazol-5-yl]-N-piperidin-4-ylpyrimidin-2-amine | 282-286 | 3 |
| 298 | 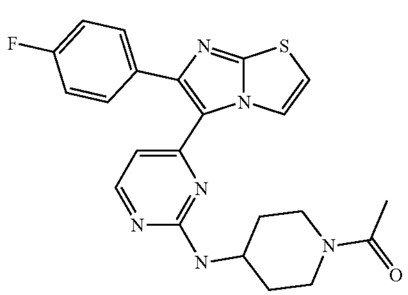 | N-(1-acetylpiperidin-4-yl)-4-[6-(4-fluorophenyl)imidazo[2,1-b][1,3]oxazol-5-yl]pyrimidin-2-amine | 214 | 59 @ 10 uM |

TABLE 2-continued

Exemplary compounds of the invention

| Cmpd # | Structure | IUPAC name | Melting point (° C.) or LCMS | Mutant B-RAF IC$_{50}$ (uM) or % inhibition |
|---|---|---|---|---|
| 299 | 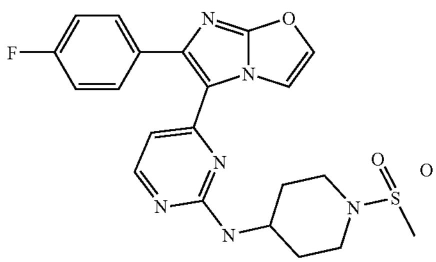 | 4-[6-(4-fluorophenyl)imidazo[2,1-b][1,3]oxazol-5-yl]-N-[1-(methylsulfonyl)piperidin-4-yl]pyrimidin-2-amine | 206-208 | 55 @ 10 uM |
| 300 | 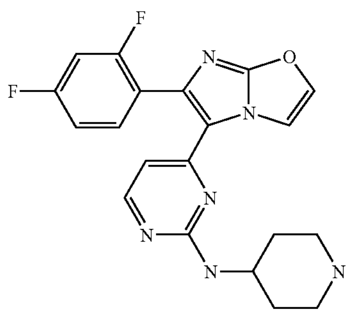 | 4-[6-(2,4-difluorophenyl)imidazo[2,1-b][1,3]oxazol-5-yl]-N-piperidin-4-ylpyrimidin-2-amine | 212-215 | 65 @ 10 uM |
| 301 | 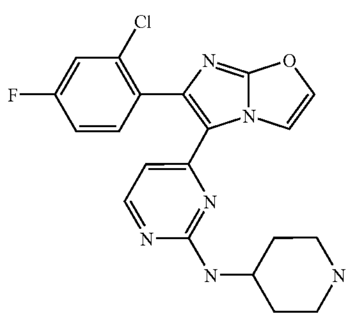 | 4-[6-(2-chloro-4-fluorophenyl)imidazo[2,1-b][1,3]oxazol-5-yl]-N-piperidin-4-ylpyrimidin-2-amine | 216-218 | 39 @ 10 uM |
| 302 | 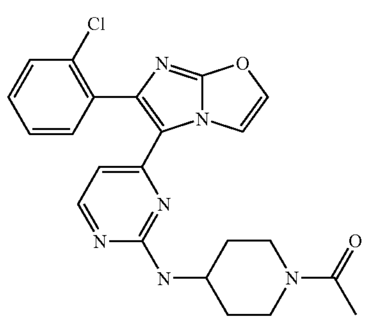 | N-(1-acetylpiperidin-4-yl)-4-[6-(2-chlorophenyl)imidazo[2,1-b][1,3]oxazol-5-yl]pyrimidin-2-amine | 155-163 | 39 @ 10 uM |

TABLE 2-continued

Exemplary compounds of the invention

| Cmpd # | Structure | IUPAC name | Melting point (° C.) or LCMS | Mutant B-RAF IC$_{50}$ (uM) or % inhibition |
|---|---|---|---|---|
| 303 | 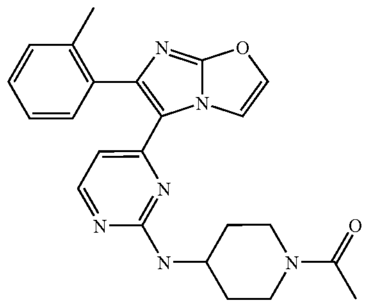 | N-(1-acetylpiperidin-4-yl)-4-[6-(2-methylphenyl)imidazo[2,1-b][1,3]oxazol-5-yl]pyrimidin-2-amine | 152-159 | 42 @ 10 uM |
| 304 | 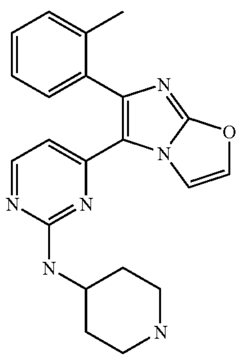 | 4-[6-(2-methylphenyl)imidazo[2,1-b][1,3]oxazol-5-yl]-N-piperidin-4-ylpyrimidin-2-amine | 217-220 | 56 @ 10 uM |
| 305 | 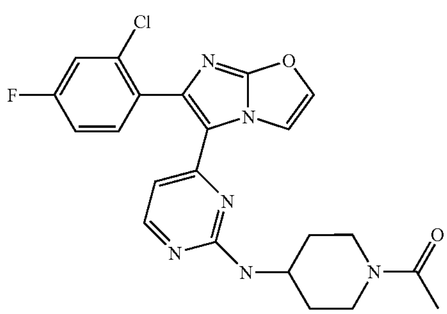 | N-(1-acetyl piperidin-4-yl)-4-[6-(2-chloro-4-fluorophenyl)imidazo[2,1-b][1,3]oxazol-5-yl]pyrimidin-2-amine | 143-145 | 47 @ 10 uM |
| 306 | 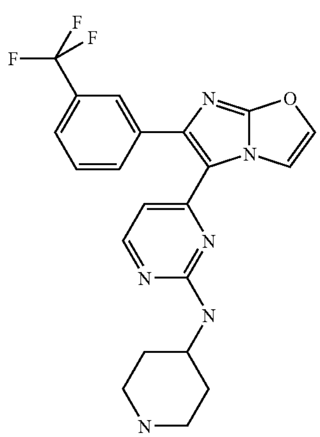 | N-piperidin-4-yl-4-{6-[3-(trifluoromethyl)phenyl]imidazo[2,b][1,3]oxazol-5-yl}pyrimidin-2-amine | 176-180 | 32 @ 10 uM |

TABLE 2-continued

Exemplary compounds of the invention

| Cmpd # | Structure | IUPAC name | Melting point (° C.) or LCMS | Mutant B-RAF IC$_{50}$ (uM) or % inhibition |
|---|---|---|---|---|
| 307 | 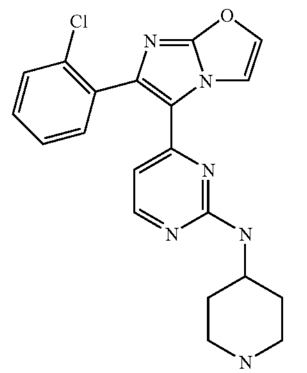 | 4-[6-(2-chlorophenyl)imidazo[2,1-b][1,3]oxazol-5-yl]-N-piperidin-4-ylpyrimidin-2-amine | 216-220 | 55 @ 10 uM |
| 308 | 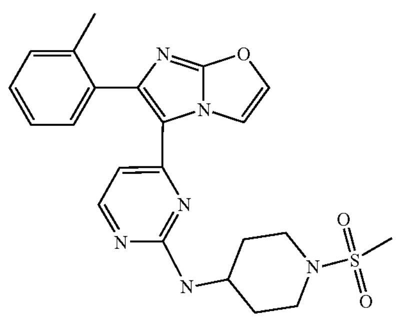 | 4-[6-(2-methylphenyl)imidazo[2,1-b][1,3]oxazol-5-yl]-N-(1-(methylsulfonyl)piperidin-4-yl]pyrimidin-2-amine | 121-123 | 45 @ 10 uM |
| 309 | 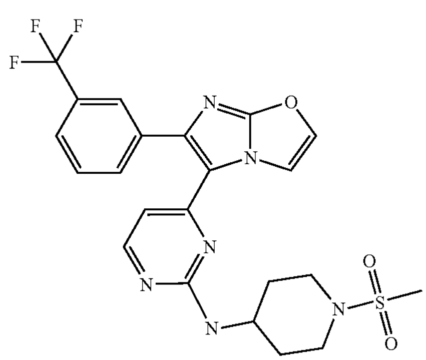 | N-[1-(methylsulfonyl)piperidin-4-yl]-4-{6-(3-(trifluoromethyl)phenyl]imidazo[2,b][1,3]oxazol-5-yl)pyrimidin-2-amine | 165-167 | 33 @ 10 uM |
| 310 | 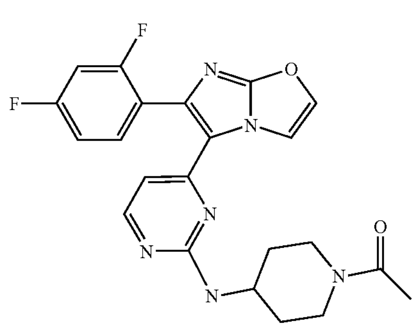 | N-(1-acetylpiperidin-4-yl)-4-[6-(2,4-difluorophenyl)imidazo[2,1-b][1,3]oxazol-5-yl]pyrimidin-2-amine | 255-258 | 33 @ 10 uM |

TABLE 2-continued

Exemplary compounds of the invention

| Cmpd # | Structure | IUPAC name | Melting point (° C.) or LCMS | Mutant B-RAF IC$_{50}$ (uM) or % inhibition |
|---|---|---|---|---|
| 311 | 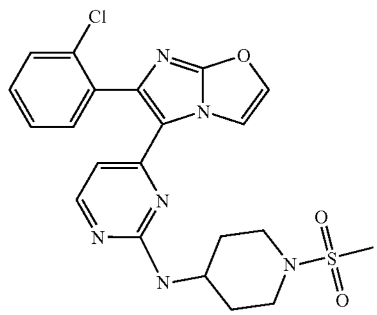 | 4-[6-(2-chlorophenyl)imidazo[2,1-b][1,3]oxazol-5-yl]-N-[1-(methylsulfonyl)piperidin-4-yl]pyrimidin-2-amine | 145-148 | 61 @ 10 uM |
| 312 | 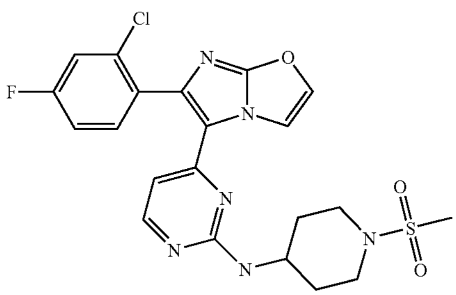 | 4-[6-(2-chloro-4-fluorophenyl)imidazo[2,1-b][1,3]oxazol-5-yl]-N-[1-(methylsulfonyl)piperidin-4-yl]pyrimidin-2-amine | 210-212 | 73 @ 10 uM |
| 313 | Chiral | 4-[6-(2,5-dimethoxyphenyl)imidazo[2,1-b][1,3]thiazol-5-yl]-N-[(3R)-piperidin-3-yl]pyrimidin-2-amine | 195-200 | 3 |
| 314 | Chiral | methyl 4-{[(3R)-3-({4-[6-(3-hydroxyphenyl)imidazo[2,1-b][1,3]thiazol-5-yl]pyrimidin-2-yl}amino)piperidin-1-yl]sulfonyl}benzoate | 184-186 | 0.03 |

TABLE 2-continued

Exemplary compounds of the invention

| Cmpd # | Structure | IUPAC name | Melting point (° C.) or LCMS | Mutant B-RAF IC$_{50}$ (uM) or % inhibition |
|---|---|---|---|---|
| 315 | 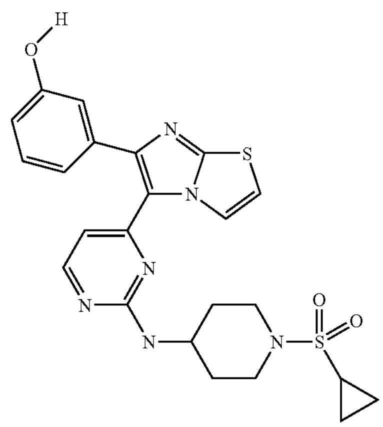 | 3-[5-(2-{[1-(cyclopropylsulfonyl)piperidin-4-yl]amino}pyrimidin-4-yl)imidazo[2,1-b][1,3]thiazol-6-yl}phenol | 166-171 | 0.011 |
| 316 | 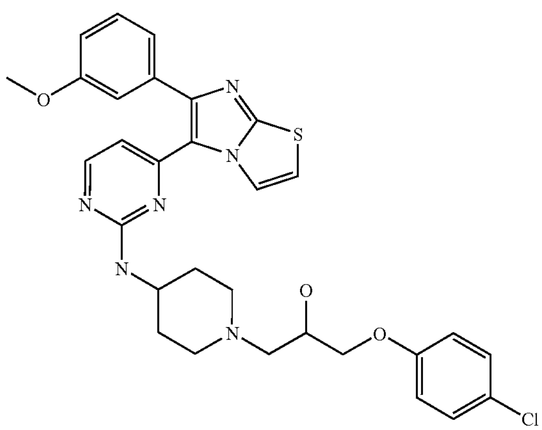 | 1-(4-chlorophenoxy)-3-[4-({4-[6-(3-methoxyphenyl)imidazo[2,1-b][1,3]thiazol-5-yl]pyrimidin-2-yl}amino)piperidin-1-yl]propan-2-ol | 109-111 | 3 |
| 317 | 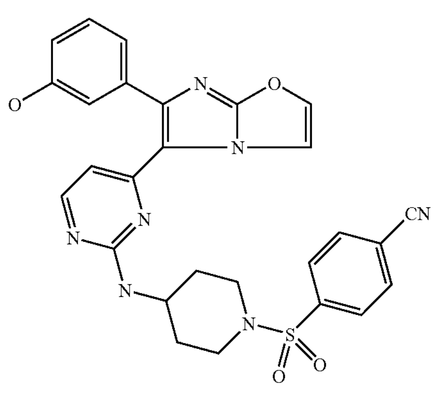 | 4-{[4-({4-[6-(3-hydroxyphenyl)imidazo[2,1-b][1,3]oxazol-5-yl]pyrimidin-2-yl}amino)piperidin-1-yl]sulfonyl}benzonitrile | 224-226 | 0.022 |

TABLE 2-continued

Exemplary compounds of the invention

| Cmpd # | Structure | IUPAC name | Melting point (° C.) or LCMS | Mutant B-RAF IC$_{50}$ (uM) or % inhibition |
|---|---|---|---|---|
| 318 | 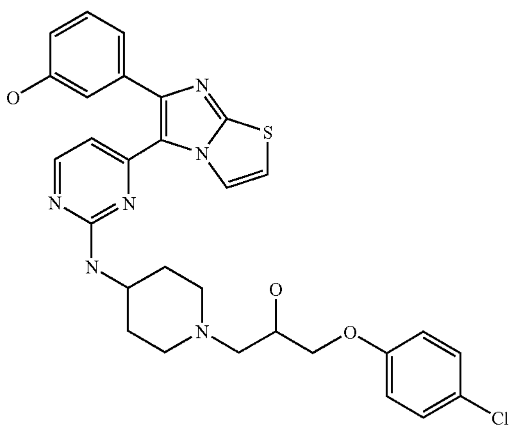 | 3-{5-[2-({1-[3-(4-chlorophenoxy)-2-hydroxypropyl]piperidin-4-yl}amino)pyrimidin-4-yl]imidazo[2,1-b][1,3]thiazol-6-yl}phenol | 130-132 | 0.422 |
| 319 | 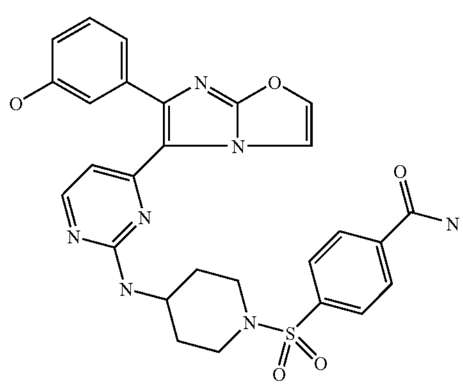 | 4-{[4-({4-[6-(3-hydroxyphenyl)imidazo[2,1-b][1,3]oxazol-5-yl]pyrimidin-2-yl}amino)piperidin-1-yl]sulfonyl)benzamide | 242-250 | 0.018 |
| 320 | Chiral | 4-{[(3R)-3-({4-[6-(3-hydroxyphenyl)imidazo[2,1-b][1,3]oxazol-5-yl]pyrimidin-2-yl}amino)piperidin-1-yl]sulfonyl}benzonitrile | 178-180 | 0.01 |

TABLE 2-continued

Exemplary compounds of the invention

| Cmpd # | Structure | IUPAC name | Melting point (° C.) or LCMS | Mutant B-RAF IC$_{50}$ (uM) or % inhibition |
|---|---|---|---|---|
| 321 | 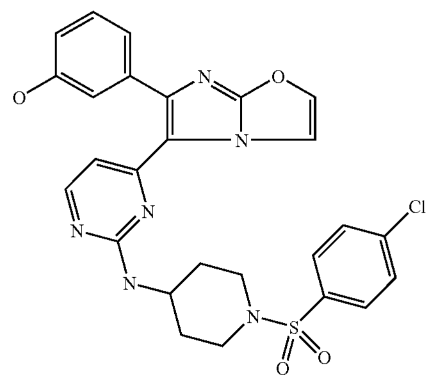 | 3-{5-[2-({1-[(4-chlorophenyl)sulfonyl]piperidin-4-yl}amino)pyrimidin-4-yl]imidazo[2,1-b][1,3]oxazol-6-yl}phenol | 175-177 | 0.126 |
| 322 | 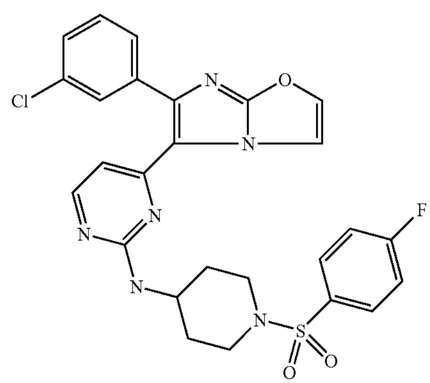 | 3-{5-[2-({1-[(4-fluorophenyl)sulfonyl]piperidin-4-yl}amino)pyrimidin-4-yl]imidazo[2,1-b][1,3]oxazol-6-yl}phenol | 173-176 | 0.046 |
| 323 | 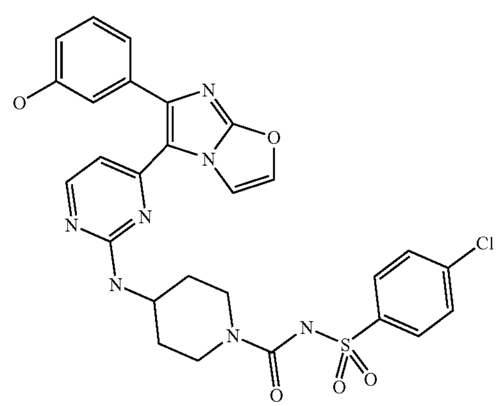 | N-[(4-chlorophenyl)sulfonyl]-4-({4-[6-(3-hydroxyphenyl)imidazo[2,1-b][1,3]oxazol-5-yl]pyrimidin-2-yl}amino)piperidine-1-carboxamide | 204-208 | 1.22 |

TABLE 2-continued

Exemplary compounds of the invention

| Cmpd # | Structure | IUPAC name | Melting point (° C.) or LCMS | Mutant B-RAF IC$_{50}$ (uM) or % inhibition |
|---|---|---|---|---|
| 324 | 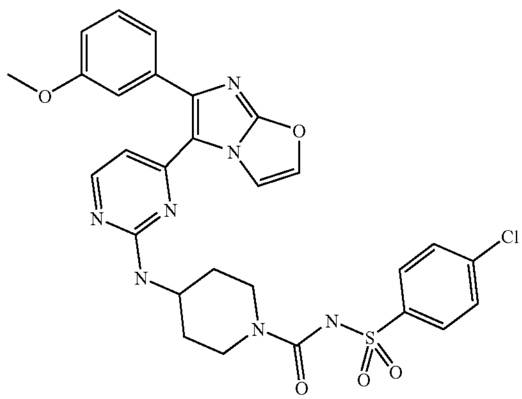 | N-[(4-chlorophenyl)sulfonyl]-4-({4-[6-(3-methoxyphenyl)imidazo[2,1-b][1,3]oxazol-5-yl]pyrimidin-2-yl}amino)piperidine-1-carboxamide | 165-166 | 4 |
| 325 | Chiral | N-[(3R)-1-(cyclopropylsulfonyl)piperidin-3-yl]-4-[6-(3-methoxyphenyl)imidazo[2,1-b][1,3]thiazol-5-yl]pyrimidin-2-amine | 107-115 | 4 |
| 326 | 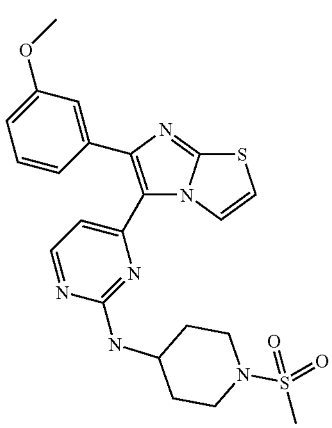 | 4-[6-(3-methoxyphenyl)imidazo[2,1-b][1,3]thiazol-5-yl]-N-[1-(methylsulfonyl)piperidin-4-yl]pyrimidin-2-amine | 110-118 | 4 |

TABLE 2-continued

Exemplary compounds of the invention

| Cmpd # | Structure | IUPAC name | Melting point (° C.) or LCMS | Mutant B-RAF IC$_{50}$ (uM) or % inhibition |
|---|---|---|---|---|
| 327 | Chiral | (3R)-N-(4-fluorophenyl)-3-({4-[6-(3-methoxyphenyl)imidazo[2,1-b][1,3]thiazol-5-yl]pyrimidin-2-yl}amino)piperidine-1-carboxamide | 120-122 | 4 |
| 328 | Chiral | (3R)-N-cyclohexyl-3-({4-[6-(3-methoxyphenyl)imidazo[2,1-b][1,3]thiazol-5-yl]pyrimidin-2-yl}amino)piperidine-1-carboxamide | 123-125 | 4 |
| 329 | Chiral | (3R)-N-(4-ethoxyphenyl)-3-({4-[6-(3-methoxyphenyl)imidazo[2,1-b][1,3]thiazol-5-yl]pyrimidin-2-yl}amino)piperidine-1-carboxamide | 122-124 | 4 |

TABLE 2-continued

Exemplary compounds of the invention

| Cmpd # | Structure | IUPAC name | Melting point (° C.) or LCMS | Mutant B-RAF IC$_{50}$ (uM) or % inhibition |
|---|---|---|---|---|
| 330 | Chiral | (3R)-3-({4-[6-(3-methoxyphenyl)imidazo[2,1-b][1,3]thiazol-5-yl]pyrimidin-2-yl}amino)-N-[4-(methylthio)phenyl]piperidine-1-carboxamide | 128-130 | 4 |
| 331 | Chiral | 3-{5-[2-({(3R)-1-[3-(4-chlorophenoxy)-2-hydroxypropyl]piperidin-3-yl}amino)pyrimidin-4-yl]imidazo[2,1-b][1,3]thiazol-6-yl}phenol | 130-135 | 1.04 |
| 332 | 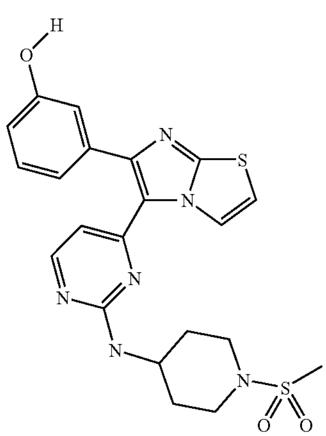 | 3-[5-(2-{[1-(methylsulfonyl)piperidin-4-yl]amino}pyrimidin-4-yl)imidazo[2,1-b][1,3]thiazol-6-yl}phenol | 220-226 | 0.01 |

TABLE 2-continued

Exemplary compounds of the invention

| Cmpd # | Structure | IUPAC name | Melting point (° C.) or LCMS | Mutant B-RAF IC$_{50}$ (uM) or % inhibition |
|---|---|---|---|---|
| 333 | Chiral | 3-(5-{2-[(3R)-piperidin-3-ylamino]pyrimidin-4-yl}imidazo[2,1-b][1,3]oxazol-6-yl)phenol | 220-225 | 0.906 |
| 334 | Chiral | (3R)-3-({4-[6-(3-hydroxyphenyl)imidazo[2,1-b][1,3]thiazol-5-yl]pyrimidin-2-yl}amino)-N-isopropylpiperidine-1-carboxamide | 170-172 | 0.65 |
| 335 | Chiral | (3R)-N-(4-fluorophenyl)-3-({4-[6-(3-hydroxyphenyl)imidazo[2,1-b][1,3]thiazol-5-yl]pyrimidin-2-yl}amino)piperidine-1-carboxamide | 160-162 | 3.26 |
| 336 | 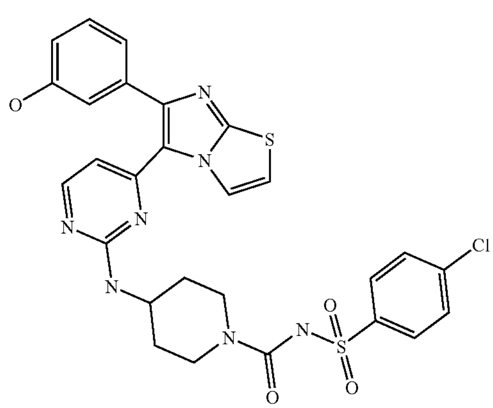 | N-[(4-chlorophenyl)sulfonyl]-4-({4-[6-(3-hydroxyphenyl)imidazo[2,1-b][1,3]thiazol-5-yl]pyrimidin-2-yl}amino)piperidine-1-carboxamide | 185-189 | 1.05 |

TABLE 2-continued

Exemplary compounds of the invention

| Cmpd # | Structure | IUPAC name | Melting point (° C.) or LCMS | Mutant B-RAF IC$_{50}$ (uM) or % inhibition |
|---|---|---|---|---|
| 337 | 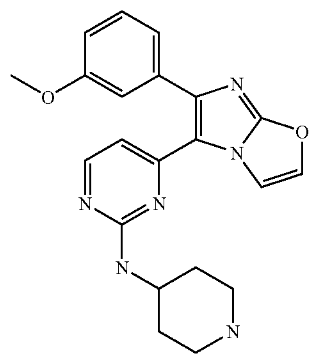 | 4-[6-(3-methoxyphenyl)imidazo[2,1-b][1,3]oxazol-5-yl]-N-piperidin-4-ylpyrimidin-2-amine | 230-232 | 3.21 |
| 338 | 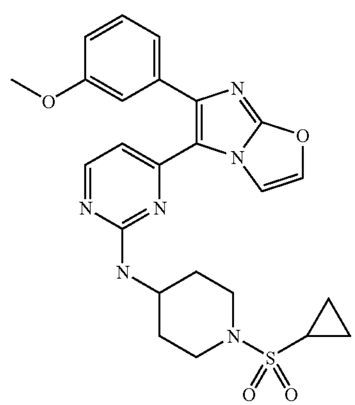 | N-[1-(cyclopropylsulfonyl)piperidin-4-yl]-4-[6-(3-methoxyphenyl)imidazo[2,1-b][1,3]oxazol-5-yl]pyrimidin-2-amine | 165-166 | 6.99 |
| 339 | 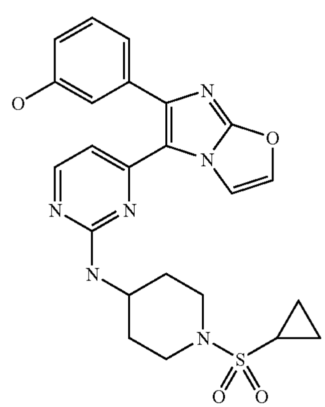 | 3-[5-(2-{[1-(cyclopropylsulfonyl)piperidin-4-yl]amino}pyrimidin-4-yl)imidazo[2,1-b][1,3]oxazol-6-yl]phenol | 152-154 | 0.046 |

TABLE 2-continued

Exemplary compounds of the invention

| Cmpd # | Structure | IUPAC name | Melting point (° C.) or LCMS | Mutant B-RAF IC$_{50}$ (uM) or % inhibition |
|---|---|---|---|---|
| 340 | 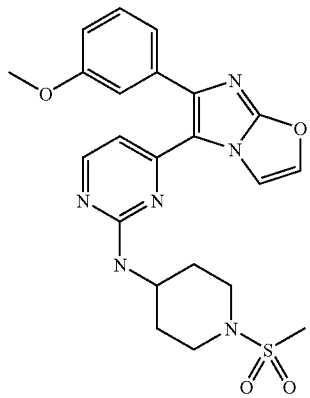 | 4-[6-(3-methoxyphenyl)imidazo[2,1-b][1,3]oxazol-5-yl]-N-[1-(methylsulfonyl)piperidin-4-yl]pyrimidin-2-amine | 206-207 | 10 |
| 341 | Chiral | (2R)-2,3-dihydroxypropyl 4-{[(3R)-3-({4-[6-(3-hydroxyphenyl)imidazo[2,1-b][1,3]thiazol-5-yl]pyrimidin-2-yl}amino)piperidin-1-yl]sulfonyl}benzoate | 182-184 | 0.033 |
| 342 | 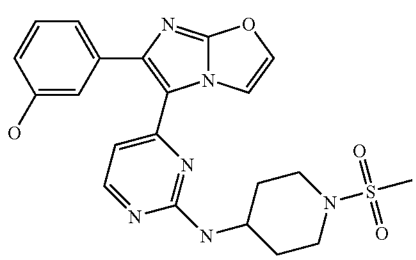 | 3-[5-(2-{[1-(methylsulfonyl)piperidin-4-yl]amino}pyrimidin-4-yl)imidazo[2,1-b][1,3]oxazol-6-yl]phenol | 237-239 | 0.258 |
| 343 | Chiral | (3R)-N-(4-hydroxyphenyl)-3-({4-[6-(3-hydroxyphenyl)imidazo[2,1-b][1,3]thiazol-5-yl]pyrimidin-2-yl}amino)piperidine-1-carboxamide | 205-207 | 1.44 |

TABLE 2-continued

Exemplary compounds of the invention

| Cmpd # | Structure | IUPAC name | Melting point (° C.) or LCMS | Mutant B-RAF IC$_{50}$ (uM) or % inhibition |
|---|---|---|---|---|
| 344 | Chiral | (3R)-3-({4-[6-(3-hydroxyphenyl)imidazo[2,1-b][1,3]thiazol-5-yl]pyrimidin-2-yl}amino)-N-[4-(methylthio)phenyl]piperidine-1-carboxamide | 172-174 | 2.45 |
| 345 | Chiral | 3-{5-[2-({(3R)-1-[(4-chlorophenyl)sulfonyl]piperidin-3-yl}amino)pyrimidin-4-yl]imidazo[2,1-b][1,3]thiazol-6-yl}-N'-hydroxybenzene-carboximidamide | 272-273 | 30 |
| 346 | Chiral | N-(3-{5-[2-({(3R)-1-[(4-chlorophenyl)sulfonyl]piperidin-3-yl}amino)pyrimidin-4-yl]imidazo[2,1-b][1,3]thiazol-6-yl}phenyl)methanesulfonamide | 170-172 | 0.88 |
| 347 | Chiral | 1-(3-{5-[2-({(3R)-1-[(4-chlorophenyl)sulfonyl]piperidin-3-yl}amino)pyrimidin-4-yl]imidazo[2,1-b][1,3]thiazol-6-yl}phenyl)-3-ethyl urea | 165-167 | 0.546 |

TABLE 2-continued

Exemplary compounds of the invention

| Cmpd # | Structure | IUPAC name | Melting point (° C.) or LCMS | Mutant B-RAF IC$_{50}$ (uM) or % inhibition |
|---|---|---|---|---|
| 348 | 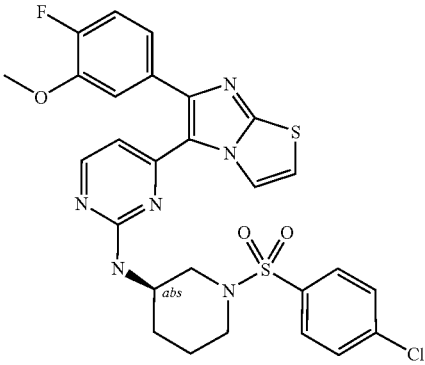 Chiral | N-{(3R)-1-[(4-chlorophenyl)sulfonyl]piperidin-3-yl}-4-[6-(4-fluoro-3-methoxyphenyl)imidazo[2,1-b][1,3]thiazol-5-yl]pyrimidin-2-amine | 142-143 | 0.105 |
| 349 | 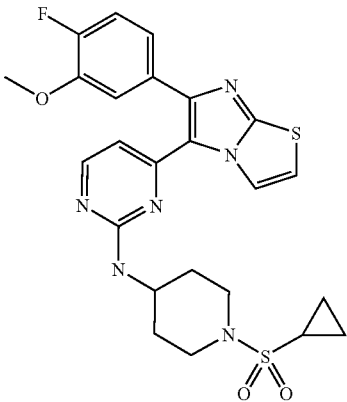 | N-[1-(cyclopropylsulfonyl)piperidin-4-yl]-4-[6-(4-fluoro-3-methoxyphenyl)imidazo[2,1-b][1,3]thiazol-5-yl]pyrimidin-2-amine | 146-148 | 2.6 |
| 350 | 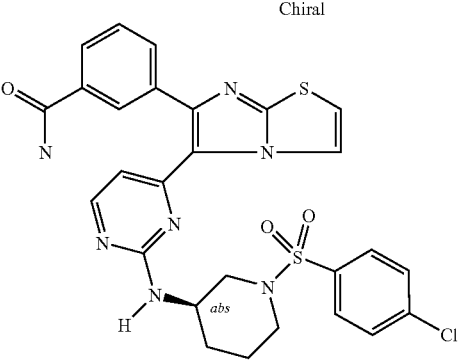 Chiral | 3-{5-[2-({(3R)-1-[(4-chlorophenyl)sulfonyl]piperidin-3-yl}amino)pyrimidin-4-yl]imidazo[2,1-b][1,3]thiazol-6-yl}benzamide | 168-170 | 0.14 |

TABLE 2-continued

Exemplary compounds of the invention

| Cmpd # | Structure | IUPAC name | Melting point (° C.) or LCMS | Mutant B-RAF IC$_{50}$ (uM) or % inhibition |
|---|---|---|---|---|
| 351 | 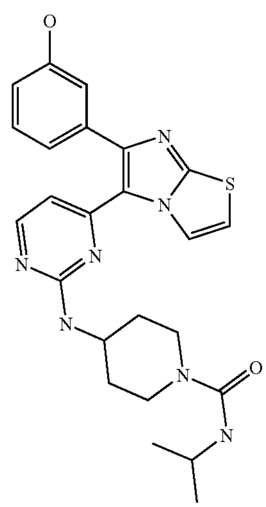 | 4-({4-[6-(3-hydroxyphenyl)imidazo[2,1-b][1,3]thiazol-5-yl]pyrimidin-2-yl}amino)-N-isopropylpiperidine-1-carboxamide | 280-290 | 0.94 |
| 352 | 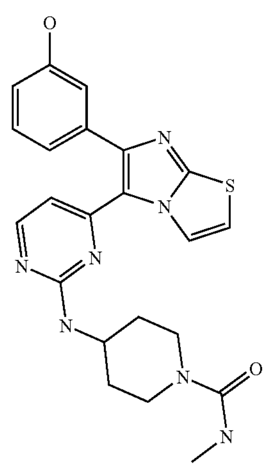 | 4-({4-[6-(3-hydroxyphenyl)imidazo[2,1-b][1,3]thiazol-5-yl]pyrimidin-2-yl}amino)-N-methylpiperidine-1-carboxamide | 285-295 | 0.67 |
| 353 | Chiral | 5-{5-[2-({(3R)-1-[(4-chlorophenyl)sulfonyl]piperidin-3-yl}amino)pyrimidin-4-yl]imidazo[2,1-b][1,3]thiazol-6-yl}-2-fluorophenol | 172-175 | 0.003 |

TABLE 2-continued

Exemplary compounds of the invention

| Cmpd # | Structure | IUPAC name | Melting point (° C.) or LCMS | Mutant B-RAF IC$_{50}$ (uM) or % inhibition |
|---|---|---|---|---|
| 354 | 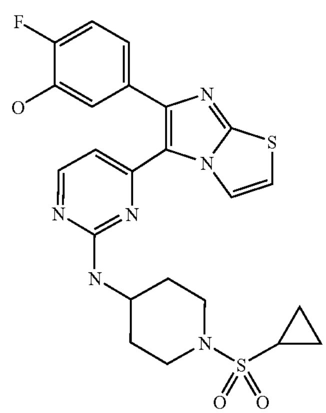 | 5-[5-(2-{[1-(cyclopropylsulfonyl)piperidin-4-yl]amino}pyrimidin-4-yl)imidazo[2,1-b][1,3]thiazol-6-yl]-2-fluorophenol | 224-225 | 0.00003 |
| 355 | 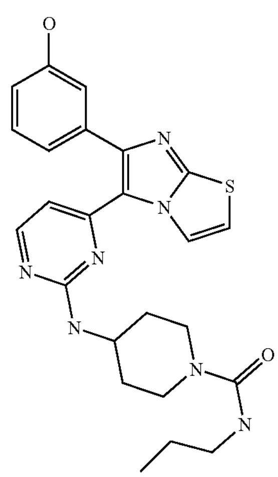 | 4-({4-[6-(3-hydroxyphenyl)imidazo[2,1-b][1,3]thiazol-5-yl]pyrimidin-2-yl}amino)-N-propylpiperidine-1-carboxamide | 235-240 | 1.79 |
| 356 | 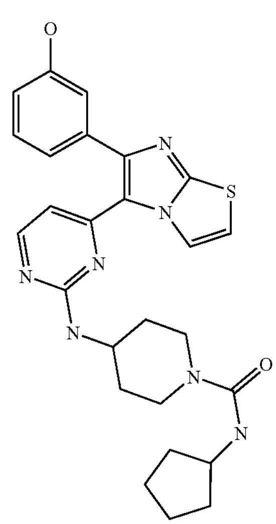 | N-cyclopentyl-4-({4-[6-(3-hydroxyphenyl)imidazo[2,1-b][1,3]thiazol-5-yl]pyrimidin-2-yl}amino)piperidine-1-carboxamide | 282-295 | 2.54 |

TABLE 2-continued

Exemplary compounds of the invention

| Cmpd # | Structure | IUPAC name | Melting point (° C.) or LCMS | Mutant B-RAF IC$_{50}$ (uM) or % inhibition |
|---|---|---|---|---|
| 357 | 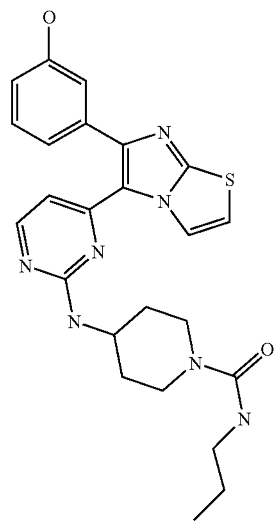 | N-butyl-4-({4-[6-(3-hydroxyphenyl)imidazo[2,1-b][1,3]thiazol-5-yl]pyrimidin-2-yl}amino)piperidine-1-carboxamide | 265-270 | 3 |
| 358 | Chiral | 4-(5-{2-[(3R)-piperidin-3-ylamino]pyrimidin-4-yl}imidazo[2,1-b][1,3]thiazol-6-yl)benzonitrile | 215-216 | 30 |
| 359 | Chiral | ethyl 4-(5-{2-[(3R)-piperidin-3-ylamino]pyrimidin-4-yl}imidazo[2,1-b][1,3]thiazol-6-yl)benzoate | 224-226 | 30 |

TABLE 2-continued

Exemplary compounds of the invention

| Cmpd # | Structure | IUPAC name | Melting point (° C.) or LCMS | Mutant B-RAF IC$_{50}$ (uM) or % inhibition |
|---|---|---|---|---|
| 360 | Chiral | 4-{5-[2-({(3R)-1-[(4-chlorophenyl)sulfonyl]piperidin-3-yl}amino)pyrimidin-4-yl]imidazo[2,1-b][1,3]thiazol-6-yl}benzonitrile | 241-244 | 2.47 |
| 361 | Chiral | ethyl 4-{5-[2-({(3R)-1-[(4-chlorophenyl)sulfonyl]piperidin-3-yl}amino)pyrimidin-4-yl]imidazo[2,1-b][1,3]thiazol-6-yl}benzoate | 129-131 | 3.25 |

TABLE 2-continued

Exemplary compounds of the invention

| Cmpd # | Structure | IUPAC name | Melting point (° C.) or LCMS | Mutant B-RAF IC$_{50}$ (uM) or % inhibition |
|---|---|---|---|---|
| 362 | 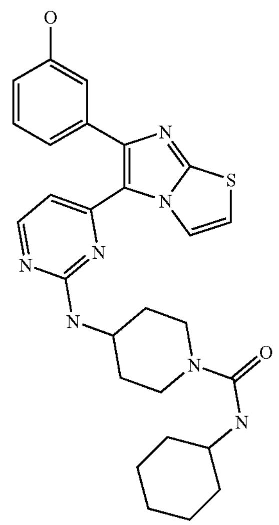 | N-cyclohexyl-4-({4-[6-(3-hydroxyphenyl)imidazo[2,1-b][1,3]thiazol-5-yl]pyrimidin-2-yl}amino)piperidine-1-carboxamide | 190-200 | 3 |
| 363 | Chiral | 4-{5-[2-({(3R)-1-[(4-chlorophenyl)sulfonyl]piperidin-3-yl}amino)pyrimidin-4-yl]imidazo[2,1-b][1,3]thiazol-6-yl}-N'-hydroxybenzene-carboximidamide | 177-179 | 8 |
| 364 | Chiral | 3-{5-[2-({(3R)-1-[(4-chlorophenyl)sulfonyl]piperidin-3-yl}amino)pyrimidin-4-yl]imidazo[2,1-b][1,3]thiazol-6-yl}phenyl carbamate | 118-120 | 0.007 |

TABLE 2-continued

Exemplary compounds of the invention

| Cmpd # | Structure | IUPAC name | Melting point (° C.) or LCMS | Mutant B-RAF IC$_{50}$ (uM) or % inhibition |
|---|---|---|---|---|
| 365 | Chiral | 4-{6-[3-(5-methyl-1,2,4-oxadiazol-3-yl)phenyl]imidazo[2,1-b][1,3]thiazol-5-yl}-N-[(3R)-piperidin-3-yl]pyrimidin-2-amine | 203-207 | 0.03 |
| 366 | Chiral | 3-{5-[2-({(3R)-1-[(1-methyl-1H-imidazol-4-yl)sulfonyl]piperidin-3-yl}amino)pyrimidin-4-yl]imidazo[2,1-b][1,3]thiazol-6-yl}phenol | 183-191 | 0.011 |
| 367 | Chiral | 3-[5-(2-{[(3R)-1-(3-thienylsulfonyl)piperidin-3-yl]amino}pyrimidin-4-yl)imidazo[2,1-b][1,3]thiazol-6-yl]phenol | 180-185 | 0.003 |

TABLE 2-continued

Exemplary compounds of the invention

| Cmpd # | Structure | IUPAC name | Melting point (° C.) or LCMS | Mutant B-RAF IC$_{50}$ (uM) or % inhibition |
|---|---|---|---|---|
| 368 | Chiral | 3-[5-(2-{[(3R)-1-(isopropylsulfonyl)piperidin-3-yl]amino}pyrimidin-4-yl)imidazo[2,1-b][1,3]thiazol-6-yl]phenol | 165-170 | >3 |
| 369 | Chiral | 3-[5-(2-{[(3R)-1-(benzylsulfonyl)piperidin-3-yl]amino}pyrimidin-4-yl)imidazo[2,1-b][1,3]thiazol-6-yl]phenol | 165-170 | >3 |
| 370 | Chiral | 3-[5-(2-{[(3R)-1-(propylsulfonyl)piperidin-3-yl]amino}pyrimidin-4-yl)imidazo[2,1-b][1,3]thiazol-6-yl]phenol | 150-155 | 1.2 |

TABLE 2-continued

Exemplary compounds of the invention

| Cmpd # | Structure | IUPAC name | Melting point (° C.) or LCMS | Mutant B-RAF IC$_{50}$ (uM) or % inhibition |
|---|---|---|---|---|
| 371 | Chiral | 3-[5-(2-{[(3R)-1-(2-thienylsulfonyl)piperidin-3-yl]amino}pyrimidin-4-yl)imidazo[2,1-b][1,3]thiazol-6-yl]phenol | 158-168 | 0.003 |
| 372 | Chiral | 3-[5-(2-{[(3R)-1-(phenylsulfonyl)piperidin-3-yl]amino}pyrimidin-4-yl)imidazo[2,1-b][1,3]thiazol-6-yl]phenol | 180-185 | 0.003 |
| 373 | Chiral | 3-[5-(2-{[(3R)-1-(ethylsulfonyl)piperidin-3-yl]amino}pyrimidin-4-yl)imidazo[2,1-b][1,3]thiazol-6-yl]phenol | 162-170 | >3 |

TABLE 2-continued

Exemplary compounds of the invention

| Cmpd # | Structure | IUPAC name | Melting point (° C.) or LCMS | Mutant B-RAF IC$_{50}$ (uM) or % inhibition |
|---|---|---|---|---|
| 374 | Chiral | N-(4-{[(3R)-3-({4-[6-(3-hydroxyphenyl)imidazo[2,1-b][1,3]thiazol-5-yl]pyrimidin-2-yl}amino)piperidin-1-yl]sulfonyl}phenyl)acetamide | 180-192 | 0.001 |
| 375 | Chiral | 3-{5-[2-({(3R)-1-[(2,2,2-trifluoroethyl)sulfonyl]piperidin-3-yl}amino)pyrimidin-4-yl]imidazo[2,1-b][1,3]thiazol-6-yl}phenol | >300 | >3 |
| 376 | Chiral | 3-{5-[2-({(3R)-1-[(1-methyl-1H-pyrazol-3-yl)sulfonyl]piperidin-3-yl}amino)pyrimidin-4-yl]imidazo[2,1-b][1,3]thiazol-6-yl}phenol | 196-210 | 0.001 |

TABLE 2-continued

Exemplary compounds of the invention

| Cmpd # | Structure | IUPAC name | Melting point (° C.) or LCMS | Mutant B-RAF IC$_{50}$ (uM) or % inhibition |
|---|---|---|---|---|
| 377 | Chiral | 3-{5-[2-({(3R)-1-{(4-chlorophenyl)sulfonyl]piperidin-3-yl}amino)pyrimidin-4-yl]imidazo[2,1-b][1,3]thiazol-6-yl}phenyl sulfamate | 133-135 | 0.085 |
| 378 | Chiral | (4-{5-[2-({(3R)-1-[(4-chlorophenyl)sulfonyl]piperidin-3-yl}amino)pyrimidin-4-yl]imidazo[2,1-b][1,3]thiazol-6-yl}phenyl)methanol | 136-137 | 2.26 |
| 379 | Chiral | 4-{5-[2-({(3R)-1-[(4-chlorophenyl)sulfonyl]piperidin-3-yl}amino)pyrimidin-4-yl]imidazo[2,1-b][1,3]thiazol-6-yl}benzamide | 177-179 | 2.67 |

TABLE 2-continued

Exemplary compounds of the invention

| Cmpd # | Structure | IUPAC name | Melting point (° C.) or LCMS | Mutant B-RAF IC$_{50}$ (uM) or % inhibition |
|---|---|---|---|---|
| 380 | Chiral | 3-{5-[2-({(3R)-1-[(4-chlorophenyl)sulfonyl]piperidin-3-yl}amino)pyrimidin-4-yl]imidazo[2,1-b][1,3]oxazol-6-yl}phenyl sulfamate | 142-145 | 1.59 |
| 381 | Chiral | 3-[5-(2-{[(3R)-1-(4H-1,2,4-triazol-3-ylsulfonyl)piperidin-3-yl]amino}pyrimidin-4-yl)imidazo[2,1-b][1,3]thiazol-6-yl]phenol | 218-240 | 0.015 |
| 382 | Chiral | 3-{5-[2-({(3R)-1-[(4-chlorophenyl)sulfonyl]piperidin-3-yl}amino)pyrimidin-4-yl]imidazo[2,1-b][1,3]thiazol-6-yl}benzoic acid | 190-195 | 1.19 |

TABLE 2-continued

Exemplary compounds of the invention

| Cmpd # | Structure | IUPAC name | Melting point (° C.) or LCMS | Mutant B-RAF IC$_{50}$ (uM) or % inhibition |
|---|---|---|---|---|
| 383 | Chiral | 3-(5-{2-[(3R)-piperidin-3-ylamino]pyrimidin-4-yl}imidazo[2,1-b][1,3]thiazol-6-yl)benzamide | 202-205 | 3 |
| 384 | Chiral | 1-(3-{5-[2-({(3R)-1-[(4-chlorophenyl)sulfonyl]piperidin-3-yl}amino)pyrimidin-4-yl]imidazo[2,1-b][1,3]thiazol-6-yl}phenyl)ethanone | 124-127 | 1.3 |
| 385 | Chiral | 4-{5-[2-({(3R)-1-[(4-chlorophenyl)sulfonyl]piperidin-3-yl}amino)pyrimidin-4-yl]imidazo[2,1-b][1,3]thiazol-6-yl}benzaldehyde | 155-159 | 0.876 |
| 386 | Chiral | 3-{5-[2-({(3R)-1-[(4-chlorophenyl)sulfonyl]piperidin-3-yl}amino)pyrimidin-4-yl]imidazo[2,1-b][1,3]oxazol-6-yl}phenyl carbamate | 144-147 | 0.109 |

TABLE 2-continued

Exemplary compounds of the invention

| Cmpd # | Structure | IUPAC name | Melting point (° C.) or LCMS | Mutant B-RAF IC$_{50}$ (uM) or % inhibition |
|---|---|---|---|---|
| 387 | 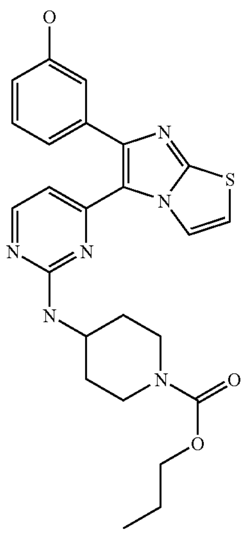 | propyl 4-({4-[6-(3-hydroxyphenyl)imidazo[2,1-b][1,3]thiazol-5-yl]pyrimidin-2-yl}amino)piperidine-1-carboxylate | 135-143 | >3 |
| 388 | Chiral | 3-[5-(2-{[(3R)-1-(2-thienylsulfonyl)piperidin-3-yl]amino}pyrimidin-4-yl)imidazo[2,1-b][1,3]oxazol-6-yl]phenol | 162-174 | 0.009 |
| 389 | Chiral | (1E)-1-(3-{5-[2-({(3R)-1-[(4-chlorophenyl)sulfonyl]piperidin-3-yl}amino)pyrimidin-4-yl]imidazo[2,1-b][1,3]thiazol-6-yl}phenyl)ethanone oxime | 156-158 | 0.034 |

TABLE 2-continued

Exemplary compounds of the invention

| Cmpd # | Structure | IUPAC name | Melting point (° C.) or LCMS | Mutant B-RAF IC$_{50}$ (uM) or % inhibition |
|---|---|---|---|---|
| 390 | Chiral | 3-{5-[2-({(3R)-1-[(4-chlorophenyl)sulfonyl]piperidin-3-yl}amino)pyrimidin-4-yl]imidazo[2,1-b][1,3]thiazol-6-yl}benzaldehyde | 124-126 | 0.28 |
| 391 | Chiral | 3-[5-(2-{[(3R)-1-(benzylsulfonyl)piperidin-3-yl]amino}pyrimidin-4-yl)imidazo[2,1-b][1,3]oxazol-6-yl]phenol | 222-227 | >3 |
| 392 | Chiral | 4-{5-[2-({(3R)-1-[(4-chlorophenyl)sulfonyl]piperidin-3-yl}amino)pyrimidin-4-yl]imidazo[2,1-b][1,3]thiazol-6-yl}benzaldehyde oxime | 174-177 | 0.698 |

TABLE 2-continued

Exemplary compounds of the invention

| Cmpd # | Structure | IUPAC name | Melting point (° C.) or LCMS | Mutant B-RAF IC$_{50}$ (uM) or % inhibition |
|---|---|---|---|---|
| 393 | Chiral | 3-[5-(2-{[(3R)-1-(propylsulfonyl)piperidin-3-yl]amino}pyrimidin-4-yl)imidazo[2,1-b][1,3]oxazol-6-yl]phenol | 144-155 | 0.33 |
| 394 | 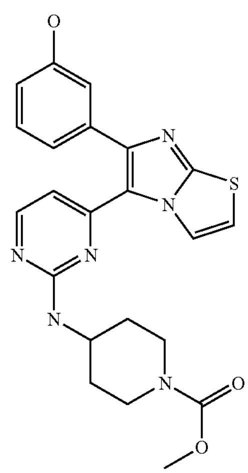 | methyl 4-({4-[6-(3-hydroxyphenyl)imidazo[2,1-b][1,3]thiazol-5-yl]pyrimidin-2-yl}amino)piperidine-1-carboxylate | 275-280 | >3 |
| 395 | Chiral | 3-{5-[2-({(3R)-1-[(4-chlorophenyl)sulfonyl]piperidin-3-yl}amino)pyrimidin-4-yl]imidazo[2,1-b][1,3]thiazol-6-yl}benzaldehyde oxime | 238-240 | 0.018 |

TABLE 2-continued

Exemplary compounds of the invention

| Cmpd # | Structure | IUPAC name | Melting point (° C.) or LCMS | Mutant B-RAF IC$_{50}$ (uM) or % inhibition |
|---|---|---|---|---|
| 396 | Chiral | (3-{5-[2-({(3R)-1-[(4-chlorophenyl)sulfonyl]piperidin-3-yl}amino)pyrimidin-4-yl]imidazo[2,1-b][1,3]thiazol-6-yl}phenyl)methanol | 150-155 | 1.6 |
| 397 | Chiral | 3-[5-(2-{[(3R)-1-(cyclopropylsulfonyl)piperidin-3-yl]amino}pyrimidin-4-yl)imidazo[2,1-b][1,3]oxazol-6-yl]phenol | 163-169 | 2.3 |
| 398 | Chiral | 3-[5-(2-{[(3R)-1-(phenylsulfonyl)piperidin-3-yl]amino}pyrimidin-4-yl)imidazo[2,1-b][1,3]oxazol-6-yl]phenol | 152-157 | 0.042 |
| 399 | Chiral | 3-[5-(2-{[(3R)-1-(3-thienylsulfonyl)piperidin-3-yl]amino}pyrimidin-4-yl)imidazo[2,1-b][1,3]oxazol-6-yl]phenol | 161-168 | >3 |

TABLE 2-continued

Exemplary compounds of the invention

| Cmpd # | Structure | IUPAC name | Melting point (° C.) or LCMS | Mutant B-RAF IC$_{50}$ (uM) or % inhibition |
|---|---|---|---|---|
| 400 | 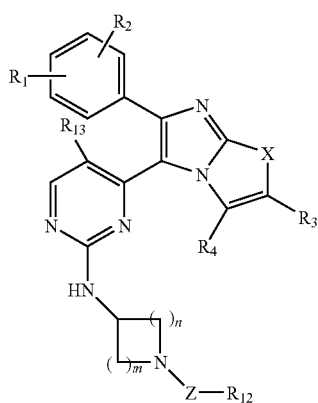 Chiral | 1-(4-{5-[2-({(3R)-1-[(4-chlorophenyl)sulfonyl]piperidin-3-yl}amino)pyrimidin-4-yl]imidazo[2,1-b][1,3]thiazol-6-yl}phenyl)ethanone | 137-139 | 1.3 |

Other embodiments are within the following claims. While several embodiments have been shown and described, various modifications may be made without departing from the spirit and scope of the present invention.

What is claimed is:

1. A compound of formula II, or pharmaceutically acceptable salts thereof:

(II)

wherein

X is O, S(O)$_p$;

m is an integer from 1 to 3;

n is an integer from 1 to 3;

p is an integer from 0 to 2;

Z is hydrogen, a bond, —C(O)—, —C(O)NR$_{11}$—, —S(O)$_2$—, —C(O)NH—S(O)$_2$—, or CH(OH)—CH$_2$—Y—, wherein Y is CH$_2$, O, S, NH, or a bond;

R$_1$ is —(CH$_2$)$_{0-3}$—C(O)NR$_6$R$_7$, —NR$_8$SO$_2$R$_9$, —NR$_8$C(O)NR$_6$R$_7$, —NR$_8$C(S)NR$_6$R$_7$, —OSO$_2$NR$_6$R$_7$, —C(N—OH)NH$_2$, —C(N—OH)R$_8$, —CH$_2$OR$_8$, —OC(O)NR$_6$R$_7$, —SR$_9$, or —C(O)NR$_8$SO$_2$R$_9$;

R$_2$ is hydrogen, —(CH$_2$)$_{0-3}$—C(O)NR$_6$R$_7$, —NR$_8$SO$_2$R$_9$, —NR$_8$C(O)NR$_6$R$_7$, —NR$_8$C(S)NR$_6$R$_7$, —OSO$_2$NR$_6$R$_7$, —C(N—OH)NH$_2$, —C(N—OH)R$_8$, —CH$_2$OR$_8$, —OC(O)NR$_6$R$_7$, —SR$_9$, or —C(O)NR$_8$SO$_2$R$_9$, or R$_1$ and R$_2$, taken together, may form a ring;

R$_3$ and R$_4$ are independently hydrogen, substituted or unsubstituted lower alkyl, —COOH, —COOR$_8$, or —C(O)NR$_{10}$R$_{11}$;

each R$_6$ and each R$_7$ are independently hydrogen, substituted or unsubstituted alkyl, substituted or unsubstituted aryl, or substituted or unsubstituted heterocyclyl, or R$_6$ and R$_7$, taken together, may form a ring;

each R$_8$ is independently hydrogen, or substituted or unsubstituted lower alkyl;

each R$_9$ is independently substituted or unsubstituted alkyl, substituted or unsubstituted aryl, substituted or unsubstituted heterocyclyl, or substituted or unsubstituted heteroaryl;

R$_{10}$ is substituted or unsubstituted lower alkyl, or substituted or unsubstituted aryl;

R$_{11}$ is hydrogen, substituted or unsubstituted alkyl, substituted or unsubstituted aryl, substituted or unsubstituted heterocyclyl, or substituted or unsubstituted heteroaryl, or R$_{11}$, taken together with R$_{10}$, may form a ring;

R$_{12}$ is substituted or unsubstituted alkyl, substituted or unsubstituted aryl, substituted or unsubstituted heterocyclyl, or substituted or unsubstituted heteroaryl; and R$_{13}$ is independently selected from the group consisting of hydrogen, C$_1$-C$_8$ alkyl, C$_1$-C$_8$ fluoro-substituted alkyl, C$_3$-C$_8$ cycloalkyl, C$_3$-C$_8$ fluoro-substituted cycloalkyl, aryl, halogen-substituted aryl, heteroaryl, and halogen-substituted heteroaryl.

2. The compound of claim 1 wherein R$_3$ and R$_4$ are hydrogen.

3. The compound of claim 1 wherein R$_{13}$ is hydrogen.

4. The compound of claim 1 wherein m+n=4, if m is not equal to n, then the preferred configuration is R.

5. The compound of claim 1 wherein Z is —S(O)$_2$— and R$_{12}$ is 4-chlorophenyl, 4-fluorophenyl, 4-cyanophenyl, methyl, or cyclopropyl.

6. The compound of claim 1 wherein the compound of formula II is selected from the group consisting of 3-{5-[2-({(3R)-1-[(4-chlorophenyl)sulfonyl]piperidin-3-yl}amino) pyrimidin-4-yl]imidazo[2,1-b][1,3]thiazol-6-yl}phenyl carbamate, 3-{5-[2-({(3R)-1-[(4-chlorophenyl)sulfonyl]

piperidin-3-yl}amino)pyrimidin-4-yl]imidazo[2,1-b][1,3]thiazol-6-yl}phenyl sulfamate, 3-{5-[2-({(3R)-1-[(4-chlorophenyl)sulfonyl]piperidin-3-yl}amino)pyrimidin-4-yl]imidazo[2,1-b][1,3]oxazol-6-yl}phenyl sulfamate, 3-{5-[2-({(3R)-1-[(4-chlorophenyl)sulfonyl]piperidin-3-yl}amino)pyrimidin-4-yl]imidazo[2,1-b][1,3]oxazol-6-yl}phenyl carbamate, and (1E)-1-(3-{5-[2-({(3R)-1-[(4-chlorophenyl)sulfonyl]piperidin-3-yl}amino)pyrimidin-4-yl]imidazo[2,1-b][1,3]thiazol-6-yl}phenyl)ethanone oxime.

7. A compound selected from the group consisting of 3-[5-(2-{[1-(cyclopropylsulfonyl)piperidin-4-yl]amino}pyrimidin-4-yl)imidazo[2,1-b][1,3]thiazol-6-yl]phenol, 3-[5-(2-{[1-(methylsulfonyl)piperidin-4-yl]amino}pyrimidin-4-yl)imidazo[2,1-b][1,3]thiazol-6-yl]phenol, 3-[5-(2-{[1-(cyclopropylsulfonyl)piperidin-4-yl]amino}pyrimidin-4-yl)imidazo[2,1-b][1,3]oxazol-6-yl]phenol, 3-[5-(2-{[1-(methylsulfonyl)piperidin-4-yl]amino}pyrimidin-4-yl)imidazo[2,1-b][1,3]oxazol-6-yl]phenol, 5-[5-(2-{[1-(cyclopropylsulfonyl)piperidin-4-yl]amino}pyrimidin-4-yl)imidazo[2,1-b][1,3]thiazol-6-yl]-2-fluorophenol, and 3-[5-(2-{[(3R)-1-(cyclopropylsulfonyl)piperidin-3-yl]amino}pyrimidin-4-yl)imidazo[2,1-b][1,3]oxazol-6-yl]phenol.

8. A pharmaceutical composition comprising a compound as claimed in claim 1 or claim 7 or a pharmaceutically acceptable salt thereof together with one or more pharmaceutically acceptable carriers or excipients.

9. The pharmaceutical composition of claim 8 further comprising a second chemotherapeutic agent.

10. The pharmaceutical composition of claim 9, wherein said second chemotherapeutic agent is selected from the group consisting of tamoxifen, raloxifene, anastrozole, exemestane, letrozole, cisplatin, carboplatin, paclitaxel, cyclophosphamide, lovastatin, minosine, gemcitabine, araC, 5-fluorouracil, methotrexate, docetaxel, goserelin, vincristin, vinblastin, nocodazole, teniposide, etoposide, epothilone, navelbine, camptothecin, daunonibicin, dactinomycin, mitoxantrone, amsacrine, doxorubicin, epirubicin, idarubicin imatanib, gefitinib, erlotinib, sorafenib, sunitinib malate, trastuzumab, rituximab, cetuximab, and bevacizumab.

* * * * *